United States Patent
McDaniel

(10) Patent No.: US 10,413,769 B2
(45) Date of Patent: *Sep. 17, 2019

(54) PAINT HAVING CELL WALL PARTICULATE MATERIAL WITH A PROTECTIVE ORGANOPHOSPHORUS ESTERASE

(71) Applicant: C. Steven McDaniel, Austin, TX (US)

(72) Inventor: C. Steven McDaniel, Austin, TX (US)

(73) Assignee: Reactive Surfaces, Ltd., LLP, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/795,608

(22) Filed: Jul. 9, 2015

(65) Prior Publication Data

US 2015/0328490 A1 Nov. 19, 2015

Related U.S. Application Data

(62) Division of application No. 10/655,345, filed on Sep. 4, 2003, now abandoned.

(60) Provisional application No. 60/409,102, filed on Sep. 9, 2002.

(51) Int. Cl.

| | | |
|---|---|---|
| A62D 5/00 | (2006.01) | |
| A62D 3/02 | (2007.01) | |
| C09D 5/00 | (2006.01) | |
| C12N 9/16 | (2006.01) | |
| C12N 11/08 | (2006.01) | |
| C09D 5/34 | (2006.01) | |
| C09J 11/02 | (2006.01) | |
| C12N 11/16 | (2006.01) | |
| C09D 7/63 | (2018.01) | |
| A62D 101/02 | (2007.01) | |
| A62D 101/26 | (2007.01) | |

(52) U.S. Cl.
CPC ............. *A62D 5/00* (2013.01); *A62D 3/02* (2013.01); *C09D 5/00* (2013.01); *C09D 5/34* (2013.01); *C09D 7/63* (2018.01); *C09J 11/02* (2013.01); *C12N 9/16* (2013.01); *C12N 11/08* (2013.01); *C12N 11/16* (2013.01); *A62D 2101/02* (2013.01); *A62D 2101/26* (2013.01)

(58) Field of Classification Search
None
See application file for complete search history.

(56) References Cited

U.S. PATENT DOCUMENTS

| | | |
|---|---|---|
| 3,437,514 A | 4/1969 | Burlant |
| 4,155,887 A | 5/1979 | Hetson |
| 4,166,804 A | 9/1979 | Bleha et al. |
| 4,244,693 A | 1/1981 | Guon |
| 4,324,683 A | 4/1982 | Lim et al. |
| 4,342,751 A | 8/1982 | Moore et al. |
| 4,495,239 A | 1/1985 | Pusch et al. |
| 4,598,015 A | 7/1986 | Panush |
| 4,683,202 A | 7/1987 | Mullis |
| 4,839,046 A | 6/1989 | Chandler |
| 4,879,236 A | 11/1989 | Smith et al. |
| 4,935,351 A | 6/1990 | Yamane et al. |
| 4,988,623 A | 1/1991 | Schwarz et al. |
| 5,026,650 A | 6/1991 | Schwarz et al. |
| 5,096,813 A | 3/1992 | Krumhar et al. |
| 5,137,569 A | 8/1992 | Waldron et al. |
| 5,153,131 A | 10/1992 | Wolf et al. |
| 5,169,554 A | 12/1992 | Akkara et al. |
| 5,177,012 A | 1/1993 | Kim et al. |
| 5,391,649 A | 2/1995 | Holmberg |
| 5,482,996 A | 1/1996 | Russell et al. ............... 525/54.1 |
| 5,484,728 A | 1/1996 | Serdar et al. .................. 435/196 |
| 5,559,163 A * | 9/1996 | Dawson .................... C09D 4/00 522/183 |
| 5,589,386 A | 12/1996 | Serdar ......................... 435/262.5 |
| 5,602,097 A | 2/1997 | Edwards |
| 5,627,021 A | 5/1997 | Goodwin et al. |
| 5,646,014 A | 7/1997 | Hara |
| 5,804,694 A | 9/1998 | Bruce et al. |
| 5,871,986 A | 2/1999 | Boyce |
| 5,879,440 A | 3/1999 | Sau |
| 5,882,731 A | 3/1999 | Owens |
| 5,885,782 A | 3/1999 | Edwards |
| 5,914,123 A | 6/1999 | Amtzen et al. |
| 5,919,689 A | 7/1999 | Selvig et al. |

(Continued)

FOREIGN PATENT DOCUMENTS

| | | |
|---|---|---|
| CA | 2337884 | 2/2000 |
| DE | 203926 | 11/1983 |

(Continued)

OTHER PUBLICATIONS

W. R. Grace & Co, SYLOID Matting Agent Brochure. Downloaded Sep. 15, 2017.*
Munnecke et al, Hydrolysis of Organophosphate Insecticides by an Immobilized-Enzyme System. Biotechnology and Bioengineering, vol. XXI, pp. 2247-2261 (1979).*
LeJeune et al, Dramatically Stabilized Phosphotriesterase-Polymers for Nerve Agent Degradation. Biotechnol Bioeng 54: 105-114, 1997.*
Gaberlein et al, Microbial and cytoplasmic membrane-based potentiometric biosensors for direct determination of organophosphorus insecticides. Appl Microbiol Biotechnol (2000) 54: 652-658.*

(Continued)

*Primary Examiner* — Sheridan Swope
(74) *Attorney, Agent, or Firm* — McDaniel & Associates, PC

(57) ABSTRACT

Disclosed herein are novel coatings and paints comprising a biomolecule composition, wherein the biomolecule composition comprises a phosphoric triester hydrolase. Also disclosed herein are methods of detoxification of a surface contaminated with an organophosphorus compound by contacting the surface with such a coating or paint. Also disclosed herein are novel coating and paint components derived from microorganisms.

9 Claims, No Drawings

(56) References Cited

U.S. PATENT DOCUMENTS

| | | | |
|---|---|---|---|
| 5,928,906 A | 7/1999 | Koster et al. | |
| 5,928,927 A | 7/1999 | Cheng et al. | 435/196 |
| 5,982,927 A | 11/1999 | Koljonen | |
| 5,998,200 A * | 12/1999 | Bonaventura | A01N 41/08 106/15.05 |
| 6,020,312 A | 2/2000 | Edwards | |
| 6,034,298 A | 3/2000 | Lam et al. | |
| 6,054,504 A | 4/2000 | Dalla Riva Toma | |
| 6,080,566 A | 6/2000 | Cheng et al. | |
| 6,087,558 A | 7/2000 | Howard et al. | |
| 6,136,320 A | 10/2000 | Amtzen et al. | |
| 6,291,200 B1 | 9/2001 | LeJeune et al. | 435/20 |
| 6,294,183 B1 | 9/2001 | Ito et al. | |
| 6,642,037 B2 | 11/2003 | Gordon et al. | |
| 6,730,144 B2 | 5/2004 | Tanaka et al. | |
| 7,041,285 B2 | 5/2006 | Polsenski et al. | |
| 7,125,842 B2 | 10/2006 | Kawabe et al. | |
| 7,229,819 B1 | 6/2007 | Cheng et al. | |
| 7,238,669 B2 | 7/2007 | Bishop-Hurley et al. | |
| 7,335,400 B2 | 2/2008 | Russell et al. | |
| 7,723,558 B1 | 5/2010 | Cheng et al. | |
| 2002/0010228 A1 | 1/2002 | Simendinger, III | |
| 2002/0010229 A1 | 1/2002 | Medoff et al. | |
| 2002/0013385 A1 | 1/2002 | Simendinger, III | |
| 2002/0018764 A1 | 2/2002 | Yamamori et al. | |
| 2002/0035239 A1 | 3/2002 | Andersen et al. | |
| 2002/0106361 A1 | 8/2002 | Paulsen et al. | 424/94.4 |
| 2002/0132540 A1 | 9/2002 | Soerens et al. | |
| 2003/0047508 A1 | 3/2003 | Boles et al. | |
| 2003/0113902 A1 | 6/2003 | Gordon et al. | |
| 2003/0166237 A1 | 9/2003 | Allermann et al. | |
| 2003/0194445 A1 | 10/2003 | Kuhner et al. | |
| 2004/0109853 A1 | 6/2004 | McDaniel | |
| 2004/0175407 A1 | 8/2004 | McDaniel | |
| 2004/0248783 A1 | 12/2004 | Kawabe et al. | |
| 2005/0147579 A1 | 7/2005 | Schneider et al. | |
| 2006/0160200 A1 | 7/2006 | Rathenow et al. | |
| 2008/0119381 A1 | 5/2008 | Wang et al. | |

FOREIGN PATENT DOCUMENTS

| | | |
|---|---|---|
| EP | 1174439 | 1/2002 |
| JP | 58198580 | 11/1983 |
| JP | 60218322 | 11/1985 |
| JP | 3239766 | 10/1991 |
| JP | 5247378 | 9/1993 |
| WO | 94/01459 | 1/1994 |
| WO | 95/08341 | 3/1995 |
| WO | 97/21805 | 6/1997 |
| WO | 99/43791 | 9/1999 |
| WO | 99/53037 | 10/1999 |
| WO | 00/64957 | 11/2000 |
| WO | 01/72911 | 10/2001 |
| WO | 02/064183 | 8/2002 |
| WO | 03/093462 | 11/2003 |
| WO | 2004/055044 | 7/2004 |

OTHER PUBLICATIONS

Sigma-Aldrich USPTO search "bis(1-octyloxy-2,2,6,6-tetramethyl-4-piperidinyl) ester"; "bis(I-octyloxy-2,2,6,6-tetramethyl-4-piperidinyl) sebacate". Downloaded Sep. 15, 2017.*

Wang et al., "Ginkbilobin, a Novel Antifungal Protein from Ginkgo biloba Seeds with Sequence Similarity to Embryo-Abundant Protein," Biochem. & Biophys. Res. Comm., vol. 279, 2000, pp. 407-411.

Wang et al., "Novel Antifungal Peptides from Ceylon Spinach Seeds," Biochem. & Biophys. Res. Comm., vol. 288, 2001, pp. 765-770.

Wilde et al., "Purification and Characterization of Human Neutrophil Peptide 4, a Novel Member of the Defensin Family," The Journal of Biological Chemistry, vol. 264, No. 19, Jul. 1989, pp. 11200-11203.

Yi et al., "Solution structure of an antimicrobial peptide buforin 11," FEBS Letters, vol. 398, 1996, pp. 87-90.

Yin et al., "Physical parameters of hydroxyapatite adorption and effect on candidacidal activity of histatins," Archives of Oral Biology, vol. 48, 2003, pp. 361-368.

Zhang et al., "NMR Studies of Defensin Antimicrobial Peptides: 1. Resonance Assignment and Secondary Structure Determined of Rabbit NP-2 and Human HNP-1," Biochemistry, vol. 31, 1992, pp. 11348-11356.

Zhao et al., "Identification of a new member of the protegrin family by cDNA cloning," FEBS Letters, vol. 346, 1994, pp. 285-288.

Zhao et al., "The structure of porcine protegrin genes," FEBS Letters, vol. 368, 1995, pp. 197-202.

Zhu et al., "Isolation and Mode of Action of Rabbit Corticostatic (Antiadrenocorticotropin) Peptides," Endocrinology, vol. 130, No. 3, 1992, pp. 1413-1423.

Zimmermann et al., "Solution Structure of Bovine Neutrophil β-Defensin-12:The Peptide Fold of the β-Defensin is Identical to that of the Classical Defensins," Biochemistry, vol. 34, 1995, pp. 13663-13671.

Cutuli et al., "Antimicrobial effects of α-MSH peptides," Journal of Leukocyte Biology, vol. 67, Feb. 2000, pp. 233-239.

Destoumieux et al., "Penaeidins, a family of antimicrobial peptides from penaeid shrimp (*Crustacea, Decapoda*)," CMLS, vol. 57, 2000, pp. 1260-1271.

Fiedler et al., "Nikkomycins: Microbial Inhibitors of Chitin Synthase," J. Chem. Tech. Biotechnol., vol. 32, 1982, pp. 271-280.

Goraya et al., "Peptides with antimicrobial activity from four different families isolated from the skins of the North American frogs *Rana luteiventris, Rana berlandieri* and *Rana pipiens*," Eur. J. Biochem., vol. 267, 2000, pp. 894-900.

Guichard et al., "Antigenic mimicry of natural L-peptides with retro-inverso-peptidomimetics," Proc. Natl. Acad. Sci. USA, vol. 91, Oct. 1994, pp. 9765-9769.

Iijima et al., "A novel antimicrobial peptide from the sea hare *Dolabella auricularia*," Developmental & Comparative Immunology, vol. 27, 2003, pp. 305-311.

Koo et al., "Two hevein homologs isolated from the seed of Pharbitis nil L. exhibit potent antifungal activity," Biochimica et Biophysica Acta, vol. 1382, 1998, pp. 80-90.

Jones et al., "Paneth Cells of the Human Small Intestine Express an Antimicrobial Peptide Gene," The Journal of Biological Chemistry, vol. 267, No. 32, Nov. 1992, pp. 23216-23225.

Lee et al., "Purification and cDNA Cloning of an Antifungal Protein from the Hemolymph of Holotrichia diomphalia Larvae," Biol. Pharm. Bull., vol. 18, No. 8, 1995, pp. 1049-1052.

Mandard et al., "Solution structure of thanatin, a potent bactericidal and fungicidal insect peptide, determined from proton two-dimensional nuclear magnetic resonance data," Eur. J. Biochem., vol. 256, 1998, pp. 404-410.

Mandard et al., "Androctonin, a Novel Antimicrobial Peptide from Scorpion Androctonus Australis: Solution Structure and Molecular Dynamics Simulations in the Presence of a Lipid Monolayer," Journal of Biomolecular Structure & Dynamics, vol. 17, No. 2, 1999, pp. 367-380.

Nagaoka et al., "Cloning and characterization of the guinea pig neutrophil cationic peptide-1 and -2 genes," J. DNA Sequencing & Mapping, vol. 4, 1993, pp. 123-128.

Qu et al., "Insect Immunity: Isolation and Structure of Cecropins B and D from Pupae of the Chinese Oak Silk Moth, *Antheraea pernyi*," Eur. J. Biochem., vol. 127, 1982, pp. 219-224.

Soedjanaatmadja et al., "Demonstration by mass spectrometry that pseudo-hevein and hevein have ragged C-terminal sequences," Biochimica et Biophysica Acta, vol. 1209, 1994, pp. 144-148.

Theil et al., "Purification and Spectral Characterization of Seminalplasmin, an Antimicrobial Protein from Bull Semen," Hoppe-Seyler's Z. Physiol. Chem. Bd., vol. 364, Aug. 1983, pp. 1003-1009.

Xu et al., "Primary Structure and Anticandidal Actificy of the Major Histatin from Parotid Secretion of the Subhuman Primate, *Macaca fascicularis*," J. Dent. Res., vol. 69, No. 11, Nov. 1990, pp. 1717-1723.

(56) References Cited

OTHER PUBLICATIONS

Yount et al., "Rat Neutrophil Defensins: Precursor Structures and Expression During Neutrophilic Myelopoiesis," The Journal of Immunology, vol. 155, 1995, pp. 4476-4484.
Zasloff et al., "Magainins, a class of antimicrobial peptides from Xenopus skin: Isolation, characterization of two active forms, and partial cDNA sequence of a precursor," Proc. Natl. Acad. Sci. USA, vol. 84, Aug. 1987, pp. 5449-5453.
Zhu et al., "Isolation and structure of corticostatin peptides from rabbit fetal and adult lung," Proc. Natl. Acad. Sci. USA, vol. 85, Jan. 1988, pp. 592-596.
Grau et al., "A Biophysical Study of the Interaction of the Lipopeptide Antibiotic Iturin A with Aqueous Phospholipid Bilayers," Archives of Biochemistry & Biophysics, vol. 377, No. 2, May 2000, pp. 315-323.
Gillatt, "Microbiological Protection of Waterborne Paint Formulations," Waterborne Coatings and Additives, © The Royal Society of Chemistry 1995, pp. 202-216.
Brunt, "A Silver Lining for Paints and Coatings—A Revolutionary Preservative System," Waterborne Coatings and Additives, © The Royal Society of Chemistry 1995, pp. 243-246.
Mak et al., "Isolation, Antimicrobial Activities, and Primary Structures of Hamster Neutrophil Defensins," Infection & Immunity, Nov. 1996, pp. 4444-4449.
Mandard et al., "The solution structure of gomesin, an antimicrobial cysteine-rich peptide from the spider," Eur. J. Biochem., vol. 269, 2002, pp. 1190-1198.
Martins et al., "1H NMR Study of the Solution Structure of Ac-AMP2, a Sugar Binding Antimicrobial Protein Isolated from Amaranthus caudatus," J. Mol. Biol., vol. 258, 1996, pp. 322-333.
Moerman et al., "Antibacterial and antifungal properties of α-helical,cationic peptides in the venom of scorpions from southern Africa," Eur. J. Biochem.,vol. 269, 2002, pp. 4799-4810.
Moore et al., "Antimicrobial Peptides in the Stomach of Xenopus laevis," The Journal of Biological Chemistry, vol. 266, No. 29, Oct. 1991, pp. 19851-19857.
Mor et al., "Isolation and structure of novel defensive peptides from frog skin," Eur. J. Biochem. vol. 219, 1994, pp. 145-154.
Mor et al., "Skip peptide tyrosine-tyrosine, a member of the pancreatic polypeptide family: Isolation, structure, synthesis, and endrocrine activity," Proc. Natl. Acad. Sci. USA, vol. 91, Oct. 1994, pp. 10295-10299.
Nagaoka et al., "Characterization of cDNA clones encoding guinea pig neutrophil cationic peptides," FEBS, vol. 280, No. 2, Mar. 1991, pp. 287-291.
Olson III et al., "Pseudin-2: An Antimicrobial Peptide with Low Hemolytic Activity from the Skin of the Paradixical Frog," Biochem. & Biophys. Res. Comm., vol. 288, 2001, pp. 1001-1005.
Oppenheim et al., "Histatins, a Novel Family of Histidine-rich Proteins in Human Parotid Secretion," The Journal of Biological Chemistry, vol. 263, No. 16, Jun. 1988, pp. 7472-7477.
Orivel et al., "Ponericins, New Antibacterial and Insecticidal Peptides from the Venom of the Ant Pachycondyla goeldii," The Journal of Biological Chemistry, vol. 276, No. 21, May 2001, pp. 17823-17829.
Park et al., "Antimicrobial Peptides from the Skin of a Korean Frog, Rana Rugosa," Biochem. & Biophys. Res. Comm., vol. 205, No. 1, Nov. 1994, pp. 948-954.
Park et al., "A Novel Antimicrobial Peptide from Bufo bufo gargarizans," Biochem. & Biophys. Res. Comm., vol. 218, 1996, pp. 408-413.
Park et al., "Structural study of novel antimicrobial peptides, nigrocins, isolated from Rana nigromaculata," FEBS Letters, vol. 507, 2001, pp. 95-100.
Park et al., "A novel antimicrobial peptide from the loach, Misgurnus anguillicaudatus," FEBS Letters, vol. 411, 1997, pp. 173-178.
Raj et al., "Structure of Human Salivary Histatin 5 in Aqueous and Nonaqueous Solutions," Biopolymers, vol. 45, 1998, pp. 51-67.
Tailor et al., "A Novel Family of Small Cysteine-rich Antimicrobial Peptides from Seed of Impatiens balsamina is Derives from a Single Precursor Protein," The Journal of Biological Chemistry, vol. 272, No. 39, Sep. 1997, pp. 24480-24487.
Rebuffat et al., "Tricholongins BI and BII, 19-residue peptaibols from Trichoderma longibrachiatum," Eur. J. Biochem., vol. 201, 1991, pp. 661-674.
Robinetie et al., "Antimicrobial activity in the skin of the channel catfish Ictalurus punctatus: characterization of broad-spectrum histone-like antimicrobial proteins," CMLS, vol. 54, 1998, pp. 467-475.
Rozek et al., "Structure of the Bovine Antimicrobiall Peptide Indolicidin Bound to Dodecylphosphocholine and Sodium Dodecyl Sulfate Micelles," Biochemistry, vol. 39, 2000, pp. 15765-15774.
Rozek et al., "The antibiotic and anticancer active aurein peptides from the Australian Bell Frogs Litoria aurea and Litoria raniformis," Eur. J. Biochem. vol. 267, 2000, pp. 5330-5341.
Ruissen et al., "Histatin 5 and derivatives: Their localization and effects on the ultra-structural level," Peptides, vol. 23, 2002, pp. 1391-1399.
Schibli et al., "Structure of the Antimicrobial Peptide Tritrpticin Bound to Micelles: A Distinct Membrane-Bound Peptide Fold," Biochemistry, vol. 38, 1999, pp. 16749-16755.
Schonwetter et al., "Epithelial antibiotics induced at sites of inflammation," Science, vol. 267, No. 5204, Mar. 1995, pp. 1645-1648.
Scocchi et al., "Structural organization of the bovine cathelicidin gene family and identification of a novel member," FEBS Letters, vol. 417, 1997, pp. 311-315.
Selsted et al., "Primary Structures of MCP-1 and MCP-2, Natural Peptide Antibiotics of Rabbit Lung Macrophages," The Journal of Biological Chemistry, vol. 258, No. 23, Dec. 1983, pp. 14485-14489.
Skerlavaj et al., Biological Characterization of Two Novel Cathelicidin-derived Peptides and Identification of Structural Requirements for Their Antimicrobial and Cell Lytic Activities, The Journal of Biological Chemistry, vol. 271, No. 45, Nov. 1996, pp. 28375-28381.
Tang et al., "Isolation, Characterication, cDNA Cloning, and Antimicrobial Properties of Two Distinct Subfamilies of α-Defensins from Rhesus Macaque Leukocytes," Infection & Immunity, vol. 67, No. 11, Nov. 1999, pp. 6139-6144.
Terras et al., "A new family of basic cysteine-rich plant antifungal proteins from Brassicaceae species," FEBS, vol. 316, No. 3, Feb. 1993, pp. 233-240.
Tinoco et al., "NMR Structure of PW2 Bound to SDS Micelles," The Journal of Biological Chemistry, vol. 277, No. 39, Sep. 2002, pp. 36351-36356.
Ueta et al, "A novel bovine lactoferrin peptide, FKCRRWQWRM, suppresses Candida cell growth and activates neutrophils," J. Peptide Res., vol. 57, 2001, pp. 240-249.
Vogel et al., "Towards a structure-function analysis of bovine lactoferricin and related tryptophan- and arginine-containing peptides," Biochem. Cell Biol., vol. 80, 2002, pp. 49-63.
International Search Report, PCT/US2004/021711, dated Feb. 23, 2005.
Abstract only, JP11124521, published May 1999.
Eisenberg et al., "Structure Summary Printout for 2mlt," deposited to RCSB Protein Data Bank Oct. 1990.
Bulet et al., "Sequence, Function, Subunit, Subcellular Location, Tissue Induction, Mass Spectrometry, and Amidation," submitted to Swiss-Prot. Data Bank Jul. 2002.
Michalowski et al., "Sequence from Nucleic Acid," submitted to the EMBL/GenBank/DDGB Databases Jun. 1998.
Paint and Surface Coatings, Theory and Practice, 2nd Ed., © 1999 Woodhead Publishing Ltd., pp. 2, 3, 10, 24, 51, 162, 193, 194, 371-383, 397, 448, 494-497, 533, 541-547, 700.
Handbook of Coatings Additives, © 1987 Marcel Dekker, Inc., pp. 43-63 and 177-224.
Almeida et al., "Solution Structure of Pisum sativum Defensin 1 by High Resolution NMR: Plant Defensins, Identical Backbone with Different Mechanisms of Action," J. Mol. Biol. vol. 315, 2002, pp. 749-757.
Bobek et al., "MUC7 20-Mer: Investigation of Antimicrobial Activity, Secondary Structure, and Possible Mechanism of Antifungal Action," Antimicrobial Agents & Chemotherapy, vol. 47, No. 2, Feb. 2003, pp. 643-652.

(56) References Cited

OTHER PUBLICATIONS

Cammue et al., "Isolation and Characterization of a Novel Class of Plant Antimicrobial Peptides from Mirabilis jalapa L. Seeds," The Journal of Biological Chemistry, vol. 267, No. 4, Feb. 1992, pp. 2228-2233.
Duvick et al., "Purification and Characterization of a Novel Antimicrobial Peptide from Maize (*Zea mays* L.) Kernels," The Journal of Biological Chemistry, vol. 267, No. 26, Sep. 1992, pp. 18814-18820.
Fernandes et al., "Anti-microbial properties of histone H2A from skin secretions of rainbow trout, *Oncorhynchus mykiss*," Biochem. J., vol. 368, 2002, pp. 611-620.
Fujitani et al., "Structure of the Antimicrobial Peptide Tachystatin A," The Journal of Biological Chemistry, vol. 277, No. 26, Jun. 2002, pp. 23651-23657.
Gao et al., "Solution Structure of PAFP-S: A New Knottin-Type Antifungal Peptide from the Seeds of Phytolacca americana," Biochemistry, vol. 40, 2001, pp. 10973-10978.
Gesell et al., "Two-dimensional 1H NMR experiments show that the 23-residue magainin antibiotic peptide is an ahelix in dodecylphosphocholine micelles, sodium dodecylsulfate micelles, and trifluoroethanol/water solution," Journal of Biololecular NMR, vol. 9, 1997, pp. 127-135.
Halverson et al., "Purification and characterization of antimicrobial peptides from the skin of the North American green frog *Rana clamitans*," Peptides, vol. 21, 2000, pp. 469-476.
Hara et al., "Effects of Peptide Dimerization on Pore Formation: Antiparallel Disulfide-Dimerized Magainin 2 Analogue," Biopolymers, vol. 58, 2001, pp. 437-446.
Hill et al., "Crystal Structure of Defensin HNP-3, an Amphiphilic Dimer: Mechanisms of Membrane Permeabilization," Science, New Series, vol. 251, No. 5000, Mar. 1991, pp. 1481-1485.
Hunter et al., "The Solution Structure of Human Hepcidin, α Peptide Hormone with Antimicrobial Activity that is Involved in Iron Uptake and Hereditary Hemochromatosis," The Journal of Biological Chemistry, vol. 277, No. 40, Oct. 2002, pp. 37597-37603.
Hwang et al., "Three-Dimensional Solution Structure of Lactoferricin B, an Antimicrobial Peptide Derived from Bovine Lactoferrin," Biochemistry, vol. 37, 1998, pp. 4288-4298.
Jones et al., "Defensin-6 mRNA in human Paneth cells: implications for antimicrobial peptides in host defense of the human bowel," FEBS Lett., vol. 315, No. 2, Jan. 1993, pp. 187-192.
Kokryakov et al., "Protegrins: leukocyte antimicrobial peptides that combine features of corticostatic defensins and tachyplesins," FEBS Lett., vol. 327, No. 2, Jul. 1993, pp. 231-236.
Lamberty et al., "Solution Structures of the Antifungal Heliomicin and a Selected Variant with both Antibacterial and Antifungal Activities," Biochemistry, vol. 40, 2001, pp. 11995-12003.
Lamberty et al., "Insect Immunity, Constitutive Expression of a Cysteine-Rich Antifungal and a Linear Antibacterial Peptide in a Termite Insect," The Journal of Biological Chemistry, vol. 276, No. 6, Feb. 2001, pp. 4085-4092.
Lee et al., "Antibiotic Activity of Reversed Peptides of a-Helical Antimicrobial Peptide, P18," Protein & Peptide Letters, vol. 9, No. 5, 2002, pp. 395-402.
Office Action dated Jan. 12, 2006 for U.S. Appl. No. 10/655,345.
Final Office Action dated May 18, 2007 for U.S. Appl. No. 10/655,345.
Final Office Action dated Feb. 27, 2008 for U.S. Appl. No. 10/655,345.
Office Action dated Mar. 27, 2009 for U.S. Appl. No. 10/655,345.
Office Action dated Feb. 19, 2010 for U.S. Appl. No. 10/655,345.
Office Action dated Dec. 14, 2010 for U.S. Appl. No. 10/655,345.
Office Action dated Jun. 19, 2014 for U.S. Appl. No. 10/655,345.
Office Action dated Jun. 25, 2014 for U.S. Appl. No. 10/655,345.
Office Action dated Jan. 9, 2015 for U.S. Appl. No. 10/655,345.
Office Action dated Jul. 20, 2015 for U.S. Appl. No. 10/655,345.
Office Action dated Dec. 30, 2010 for U.S. Appl. No. 11/368,087.
Lambourne, R. ed. et al. Paint and Surface Coatings, Theory and Practice, $2^{nd}$ Ed, 1999. 2-3, 10, 24, 51, 162, 193-194, 371-383, 397, 448, 494-497, 533, 541-547, 700.
Drevon G. et al. High-Activity Enzyme Polyurethane Coatings, *Biotechnology and Bioengineering* 2002, vol. 79, No. 7, 785-794.
Defrank, J. et al. Advanced Catalystic Enzyme System (ACES)—Dual Use Capabilities. U.S. Army Edgewood Chemical Biological Center Aberdeen Proving Grounds.
Paint Research Association. *Emulsion Polymer Technologies*. Apr. 2002. http://www.pra.org.uk/publications/emulsion/emulsionhighlights-2002.htm.
Green Marine Paint. *Chemical Week*, Apr. 11, 2001. 33.
"Reactive Coatings Literature Review" Department of Commerce National Technical Information Service, 2002.
Calbo, L. Handbook of Coatings Additives, 43-63, 177-224, 1987. New York: Marcel Dekker, Inc.
Flick, E. Handbook of Paint Raw Materials, $2^{nd}$ ed. 263-285. New Jersey; Noyes Publications.
Karsa, D. et al. Waterborne Coatings and Additives. 202-216, 243-251. 1995. Cambridge: Royal Society of Chemistry.
Stove, D. et al. Paints, Coatings, and Solvents, Second Completely Revised edition. 6, 12-19, 127, 165, 288-290. 1998. Weinheim: Wiley-Vch.
Rainina, E et al. The development of a new biosensor based on recombinant *E. coli* for the direct detection of organophosphorus neurotoxins. *Biosensors & Bloelectronics* 11, (10), 991-1000. 1996.
Gaberlein, S. et al. Microbial and cytoplasmic membrane-based potentiometric biosensors for direct determination organophosphorus insecticides, *Applied Microbiology and biotechnology*, 54, (5). 652-658. 2000.
Mulchandani, A. et al. A potentiometric microbial biosensor for direct determination of organophosphate nerve agents. *Electroanalysis*, 10 (11). 733-737. 1998.
Mulchandani, A. et al. Biosensor for direct determination of organophosphate nerve agents using recombinant *Escherichia coli* with surface-expressed organophosphorus hydrolase. 1. Potentiometric microbial electrode. *Analytical Chemistry*, 70 (19). 4140-4145. 1998.
Mulchandani, A. et al. Biosensor for direct determination of organophosphate nerve agents using recombinant *Escherichia coli* with surface-expressed organophosphorus hydrolase. 2. Fiber optic microbial biosensor. *Analytical Chemistry*, 70. 5042-5046. 1998.
Mulchandani, P. et al. Amperometric microbial biosensor for direct determination of organophosphate pesticides using recombinant microorganism with surface expressed organophosphorus hydrolase. *Biosensors and Bioelectronics*, 16, 433-437, 2001.
Wang, A. et al. Specific adhesion to cellulose and hydrolysis of organophosphate nerve agents by a genetically engineered *Escherichia coli* strain with a surface-expressed cellulose-bindingsdomain and organophosphorus hydrolase. *Applied & Environmental Microbiology*, 68, No. 4. 1684-1689. 2002.
Hong, M. et al. Neurotoxic Organophosphate Degradation with Polyvinyl Alcohol Gel-Immobilized Microbial Cells, *Bioremediation Journal* 2, No. 2.145-157. 1998.
Efremenko, E. et al. Addition of Polybrene improves stability of organophosphate hydrolase immobilized in polyvinyl alcohol) cryogel carrier. *J. Biochem. Biophys Methods* 51, No. 2, 195-201. 2002.
Kim, J. et al. Enhanced-rate biodegradation of organophosphate neurotoxins by immobilized nongrowing bacteria. *Biotechnol Prog.* 18(3):429-36. 2002.
Mulchandani, A. et al. Detoxification of organophosphate nerve agents by immobilized *Escherichia coli* with surface-expressed organophosphorus hydrolase. *Biotechnology Bioengineering*. 63(2), 216-23. 1999.
Albizo, J. et al. The Hydrolysis of GD and VX by Acetone Dried Preparations of Cured and Plasmid-Containing *Pseudomonas Diminuta*. Chemical Research, Development & Engineering Center Scientific conference on Chemical Defense Research, Nov. 18-21, pp. 643-649, 1986.
Wu, C. et al. GFP-visualized immobilized enzymes: degradation of paraoxon via organophosphorus hydrolase in a packed column, *Biotechnology & Bioengineering* 77, 212-218. 2002.
Lejeune, K. et al. Covalent binding of a nerve agent hydrolyzing enzyme within polyurethane foams. *Biotechnology and Bioengineering* 51 (4), 450-457. 1996.

(56) References Cited

OTHER PUBLICATIONS

Lejeune, K. et al. Dramatically stabilized phosphotriesterase-polymers for nerve agent degradation. *Biotechnology and Bioengineering* 54(2), 105-114. 1997.
Lejeune, K. et al. Increasing the Tolerance of Organophosphorus Hydrolase to Bleach. *Biotechnology and Bioengineering* 64(2):250-254, 1999.
Havens, P. et al. Reusable Immobilized Enzyme/Polyurethane Sponge for Removal and Detoxification of Localized Organophosphate Pesticide Spills. *Ind. Eng. Chem. Res.* 32, 2254-2258. 1993.
Gordon, R. et al. Organophosphate Skin decontamination using immobilized enzymes *Chemico-Biological Interactions* 119-120:463-470, 1999.
Munnecke, D. et al. Hydrolysis of Organophosphate Insecticides by an Immobilized-Enzyme System. *Biotechnology Bioengineering*, 21. 2247-2261. 1979.
Munnecke, D. Detoxification of pesticides using soluble or immobilized enzymes. *Process Biochemistry*. 14-16. 1978,
Mulchandani, P. et al. Biosensor for direct determination of organophosphate nerve agents. 1. Potentiometric enzyme electrode. *Biosensors & Bioelectronics* 14 77-85. 1999.
Mulchandani, A. et al. Fiber-optic enzyme biosensor for direct determination of organophosphate nerve agents. *Biotechnology Progress* 15. 130-134, 1999.
Mulchandani, P. et al. A. Flow injection arnperornetric enzyme biosensor for direct determination of organophosphate nerve agents. *Environmental Science Technology*. 35, 2562-2565. 2001.
Singh, A. et al. Development of sensors for direct detection of organophosphates. Part I: immobilization, characterization and stabilization of acetylcholinesterase and organophosphate hydrolase on silica supports. *Biosensors & Bioelectronics* 14, 703-713. 1999.
Rogers, K. et al. Organophosphorus hydrolase-based assay for organophosphate pesticides. *Biotechnology Progress* 15, 517-521. 1999.
Gaberlein S. et al. Disposable potentiometric enzyme sensor for direct determination of organophosphorus insecticides. *Analyst* 125, No. 12, 2274-2279. 2000.
Wang, J. et al. Orientation specific immobilization of organophosphorus hydrolase on magnetic particles through gene fusion. *Biomacromolecules* 2, 700-705, 2001.
Mulchandani, P. et al. Biosensors for direct determination of organophosphate pesticides. *Biosensors & Bioelectronics* 16. 225-230. 2001.
Caldwell, S. et al. Detoxification of Organophostphate Pesticides Using a Nylon Based Immobilized Phosphotriesterase From *Pseudomonas Diminuta. Applied Biochemistry & Biotechnology* 31. 59-730. 1991.
Lejeune, K. et al. Biocatalytic nerve agent detoxification in fire fighting foams. *Biotechnology & Bioengineering* 62(6), 659-665. 1999.
Lejeune, K. et al. Nerve agents degraded by enzymatic foams. *Nature* 395, 6697. 27-28. 1998.
Komives, C. et al. Degradation of pesticides in a continuous-flow two-phase niicroemulsion reactor. *Biotechnology* 10, 340-343. 1994.
Pei, L. et al. Encapsulation of Phosphotriesterase Within Murine Erythrocytes. *Toxicology and Applied Pharmacology* 124, 296-301. 1994.
Petrikovics, I. et al. Antagonism of paraoxon intoxication by recombinant phosphotriesterase encapsulated within sterically stabilized liposomes. *Toxicology & Applied Pharmacology* 156, 56-63. 1999.
Yang, F. et al. Nonaqueous biocatalytic degradation of a nerve gas mimic. *Biotechnology* 11, 471-474. 1995.
Caldwell, S. et al. Detoxicification of Organophosphate Pesticides Using an Immobilized Phosphotriesterase from *Pseudomonas diminuta. Biotechnology and Bloegineering* 37,103-109. 1991.
Andreopoulos, F. et al. Photoimmobilization of organophosphorus hydrolase within a PEG-based hydrogel. *Biotechnology Bioengineering*. 65(5), 579-588, 1999.
Lei, C. Entrapping Enzyme in a Fuctionalized Nanoporous Support. *J. American Chemical Society*, 124. 11242-11243. 2002.

Cheng, T. et al. . Alteromonas prolidase for organophosphorus G-agent decontamination. *Chemico-Biological Interactions* 119-120, 455-462. 1999.
McGuinn, W. et al. The Encapsulation of Squid Diisopropylphosphorofluoridate-Hydrolizing Enzyme within Mouse Erythrocytes. *Fundamental and Applied Toxicology* 21:38-43, 1993.
Hoskin, C. et al. Hydrolysis of Nerve Gas by Squid-Type Diisopropyl Phosphorofluoridate Hydrolyzing Enzyme on Agarose Resin. *Science*, vol. 215. 1255-1257. 1982.
Drevon, G. et al. Irreversible Immobilization of Diisopropylfluorophosphatase in Polyurethane Polymers *Biomacromolecules* 1:571-576, 2000.
Drevon, G. et al. Thermoinactivation of Diisopropylfluorophosphatase Containing Polyurethane Polymers. *Biomacromolecules* 2:664-671, 2001.
Dumas, D. et al. Purification and Properties of the Phosphotriesterase from Pseudomonas diminuta. 1-28.
Dumas, D. et al. Inactivation of organophosphorus nerve agents by the phosphotriesterase from pseudomonas diminuta. 1-14.
McDaniel, C. et al. Cloning and sequencing of a plasmid-borne gene (opd) encoding a phosphotriesterase. *J. of Bacteriology*. 170, 5. 2306-2311. 1998.
Lewis, V. et al. Mechanism and stereochemical course at phosphorus of the reaction catalyzed by a bacterial phosphotriesterase. *Biochemistry*. 27. 1591-1597. 1988.
Richins, R. et al. Expression, immobilization, and enzymatic characterization of cellulose-binding domain-organophosphorus hydrolase fusion enzymes. *Biotechnology & Bioengineering*, 69(6). 591-596. 2000.
Chen, T. et al. Combinatorial screening for enzyme-mediated coupling. Tyrosinase-catalzyed coupling to create protein-chitosan conjugates. *Biomacromolecules*, 456-462. 2001.
Shimazu, M. et al. Thermally triggered purification and immobilization of elastin-OPH fusions. , *Biotechnology & Bioengineering*, 81(1) 75-79. 2003.
Chen, W. et al. The use of live biocatalysts for pesticide detoxification, *Trends in Biotechnology* 16. 71-76. 1998.
Lejeune, K. et al. Fighting nerve agent chemical weapons with enzyme technology. *Annals New York Academy of Sciences*, 864. 153-170. 1998.
Petrikovics, I. et al. In vitro studies on sterically stabilized liposomes (SL) as enzyme carriers in organophosphorus (OP) antagonism. *Drug Delivery* 7. 83-89. 2000.
Petrikovics, I. et al. Long circulating liposomes encapsulating organophosphorus acid androlase in diisopropylflurorophosphate antagonism. *Toxicological Sciences* 57. 16-21. 2000.
ASTM D 5589-97. Standard test method for determining the resistance of paint films and related coatings to algal defacement, ASTM International.
ASTM D 5590-94. Standard test method for determining the resistance of paint films and related coatings to fungal defacement by accelerated four-week agar plate assay. ASTM International.
ASTM D 3623-78a. Standard test method for testing antifouling panels in shallow submergence. ASTM International.
ASTM D 4610-98. Standard guide for determining the presence of and removing microbial (fungal or algal) growth on paint and related coatings. ASTM International.
ASTM D 4938-89. Standard test method for erosion testing of antifouling paints using high velocity water. ASTM International.
ASTM D 4939-89. Standard test method for subjecting marine antifouling coating to biofouling and fluid shear forces in natural seawater. ASTM International.
ASTM D 5108-90. Standard test method for organotin release rates of antifouling coatings system in sea water. ASTM International.
ASTM D 5479-94. Standard practice for testing biofouling resistance of marine coatings partially immersed. ASTM International.
ASTM D 5618-94. Standard test method for measurement of barnacle adhesion strength in shear. ASTM International.
ASTM D 912-81. Standard specification for cuprous oxide for use in antifouling paints. ASTM International.
ASTM D 964-65. Standard Specification for copper powder use in antifouling paints. ASTM International.

(56) References Cited

OTHER PUBLICATIONS

ASTM D 2574-97. Standard test method for resistance of emulsion paints in the container to attack by microorganisms. ASTM International.
ASTM D 3274-95. Standard test method for evaluating degree of surface disfigurement of paint films by microbial (fungal or algal) growth or soil and dirt accumulation, ASTM International.
ASTM D 3273-94. Standard test method for resistance to growth of mold on the surface of interior coatings in an environmental chamber. ASTM International.
ASTM D 3456-86, Standard practice for determining by exterior exposure tests the suceptibility of paint films to microbiological attack. ASTM International.
Wicks, et al. Organic Coatings, Science and Technology vol. 1: Film Formation, Components, and Appearance, 318-320. 1992.
Wicks, et al, Organic Coatings, Science and Technology vol. 2: Applications, Properties, and Performance. 145, 309 319-323, 240-341. 1992.
PCI: Paint and Coatings Industry. 56, 60-66, 68-70, 72-74. Jul. 2002.
Abstract only for CN1031387, published Mar. 1, 1989.
International Search Report, PCT/US2004/007263, dated Nov. 16, 2004.
ASTM D 964, Standard Specification for Metallic Copper Powder for Use in Antifouling Paints, published May 2003, 1 page.
ASTM D 2574, Standard Test Method for Resistance of Emulsion Paints in the Container to Attack by Microorganisms, published Jun. 2006, 4 pages.
ASTM D 3273, Standard Test Method for Resistance to Growth of Mold on the Surface of Interior Coatings in an Environmental Chamber, published Feb. 2006, 4 pages.
ASTM D 3274, Standard Test Method for Evaluating Degree of Surface Disfigurement of Paint Films by Microbial (Fungal or Algal) Growth or Soil and Dirt Accumulation, published Jun. 1995, 4 pages.
ASTM D 3456, Standard Practice for Determining by Exterior Exposure Tests the Susceptibility of Paint Films to Microbiological Attack, published May 1986, 4 pages.
ASTM D 3623, Standard Test Method for Testing Antifouling Panels in Shallow Submergence, published Jun. 2004, 8 pages.
ASTM D 4610, Standard Guide for Determining the Presence of and Removing Microbial (Fungal or Algal) Growth on Paint and Related Coatings, published Jun. 2004, 2 pages.
ASTM D 4938, Standard Test Method for Erosion Testing of Antifouling Paints Using High Velocity Water, published Jun. 1989, 4 pages.
ASTM D 4939, Standard Test Method for Subjecting Marine Antifouling Coating to Biofouling and Fluid Shear Forces in Natural Seawater, published May 2003, 5 pages.
ASTM D 5108, Standard Test Method for Organotin Release Rates of Antifouling Coating Systems in Sea Water, published Feb. 1991, 6 pages.
ASTM D 5479, Standard Practice for Testing Biofouling Resistance of Marine Coatings Partially Immersed, published May 1994, 2 pages.
ASTM D 5589, Standard Practice Test Method for Determining the Resistance of Paint Films and Related Coatings to Algal Defacement, published Sep. 1997, 4 pages.
ASTM D 5590, Standard Test Method for Determining the Resistance of Paint Films and Related Coatings to Fungal Defacement by Accelerated Four-Week Agar Plate Assay, published Feb. 2006, 4 pages.
ASTM D 5618, Standard Test Method for Measurement of Barnacle Adhesion Strength in Shear, published Sep. 2005, 2 pages.
Bell et al., "Reactive Coatings Literature Review," prepared for the U.S. Army Research Office, Dec. 2001, 41 pages.
Dumas et al., "Inactivation of Organophosphorus Nerve Agents by the Phosphotriesterase from Pseudomonas diminuta," Archives of Biochemistry and Biophysics, vol. 277, No. 1, Feb. 1990, pp. 155-159.
Dumas et al., "Purification and Properties of the Phosphotriesterase from Pseudomonas diminuta," The Journal of Biological Chemistry, vol. 264, No. 33, Nov. 1989, pp. 19659-19665.
Efremenko et al., "Addition of Polybrene improves stability of organophosphate hydrolase immobilized in polyvinyl alcohol) cryogel carrier," J. Biochem. Biophys. Methods, vol. 51, 2002, pp. 195-201.
"Green Marine Paint," Chemical Week, Apr. 2001, p. 33.
Kim et al., "Enhanced-Rate Biodegradation of Organophosphate Neurotoxins by Immobilized Nongrowing Bacteria," Biotechnol. Prog., vol. 18, 2002, pp. 429-436.
Lei et al., "Entrapping Enzyme in a Functionalized Nanoporous Support," J. Am. Chem. Soc., vol. 124, 2002, pp. 11242-11243.
Munnecke, "Detoxification of Pesticides Using Soluble or Immobilised Enzymes," Process Biochemistry, Feb. 1978, pp. 14-16, 31.
Wu et al., "GFP-Visualized Immobilized Enzymes: Degradation of Paraoxon via Organophosphorus Hydrolase in a Packed Column," Biotechnology & Bioengineering, vol. 77, 2002, pp. 212-218.
Flick, *Handbook of Paint Raw Materials, 2nd Ed.*, published by Noyes Publications, Aug. 1989, pp. 263-285.
ASTM D 912, Standard Specification for Cuprous Oxide for Use in Antifouling Paints, Dec. 1981, 1 page.
Wicks et al., *Organic Coatings, Science and Technology, vol. 1: Film Formation, Components, and Appearance*, published by Wiley-Interscience, Oct. 1992, pp. 318-320.
Wicks et al., *Organic Coatings, Science and Technology, vol. 2: Applications, Properties, and Performance*, published by Wiley-Interscience, Nov. 1993, pp. 145, 309, 319-323, 340-341.
"PPG Installs Cleaning System," PCI Magazine, Jul. 2002, pp. 68-70.
"Copper-8-Quinolinolate Chemistry for Specialty Wood Preservative," PCI Magazine, Jun. 2002, 3 pages.
"Emulsion Polymer Technologies," Paint Research Association, vol. 13, No. 12, Apr. 2002, 24 pages.
"The PCI 50 & Global Top 10," PCI Magazine, Jun. 2002, 34 pages.
Winkowski, "Controlling Microbial Contamination," PCI Magazine, Jun. 2002, 6 pages.
Defrank et al., "Advanced Catalytic Enzyme System (ACES)—Dual Use Capabilities," U.S. Army Edgewood Chemical Biological Center, 2002, 7 pages.
Search Report, Application No. GB0616715.9 dated Oct. 30, 2006.
Sakuradani et al., "Identification of Δ12-fatty acid desaturase from arachidonic acid-producing Mortierella fungus by heterologous expression in the yeast *Saccharomyces cerevisiae* and the fungus *Aspergillus oryzae*," Eur. J. Biochem., vol. 261, 1999, pp. 812-820.
ASTM Document 912, "Standard Specification for Cuprous Oxide for Use in Antifouling Paints," published by ASTM International, West Conshohocken, PA, Dec. 1981, p. 1.
ASTM Document 964, "Standard Specification for Metallic Copper Powder for Use in Antifouling Paints," published by ASTM International, West Conshohocken, PA, May 2003, p. 1.
ASTM Document 2574, "Standard Test Method for Resistance of Emulsion Paints in the Container to Attack by Microorganisms," published by ASTM International, West Conshohocken, PA, Jun. 2006, pp. 1-4.
ASTM Document 3273, "Standard Test Method for Resistance to Growth of Mold on the Surface of Interior Coatings in an Environmental Chamber," published by ASTM International, West Conshohocken, PA, Feb. 2006, pp. 1-4.
ASTM Document 3274, "Standard Test Method for Evaluating Degree of Surface Disfigurement of Paint Films by Microbial (Fungal or Algal) Growth or Soil and Dirt Accumulation," published by ASTM International, West Conshohocken, PA, Jun. 1995, pp. 1-4.
ASTM Document 3456, "Standard Practice for Determining by Exterior Exposure Tests the Susceptibility of Paint Films to Microbiological Attack," published by ASTM International, West Conshohocken, PA, May 1986, pp. 1-4.
ASTM Document 3623, "Standard Test Method for Testing Antifouling Panels in Shallow Submergence," published by ASTM International, West Conshohocken, PA, Jun. 2004, pp. 1-8.
ASTM Document 4610, "Standard Guide for Determining the Presence of and Removing Microbial (Fungal or Algal) Growth on

(56) References Cited

OTHER PUBLICATIONS

Paint and Related Coatings," published by ASTM International, West Conshohocken, PA, Jun. 2004, pp. 1-2.
ASTM Document 4938, "Standard Test Method for Erosion Testing of Antifouling Paints Using High Velocity Water," published by ASTM International, West Conshohocken, PA, Jun. 1989, pp. 1-4.
ASTM Document 4939, "Standard Test Method for Subjecting Marine Antifouling Coating to Biofouling and Fluid Shear Forces in Natural Seawater," published by ASTM International, West Conshohocken, PA, May 2003, pp. 1-5.
ASTM Document 5108, "Standard Test Method for Organotin Release Rates of Antifouling Coating Systems in Sea Water," published by ASTM International, West Conshohocken, PA, Feb. 1991, p. 1-6.
ASTM Document 5479, "Standard Practice for Testing Biofouling Resistance of Marine Coatings Partially Immersed," published by ASTM International, West Conshohocken, PA, May 1994, pp. 1-2.
ASTM Document 5589, "Standard Practice Test Method for Determining the Resistance of Paint Films and Related Coatings to Algal Defacement," published by ASTM International, West Conshohocken, PA, Sep. 1997, pp. 1-4.
ASTM Document 5590, "Standard Test Method for Determining the Resistance of Paint Films and Related Coatings to Fungal Defacement by Accelerated Four-Week Agar Plate Assay," published by ASTM International, West Conshohocken, PA, Feb. 2006, pp. 1-4.
ASTM Document 5618, "Standard Test Method for Measurement of Barnacle Adhesion Strength in Shear," published by ASTM International, West Conshohocken, PA, Sep. 2005, pp. 1-2.
Bell et al., "Reactive Coatings Literature Review," prepared by TDA Research, Inc. for the U.S. Army Research Office, Dec. 2001, pp. i-vi, 1-20, Appendix A pp. 1-15.
Office Action dated May 26, 2008 for Canadian Patent Application No. 2538124.
Office Action dated Aug. 18, 2008 for Australian Patent Application No. 2003304222.
Plueddemann, Silane Coupling Agents, © 1982 Plenum Press, pp. 224-229.
U.S. Appl. No. 07/898,973 entitled "Parathion Hydrolase Analogs and Methods for Production and Purification," filed Jun. 15, 1992.
Office Action dated Jun. 28, 2007 for U.S. Appl. No. 10/792,516.
Office Action dated May 13, 2009 for U.S. Appl. No. 10/792,516.
Abstract only for CN1031387, Applicant: Qingdao Oceanology Univ., published Mar. 1, 1989.
Final Office Action dated Oct. 23, 2009 for U.S. Appl. No. 11/344,582.
Broun et al., "Catalytic Plasticity of Fatty Acid Modification Enzymes Underlying Chemical Diversity of Plant Lipids," Science, vol. 282, 1998, pp. 1315-1317.
Devos et al., "Practical Limits of Function Prediction," Proteins: Structure, Function, and Genetics, vol. 41, 2000, pp. 98-107.
Kisselev, "Polypeptide Release Factors in Prokaryotes and Eukaryotes: Same Function, Different Structure," Structure, vol. 10, 2002, pp. 8-9.
McDaniel et al., "Enzyme-based additives for paints and coatings," Progress in Organic Coatings, vol. 55, 2006, pp. 182-188.
Seffernick et al., "Melamine Deaminase and Atrazine Chlorohydrolase: 98 Percent Identical but Functionally Different," Journal of Bacteriology, vol. 183, No. 8, 2001, pp. 2405-2410.
Whisstock et al., "Prediction of protein function from protein sequence and structure," Quarterly Review of Biophysics, vol. 36, No. 3, 2006, pp. 307-340.
Witkowski et al., "Conversion of a β-Ketoacyl Synthase to a Malonyl Decarboxylase by Replacement of the Active-Site Cysteine with Glutamine," Biochemistry, vol. 38, 1999, pp. 11643-11650.
Gordon et al., "Organophosphate skin decontamination using immobilized enzymes," Chemico-Biological Interactions, vols. 119-120, 1999, pp. 463-470.
Lejeune et al., "Fighting Nerve Agent Chemical Weapons with Enzyme Technology," pp. 153-170.

Mulchandani et al., "Detoxification of Organophosphate Nerve Agents by Immobilized *Escherichia coli* with Surface-Expressed Organophosphorus Hydrolase," 1999, pp. 216-223.
Cheng et al., "Alteromonas prolidase for organophosphorus G-agent decontamination," Chemico-Biological Interactions, vols. 119-120, 1999, pp. 455-462.
Elashvili et al., "phnE and glpT Genes Enhance Utilization of Organophosphates in *Escherichia coli* K-12," Applied and Environmental Microbiology, vol. 64, No. 7, 1998, pp. 2601-2608.
D'Acunzo et al., "D-Amino Acid Oxidase from Trigonopsis variabilis: Immobilization of Whole Cells in Natural Polymeric Gels for Glutaryl-7-Aminocephalosporanic Acid Production," Journal of Fermentation and Bioengineering, vol. 81, No. 2, 1996, pp. 138-142.
Hoskin et al., "Degradation of nerve gases by CLECS and cells: kinetics of heterogenous systems," Chemico-Biological Interactions, vols. 119-120, 1999, pp. 439-444.
Kaneva et al., "Factors Influencing Parathion Degradation by Recombinant *Escherichia coli* with Surface-Expressed Organophosphorus Hydrolase," Biotechnol. Prog., vol. 14, 1998, pp. 275-278.
Sanders et al., "Stand-off tissue-based biosensors for the detection of chemical warfare agents using photosynthetic fluorescence induction," Biosensors& Bioelectronics, vol. 16, 2001, pp. 439-446.
Richins et al., "Biodegradation of organophosphorus pesticides by surface-expressed organophosphorus hydrolase," Nature Biotechnology, vol. 15, 1997, pp. 964-987.
Richins et al., "Biodegradation of organophosphorus pesticides by surface-expressed organophosphorus hydrolase," Nature Biotechnology, vol. 15, 1997, pp. 964-987.
Kim et al., "Processing Efficiency of Immobilized Non-Growing Bacteria: Biocatalytic Modeling and Experimental Analysis," Canadian Journal of Chemical Engineering, vol. 77, 1999, pp. 883-892.
Office Action dated Apr. 28, 2010 for U.S. Appl. No. 12/243,755.
Office Action dated May 26, 2008 for CA Patent Application No. 2,538,124.
Office Action dated Feb. 3, 2009 for CA Patent Application No. 2,538,124.
Office Action dated Sep. 29, 2005 for GB Patent Application No. 0506979.4.
Office Action dated Aug. 18, 2008 for AU Patent Application No. 2003304222.
Office Action dated Aug. 27, 2009 for AU Patent Application No. 2003304222.
Office Action dated Aug. 13, 2010 for EP Patent Application No. 03816944.7.
Final Office Action dated Mar. 17, 2008 for U.S. Appl. No. 10/792,516.
Final Office Action dated Feb. 3, 2010 for U.S. Appl. No. 10/792,516.
Office Action dated Oct. 31, 2006 for GB Patent Application No. 0616715.9.
Office Action dated Feb. 17, 2009 for U.S. Appl. No. 11/344,582.
Office Action dated Oct. 13, 2011 for U.S. Appl. No. 11/368,087.
Office Action dated Sep. 4, 2013 for U.S. Appl. No. 11/368,087.
Office Action dated Apr. 4, 2014 for U.S. Appl. No. 11/368,087.
Jamieson, "New Perspectives on Seed Enhancement," Acta Hort.., vol. 782, ISHS 2008, pp. 143-150.
Johnson, "Germination," Seed Development, Copyright 2003 by Elsevier Ltd., pp. 1298-1304.
Scott, "Seed Coatings and Treatments and Their Effects on Plant Establishment," Advances in Agronomy, vol. 42, 1989, pp. 43-83.
Taylor et al., "Concepts and Technologies of Selected Seed Treatments," Annu. Rev. Phytopathol., 1990 Annu. Rev. Phytopathol., pp. 321-339.
Taylor, "Seed Treatments," Seed Development, 2003, pp. 1291-1298.
Grimsley et al., "Structural and mutational studies of organophosphorus hydrolase reveal a cryptic and functional allosteric binding site," Arch. Biochem. Biophys.,vol. 442, No. 2, 2005, pp. 169-179.
Yang et al., "Evolution of an organophosphate-degradi ng enzyme: a comparison of natural and directed evolution," Protein Eng., vol. 16, No. 2, 2003, pp. 135-145.
Newcomb et al., "A single amino acid substitution converts a carboxylesterase to an organophosphorus hydrolase and confers

(56) References Cited

OTHER PUBLICATIONS insecticide resistance on a blowfly," Proc. Natl. Acad. Sci. USA, vol. 94, No. 14, 1997, pp. 7464-7468.

Mulbry et al., "Parathion hydrolase specified by the Flavobacterium opd gene: relationship between the gene and protein," J. Bacterial., vol. 171, No. 12, 1989, pp. 6740-6746.

Gayle et al., "Identification of Regions in Interleukin-1a Important for Activity," The Journal of Biological Chemistry, vol. 268, No. 29, Oct. 1993, pp. 22105-22111.

Ausubel et al., Current Protocols in Molecular Biology, Chapter 16 entitled "Protein Expression," 1987.

Office Action dated Jun. 19, 2013 for U.S. Appl. No. 10/792,516.
Final Office Action dated Mar. 6, 2014 for U.S. Appl. No. 10/792,516.
Office Action dated May 20, 2014 for U.S. Appl. No. 10/792,516.
Office Action dated Jun. 18, 2012 for European Patent Application No. 04718588.9.

Mulbry et al., "Parathion hydrolase specified by the Flavobacterium opd gene: relationship between the gene and protein." J. Bacterial. Dec. 1999; 171(12):6740-6748.

Di Sioudi et al., "Rational design of organophosphorus hydrolase for altered substrate specificities." Chemico-Biological Interactions vols. 119-120. May 14, 1999 pp. 211-223.

Doelle et al., "Electron microscopic investigations of Zymomonas mobilis cells grown in low and high glucose concentrations." European Journal of Applied Microbiology and Technology 16:136-141, 1982.

Rastogi et al., "Enzymatic hydrolysis of Russian-VX by organophosphorus hydrolase." Biochem. Biophys. Res. Commun. Dec. 18, 1997:241(2):294-296.

Szafraniec et al., "Decomtamination Chemistry of Russian VX," In Proceedings of the 1995 ERDEC Scientific Conference on Chemical and Biological Defense Research, Nov. 14-17, 1995; Berg, D.A., Ed.: ERDEC-SP-043, Aberdeen Proving Ground, MD, Jul. 1996; pp. 855-861.

Bernard et al., "Fermentation and Growth of *Escherichia coli* for Optimal Protein Production." In: Current Protocols in Protein Science (1995) John Wiley & Sons, Inc. pp. 5.3.1-5.3.18.

Piesecki et al., Immobilization of β-galactosidase for application in organic chemistry using a chelating peptide. Biotech & Bioeng. Jun. 1993; 42(2): 178-184.

EsPASY proteomics server/ENZYME/SIB E.C.3.1.8. Downloaded Jan. 26, 2010.

Hydrogel information sheet. W.R. Grace & Co. Downloaded Jan. 27, 2010.

DiBasic Phosphate Buffer, Sigma, Inc. Downloaded Jan. 31, 2010.
Ye et al., "The bile acid-inducible baiF gene from Eubacterium sp. strain VPI 12708 encodes a bile acid-coenzyme A hydrolase," J. Lipid Research, vol. 40, 1999, pp. 17-23.

Office Action dated Jan. 9, 2011 for Israel Patent Application No. 174122.

Gill, I. and Ballesteros, A. "Degradation of Organophosphorous Nerve Agents by Enzyme-Polymer Nanocomposites: Efficient Biocatalytic Materials for Personal Protection and Large-Scale Detoxification," Biotech. Bioengineer. vol. 70, No. 4, 2000, pp. 400-410.

LeJeune et al., "Dramatically Stabilized Phosphotriesterase-Polymers for Nerve Agent Degradation," Biotech. Bioengineer. vol. 54, No. 2, 1997, pp. 105-114.

* cited by examiner

PAINT HAVING CELL WALL PARTICULATE MATERIAL WITH A PROTECTIVE ORGANOPHOSPHORUS ESTERASE

This application is a divisional application of U.S. Ser. No. 10/655,345 filed Sep. 4, 2003, which claims the benefit of Provisional Patent Application Entitled "Bioactive Protein Paint Additive, Paint, and Painted Various," Ser. No. 60/409,102, filed Sep. 9, 2002, which are incorporated herein in their entirety by reference.

TABLE OF CONTENTS

| | |
|---|---|
| Title Page | 1 |
| Table of Contents | 2 |
| Priority Statement | 7 |
| Background of the Invention | 7 |
| A. Field of the Invention | 7 |
| B. Description of the Related Art | 7 |
| Summary of Invention | 15 |
| Detailed Description of the Invention | 38 |
| A. Biomolecules | 40 |
| B. Enzymes | 42 |
| 1. Preferred Enzymes | 46 |
| a. OPH | 51 |
| b. Paraoxonase | 54 |
| c. Carboxylases | 54 |
| d. OPAAs, Prolidases, Aminopeptideases and PepQ | 59 |
| e. Squid-Type DFPases | 57 |
| f. Mazur-Type DFPases | 57 |
| g. Other Phosphoric Triester Hydrolases | 58 |
| 2. Functional Equivalents of Wild-Type Enzymes | 58 |
| a. OPH Functional Equivalents | 66 |
| b. Paraoxonase Functional Equivalents | 76 |
| c. Squid-type DFPase Functional Equivalents | 76 |
| 3. Combinations of Biomolecules | 77 |
| C. Recombinantly Produced Enzymes | 78 |
| 1. General Expression Vector Components and Use | 80 |
| 2. Prokaryotic Expression Vectors and Use | 90 |
| D. Host Cells | 94 |
| E. Production of Expressed Proteinaceous Molecules | 97 |
| F. Processing of Expressed Proteinaceous Molecules | 98 |
| 1. Cell Permeabilization/Disruption | 100 |
| 2. Sterilization | 102 |
| 3. Concentrating a Biomolecule Composition | 102 |
| 4. Drying a Biomolecule Composition | 103 |
| 5. Resuspending Biomolecule Composition | 103 |
| 6. Temperatures | 104 |
| 7. Other Processing Steps | 104 |
| G. Coatings | 106 |
| 1. Paints | 115 |
| 2. Clear-coatings | 115 |
| a. Varnishes | 116 |
| b. Lacquers | 116 |
| c. Shellacs | 117 |
| d. Stains | 117 |
| e. Water repellent-coatings | 118 |
| 3. Coating Categories by Use | 119 |
| a. Architectural Coatings | 120 |
| (1) Wood Coatings | 123 |
| (2) Masonry Coatings | 124 |
| (3) Artist's Coatings | 125 |
| b. Industrial Coatings | 126 |
| (1) Automotive Coatings | 127 |
| (2) Can Coatings | 129 |
| (3) Sealant Coatings | 130 |
| (4) Marine Coatings | 132 |
| c. Specification Coatings | 133 |
| (1) Pipeline Coatings | 134 |
| (2) Traffic Marker Coatings | 135 |
| (3) Aircraft Coatings | 136 |
| (4) Nuclear Power Plant Coatings | 136 |
| H. Coating Components | 136 |
| 1. Binders | 138 |
| a. Oil-based binders | 140 |
| (1) Oils | 142 |
| (2) Alkyd Resins | 146 |
| (i) Oil Length Alkyd Binders | 148 |

-continued

TABLE OF CONTENTS

| | |
|---|---|
| (ii) High Solid Alkyd Coatings | 149 |
| (iii) Uralkyd Coatings | 150 |
| (iv) Water-Borne Alkyd Coatings | 151 |
| (3) Oleoresinous Binders | 151 |
| (4) Fatty Acid Epoxy Esters | 152 |
| b. Polyester Resins | 152 |
| c. Modified Cellulose Binders | 155 |
| d. Polyamide and amidoamine binders | 157 |
| e. Amino Resins | 160 |
| f. Urethane Binders | 162 |
| (1) Water-Borne Urethanes | 166 |
| (2) Urethane Powder Coatings | 166 |
| g. Phenolic Resins | 167 |
| (1) Resole | 168 |
| (2) Novolak | 169 |
| h. Epoxy Resins | 170 |
| (1) Ambient Condition Curing Epoxies | 171 |
| (2) Bake Curing Epoxies | 172 |
| (3) Electrodeposition Epoxies | 173 |
| (4) Powder Coating Epoxies | 173 |
| (5) Cycloaliphatic Epoxies | 173 |
| i. Polyhydroxyether Binders | 174 |
| j. Acrylic Resins | 175 |
| (1) Thermoplastic Acrylic Resins | 176 |
| (2) Water-Borne Thermoplastic Acrylic Coatings | 178 |
| (i) Architectural Coatings | 179 |
| (ii) Industrial Coatings | 180 |
| (3) Thermosetting Acrylic Resins | 180 |
| (i) Acrylic-Epoxy Combinations | 181 |
| (ii) Acrylic-Amino Combinations | 182 |
| (iii) Acrylic-Urethane Combinations | 183 |
| (iv) Water-Borne Thermosetting Acrylics | 183 |
| k. Polyvinyl Binders | 184 |
| (1) Plastisols and Organisols | 186 |
| (2) Powder Coatings | 188 |
| (3) Water-Borne Coatings | 188 |
| l. Rubber Resins | 188 |
| (1) Chlorinated Rubber Resins | 189 |
| (2) Synthetic Rubber Resins | 190 |
| m. Bituminous Binders | 191 |
| n. Polysulfide Binders | 192 |
| o. Silicone Binders | 193 |
| 2. Liquid Components | 195 |
| a. Solvents, Thinners, and Diluents | 200 |
| (1) Hydrocarbons | 205 |
| (i) Aliphatic Hydrocarbons | 206 |
| (ii) Cycloaliphatic Hydrocarbons | 207 |
| (iii) Terpene Hydrocarbons | 208 |
| (iv) Aromatic Hydrocarbons | 209 |
| (2) Oxygenated Solvents | 210 |
| (i) Alcohols | 210 |
| (ii) Ketones | 210 |
| (iii) Esters | 212 |
| (iv) Glycol Ethers | 213 |
| (v) Ethers | 214 |
| (3) Cholrinated Hydrocarbons | 214 |
| (4) Nitrated Hydrocarbon | 215 |
| (5) Miscellaneous Organic Liquids | 216 |
| b. Plasticizers | 216 |
| c. Water-Borne Coatings | 218 |
| 3. Colorants | 220 |
| a. Pigments | 221 |
| (1) Corrosion Resistance Pigments | 223 |
| (2) Camouflage Pigments | 227 |
| (3) Color Property Pigments | 227 |
| (i) Black Pigments | 227 |
| (ii) Brown Pigments | 229 |
| (iii) White Pigments | 229 |
| (iv) Pearlescent Pigments | 230 |
| (v) Violet Pigments | 230 |
| (vi) Blue Pigments | 231 |
| (vii) Green Pigments | 232 |
| (viii) Yellow Pigments | 233 |
| (ix) Orange Pigments | 236 |
| (x) Red Pigments | 237 |
| (xi) Metallic Pigments | 239 |

-continued

TABLE OF CONTENTS

| | |
|---|---|
| (4) Extender Pigments | 239 |
| b. Dyes | 242 |
| 4. Coating Additives | 242 |
| a. Preservatives | 242 |
| b. Wetting Additives and Dispersants | 249 |
| (1) Wetting Additives | 249 |
| (2) Dispersants | 251 |
| c. Buffers | 252 |
| d. Rheology Modifiers | 253 |
| e. Defoamers | 256 |
| f. Catalysts | 257 |
| (1) Driers | 257 |
| (2) Acids | 259 |
| (3) Bases | 260 |
| (4) Urethane Catalysts | 260 |
| g. Antiskinning Agent | 260 |
| h. Light Stabilizers | 261 |
| i. Corrosion Inhibitors | 262 |
| j. Dehydrators | 263 |
| k. Electrical Additives | 263 |
| l. Anti-Insect Additives | 264 |
| 5. Coating Preparation | 264 |
| 6. Empirically Determining the Properties of Biomolecule Coatings and/or Film | 270 |
| 7. Preferred Use of the Invention | 286 |
| 8. Combinations of Decontamination Compositions and Methods | 288 |
| 9. Removing a Coating of Film | 291 |
| Example 1 | |
| Assay for Active Phosphoric Triester Hydrolase Expression in Cells | 291 |
| Example 2 | |
| Preparation of Enzyme Powder | 292 |
| Example 3 | |
| Two-Pack OPH Paint Coating: OPH Powder and Latex Paint | 292 |
| Example 4 | |
| Application of OPH Paint to a Surface | 292 |
| Example 5 | |
| Buffered Enzyme Paint | 293 |
| Example 6 | |
| NATO Demonstration of Soman Detoxification Using OPH-Painted Surfaces | 294 |
| Example 7 | |
| Aberdeen Proving Ground | 295 |
| Example 8 | |
| NATO Protocols for Organophosphorus CWA Decontamination | 296 |
| A. Coated Surface | 296 |
| B. Contamination | 297 |
| C. Incubation | 297 |
| D. Decontamination | 297 |
| E. Sampling | 297 |
| F. Analysis | 297 |
| Example 9 | |
| Large-Scale Batch Fermentation of Produce OPH | 298 |
| Example 10 | |
| Large-Scale Fed-Batch Fermentation to Produce OPH | 299 |
| Example 11 | |
| Exterior Gloss Alkyd Paint Formulation | 299 |
| Example 12 | |
| Ranges | 302 |
| Example 13 | |
| Elastomers | 304 |
| Example 14 | |

-continued

TABLE OF CONTENTS

| | |
|---|---|
| Fillers and Flled Polymers | 304 |
| Example 15 | |
| Adhesives and Sealants | 305 |
| Example 16 | |
| Textiles | 306 |
| Example 17 | |
| Waxes | 307 |
| Example 18 | |
| Additional OPAAs | 307 |
| Example 19 | |
| Dowel Assay-Paraoxonase | 308 |
| References | 310 |
| Claims | |
| Abstract | 331 |

BACKGROUND OF THE INVENTION

A. Field of the Invention

The present invention relates generally to the field of biological molecules as components of coatings conferring an activity or other advantage to the coating proteinaceous molecule related to the biological molecule. More specifically, the present invention relates to proteins as such components of coatings. In one specific regard, the present invention relates to protein compositions capable of organophosphorus detoxification, and methods of reducing organophosphorus compounds on surfaces. More specifically, the present invention relates to coatings such as paints that degrade organophosphorus compounds such as pesticides and chemical warfare agents. The present invention further relates to paint and coating compositions and methods of their use to detoxify organophosphorus chemical warfare agents.

B. Description of the Related Art

Organophosphorus compounds ("organophosphate compounds" or "OP compounds") and organosulfur ("OS") compounds are used extensively as insecticides and are highly toxic to many organisms, including humans. OP compounds function as nerve agents. The primary effects of exposure to these agents are very similar, including inhibition of acetylcholinesterase and butyrylcholinesterase, with the subsequent breakdown of the normal operation of the autonomic and central nervous systems (Gallo and Lawryk, 1991).

Over 40 million kilograms of OP pesticides are used in the United States annually (Mulchandani, A. et al., 1999a). The number of people accidentally poisoned by OP pesticides has been estimated to be upwards of 500,000 persons a year (LeJeune, K. E. et al., 1998). Depending on the toxicity to the organism (e.g., humans), repeated, prolonged and/or low-dose exposure to an OP compound can cause neurotoxicity and delayed cholinergic toxicity. High-dose exposure can produces a fatal response (Tuovinen, K. et al., 1994).

Arguably of greater danger to humans, however, is the fact that some of the most toxic OP compounds are used as chemical warfare agents ("CWA"). Chemical warfare agents are classified into G agents, such as GD ("soman"), GB ("sarin"), GF ("cyclosarin") and GA ("tabun"), and the methyl phosphonothioates, commonly known as V agents, such as VX and Russian VX ("R-VX" or "VR"). The most important CWAs are as follows: tabun (O-methyl dimethylamidophosphorylcyanide), which is the easiest to manufacture; sarin ("isopropyl methylphosphonofluoridate"), which is a volatile substance mainly taken up through inhalation; soman ("pinacolyl methylphosphonofluoridate"), a moderately volatile substance that can be taken up by inhalation or skin contact; cyclosarin ("cyclohexyl methylphosphonofluoridate"), a substance with low volatility that is taken up through skin contact and inhalation of the substance as a gas or aerosol; and VX ("O-ethyl S-diisopropylaminomethyl methylphosphonothioate") and its isomeric analog R-VX ["O-isobutyl S-(2-diethylamino)-methylphosphonothioate, R-VX or VR"], both of which can remain on material, equipment and terrain for long periods, such as weeks, with R-VX being an especially persistent substance. All CWAs are colorless liquids with volatility varying from VX to sarin. VX is an involatile oil-like liquid, while sarin is a water-like, easily volatilized liquid. By addition of a thickener (e.g., a variety of carbon polymers), soman or other more volatile agents may be made to be less volatile and more persistent.

The CWAs are extremely toxic and have a rapid effect. Such agents enter the body through any of the following manners: inhalation, direct contact to the skin with a gas or with a contaminated surface, or through ingestion of contaminated food or drink. The poisoning effect takes longer when the agents enter through the skin, but is much faster when they are inhaled because of the rapid diffusion in the blood from the lungs. These toxins are fat-soluble and can penetrate the skin, but take longer to reach the deep blood vessels. Because of this, the first symptoms may not appear for 20-30 minutes after initial contact with a contaminated surface. This increases the danger for personnel entering a contaminated area, because the contamination may not be detected for 30 minutes or more (depending on concentrations) after the contaminated area is entered.

The first and most important method of protection from nerve agents is to prevent exposure. For military personnel and other first responders, masks and full body protective gear are available, but this equipment has certain drawbacks. Impermeable suits and even some air permeable suits are bulky and hot. The equipment inhibits free movement and tasks are harder and take longer to complete. In addition to those factors, hard physical work in these suits this may cause heat stress or even collapse. There may also be long delays before decontamination can be completed so the protective gear must be worn for long periods. This makes for a marginally acceptable first defense against a chemical warfare agent attack. Decontamination is also time-consuming so the equipment must often be destroyed and new equipment provided. It is also difficult to provide everyone with such protective equipment in the general population, and the effectiveness of such equipment diminishes during use. Tasks requiring detailed work using fingers and hands such as keystrokes on a keyboard, or pushing buttons on phones or equipment can be severely hampered by such bulky protective gear.

In addition to direct contact with a gaseous agent during an attack, surfaces that are exposed to the gas retain their toxicity for long periods of time. The OP nerve agents are soluble in materials such as paint, plastics, and rubber, allowing agents to remain in those materials and be released over long time periods. Nerve agents with thickening agents are even more persistent and difficult to decontaminate from a painted surface such as a wall, vehicle, or even a computer keyboard. It is understood that on painted metal surfaces, soman may persist for from one to five days, and that the less volatile VX may persist for 12 to 15 days. Under certain environmental conditions, OP compounds have been shown to persist indefinitely. On surfaces that are convoluted such as the surface of a military vehicle, the hidden surfaces that are less exposed to the environment can be especially difficult to decontaminate. Decontamination also requires detection, which is often not possible, and so resources and time may be wasted treating uncontaminated surfaces.

Historically, most approaches to chemical agent decontamination have focused on the treatment of surfaces after chemical exposure, whether real or merely suspected, has occurred. There are several current methods of decontamination of surfaces. One method is post-exposure washing with hot water with or without addition of detergents or organic solvents, such as caustic solutions (e.g., DS2, bleach) or foams (e.g., Eco, Sandia, Decon Green). Additional types of methods are an application of use of intensive heat and carbon dioxide applied for sustained periods, and incorporation of oxidizing materials (e.g., $TiO_2$ and porphyrins) into coatings that, when exposed to sustained high levels of UV light, degrade chemical agents (Buchanan, J. H. et al., 1989; Fox, M. A., 1983). Chemical agent resistant coatings ("CARCs") have been developed to withstand repeated decontamination efforts with such caustize and organic solvents. However, the resulting "decontaminated" materials are often still contaminated. Moreover, many decontamination procedures aerosolize contaminants on surfaces to be cleaned. In addition, it is often hard to clean certain kinds of surfaces such as those with rough texture, or with deep crevasses and other hard to reach areas that must often "self-decontaminate."

Although each of these approaches can be effective under specific conditions, a number of additional limitations exist. Caustic solutions degrade surfaces, create personnel handling and environmental risks, and require transport and mixing logistics. Additionally, alkaline solutions, such as a bleaching agent, is both relatively slow in chemically degrading VX OPs and can produce decontamination products nearly as toxic as the OP itself (Yang, Y.-C. et al., 1990). While foams may have both non-specific biocidal and chemical decontamination properties, they require transport and mixing logistics, may have personnel handling and environmental risks, and are not effective on sensitive electronic equipment or interior spaces. CARCs have been shown to become porous after sustained UV light exposure that can create a sponge effect that may actually trap chemical agents and delay decontamination. Moreover, these approaches are not well suited for decontamination of convoluted surfaces. Decontamination with heat and carbon dioxide presents logistical requirements and does not allow rapid reclamation of equipment. UV-based approaches can be costly and have logistical requirements, including access to UV-generating equipment and power, as well as the production of toxic byproducts of degradation (Yang, Y.-C. et al., 1992; Buchanan, J. H. et al., 1989; Fox, M. A., 1983).

One attempted solution to the problem of surface contamination has been to provide paints with shedding ("chalking") properties such as an acrylic surface that may shed, or at least not be penetrated by a CWA, making decontamination easier. This has been unsatisfactory solution, however, because the area remains contaminated and there is no way to know if the surface is or is not poisonous. In addition, shedding coatings over existing painted surfaces require additional materials and labor over a single coating. Shedding may or may not occur over timeframes necessary to protect personnel from residual nerve agents on contaminated surfaces, and in many instances may require washing despite the shedding characteristic.

Various enzymes have been identified that detoxify OP compounds, such as organophosphorus hydrolase ("OPH"), organophosphorus acid anhydrolase ("OPAA"), and DFPase, which detoxifies O,O-diisopropyl phosphorofluoridate ("DFP"). A number of civilian (e.g., Texas A&M University, private sector), and military laboratories [e.g., the Army research facilities at Edgewood (SBCCOM)] have worked on enzyme-based detection or decontamination systems for OP compounds. Various approaches taken in such laboratories include dispersion systems or immobilization systems of one or more OP degrading enzymes for use in detection or decontamination of OP compounds, as well as for convenience of handling of the enzyme preparation.

Sensors of OP compounds using an OP compound degrading enzyme have been described primarily for the detection of OP pesticides. OP compound sensors have been described that detect pH changes upon OP compound degradation using recombinant *Escherichia coli* cells expressing OPH cryoimmobilized in poly(vinyl)alcohol gel spheres (Rainina, E. I. et al., 1996). Endogenously expressed OPH from whole *Flavobacterium* sp. cells or cell membranes have been described as immobilized to glass membrane using poly(carbamoyl sulfonate) and poly(ethyleneimine) to produce a sensor of pH changes due to OP compound degradation (Gaberlein, S. et al., 2000a). OP compound sensors have been described that detect pH changes upon OP compound degradation using recombinant *Escherichia coli* cells, expressing OPH cytosolically or at the cell surface, that were fixed behind a polycarbonate membrane (Mulchandani, A. et al., 1998a; Mulchandani, A. et al., 1998b). An OP compound sensor has been described that detects optical changes upon OP compound degradation using recombinant *Escherichia coli* cells, expressing OPH at the cell surface, that were admixed in low melting point agarose and applied to membrane that was affixed to a fiber optic sensor (Mulchandani, A. et al., 1998c).

An OP compound sensor has been described that detects pH changes upon OP compound degradation using purified OPH chemically cross-linked with bovine serum albumin by glutaraldehyde on an electrode's glass membrane and covered with a dialysis membrane (Mulchandani, P. et al., 1999). Such chemically cross-linked OPH has been placed on a nylon membrane, and the membrane affixed to a fiber optic sensor to detect optical changes upon OP compound degradation (Mulchandani, A. et al., 1999a). Purified OPH has been immobilized by glutaraldehyde to glass-beads having aminopropyl groups in the construction of an OP compound degradation sensor (Mulchandani, P. et al., 2001a). An OP compound sensor has been described that detects optical changes upon OP compound degradation using recombinant *Moraxella* sp. cells, expressing OPH at the cell surface, that were admixed in 75% (w/w) graphite powder and 25% (w/w) mineral oil and placed into an electrode cavity (Mulchandani, P. et al., 2001b). Purified OPH was attached to silica beads by glutaraldehyde or N-γ-maleimidobutyrylozy succinimide ester linkages, and the beads placed as a layer on a glass slide to construct a sensor (Singh, A. K. et al., 1999). Purified OPH has been labeled with fluorescein isothiocyanate and absorbed to poly(methyl methacrylate) beads that were placed on a nylon membrane to construct a sensor that detects OP compound cleavage by decreased fluorescence (Rogers, K. R. et al., 1999). Purified OPH has been immobilized by placement within a poly(carbamoyl sulfonate) prepolymer that was allowed to polymerize on a heat-sealing film in the construction of a sensor (Gaberlein, S. et al., 2000b). A purified fusion protein comprising OPH and a FLAG octapeptide sequence was immobilized to magnetic particles (Wang, J. et al., 2001). Additional sensors using OPH have been described (Mulchandani, A. et al., 2001).

Different OP compound degrading enzyme compositions have been described, primarily for the detoxification of OP pesticides (Chen, W. and Mulchandani, A., 1998; LeJeune, K. E. et al., 1998a). A parathion hydrolase enzyme degrading cell extract has been immobilized onto silica beads and porous glass (Munnecke, D. M., 1979; Munnecke, D. M., 1978). OPH has also been immobilized onto porous glass and silica beads (Caldwell, S. R. and Raushel, F. M., 1991b). Purified OPH has been mixed with fire fighting foams in an attempt to create a readily dispersible decontamination composition (LeJeune, K. E., and Russell, A. J., 1999; LeJeune, K. E. et al., 1998b). Purified OPH has been incorporated into micelles in an OP compound degradation device (Komives, C. et al., 1994). Purified OPH has been encapsulated in a liposome for use in OP compound degradation (Pei, L. et al., 1994; Petrikovics, I. et al., 1999). OPH enzyme supported by glass wool in a biphasic solvent and gas phase reactor for OP compound detoxification has been described (Yang, F. et al., 1995). Purified OPH has also been immobilized onto trityl agarose and nylon (Caldwell, S. R. and Raushel, F. M., 1991a). Recombinant *Escherichia coli* cells co-expressing OPH and a surface expressed cellulose-binding domain have been immobilized to cellulose supports (Wang, A. A. et al., 2002). Partly purified OPH, acetylcholinesterase or butyrylcholinesterase has been incorporated into polyurethane foam sponges (Havens, P. L. and Rase, H. F., 1993; Gordon, R. K. et al., 1999). Partly purified or purified OPH has been incorporated into solid polyurethane foam (LeJeune, K. E. and Russell, A. J., 1996; LeJeune, K. E. et al., 1997; LeJeune, K. E. et al., 1999). Recombinant *Escherichia coli* cells expressing OPH have been immobilized in a poly (vinylalcohol) cryogel (Hong, M. S. et al., 1998; Efremenko, E. N. et al., 2002; Kim, J.-W. et al., 2002). Purified OPH has been immobilized in polyethylene glycol hydrogels (Andreopoulos, F. M. et al., 1999). Recombinant *Escherichia coli* expressing OPH at the cell surface has been immobilized to polypropylene fabric by absorption of the cells to the fabric (Mulchandani, A. et al., 1999b). Purified OPH was immobilized to mesoporous silica by Tris-(methoxy)carboxylethylsilane or Tris-(methoxy)aminopropylsilane (Lei, C. et al., 2002). A fusion protein comprising OPH and a cellulose-binding domain has been immobilized to cellulose supports (Richins, R. D. et al., 2000). Sonicated *Escherichia coli* cells expressing a fusion protein comprising OPH, a green fluorescent protein, and a polyhistidine sequence as an affinity tag, have been attached to a nickel-iminodiacetic acid-agarose bead resin (Wu, C.-F. et al., 2002). A fusion protein comprising OPH and a polyhistidine sequence as an affinity tag has been attached to a chitosan film (Chen, T. et al., 2001). A purified fusion protein comprising an elastin-like polypeptide and OPH has shown to reversibly bind to the hydrophobic surface of polystyrene plates at temperatures above 37° C. (Shimazu, M. et al., 2002).

In addition to OPH, other OP compound enzyme compositions have been described. Purified OPAA has been encapsulated in a liposome for use in OP compound degradation (Petrikovics, I. et al., 2000a; Petrikovics, I. et al., 2000b). Purified OPAA has been mixed with fire fighting foams, detergents, and a skin care lotion in an attempt to create a readily dispersible decontamination composition (Cheng, T.-C. et al., 1999). Purified squid-type DFPase has been encapsulated in erythrocytes for use in OP compound degradation (McGuinn, W. D. et al., 1993). Purified squid-type DFPase has been coupled to agarose beads (Hoskin, F. C. G. and Roush, A. H., 1982). Purified squid-type DFPase has also been incorporated into a polyurethane matrix (Drevon, G. F. et al., 2002; Drevon, G. F. et al., 2001; Drevon, G. F. and Russell, A. J., 2000).

US. Patent Publication no. US 2002/0106361 A1 discusses a marine anti-fungal enzyme for use in a marine coating. However, the substrate for the enzyme was incorporated into the marine coating, and the enzyme was in a marine environment as the organism from which it was obtained. Immobilized enzymes in an latex are discussed in the April, 2002 edition of "Emulsion Polymer Technologies," by the Paint Research Association However, to date, there has been limited success in using these and other approaches to harness the potential of these enzymes in systems that can be readily and cost effectively used in field-based military or civilian applications. Thus, despite the current understanding of the various OP compound degrading compositions and techniques, whether based on caustic chemicals or enzymes, there is a clear and present need for compositions and methods that can readily be used in OP compound degradation. This is particularly true for the detoxification of OP chemical warfare agents. In particular, compositions and methods are needed that will detoxify surfaces contaminated with OP compounds.

SUMMARY OF THE INVENTION

The present invention provides compositions and methods for their use as—components of surface treatments such as coatings. More specifically, the present invention provides compositions and methods for incorporating biological molecules into coatings in a manner to retain biological activity conferred by such biological molecule.

The present invention provides compositions and methods capable of effective decontamination of OP compounds, as well as prophalactic protection of buildings, equipment, and personnel that contact such objects, from OP compounds, including CWAs. As they relate to detoxification of OPs, the compositions and methods disclosed herein differ substantially from prior efforts, which focus on enzymatic detoxification of chemical compounds by application of a decontamination composition or method to the site of contamination after contact with the chemical compound. The preferred embodiments of the present invention represent a paradigm shift in chemical decontamination. They demonstrate usable compositions and methods for prophylactic protection of a site prior to contact with a chemical by prior application of a protective coating comprising an enzyme composition of the present invention. While prophylactic treatment with the coatings of the invention are a preferred embodiment, such a coating can also be used to coat a surface after contamination occurs. A preferred coating comprises a paint. Specifically, a paint comprising a preferred enzyme composition of the present invention degrades an organophosphorus compound, including a chemical warfare agent, into a significantly less toxic compound. Another preferred coating comprises a clear coat, a textile treatment, a wax, elastomer, or a sealant.

Further, the present disclosure is the first composition of which Applicant is aware that comprises a bioactive molecule such as an enzyme composition that retains activity after being admixed with paint. In addition, it still retains activity after the paint is applied to a surface, and renders the surface bioactive.

In light of these and additional disclosures herein, it is now possible to produce paints and other coatings that detoxify chemical compounds for extended periods. Remarkably, a preferred enzyme composition of the present invention remained stable in the coating for an extended period of time (e.g., months) at ambient conditions. It is contemplated that the extended period of activity may further comprise time periods in excess of a year. In particular, stabilized embodiments of the enzyme composition are designed to enhance the life time of the biomolecule composition in a coating and on a surface. In a preferred embodiment, the invention comprises at least one polymer-based compound that provides prophylactic protection and continuous detoxification of an organophosphorus nerve agent.

In certain embodiments, it is contemplated that the compositions and methods of the present invention may be used to produce self-decontaminating surfaces that remain active for extended periods. In a specific aspect, it is contemplated that such a self-decontaminating surface will not need additional decontamination compositions or methods to effect decontamination, thereby minimizing logistical requirement. In a particular aspect, it is contemplated that the compositions and methods of the present invention may be easily applied in advance of, during or after exposure to a chemical compound. In another preferred aspect, the compositions and methods of the present invention will be used in conjunction with existing other decontamination compositions and methods. In a preferred facet, the compositions and methods of the present invention are applied in advance of, during or after a field-based military operation to protect troops against a chemical warfare agent.

A recombinant phosphoric triester hydrolase may be produced using specific expression vectors in a variety of host cells. In the practice of the present invention, any of the described cells, nucleic acid sequences, genes, gene fragments, vectors and transcriptional or translational signals may be used, or any others that are known in the art. In preferred facets, the enzyme is grown in bacterial, fungal, plant (e.g., corn), or insect cells. In preferred embodiments, an expression vector includes an opd DNA fragment in the correct orientation and reading frame with respect to the promoter sequence to allow translation of the opd gene or gene fragment. In a specific aspect, the expression vector produces heterologous expression of the opd gene or gene fragment. In particularly preferred embodiments of the composition, the enzyme is an OPH enzyme. In other preferred embodiments the enzyme is an OPAA enzyme. In other preferred embodiments, the enzyme is a DFPase. Examples of the cloning and expression of exemplary opd gene and gene fragments are described (McDaniel, S. et al., 1988; McDaniel, 1985; Wild, J. R. et al., 1986; each incorporated herein in its entirety by reference).

In general embodiments, a biomolecule of the present invention refers to a compound comprising one or more chemical moieties normally produced by a living organism such as an amino acid, a nucleic acid, a sugar, a lipid, or a combination thereof. The invention provides a coating comprising a biomolecule composition, wherein the biomolecule composition comprises an active biomolecule. A biomolecule typically has a function in or upon a living organism, such as binding another molecule, catalyzing a chemical reaction, or a combination thereof. Specific examples of such activity by a biomolecule include an antibody binding an antigen, a cell receptor binding a ligand, an enzyme binding a substrate, a transport protein may bind a ligand, etc. In some aspects, binding a ligand may be a desired activity such as, for example, to sequester an undesired molecule, such as a toxin, to the biomolecule. Often, a biomolecule's activity further comprises a specific chemical reaction in addition to a physical/chemical affinity for another molecule. For example, an enzyme may accelerate a chemical reaction upon the bound substrate, a cell receptor may change conformation and/or become enzymatically active or inactive toward a second substrate, a transport protein may mitigate the movement of a molecule, etc. In another example, a biomolecule may comprise a ligand that induces or inhibits such activity in an enzyme, a cell receptor, a transport protein, and the like.

An "active biomolecule" refers to biomolecule that retains these types of properties in a coating of the present invention. The ability to confer bioactivity to a coating provides numerous uses in addition to the preferred bioactivity of detoxification of OP compounds.

Further, disclosed herein is the discovery that an active biomolecule may function in a coating in environments differing from the native environment of the organism from which it was obtained or derived. For example, an active biomolecule may retain activity in a coating under conditions of temperature, salinity, pH, moisture, or a combination thereof that differ from the organism's native environment.

The ability of a biomolecule to retain its function as an active biomolecule in a composition of the present invention, particularly a coating, may be detected and measured by any technique known to one of ordinary skill the art, including the various assays described herein.

A further disclosure of the present invention is the preparation of an active biomolecule with a limited number of processing and/or purification steps from other cellular molecules of the organism in which it was produced. Typically, the organism is a microorganism. The combination of an active biomolecule and such cellular molecules is known herein as a "biomolecule composition". It is contemplated that the inclusion of such cellular molecules may provide a protective or stabilizing effect for the activity of the active biomolecule. An example would be the protective encapsulation of an active biomolecule by a cell wall and/or cell membrane of the organism. Such additional cellular molecules contribute to the particulate nature of a biomolecule composition, which may grant utility for such material as a particulate component of a coating or paint, such as a pigment, an dispersant, a rheological agent, or a combination thereof.

The invention provides various additional embodiments. In general embodiments, a biomolecular composition comprises 0.001% to 40% of the coating composition by weight or volume, including all intermediate ranges and combinations thereof. In other embodiments, the biomolecule composition comprises a microorganism based particulate material. In some aspects, the microorganism based particulate material comprises a whole cell material. In alternative aspects, the microorganism based particulate material is a cell fragment microorganism based particulate material. In certain aspects, the active biomolecule comprises 0.001% to 40% of the coating composition by weight or volume, including all intermediate ranges and combinations thereof.

In certain embodiments, the active biomolecule comprises a proteinaceous molecule. In some aspects, a proteinaceous molecule comprises a peptide, a polypeptide, a protein, or a combination thereof. In specific aspects, the proteinaceous molecule comprises an enzyme, an antibody, a receptor, a transport protein, a structural protein, or a combination thereof. In other embodiments, the proteinaceous molecule binds a ligand, contacts a living organism, or a combination thereof. In particular aspects, the proteinaceous molecule binds a ligand. The ligand may comprise an antigen, a substrate, an inhibitor, or a combination thereof. In certain preferred facets, the ligand comprises a chemical toxic to humans, such as, for example, an organophosphorus compound. In further aspects, the proteinaceous molecule contacts a living organism. In particular facets, the proteinaceous molecule comprises a ligand capable of binding to an active biomolecule of the living organism. In specific facets, the active biomolecule of the living organism comprises a receptor, an enzyme, a transport protein, or a combination thereof.

In certain embodiments, the active biomolecule comprises a combination of active biomolecules. The combination of biomolecules may be of the same type, such as a combination of enzymes. The combination may be of different biomolecules or may be of different types of biomolecules such as a receptor ligand and an enzyme, a receptor and an antibody, an enzyme and an combination of antibodies, etc. All iterations of active biomolecules may be selected to confer to a coating a combination of bioactivities as desired. In general embodiments, a composition of the present invention may comprise 1 to 100 or more different selected biomolecules of interest, including all intermediate ranges and combinations thereof.

In some embodiments, the proteinaceous molecule comprises an enzyme. In particular embodiments, the enzyme comprises an oxidoreductase, a transferase, a hydrolase, a lyase, an isomerase, a ligase, or a combination thereof. In certain aspects, the enzyme comprises a hydrolase. In further aspects, the hydrolase comprises an esterase. In specific aspects, the esterase comprises a phosphoric triester hydrolase. The phosphoric triester hydrolase may comprise, for example, an aryldialkylphosphatase, a diisopropyl-fluorophosphatase, or a combination thereof.

In one preferred embodiment, the combination of biomolecules comprises a combination of phosphoric triester hydrolases. The combination of phosphoric triester hydrolases may be of the similar types, such as, for example, an organophosphorus hydrolase that possesses an enzymatic activity superior in, for example, binding affinity and/or rate of substrate cleavage in combination with one or more additional an organophosphorus hydrolases, each with a different enzymatic activity relative to the substrate. The combination of phosphoric triester hydrolases may comprise phosphoric triester hydrolases of different types, such as, for example, a Mazur-type DFPase and an aryldialkylphosphatase, or an OPAA and a human paraoxonase, or an organophosphorus hydrolase, a human paraoxonase and an animal carboxylase, etc. All iterations of selection of phosphoric triester hydrolases are contemplated to produce a coating with a combination of phosphoric triester hydrolase activities as desired.

In certain embodiments, the phosphoric triester hydrolase comprises an aryldialkylphosphatase. In some aspects, the aryldialkylphosphatase comprises an organophosphorus hydrolase, a human paraoxonase, an animal carboxylase, or a functional equivalent thereof. In additional aspects, the aryldialkylphosphatase comprises an organophosphorus hydrolase or a functional equivalent thereof. In specific aspects, the organophosphorus hydrolase comprises an *Agrobacterium radiobacter* P230 organophosphate hydrolase, a *Flavobacterium balustinum* parathion hydrolase, a *Pseudomonas diminuta* phosphodiesterase, a *Flavobacterium* sp opd gene product, a *Flavobacterium* sp. parathion hydrolase opd gene product, or a functional equivalent thereof. In certain facets, the organophosphorus hydrolase comprises a functional equivalent of *Agrobacterium radiobacter* P230 organophosphate hydrolase, a *Flavobacterium balustinum* parathion hydrolase, a *Pseudomonas diminuta* phosphodiesterase, a *Flavobacterium* sp opd gene product, or a *Flavobacterium* sp. parathion hydrolase opd gene product. In particular facets, the functional equivalent is a structural analog, a sequence analog, or a combination thereof. In specific facets, the functional equivalent is a structural analog. In further facets, the structural analog comprises a $Co^{2+}$, $Fe^{2+}$, $Cu^{2+}$, $Mn^{2+}$, $Cd^{2+}$ or $Ni^{2+}$ at the enzyme active site. In other facets, the functional equivalent is a sequence analog. In other facets, the functional equivalent is a structural analog. In particular facets, the sequence analog is an alteration in sequence length. In specific facets, the sequence analog lacks a leader peptide sequence, the sequence analog comprises a fusion protein, or a combination thereof.

In certain embodiments, the organophosphorus hydrolase comprises a *Pseudomonas diminuta* phosphotriesterase, or a functional equivalent thereof. In some aspects, the organophosphorus hydrolase comprises a *Pseudomonas diminuta* phosphotriesterase. In other embodiments, a preferred organophosphorus hydrolase comprises a *Pseudomonas diminuta* phosphotriesterase functional equivalent. In certain aspects the *Pseudomonas diminuta* phosphotriesterase functional equivalent comprises a sequence analog, a structural analog, or a combination thereof. In particular facets, the *Pseudomonas diminuta* phosphodiesterase functional equivalent comprises a sequence analog. In some facets, the sequence analog comprises an amino acid substitution. In specific facets, the sequence analog comprises H55C, H57C, C59A, G60A, S61A, I106A, I106G, W131A, W131F, W131K, F132A, F132H, F132Y, L136Y, L140Y, H201C, H230C, H254A, H254R, H254S, H257A, H257L, H257Y, L271A, L271Y, L303A, F306A, F306E, F306H, F306K, F306Y, S308A, S308G, Y309A, M317A, M317H, M317K, M317R, H55C/H57C, H55C/H201C, H55C/H230C, H57C/H201C, H57C/H230C, A80V/S365P, I106A/F132A, I106A/S308A, I106G/F132G, I106G/S308G, F132Y/F306H, F132H/F306H, F132H/F306Y, F132Y/F306Y, F132A/S308A, F132G/S308G, L182S/V310A, H201C/H230C, H254R/H257L, H55C/H57C/H201C, H55C/H57C/H230C, H55C/H201C/H230C, I106A/F132A/H257Y, I106A/F132A/H257W, I106G/F132G/S308G, L130M/H257Y/I274N, H257Y/I274N/S365P, H55C/H57C/H201C/H230C, I106G/F132G/H257Y/S308G, A14T/A80V/L185R/H257Y/I274N, or a combination thereof.

In additional embodiments, the aryldialkylphosphatase comprises a paraoxonase, such as, for example, a human paraoxonase or a functional equivalent thereof. In some aspects, the human paraoxonase comprises an HPON1 gene product or a functional equivalent thereof. In certain facets, the human paraoxonase comprises a HPON1 gene product functional equivalent. In specific facets, the HPON1 gene product functional equivalent comprises a sequence analog. In particular facets, the sequence analog comprises an amino acid substitution. In further facets, the sequence analog is E32A, E48A, E52A, D53A, D88A, D107A, H114N, D121A, H133N, H154N, H160N, W193A, W193F, W201A, W201F, H242N, H245N, H250N, W253A, W253F, D273A, W280A, W280F, H284N, H347N or a combination thereof.

In further embodiments, the aryldialkylphosphatase comprises an animal carboxylase. In particular aspects, the animal carboxylase comprises an insect carboxylase or a functional equivalent thereof. In additional aspects, the insect carboxylase comprises a *Plodia interpunctella* carboxylase, *Chrysomya putoria* carboxylase, *Lucilia cuprina* carboxylase, *Musca domestica* carboxylase carboxylase, or a functional equivalent thereof.

In other embodiments, the phosphoric triester hydrolase comprises a diisopropyl-fluorophosphatase. In some aspects, the diisopropyl-fluorophosphatase comprises an organophosphorus acid anhydrolase, a squid-type DFPase, a Mazur-type DFPase, or a functional equivalent thereof. In further aspects, the diisopropyl-fluorophosphatase comprises an organophosphorus acid anhydrolase or a functional equivalent thereof. In additional aspects, the organophosphorus acid anhydrolase comprises an *Altermonas* organophosphorus acid anhydrolase, a prolidase, or a functional equivalent thereof. In some facets, the organophosphorus acid anhydrolase comprises an *Altermonas* organophosphorus acid anhydrolase or a functional equivalent thereof. In particular facets, the *Altermonas* organophosphorus acid anhydrolase comprises an *Alteromonas* sp JD6.5 organophosphorus acid anhydrolase, an *Alteromonas haloplanktis* organophosphorus acid anhydrolase, an *Altermonas undina* organophosphorus acid anhydrolase, or a functional equivalent thereof. In additional facets, the organophosphorus acid anhydrolase comprises a prolidase or a functional equivalent thereof. In specific facets, the prolidase comprises a human prolidase, a *Mus musculus* prolidase, a *Lactobacillus helveticus* prolidase, an *Escherichia coli* prolidase, an *Escherichia coli* aminopeptidase P, or a functional equivalent thereof.

In certain embodiments, the diisopropyl-fluorophosphatase comprises a squid-type DFPase, or a functional equivalent thereof. In some aspects, the squid-type DFPase comprises a *Loligo vulgaris* DFPase, a *Loligo pealei* DFPase, a *Loligo opalescens* DFPase, or a functional equivalent thereof. In specific aspects, the squid-type DFPase comprises a *Loligo vulgaris* DFPase, or a functional equivalent thereof. In some facets, the squid-type DFPase comprises a *Loligo vulgaris* DFPase, or a functional equivalent thereof. In additional facets, the squid-type DFPase comprises a *Loligo vulgaris* DFPase functional equivalent. In particular facets, the *Loligo vulgaris* DFPase functional equivalent comprises a sequence analog. In continuing facets, the sequence analog comprises an amino acid substitution. In some facets, the sequence analog is H181N, H224N, H274N, H219N, H248N, or H287N. In other facets, the sequence analog is an alteration in sequence length. In specific facets, the sequence analog is a fusion protein.

In other embodiments, the diisopropyl-fluorophosphatase comprises a Mazur-type DFPase, or a functional equivalent thereof. In some aspects, the Mazur-type DFPase comprises a mouse liver DFPase, a hog kidney DFPase, a *Bacillus stearothermophilus* strain OT DFPase, an *Escherichia coli* DFPase, or a functional equivalent thereof.

In additional embodiments, the phosphoric triester hydrolase comprises a *Plesiomonas* sp. strain M6 mpd gene product, a *Xanthomonas* sp. phosphoric triester hydrolase, a *Tetrahymena* phosphoric triester hydrolase, or a functional equivalent thereof.

In other embodiments, the coating is 5 um to 1500 um thick upon the surface, including all intermediate ranges and combinations thereof. In some aspects, the coating is 15 um to 500 um thick upon the surface, including all intermediate ranges and combinations thereof. In particular aspects, the coating comprises a multicoat system. In an additional aspect, the multicoat system comprises 2 to 10 layers. In a particular facet, one layer of the multicoat system comprises the biomolecular composition. In a further aspect, a plurality of layers of the multicoat system comprises the biomolecular composition. In some facets, each layer of the multicoat system is a coating 15 um to 500 um thick, including all intermediate ranges and combinations thereof. In other facets, each layer of the multicoat system is a coating 15 um to 150 um thick, including all intermediate ranges and combinations thereof. In particular aspects, the multicoat system comprises a sealer, a water repellent, a primer, an undercoat, a topcoat, or a combination thereof. In specific facets, the multicoat system comprises a topcoat. In particular facets, the topcoat comprises the biomolecular composition.

In some embodiments, the coating comprises a paint. In other embodiments, the coating comprises a clear coating. In some aspects, the clear coating comprises a lacquer, a varnish, a shellac, a stain, a water repellent coating, or a combination thereof. In general aspects, the coating comprises a binder, a liquid component, a colorant, an additive, or a combination thereof. In some facets, the coating comprises a buffer. In particular aspects, the buffer comprises a bicarbonate.

In certain embodiments, the coating undergoes film formation. In general aspects, film formation occurs at ambient conditions, baking conditions, or a combination thereof. In particular aspects, film formation occurs at baking conditions. In other aspects, baking conditions is between 40° C. and 110° C., including all intermediate ranges and combinations thereof. Examples of specific intermediate ranges for baking conditions include 40° C. and 50° C., or 40° C. and 65° C. In general aspects, the coating comprises a volatile component and a non-volatile component. In general facets, the coating undergoes film formation by loss of part of the volatile component. In other facets, the volatile component comprises a volatile liquid component. In particular facets, the volatile liquid component comprises a solvent, a thinner, a diluent, or a combination thereof. In other aspects, the non-volatile component comprises a binder, a colorant, a plasticizer, a coating additive, a biomolecular composition of the present invention, or a combination thereof. In certain aspects, film formation occurs by crosslinking of a binder. In some facets, film formation occurs by crosslinking of a plurality of binders. In further facets, film formation occurs by irradiating the coating. In some facets, the coating produces a self-cleaning film upon film formation.

In certain alternative embodiments, the coating is a non-film forming coating. In particular aspects, the non-film forming coating comprises a non-film formatting binder. In some aspects, the non-film forming coating comprises a coating component in a concentration that is insufficient to produce a solid film. In some facets, the coating component comprises a binder that contributes to thermoplastic film formation, thermosetting film formation, or a combination thereof. In particular facets, the coating component comprises a binder, catalyst, initiator, or combination thereof. Though the concentration which is insufficient for a coating component to produce film formation in a coating may be empirically determined by an assay, such as those described herein for film formation, such an insufficient concentration may easily achieved by selection of a concentration of 0%, wherein the coating lacks the film-forming component.

In other alternative embodiments, the coating produces a temporary film. In specific aspects, the temporary film has a poor resistance to a coating remover. In particular facets, the temporary film has a poor scrub resistance, a poor solvent resistance, a poor water resistance, a poor weathering property, a poor adhesion property, or a combination thereof. A poor resistance and/or poor quality property for a coating can be empirically determined by assays described herein.

In general embodiments, the coating comprises an architectural coating, an industrial coating, a specification coating, or a combination thereof. In additional aspects, the coating comprises an architectural coating. In particular aspects, the architectural coating comprises a wood coating, a masonry coating, an artist's coating, or a combination thereof. In some facets, the architectural coating has a pot life of at least 12 months at ambient conditions. In general aspects, the architectural coating undergoes film formation at ambient conditions. In other aspects, the coating comprises an industrial coating. In further aspects, the industrial coating comprises an automotive coating, a can coating, sealant coating, a marine coating, or a combination thereof. In particular facets, the industrial coating undergoes film formation at baking conditions. In additional aspects, the coating comprises a specification coating. In particular facets, the specification coating comprises a camouflage coating, a pipeline coating, traffic marker coating, aircraft coating, a nuclear power plant coating, or a combination thereof. In particular facets, the specification coating comprises a camouflage coating. In specific facets, the camouflage coating comprises a camouflage pigment.

In many embodiments, a coating comprises a water-borne coating, a solvent borne coating, or a powder coating. In particular aspects, the coating comprises a water-borne coating. In certain facets, the water-borne coating is a latex coating. In additional facets, the water-borne coating has a density of 1.20 kg/L to 1.50 kg/L, including all intermediate ranges and combinations thereof. In other aspects, the coating comprises a solvent-borne coating. In further facets, the solvent-borne coating has a density of 0.90 kg/L to 1.2 kg/L, including all intermediate ranges and combinations thereof.

In general embodiments, the coating has a viscosity during application of 72 Ku to 95 Ku, including all intermediate ranges and combinations thereof. In further aspects, the coating has a viscosity prior to application of 100 P to 1000 P, including all intermediate ranges and combinations thereof. In particular aspects, the coating has a viscosity during application of 0.5 P to 2.5 P, including all intermediate ranges and combinations thereof. In other aspects, the coating has a viscosity of 100 P to 1000 P, including all intermediate ranges and combinations thereof, upon a surface immediately after application.

In many embodiments, the coating comprises a binder. In many aspects, the binder comprises a thermoplastic binder, a thermosetting binder, or a combination thereof. In certain aspects, the coating comprises a thermoplastic binder. In particular facets, such a coating produces a film by thermoplastic film formation. In other aspects, the coating comprises a thermosetting binder. In further facets, such a coating produces a film by thermosetting film formation.

In some embodiments, the binder comprises an oil-based binder. In particular aspects, the oil-based binder comprises an oil, an alkyd, an oleoresinous binder, a fatty acid epoxide ester, or a combination thereof. In further facets, such an oil-based binder coating produces a layer 15 um to 25 μm thick upon the vertical surface, including all intermediate ranges and combinations thereof, or 15 um to 40 μm thick upon the horizontal surface, including all intermediate ranges and combinations thereof. In further aspects, the binder comprises an oil. In other aspects, the binder comprises an alkyd. In specific aspects, the binder comprises an oleoresinous binder. In some aspects, the binder comprises a fatty acid epoxide ester.

In other embodiments, the binder comprises a polyester resin. In certain aspects, polyester resin comprises a hydroxy-terminated polyester. In other aspects, the polyester resin comprises a carboxylic acid-terminated polyester. In additional facets, the coating comprises a polyester resin and a urethane, an amino resin, or a combination thereof.

In some embodiments, the binder comprises a modified cellulose. In certain aspects, the modified cellulose comprises a cellulose ester, a nitrocellulose or a combination thereof. In certain facets, the modified cellulose comprises a cellulose ester. In other facets, the modified cellulose comprises a nitrocellulose. In further aspects, the coating comprises a modified cellulose and an amino binder, an acrylic binder, urethane binder, or a combination thereof.

In additional embodiments, the binder comprises a polyamide. In specific aspects, the coating comprises a polyamide and an epoxide.

In certain embodiments, the binder comprises an amino resin. In some aspects, the coating comprises an amino resin and an acrylic binder, an alkyd resin, a polyester binder, or a combination thereof.

In additional embodiments, the binder comprises an urethane binder. In particular aspects, the coating comprises an urethane binder and a polyol, an amine, an epoxide, a silicone, a vinyl, a phenolic, a triacrylate, or a combination thereof.

In some embodiments, the binder comprises a phenolic resin. In further aspects, the coating comprises a phenolic resin and an alkyd resin, an amino resin, a blown oil, an epoxy resin, a polyamide, a polyvinyl resin, or a combination thereof.

In other embodiments, the binder comprises an epoxy resin. In additional aspects, the coating comprises an epoxy resin and an amino resin, a phenolic resin, a polyamide, a ketimine, an aliphatic amine, or a combination thereof. In particular facets, the epoxy resin comprises a cycloaliphatic epoxy binder. In further facets, the coating comprises cycloaliphatic epoxy binder and a polyol.

In additional embodiments, the binder comprises a polyhydroxyether binder. In further aspects, the coating comprises a polyhydroxyether binder and an epoxide, a polyurethane comprising an isocyanate moiety, an amino resin, or a combination thereof.

In further embodiments, the binder comprises an acrylic resin. In additional aspects, the coating comprises an acrylic resin and an epoxide, a polyurethane comprising an isocyanate moiety, an amino resin, or a combination thereof.

In some embodiments, the binder comprises a polyvinyl binder. In further embodiments, the coating comprises a polyvinyl binder and an alkyd, an urethane, an amino-resin, or a combination thereof.

In certain embodiments, the binder comprises a rubber resin. In some aspects, the rubber resin comprises a chlorinated rubber resin, a synthetic rubber resin, or a combination thereof. In additional facets, the coating comprises a rubber resin and an acrylic resin, an alkyd resin, a bituminous resin, or a combination thereof.

In specific embodiments, the binder comprises a bituminous binder. In additional aspects, the coating comprises a bituminous binder and an epoxy resin.

In further embodiments, the binder comprises a polysulfide binder. In specific aspects, the coating comprises a polysulfide binder and a peroxide, a binder comprising an isocyanate moiety, or a combination thereof.

In additional embodiments, the binder comprises a silicone binder. In further aspects, the coating comprises a silicone binder and an organic binder.

In many embodiments, the coating comprises a liquid component. In general aspects, the liquid component comprises a solvent, a thinner, a diluent, a plasticizer, or a combination thereof. In other aspects, the liquid component comprises a liquid organic compound, an inorganic compound, water, or a combination thereof.

In some embodiments, the liquid component comprises a liquid organic compound. In certain aspects, the liquid organic compound comprises a hydrocarbon, an oxygenated compound, a chlorinated hydrocarbon, a nitrated hydrocarbon, a miscellaneous organic liquid component, a plasticizer, or a combination thereof.

In particular embodiments, the liquid organic compound comprises a hydrocarbon. In certain aspects, the hydrocarbon comprises an aliphatic hydrocarbon, a cycloaliphatic hydrocarbon, a terpene, an aromatic hydrocarbon, or a combination thereof. In additional facets, the hydrocarbon comprises an aliphatic hydrocarbon. In further facets, the aliphatic hydrocarbon comprises a petroleum ether, pentane, hexane, heptane, isododecane, a kerosene, a mineral spirit, a VMP naphtha or a combination thereof. In other aspects, the hydrocarbon comprises a cycloaliphatic hydrocarbon. In some facets, the cycloaliphatic hydrocarbon comprises cyclohexane, methylcyclohexane, ethylcyclohexane, tetrahydronaphthalene, decahydronaphthalene, or a combination thereof. In other aspects, the hydrocarbon comprises a terpene. In additional facets, the terpene comprises wood terpentine oil, pine oil, $\alpha$-pinene, $\beta$-pinene, dipentene, D-limonene, or a combination thereof. In particular aspects, the hydrocarbon comprises an aromatic hydrocarbon. In some facets, the aromatic hydrocarbon comprises benzene, toluene, ethylbenzene, xylene, cumene, a type I high flash aromatic naphtha, a type II high flash aromatic naphtha, mesitylene, pseudocumene, cymol, styrene, or a combination thereof.

In other embodiments, the liquid organic compound comprises an oxygenated solvent. In certain aspects, the oxygenated solvent comprises an alcohol, an ester, a glycol ether, a ketone, an ether, or a combination thereof. In some aspects, the oxygenated solvent comprises an alcohol. In further aspects, the alcohol comprises methanol, ethanol, propanol, isopropanol, 1-butanol, isobutanol, 2-butanol, tert-butanol, amyl alcohol, isoamyl alcohol, hexanol, methylisobutylcarbinol, 2-ethylbutanol, isooctyl alcohol, 2-ethylhexanol, isodecanol, cylcohexanol, methylcyclohexanol, trimethylcyclohexanol, benzyl alcohol, methylbenzyl alcohol, furfuryl alcohol, tetrahydrofurfuryl alcohol, diacetone alcohol, trimethylcyclohexanol, or a combination thereof. In other aspects, the oxygenated solvent comprises an ester. In particular facets, the ester comprises methyl formate, ethyl formate, butyl formate, isobutyl formate, methyl acetate, ethyl acetate, propyl acetate, isopropyl acetate, butyl acetate, isobutyl acetate, sec-butyl acetate, amyl acetate, isoamyl acetate, hexyl acetate, cyclohexyl acetate, benzyl acetate, methyl glycol acetate, ethyl glycol acetate, butyl glycol acetate, ethyl diglycol acetate, butyl diglycol acetate, 1-methoxypropyl acetate, ethoxypropyl acetate, 3-methoxybutyl acetate, ethyl 3-ethoxypropionate, isobutyl isobutyrate, ethyl lactate, butyl lactate, butyl glycolate, dimethyl adipate, glutarate, succinate, ethylene carbonate, propylene carbonate, butyrolactone, or a combination thereof. In certain aspects, the oxygenated solvent comprises a glycol ether. In other facets, the glycol ether comprises methyl glycol, ethyl glycol, propyl glycol, isopropyl glycol, butyl glycol, methyl diglycol, ethyl diglycol, butyl diglycol, ethyl triglycol, butyl triglycol, diethylene glycol dimethyl ether, methoxypropanol, isobutoxypropanol, isobutyl glycol, propylene glycol monoethyl ether, 1-isopropoxy-2-propanol, propylene glycol mono-n-propyl ether, propylene glycol n-butyl ether, methyl dipropylene glycol, methoxybutanol, or a combination thereof. In specific aspects, the oxygenated solvent comprises a ketone. In some facets, the ketone comprises acetone, methyl ethyl ketone, methyl propyl ketone, methyl isopropyl ketone, methyl butyl ketone, methyl isobutyl ketone, methyl amyl ketone, methyl isoamyl ketone, diethyl ketone, ethyl amyl ketone, dipropyl ketone, diisopropyl ketone, cyclohexanone, methylcylcohexanone, trimethylcyclohexanone, mesityl oxide, diisobutyl ketone, isophorone, or a combination thereof. In particular aspects, the oxygenated solvent comprises an ether. In additional facets, the ether comprises diethyl ether, diisopropyl ether, dibutyl ether, di-sec-butyl ether, methyl tert-butyl ether, tetrahydrofuran, 1,4-dioxane, metadioxane, or a combination thereof.

In some embodiments, the liquid organic compound comprises a chlorinated hydrocarbon. In specific aspects, the chlorinated hydrocarbon comprises methylene chloride, trichloromethane, tetrachloromethane, ethyl chloride, isopropyl chloride, 1,2-dichloroethane, 1,1,1-trichloroethane, trichloroethylene, 1,1,2,2-tetrachlorethane, 1,2-dichloroethylene, perchloroethylene, 1,2-dichloropropane, chlorobenzene, or a combination thereof.

In further embodiments, the liquid organic compound comprises a nitrated hydrocarbon. In specific aspects, the nitrated hydrocarbon comprises a nitroparaffin, N-methyl-2-pyrrolidone, or a combination thereof.

In additional embodiments, the liquid organic compound comprises a miscellaneous organic liquid. In some aspects, the miscellaneous organic liquid comprises carbon dioxide, acetic acid, methylal, dimethylacetal, N, N-dimethylformamide, N,N-dimethylacetamide, dimethylsulfoxide, tetramethylene suflone, carbon disulfide, 2-nitropropane, N-methylpyrrolidone, hexamethylphosphoric triamide, 1,3-dimethyl-2-imidazolidinone, or a combination thereof.

In specific embodiments, the liquid organic compound comprises a plasticizer. In general facets, the plasticizer comprises an adipate, an azelate, a citrate, a chlorinated plasticizer, an epoxide, a phosphate, a sebacate, a phthalate, a polyester, a trimellitate, or a combination thereof.

In other embodiments, the liquid component comprises an inorganic compound. In specific aspects, the inorganic compound comprises ammonia, hydrogen cyanide, hydrogen fluoride, hydrogen cyanide, sulfur dioxide, or a combination thereof.

In many embodiments, the liquid component comprises water. In particular aspects, the liquid component comprising water further comprises methanol, ethanol, propanol, isopropyl alcohol, tert-butanol, ethylene glycol, methyl glycol, ethyl glycol, propyl glycol, butyl glycol, ethyl diglycol, methoxypropanol, methyldipropylene glycol, dioxane, tetrahydrofuran, acetone, diacetone alcohol, dimethylformamide, dimethyl sulfoxide, ethylbenzene, tetrachloroethylene, p-xylene, toluene, diisobutyl ketone, tricholorethylene, trimethylcyclohexanol, cyclohexyl acetate, dibutyl ether, trimethylcyclohexanone, 1,1,1-tricholoroethane, hexane, hexanol, isobutyl acetate, butyl acetate, isophorone, nitropropane, butyl glycol acetate, 2-nitropropane, methylene chloride, methyl isobutyl ketone, cyclohexanone, isopropyl acetate, methylbenzyl alcohol, cyclohexanol, nitroethane, methyl tert-butyl ether, ethyl acetate, diethyl ether, butanol, butyl glycolate, isobutanol, 2-butanol, propylene carbonate, ethyl glycol acetate, methyl acetate, methyl ethyl ketone, or a combination thereof.

In general embodiments, the coating comprises a colorant. In some aspects, the colorant comprises a pigment, a dye, a pH indicator, or a combination thereof. In specific aspects, the colorant comprises a pigment. In some aspects, the biomolecule composition comprises 0.001% to 100% of the pigment, including all intermediate ranges and combinations thereof. In particular facets, the pigment volume concentration of the coating is 20% to 60%, including all intermediate ranges and combinations thereof. In other aspects, the pigment comprises a corrosion resistance pigment, a camouflage pigment, a color property pigment, an extender pigment, or a combination thereof. In particular aspects, the pigment comprises a corrosion resistance pigment. In some facets, the corrosion resistance pigment comprises aluminum flake, aluminum triphosphate, aluminum zinc phosphate, ammonium chromate, barium borosilicate, barium chromate, barium metaborate, basic calcium zinc molybdate, basic carbonate white lead, basic lead silicate, basic lead silicochromate, basic lead silicosulfate, basic zinc molybdate, basic zinc molybdate-phosphate, basic zinc molybdenum phosphate, basic zinc phosphate hydrate, bronze flake, calcium barium phosphosilicate, calcium borosilicate, calcium chromate, calcium plumbate, calcium strontium phosphosilicate, calcium strontium zinc phosphosilicate, dibasic lead phosphite, lead chromosilicate, lead cyanamide, lead suboxide, lead sulfate, mica, micaceous iron oxide, red lead, steel flake, strontium borosilicate, strontium chromate, tribasic lead phophosilicate, zinc borate, zinc borosilicate, zinc chromate, zinc dust, zinc hydroxy phosphite, zinc molybdate, zinc oxide, zinc phosphate, zinc potassium chromate, zinc silicophosphate hydrate, zinc tetraoxylchromate, or a combination thereof. In specific facets, the coating comprising the corrosion resistance pigment is a metal surface coating, a primer, or a combination thereof. In other aspects, the pigment comprises a camouflage pigment. In specific facets, the camouflage pigment comprises an anthraquinone black, a chromium oxide green, or a combination thereof. In some aspects, the pH indicator is a colorimetric or a fluorimetric indicator. Examples of colorimetric include Alizarin, Alizarin S, Brilliant Yellow, Lacmoid, Neutral Red, Rosolic Red, or a combination thereof. In specific instances, the colorimetric indicator is a pH indicator that undergoes a color change between pH 8 to pH 9. For example the following fluorimetric indicators are SNARF-1, BCECF, HPTS, Fluroescein, or a combination thereof. In certain embodiments, the fluorescence indicator have reduced fluorescence at a lower pH. In specific instances, the fluorimetric indicator is a pH indicator that undergoes a fluorescence change between pH 8 to pH 9. Additional pH indicators are described, for example, in "Using Acid-Base Indicators to Visually Estimate the Ph of Solutions" by Marcia L. Gillette, Chemical Education Resources, Incorporated, 1995.

In further embodiments, the pigment comprises a color property pigment. In additional aspects, the color property pigment comprises a black pigment, a brown pigment, a white pigment, a pearlescent pigment, a violet pigment, a blue pigment, a green pigment, a yellow pigment, an orange pigment, a red pigment, a metallic pigment, or a combination thereof. In particular facets, the color property pigment comprises aniline black, anthraquinone black, carbon black; copper carbonate, graphite, iron oxide, micaceous iron oxide, manganese dioxide, azo condensation, benzimidazolone, iron oxide, metal complex brown, antimony oxide, basic lead carbonate, lithopone, titanium dioxide, white lead, zinc oxide, zinc sulphide, titanium dioxide and ferric oxide covered mica, bismuth oxychloride crystal, dioxanine violet, carbazol Blue, carbazole Blue, cobalt blue, copper phthalocyanine, dioxanine Blue, indanthrone, phthalocyanin blue, Prussian blue, ultramarine, chrome green, chromium oxide green, halogenated copper phthalocyanine, hydrated chromium oxide, phthalocyanine green, anthrapyrimidine, arylamide yellow, barium chromate, benzimidazolone yellow, bismuth vanadate, cadmium sulfide yellow, complex inorganic color pigment, diarylide yellow, disazo condensation, flavanthrone, isoindoline, isoindolinone, lead chromate, nickel azo yellow, organic metal complex, quinophthalone, yellow iron oxide, yellow oxide, zinc chromate, perinone orange, pyrazolone orange, anthraquinone, benzimidazolone, BON arylamide, cadmium red, cadmium selenide, chrome red, dibromanthrone, diketopyrrolo-pyrrole pigment, disazo condensation pigment, lead molybdate, perylene, pyranthrone, quinacridone, quinophthalone, red iron oxide, red lead, toluidine red, tonor pigment, β-naphthol red, aluminum flake, aluminum non-leafing, gold bronze flake, zinc dust, stainless steel flake, nickel flake, nickel powder, or a combination thereof.

In general embodiments, the pigment comprises an extender pigment. In some aspects, the extender pigment comprises a barium sulphate, a calcium carbonate, a kaolin, a calcium sulphate, a silicate, a silica, an alumina trihydrate, or a combination thereof.

In general embodiments, the coating comprises an additive. In some aspects, the additive comprises 0.001% to 20.0% by weight, including all intermediate ranges and combinations thereof, of the coating. In specific facets, the additive comprises an accelerator, an adhesion promoter, an antifoamer, anti-insect additive, an antioxidant, an antiskinning agent, a buffer, a catalyst, a coalescing agent, a corrosion inhibitor, a defoamer, a dehydrator, a dispersant, a drier, electrical additive, an emulsifier, a filler, a flame/fire retardant, a flatting agent, a flow control agent, a gloss aid, a leveling agent, a marproofing agent, a preservative, a silicone additive, a slip agent, a surfactant, a light stabilizer, a rheological control agent, a wetting additive, or a combination thereof. In additional aspects, the additive comprises a preservative. In specific aspects, the preservative comprises an in-can preservative, an in-film preservative, or a combination thereof. In general aspects, the preservative comprises a biocide. In particular facets, the biocide comprises a bactericide, a fungicide, an algaecide, or a combination thereof. In other aspects, the additive comprises a wetting additive, a dispersant, or a combination thereof. In further aspects, the additive comprises an anti-foamer, a defoamer, or a combination thereof. In additional aspects, the additive comprises a rheological control agent. In particular facets, the rheological control agent comprises a thickener, a viscosifier, or a combination thereof. In specific aspects, the additive comprises a corrosion inhibitor. In some facets, the corrosion inhibitor comprises an in-can corrosion inhibitor, a flash corrosion inhibitor, or a combination thereof. In particular aspects, the additive comprises a light stabilizer. In specific facets, the light stabilizer comprises a UV absorber, a radical scavenger, or a combination thereof.

In some embodiments, the coating is a multi-pack coating. In particular aspects, the coating is stored in a two to five containers prior to application to the surface. In specific aspects, 0.001% to 100% of the biomolecular composition, including all intermediate ranges and combinations thereof, is stored in a container of a multipack coating, and at least one additional coating component is stored in another container of a multipack coating. In some aspects, the container comprising the biomolecular composition further comprises an additional coating component. In particular facets, the additional coating component comprises a preservative, a wetting agent, a dispersing agent, a buffer, a liquid component, a rheological modifier, or a combination thereof. In specific facets, the additional coating component comprises glycerol.

The invention provides a method of detoxification of a surface contaminated with an organophosphorus compound, comprising the step of: contacting a surface contaminated with an organophosphorous compound with a coating comprising a biomolecule composition, wherein the biomolecule composition comprises a phosphoric triester hydrolase. In some aspects, the method further comprises the step of contacting the surface with a caustic agent; a decontaminating foam, a combination of baking condition heat and carbon dioxide, or a combination thereof.

The invention provides a method of detoxification of an organophosphorus compound, comprising the step of: contacting an organophosphorous compound with a coating comprising a biomolecule composition, wherein the biomolecule composition comprises a phosphoric triester hydrolase. In some aspects, the method further comprises the step of contacting the organophosphorus compound with a caustic agent; a decontaminating foam, a combination of baking condition heat and carbon dioxide, or a combination thereof.

The invention provides methods of reducing the concentration of an organophosphorus compound upon a surface, comprising the steps of: applying to the surface a coating comprising a biomolecule composition, wherein the biomolecule composition comprises a phosphoric triester hydrolase, and contacting the surface with an organophosphorus compound. In some aspects, the method further comprises the step of contacting the surface with a caustic agent; a decontaminating foam, a combination of baking condition heat and carbon dioxide, or a combination thereof.

In certain embodiments, the organophosphorus compound comprises a chemical warfare agent. In some aspects, the chemical warfare agent comprises a persistent agent. In additional aspects, the chemical warfare agent comprises a G-agent, a V agent, or a combination thereof. In particular facets, the G-agent comprises soman, sarin, cyclosarin, tabun, or a combination thereof. In further facets, the V-agent comprises VX, Russian VX, or a combination thereof. In other facets, the organophosphorus compound comprises a pesticide. In particular facets, the pesticide comprises a persistent organophosphorous compound. In general facets, the pesticide comprises bromophos-ethyl, chlorpyrifos, chlorfenvinphos, chlorothiophos, chlorpyrifos-methyl, coumaphos, crotoxyphos, crufomate, cyanophos, diazinon, dichlofenthion, dichlorvos, dursban, EPN, ethoprop, ethyl-parathion, etrimifos, famphur, fensulfothion, fenthion, fenthrothion, isofenphos, jodfenphos, leptophos-oxon, malathion, malaoxon, methyl-parathion, mevinphos, paraoxon, parathion, parathion-methyl, pirimiphos-ethyl, pirimiphos-methyl, pyrazophos, quinalphos, ronnel, sulfopros, sulfotepp, trichloronate, or a combination thereof.

The invention provides a coating or a paint comprising, in various aspects, 0.001% to 40% by weight or volume a biomolecule composition, including all intermediate ranges and combinations thereof, wherein the biomolecule composition comprises an active biomolecule. The invention provides a coating or a paint comprising a biomolecule composition that comprise, in various aspects, a proteinaceous molecule that binds a ligand, an enzyme, a phosphoric triester hydrolase, an organophosphorus hydrolase, an organophosphorus hydrolase and a buffer, or a combination thereof. The invention further provides a coating or a paint comprising, in various further aspects, a microorganism based particulate material, a whole cell material, or a combination thereof, wherein the material comprises an active biomolecule, an enzyme, a phosphoric triester hydrolase, an organophosphorus hydrolase, an organophosphorus hydrolase and a buffer, or a combination thereof. The invention specifically provides a coating or paint comprising 0.001% to 40% by weight or volume, including all intermediate ranges and combinations thereof, a microorganism based particulate material, a whole cell material, or a combination thereof, wherein the material comprises an active biomolecule.

The invention provides a coating or paint, the improvement comprising inclusion of a biomolecule composition, wherein the biomolecule composition comprises an active biomolecule.

The invention provides a coating or paint, the improvement comprising inclusion of 0.001% to 40% by weight or volume a biomolecule composition, wherein the biomolecule composition comprises an active biomolecule, a proteinaceous molecule that binds a ligand, an enzyme, a phosphoric triester hydrolase, an organophosphorus hydrolase, an organophosphorus hydrolase and a buffer, or any combination thereof.

The invention provides a coating or paint, the improvement comprising inclusion of a microorganism based particulate material, wherein the microorganism based particulate material that comprises an active biomolecule.

The invention provides a coating or paint, the improvement comprising inclusion of a whole cell particulate material, wherein the particulate material comprises an active biomolecule.

The invention provides a coating or paint, the improvement comprising inclusion of 0.001% to 40% by weight or volume of a whole cell particulate material, including all intermediate ranges and combinations thereof, wherein the whole cell particulate material comprises an active biomolecule.

The invention provides a coating or paint, the improvement comprising inclusion of a whole cell particulate material, wherein the particulate material comprises an enzyme.

The invention provides a coating or paint, the improvement comprising inclusion of a whole cell particulate material, wherein the particulate material comprises a phosphoric triester hydrolase.

The invention provides a coating or paint, the improvement comprising inclusion of a whole cell particulate material, wherein the particulate material comprises an organophosphorus hydrolase.

The invention provides a coating or paint, the improvement comprising inclusion of a whole cell particulate material, wherein the particulate material comprises an organophosphorus hydrolase and a buffer.

The invention provides a water-borne or a solvent-borne coating or paint comprising a biomolecule composition, wherein the biomolecule composition comprises an active biomolecule.

The invention provides a latex or oil-based coating or paint comprising a whole cell particulate material, wherein the whole cell particulate material comprises a phosphoric triester hydrolase. In certain aspect the coating or paint comprises a buffer.

The invention provides a latex or oil-based coating or paint comprising a whole cell particulate material and a buffer, wherein the whole cell particulate material comprises a phosphoric triester hydrolase. In specific aspects, the coating or paint comprises 0.001% to 40% by weight or volume, including all intermediate ranges and combinations thereof, of a whole cell particulate material, wherein the whole cell particulate material comprises a phosphoric triester hydrolase. In certain aspects the coating or paint is a multipack coating. In some facets, one container of the multipack coating comprises 0.001% to 40%, by weight or volume of the coating or paint, including all intermediate ranges and combinations thereof, the whole cell particulate material. In certain aspects, the container comprising the whole cell particulate material further comprises a preservative, a wetting agent, a dispersing agent, the buffer, a liquid component, a rheological modifier, or a combination thereof.

The invention provides a two-pack a latex or oil-based coating or paint, wherein one container comprises 100 parts by volume coating or paint, wherein a second container comprises 3 parts by volume of a biomolecular composition comprising a whole cell particulate material, wherein the whole cell particulate material comprises an organophosphorus hydrolase, and wherein each part of the biomolecular composition comprises 1 mg of whole cell particulate material and 50% glycerol and/or a buffer, and wherein the buffer comprises ammonium bicarbonate, a monobasic buffer, a dibasic phosphate buffer, Trizma base, a 5 zwitterionic buffer, or a combination thereof.

The invention also provides a non-film forming coating comprising a biomolecule composition, wherein the biomolecule composition comprises an active biomolecule.

The invention provides an elastomer comprising a biomolecule composition, wherein the biomolecule composition comprises an active biomolecule.

The invention provided a filler comprising a biomolecule composition, wherein the biomolecule composition comprises an active biomolecule.

The invention provides an adhesive comprising a biomolecule composition, wherein the biomolecule composition comprises an active biomolecule.

The invention provides a sealant comprising a biomolecule composition, wherein the biomolecule composition comprises an active biomolecule.

The invention provides a material applied to a textile, comprising a biomolecule composition, wherein the biomolecule composition comprises an active biomolecule.

The invention provides a wax comprising a biomolecule composition, wherein the biomolecule composition comprises an active biomolecule.

The invention provides a surface treatment comprising a biomolecule composition, wherein the biomolecule composition comprises an active biomolecule. In certain embodiments, the surface treatment is a coating, a paint, a non-film forming coating, an elastomer, an adhesive, an sealant, a material applied to a textile, or a wax. In other aspects, the surface treatment comprises a pH indicator.

DETAILED DESCRIPTION OF THE INVENTION

One skilled in the art will readily appreciate that the present invention is well adapted to carry out the objects and obtain the ends and advantages mentioned as well as those inherent therein. It should be understood, however, that the enzyme compositions, enzymes, microorganism-based particulate materials, compounds, coatings, paints, films, methods, procedures, and techniques described herein are presently representative of preferred embodiments. These techniques are intended to be exemplary, are given by way of illustration only, and are not intended as limitations on the scope. Other objects, features, and advantages of the present invention will be readily apparent to one skilled in the art from the following detailed description; specific examples and claims; and various changes, substitutions, other uses and modifications that may be made to the invention disclosed herein without departing from the scope and spirit of the invention or as defined by the scope of the appended claims.

As used herein other than the claims, the terms "a," "an," "the," and "said" means one or more. As used herein in the claim(s), when used in conjunction with the words "comprises" or "comprising," the words "a," "an," "the," or "said" may mean one or more than one. As used herein "another" may mean at least a second or more.

All patents and publications mentioned in this specification are indicative of the levels of those skilled in the art to which the invention pertains. All patents and publications so referenced are herein incorporated by reference to the same extent as if each individual publication was specifically and individually indicated to be incorporated by reference.

As would be known to one of ordinary skill in the art, many variations of nomenclature are commonly used to refer to a specific chemical composition. Accordingly, several common alternative names may be provided herein in quotations and parentheses/brackets, or other grammatical technique, adjacent to a chemical composition's preferred designation when referred to herein. Additionally, many chemical compositions referred to herein are further identified by a Chemical Abstracts Service registration number. As would be known to those of ordinary skill in the art, the Chemical Abstracts Service provides a unique numeric designation, denoted herein as "CAS No.," for specific chemicals and some chemical mixtures, which unambiguously identifies a chemical composition's molecular structure.

In various embodiments described herein, exemplary values are specified as a range. Examples of such ranges cited herein include, for example, a size of a biomolecule, a temperature for growth and/or preparation of a microorganism, a chemical moiety's content in a coating component, a coating component's content in a coating composition and/or film, a coating component's mass, a glass transition temperature ("$T_g$"), a temperature for a chemical reaction (e.g., film formation, chemical modification of a coating component), the thickness of a coating and/or film upon a surface, etc. It will be understood that herein the phrase "including all intermediate ranges and combinations thereof" associated with a given range is all integers and sub-ranges comprised within a cited range. For example, citation of a range "0.03% to 0.07%, including all intermediate ranges and combinations thereof" is specific values within the sited range, such as, for example, 0.03%, 0.04%, 0.05%, 0.06%, and 0.07%, as well as various combinations of such specific values, such as, for example, 0.03%, 0.06% and 0.07%, 0.04% and 0.06%, or 0.05% and 0.07%, as well as sub-ranges such as 0.03% to 0.05%, 0.04% to 0.07%, or 0.04% to 0.06%, etc. Additionally, example 12 provides additional descriptions of specific numeric values within a cited range.

A. Biomolecules

As used herein, a "biomolecule composition" of the present invention refers to a composition comprising a biomolecule. As used herein, a "biomolecule" refers to a compound comprising of one or more chemical moieties typically synthesized in living organisms, including but not limited to, an amino acid, a nucleotide, a polysaccharide or simple sugar, a lipid, or a combination thereof. A preferred biomolecule of the present invention comprises a proteinaceous molecule. As used herein a "proteinaceous molecule" comprises a polymer formed from amino acids, such as a peptide or a polypeptide. Examples of proteinaceous molecules include an enzyme, an antibody, a receptor, a transport protein, structural protein, or a combination thereof. Examples of a peptide include inhibitory peptides of 3-15 amino acids.

In addition to the sources described herein for biomolecules, reagents, living cells, etc., one of ordinary skill in the art may obtain such materials and/or chemical formulas thereof for use in the present invention from convenient source such as a public database, a biological depository, and/or a commercial vendor. For example, various nucleotide sequences, including those that encode amino acid sequences, may be obtained at a public database, such as the Entrez Nucleotides database, which includes sequences from other databases including GenBank, RefSeq, and PDB. In another example, various amino acid sequences may be obtained at a public database, such as the Entrez databank, which includes sequences from other databases including SwissProt, PIR, PRF, PDB, GenBank, and RefSeq. Numerous nucleic acid sequences and/or encoded amino acid sequences can be obtained from such sources. In a further example, biological materials that comprise, or are capable of comprising such biomolecules (including living cells), may be obtained from a depository such as the American Type Culture Collection ("ATCC"), P.O. Box 1549 Manassas, Va. 20108, USA. In an additional example, biomolecules, chemical reagents, biological materials, and equipment may be obtained, as is well known to those of ordinary skill in the art, from commercial vendors such as Amersham Biosciences®, 800 Centennial Avenue, P.O. Box 1327, Piscataway, N.J. 08855-1327 USA; BD Biosciences®, including Clontech®, Discovery Labware®, Immunocytometry Systems® and Pharmingen®, 1020 East Meadow Circle, Palo Alto, Calif. 94303-4230 USA; Invitrogen™, 1600 Faraday Avenue, PO Box 6482, Carlsbad, Calif. 92008 USA; New England Biolabs®, 32 Tozer Road, Beverly, Mass. 01915-5599 USA; Merck®, One Merck Drive, P.O. Box 100, Whitehouse Station, N.J. 08889-0100 USA; Novagene®, 441 Charmany Dr., Madison, Wis. 53719-1234 USA; Promega®, 2800 Woods Hollow Road, Madison Wis. 53711 USA; Pfizer®, including Pharmacia®, 235 East 42nd Street, New York, N.Y. 10017 USA; Quiagen®, 28159 Avenue Stanford, Valencia, Calif. 91355 USA; Sigma-Aldrich®, including Sigma, Aldrich, Fluka, Supelco and Sigma-Aldrich Fine Chemicals, PO Box 14508, Saint Louis, Mo. 63178 USA; Stratagene®, 11011 N. Torrey Pines Road, La Jolla, Calif. 92037 USA, etc.

In addition to those techniques specifically described herein, one of ordinary skill in the art may manipulate a cell, nucleic acid sequence, amino acid sequence, and the like, in light of the present disclosures, using standard techniques known in the art [see, for example, In "Molecular Cloning" (Sambrook, J., and Russell, D. W., Eds.) 3rd Edition, Cold Spring Harbor, N.Y.: Cold Spring Harbor Laboratory Press, 2001; In "Current Protocols in Molecular Biology" (Chanda, V. B. Ed.) John Wiley & Sons, 2002; In "Current Protocols in Nucleic Acid Chemistry" (Harkins, E. W. Ed.) John Wiley & Sons, 2002; In "Current Protocols in Protein Science" (Taylor, G. Ed.) John Wiley & Sons, 2002; In "Current Protocols in Cell Biology" (Morgan, K. Ed.) John Wiley & Sons, 2002; In "Current Protocols in Pharmacology" (Taylor, G. Ed.) John Wiley & Sons, 2002; In "Current Protocols in Cytometry" (Robinson, J. P. Ed.) John Wiley & Sons, 2002; In "Current Protocols in Immunology" (Coico, R. Ed.) John Wiley & Sons, 2002].

B. Enzymes

The selection of a biomolecule for use in the present invention depends on the desired property that is to be conferred to a composition of the present invention. A preferred biomolecule of the present invention comprises an enzyme, as enzymatic activity is a preferred property to be conferred to a biomolecule composition, coating and/or paint in the present invention. As used herein, the term "enzyme" refers to a molecule that possesses the ability to accelerate a chemical reaction, and comprises one or more chemical moieties typically synthesized in living organisms, including but not limited to, an amino acid, a nucleotide, a polysaccharide or simple sugar, a lipid, or a combination thereof. As used herein, the term "bioactive" refers to the ability of an enzyme to accelerate a chemical reaction differentiating such activity from a like ability of a composition, and/or a method that does not comprise an enzyme to accelerate a chemical reaction.

In preferred embodiments, an enzyme comprises a proteinaceous molecule. It is contemplated that any proteinaceous molecule that functions as an enzyme, whether identical to the wild-type amino acid sequence encoded by an isolated gene, a functional equivalent of such a sequence, or a combination thereof, may be used in the present invention. As used herein, a "wild-type enzyme" refers to an amino acid sequence that functions as an enzyme and is identical to the sequence encoded by an isolated gene from a natural source. As used herein, a "functional equivalent" to the wild-type enzyme is a proteinaceous molecule comprising a sequence and/or a structural analog of a wild-type enzyme's sequence and/or structure and functions as an enzyme. The functional equivalent enzyme may possess similar or the same enzymatic properties, such as catalyzing chemical reactions of the wild-type enzyme's EC classification, or may possess other desired enzymatic properties, such as catalyzing the desirable chemical reactions of an enzyme that is related to the wild-type enzyme by sequence and/or structure. Examples of a functional equivalent of a wild-type enzyme are described herein, and include mutations to a wild-type enzyme sequence, such as a sequence truncation, an amino acid substitution, an amino acid modification, a fusion protein, or a combination thereof, wherein the altered sequence functions as an enzyme.

In certain embodiments, an enzyme may comprise a simple enzyme, a complex enzyme, or a combination thereof. As known herein, a "simple enzyme" is an enzyme wherein the chemical properties of moieties found in its amino acid sequence is sufficient for producing enzymatic activity. As known herein, a "complex enzyme" is an enzyme whose catalytic activity functions only when an apo-enzyme is combined with a prosthetic group, a co-factor, or a combination thereof. An "apo-enzyme" is a proteinaceous molecule and is catalytically inactive without the prosthetic group and/or co-factor. As known herein, a "prosthetic group" or "co-enzyme" is non-proteinaceous molecule that is attached to the apo-enzyme to produce a catalytically active complex enzyme. As known herein, a "holo-enzyme" is a complex enzyme that comprises an apo-enzyme and a co-enzyme. As known herein, a "co-factor" is a molecule that acts in combination with the apo-enzyme to produce a catalytically active complex enzyme. In some aspects, a prosthetic group is one or more bound metal atoms, a vitamin derivative, or a combination thereof. Examples of metal atoms that may be used as a prosthetic group and/or a co-factor include Ca, Cd, Co, Cu, Fe, Mg, Mn, Ni, Zn, or a combination thereof. Usually the metal atom is an ion, such as $Ca^{2+}$, $Cd^{2+}$, $Co^{2+}$, $Cu^{2+}$, $Fe^{+2}$, $Mg^{2+}$, $Mn^{2+}$, $Ni^{2+}$, $Zn^{2+}$, or a combination thereof. As known herein, a "metalloenzyme" is a complex enzyme that comprises an apo-enzyme and a prosthetic group, wherein the prosthetic group comprises a metal atom. As known herein, a "metal activated enzyme" is a complex enzyme that comprises an apo-enzyme and a co-factor, wherein the co-factor comprises a metal atom.

A chemical that binds a proteinaceous molecule is known herein as a "ligand." As used herein, "bind" or "binding" refers to a physical contact between the proteinaceous molecule at a specific region of the proteinaceous molecule and the ligand in a reversible fashion. Examples of binding interactions are well known in the art, and include such interactions as a ligand known as an "antigen" binding an antibody, a ligand binding a receptor, and the like. A portion of the proteinaceous molecule wherein substrate binding occurs is known herein as a "binding site." A ligand that is acted upon by the enzyme in the accelerated chemical reaction is known herein as a "substrate." A contact between the enzyme and a substrate in a fashion suitable for the accelerated chemical reaction to proceed is known herein as "substrate binding." A portion of the enzyme involved in the chemical interactions that contributed to the accelerated chemical reaction is known herein as an "active site."

A chemical that slows or prevents the enzyme from conducting the accelerated chemical reaction is known herein as an "inhibitor." A contact between the enzyme and the inhibitor in a fashion suitable for slowing or preventing the accelerated chemical reaction to proceed upon a target substrate is known herein as "inhibitor binding." In some embodiments, inhibitor binding occurs at a binding site, an active site, or a combination thereof. In some aspects, an inhibitor's binding occurs without the inhibitor undergoing the chemical reaction. In specific aspects, the inhibitor may also be a substrate such as in the case of an inhibitor that precludes the enzyme from catalyzing the chemical reaction of a target substrate for the period of time inhibitor binding occurs at an active and/or binding site. In other aspects, an inhibitor undergoes the chemical reaction at a rate that is slower relative to a target substrate.

In some embodiments, enzymes may be described by the classification system of The International Union of Biochemistry and Molecular Biology ("IUBMB"). The IUBMB classifies enzymes by the type of reaction catalyzed and enumerates each sub-class by a designated enzyme commission number ("EC"). Based on these broad categories, an enzyme may comprise an oxidoreductase (EC 1), a transferase (EC 2), a hydrolase (EC 3), a lyase (EC 4), an isomerase (EC 5), a ligase (EC 6), or a combination thereof. Often, an enzyme may be able to catalyze multiple reactions, and thus have multiple EC classifications.

Generally, the chemical reaction catalyzed by an enzyme alters a moiety of a substrate. As used herein, a "moiety" or "group," in the context of the field of chemistry, refers to a chemical sub-structure that is a part of a larger molecule. Examples of moiety include an acid halide, an acid anhydride, an alcohol, an aldehyde, an alkane, an alkene, an alkyl halide, an alkyne, an amide, an amine, an arene, an aryl halide, a carboxylic acid, an ester, an ether, a ketone, a nitrile, a phenol, a sulfide, a sulfonic acid, a thiol, etc.

An oxidoreductase catalyzes an oxido-reduction of a substrate, wherein the substrate is either a hydrogen donor and/or an electron donor. An oxidoreductase is generally classified by the substrate moiety that is the donor or acceptor. Examples of oxidoreductases include an oxidoreductase that acts on a donor CH—OH moiety, (EC 1.1); an donor aldehyde or a donor oxo moiety, (EC 1.2); a donor CH—CH moiety, (EC 1.3); a donor CH—NH₂ moiety, (EC 1.4); a donor CH—NH moiety, (EC 1.5); a donor nicotinamide adenine dinucleotide ("NADH") or a donor nicotinamide adenine dinucleotide phosphate ("NADPH"), (EC 1.6); a donor nitrogenous compound, (EC 1.7); a donor sulfur moiety, (EC 1.8); a donor heme moiety, (EC 1.9); a donor diphenol or a related moiety as donor, (EC 1.10); a peroxide as an acceptor, (EC 1.11); a donor hydrogen, (EC 1.12); a single donor with incorporation of molecular oxygen ("oxygenase"), (EC 1.13); a paired donor, with incorporation or reduction of molecular oxygen, (EC 1.14); a superoxide radical as an acceptor, (EC 1.15); an oxidoreductase that oxidises a metal ion, (EC 1.16); an oxidoreductase that acts on a donor CH₂ moiety, (EC 1.17); a donor iron-sulfur protein, (EC 1.18); a donor reduced flavodoxin, (EC 1.19); a donor phosphorus or donor arsenic moiety, (EC 1.20); an oxidoreductase that acts on an X—H and an Y—H to form an X—Y bond, (EC 1.21); as well as a other oxidoreductase, (EC 1.97)[Is this the right number?]; or a combination thereof.

A transferase catalyzes the transfer of a moiety from a donor compound to an acceptor compound. A transferase is generally classified based on the chemical moiety transferred. Examples of transferases include an transferase that catalyzes the transfer of a one-carbon moiety, (EC 2.1); an aldehyde or a ketonic moiety, (EC 2.2); an acyl moiety, (EC 2.3); a glycosyl moiety, (EC 2.4); an alkyl or an aryl moiety other than a methyl moiety, (EC 2.5); a nitrogenous moiety, (EC 2.6); a phosphorus-containing moiety, (EC 2.7); a sulfur-containing moiety, (EC 2.8); a selenium-containing moiety, (EC 2.9); or a combination thereof.

A hydrolase catalyses the hydrolysis of a chemical bond. A hydrolase is generally classified based on the chemical bond cleaved or the moiety released or transferred by the hydrolysis reaction. Examples of hydrolases include a hydrolase that catalyzes the hydrolysis of an ester bond, (EC 3.1); a glycosyl released/transferred moiety, (EC 3.2); an ether bond, (EC 3.3); a peptide bond, (EC 3.4); a carbon-nitrogen bond, other than a peptide bond, (EC 3.5); an acid anhydride, (EC 3.6); a carbon-carbon bond, (EC 3.7); a halide bond, (EC 3.8); a phosphorus-nitrogen bond, (EC 3.9); a sulfur-nitrogen bond, (EC 3.10); a carbon-phosphorus bond, (EC 3.11); a sulfur-sulfur bond, (EC 3.12); a carbon-sulfur bond, (EC 3.13); or a combination thereof.

A lyase catalyzes the cleavage of a chemical bond by reactions other than hydrolysis or oxidation. A lyase is generally classified based on the chemical bond cleaved. Examples of lyases include a lyase that catalyzes the cleavage of a carbon-carbon bond, (EC 4.1); a carbon-oxygen bond, (EC 4.2); a carbon-nitrogen bond, (EC 4.3); a carbon-sulfur bond, (EC 4.4); a carbon-halide bond, (EC 4.5); a phosphorus-oxygen bond, (EC 4.6); a other lyase, (EC 4.99) [Is this the right number?]; or a combination thereof.

An isomerase catalyzes a change within one molecule. Examples of isomerases include a racemase or an epimerase, (EC 5.1); a cis-trans-isomerases, (EC 5.2); an intramolecular isomerase, (EC 5.3); an intramolecular transferase, (EC 5.4); an intramolecular lyase, (EC 5.5); a other isomerases, (EC 5.99) [Is this the right number?]; or a combination thereof.

A ligase catalyses the formation of a chemical bond between two substrates with the hydrolysis of a diphosphate bond of a triphosphate such as ATP. A ligase is generally classified based on the chemical bond created. Examples of lyases include a ligase that form a carbon-oxygen bond, (EC 6.1); a carbon-sulfur bond, (EC 6.2); a carbon-nitrogen bond, (EC 6.3); a carbon-carbon bond, (EC 6.4); a phosphoric ester bond, (EC 6.5); or a combination thereof.

1. Preferred Enzymes

A preferred enzyme for use in the present invention comprises a hydrolase. A preferred hydrolase comprises an esterase. A preferred esterase comprises an esterase that catalyzes the hydrolysis of an organophosphorus compound. Examples of such preferred esterases are those identified by enzyme commission number EC 3.1.8, the phosphoric triester hydrolases. As used herein, a phosphoric triester hydrolase catalyzes the hydrolytic cleavage of an ester from a phosphorus moiety. Examples of a phosphoric triester hydrolase include an aryldialkylphosphatase, a diisopropyl-fluorophosphatase, or a combination thereof.

An aryldialkylphosphatase (EC 3.1.8.1) is also known by its systemic name "aryltriphosphate dialkylphosphohydrolase," and various enzymes in this category have been known in the art by names such as "organophosphate hydrolase"; "paraoxonase"; "A-esterase"; "aryltriphosphatase"; "organophosphate esterase"; "esterase B1"; "esterase E4"; "paraoxon esterase"; "pirimiphos-methyloxon esterase"; "OPA anhydrase"; "organophosphorus hydrolase"; "phosphotriesterase"; "PTE"; "paraoxon hydrolase"; "OPH"; and "organophosphorus acid anhydrase." An aryldialkylphosphatase catalyzes the following reaction: aryl dialkyl phosphate+H₂O=an aryl alcohol+dialkyl phosphate. Examples of an aryl dialkyl phosphate include an organophosphorus compound comprising a phosphonic acid ester, a phosphinic acid ester, or a combination thereof.

A diisopropyl-fluorophosphatase (EC 3.1.8.2) is also known by its systemic name "diisopropyl-fluorophosphate fluorohydrolase," and various enzymes in this category have been known in the art by names such as "DFPase"; "tabunase"; "somanase"; "organophosphorus acid anhydrolase"; "organophosphate acid anhydrase"; "OPA anhydrase"; "diisopropylphosphofluoridase"; "dialkylfluorophosphatase"; "diisopropyl phosphorofluoridate hydrolase"; "isopropylphosphorofluoridase"; and "diisopropylfluorophosphonate dehalogenase." A diisopropyl-fluorophosphatase catalyzes the following reaction: diisopropyl fluorophosphate+H₂O=fluoride+diisopropyl phosphate. Examples of a diisopropyl fluorophosphates include an organophosphorus compound comprising a phosphorus-halide, a phosphorus-cyanide, or a combination thereof.

Examples of phosphoric triester hydrolases and cleaved OP compounds and bond types are shown at Table 1.

TABLE 1

Phosphoric Triester Hydrolases

| | OP Compound Phosphoryl Bond-Type and Phosphoryl Bond Types Cleaved by Enzyme | | | | |
|---|---|---|---|---|---|
| | Various OP Pesticides | Sarin, Soman | VX, R-VX | | Tabun |
| Enzyme | P—C | P—O | P—F | P—S | P—CN |
| OPH[a,b,c,d,e,f,g] | − | + | + | + | + |
| Human | + | + | + | − | + |

TABLE 1-continued

Phosphoric Triester Hydrolases

OP Compound Phosphoryl Bond-Type and
Phosphoryl Bond Types Cleaved by Enzyme

| Enzyme | Various OP Pesticides P—C | Sarin, Soman P—O | VX, R-VX P—F | P—S | Tabun P—CN |
|---|---|---|---|---|---|
| Paraoxonase[h,i,j] | | | | | |
| OPAA-2[k,l] | − | + | + | − | + |
| Squid DFPase[m] | − | − | + | − | − |

[a]Dumas, D. P. et al., 1989a;
[b]Dumas, D. P. et al., 1989b;
[c]Dumas, D. P. et al., 1990;
[d]Dave, K. I. et al., 1993;
[e]Chae, M. Y. et al., 1994;
[f]Lai, K. et al., 1995;
[g]Kolakowski, J. E. et al., 1997;
[h]Hassett, C. et al., 1991;
[i]Josse, D. et al., 2001;
[j]Josse, D. et al., 1999;
[k]DeFrank, J. J. et al. 1993;
[l]Cheng, T.-C. et al., 1996;
[m]Hoskin, F. C. G. and Roush, A. H., 1982.

A preferred substrate for a composition of the present invention comprises an organophosphorus compound. As used herein, an "organophosphorus compound" is a compound comprising a phosphoryl center, and further comprises two or three ester linkages. In some aspects, the type of phosphoester bond and/or additional covalent bond at the phosphoryl center classifies an organophosphorus compound. In embodiments wherein the phosphorus is linked to an oxygen by a double bond (P=O), the OP compound is known as an "oxon OP compound" or "oxon organophosphorus compound." In embodiments wherein the phosphorus is linked to a sulfur by a double bond (P=S), the OP compound is known as a "thion OP compound" or "thion organophosphorus compound." Additional examples of bond-type classified OP compounds include a phosphonocyanate, which comprises a P—CN bond; a phosphoroamidate, which comprises a P—N bond; a phosphotriester, which comprises a P—O bond; a phosphodiester, which comprises a P—O bond; a phosphonofluoridate, which comprises a P—F bond; and a phosphonothiolate, which comprises a P—S bond. A "dimethyl OP compound" comprises two methyl moieties covalently bonded to the phosphorus atom, such as, for example, malathion. A "diethyl OP compound" comprises two ethoxy moieties covalently bonded to the phosphorus atom, such as, for example, diazinon.

In general embodiments, an OP compound comprises an organophosphorus nerve agent or an organophosphorus pesticide. As used herein, a "nerve agent" is an inhibitor of a cholinesterase, including but not limited to, an acetyl cholinesterase, a butyl cholinesterase, or a combination thereof. The toxicity of an OP compound depends on the rate of release of its phosphoryl center (e.g., P—C, P—O, P—F, P—S, P—CN) from the target enzyme (Millard, C. B. et al., 1999). Preferred nerve agents are inhibitors of a cholinesterase (e.g., acetyl cholinesterase) whose catalytic activity is often critical for health and survival in animals, including humans.

Certain OP compounds are so toxic to humans that they have been adapted for use as chemical warfare agents, such as tabun, soman, sarin, cyclosarin, VX, and R-VX. A CWA may be in airborne form and such a formulation is known herein as an "OP-nerve gas." Examples of airborne forms include a gas, a vapor, an aerosol, a dust, or a combination thereof. Examples of an OP compounds that may be formulated as an OP nerve gas include tabun, sarin, soman, VX, GX, or a combination thereof.

In addition to the initial inhalation route of exposure common to such agents, CWAs, especially persistent agents such as VX and thickened soman, pose threats through dermal absorption [In "Chemical Warfare Agents: Toxicity at Low Levels," (Satu M. Somani and James A. Romano, Jr., Eds.) p. 414, 2001]. As used herein, a "persistent agent" is a CWA formulated to be non-volatile and thus remain as a solid or liquid while exposed to the open air for more than three hours. Often after release, a persistent agent may convert from an airborne dispersal form to a solid or liquid residue on a surface, thus providing the opportunity to contact the skin of a human. The toxicities for common OP chemical warfare agents after contact with skin are shown at Table 2.

TABLE 2

| $LD_{50}$ Values* of Common Organophosphorus Chemical Warfare Agents | |
|---|---|
| Common OP CWA | Estimated human $LD_{50}$ - percutaneous (skin) administration |
| Tabun | 1000 milligrams ("mg") |
| Sarin | 1700 mg |
| Soman | 100 mg |
| VX | 10 mg |

*$LD_{50}$ - the dose need to kill 50% of individuals in a population after administration, wherein the individuals weigh approximately 70 kg.

In some embodiments, an OP compound may be a particularly poisonous organophosphorus nerve agent. As used herein, a "particularly poisonous" agent is a composition with a $LD_{50}$ of 35 mg/kg or less for an organism after percutaneous ("skin") administration of the agent. Examples of a particularly poisonous OP nerve agent include tabun, sarin, cyclosarin, soman, VX, R-VX, or a combination thereof.

As used herein, "detoxification," "detoxify," "detoxified," "degradation," "degrade," and "degraded" refers to a chemical reaction of a compound that produces a chemical byproduct that is less harmful to the health or survival of a target organism contacted with the chemical product relative to contact with the parent compound. OP compounds may be detoxified using chemical hydrolysis or through enzymatic hydrolysis (Yang, Y.-C. et al., 1992; Yang, Y.-C. et al., 1996; Yang, Y.-C. et al., 1990; LeJeune, K. E. et al., 1998a). In general embodiments, the enzymatic hydrolysis is a specifically targeted reaction wherein the OP compound is cleaved at the phosphoryl center's chemical bond resulting in predictable byproducts that are acidic in nature but benign from a neurotoxicity perspective (Kolakowski, J. E. et al., 1997; Rastogi, V. K. et al., 1997; Dumas, D. P. et al., 1990; Raveh, L. et al., 1992). By comparison, chemical hydrolysis can be much less specific, and in the case of VX may produce some quantity of byproducts that approach the toxicity of the intact agent (Yang, Y.-C. et al., 1996; Yang, Y.-C. et al., 1990). In preferred facets, an enzyme composition of the present invention degrades a CWA, a particularly poisonous organophosphorus nerve agent, or a combination thereof into byproduct that is not particularly poisonous.

Many OP compounds are pesticides that are not particularly poisonous to humans, though they do possess varying degrees of toxicity to humans and other animals. Examples of an OP pesticide include bromophos-ethyl, chlorpyrifos, chlorfenvinphos, chlorothiophos, chlorpyrifos-methyl, coumaphos, crotoxyphos, crufomate, cyanophos, diazinon, dichlofenthion, dichlorvos, dursban, EPN, ethoprop, ethyl-parathion, etrimifos, famphur, fensulfothion, fenthion, fenthrothion, isofenphos, jodfenphos, leptophos-oxon, malathion, methyl-parathion, mevinphos, paraoxon, parathion, parathion-methyl, pirimiphos-ethyl, pirimiphos-methyl, pyrazophos, quinalphos, ronnel, sulfopros, sulfotepp, trichloronate, or a combination thereof. In some embodiments, a composition of the present invention degrades a pesticide into a byproduct that is less toxic to an organism. In specific aspects, the organism is an animal, such as a human.

a. OPH

Organophosphorus hydrolase (E.C.3.1.8.1) has been also referred to in that art as "organophosphate-hydrolyzing enzyme," "phosphotriesterase," "PTE," "organophosphate-degrading enzyme," "OP anhydrolase," "OP hydrolase," "OP thiolesterase," "organophosphorus triesterase," "parathion hydrolase," "paraoxonase," "DFPase," "somanase," "VXase," and "sarinase." As used herein, this type of enzyme will be referred to herein as "organophosphorus hydrolase" or "OPH."

The initial discovery of OPH was from two bacterial strains from the closely related genera: *Pseudomonas diminuta* and *Flavobacterium* spp. (McDaniel, S. et al., 1988; Harper, L. et al., 1988), which encoded identical organophosphorus degrading opd genes on large plasmids (Genbank accession no. M20392 and Genbank accession no. M22863) (copending U.S. patent application Ser. No. 07/898,973, incorporated herein in its entirety by reference). It is likely that *Pseudomonas diminuta* was derived from the *Flavobacterium* spp. Subsequently, other such OPH encoding genes have been discovered. The use of any opd gene or their gene product in the described compositions and methods is contemplated. Examples of opd genes and gene products that may be used include the *Agrobacterium radiobacter* P230 organophosphate hydrolase gene, opdA (Genbank accession no. AY043245; Entrez databank no. AAK85308); the *Flavobacterium balustinum* opd gene for parathion hydrolase (Genbank accession no. AJ426431; Entrez databank no. CAD19996); the *Pseudomonas diminuta* phosphodiesterase opd gene (Genbank accession no. M20392; Entrez databank no. AAA98299; Protein Data Bank entries 1JGM, 1DPM, 1EYW, 1EZ2, 1HZY, 1IOB, 1IOD, 1PSC and 1PTA); the *Flavobacterium* sp opd gene (Genbank accession no. M22863; Entrez databank no. AAA24931; ATCC 27551); the *Flavobacterium* sp. parathion hydrolase opd gene (Genbank accession no. M29593; Entrez databank no. AAA24930; ATCC 27551); or a combination thereof (Horne, I. et al., 2002; Somara, S. et al., 2002; McDaniel, C. S. et al., 1988a; Harper, L. L. et al., 1988; Mulbry, W. W. and Karns, J. S., 1989).

Because OPH possesses the desirable property of cleaving a broad range of OP compounds (Table 1), it is the OP detoxifying enzyme that has been most studied and characterized, with the enzyme obtained from *Pseudomonas* being the target of focus for most studies. This OPH was initially purified following expression from a recombinant baculoviral vector in insect tissue culture of the Fall Armyworm, *Spodoptera frugiperda* (Dumas, D. P. et al., 1989b). Purified enzyme preparations have been shown to be able to detoxify via hydrolysis a wide spectrum of structurally related insect and mammalian neurotoxins that function as acetylcholinesterase inhibitors. Of great interest, this detoxification ability included a number of organophosphorofluoridate nerve agents such as sarin and soman. This was the first recombinant DNA construction encoding an enzyme capable of degrading these potent nerve gases. This enzyme was capable of degrading the common organophosphorus insecticide analog (paraoxon) at rates exceeding $2 \times 10^7$ M$^{-1}$ (mole enzyme)$^{-1}$, which is equivalent to the most catalytically efficient enzymes observed in nature. The purified enzyme preparations are capable of detoxifying sarin and the less toxic model mammalian neurotoxin O,O-diisopropyl phosphorofluoridate ("DFP") at the equivalent rates of 50-60 molecules per molecule of enzyme-dimer per second. In addition, the enzyme can hydrolyze soman and VX at approximately 10% and 1% of the rate of sarin, respectively. The breadth of substrate utility (e.g., V agents, sarin, soman, tabun, cycosarin, OP pesticides) and the efficiency for the hydrolysis exceeds the known abilities of other prokaryotic and eukaryotic organophosphorus acid anydrases, and it is clear that this detoxification is due to a single enzyme rather than a family of related, substrate-limited proteins.

The X-ray crystal structure of *Pseudomonas* OPH has been determined (Benning, M. M. et al., 1994; Benning, M. M. et al., 1995; Vanhooke, J. L. et al., 1996). Each OPH monomer's active site binds two atoms of $Zn^{2+}$; however, OPH is usually prepared wherein $Co^{2+}$ replaces $Zn^{2+}$, which enhances catalytic rates. Examples of the catalytic rates ($k_{cat}$) and specificities ($k_{cat}/K_m$) for $Co^{2+}$ substituted OPH against various OP compounds are shown at Table 3 below.

TABLE 3

Catalytic Activity of Wild-Type OPH binding $Co^{2+}$

|  | $k_{cat}$ (s$^{-1}$) | $k_{cat}/K_m$ (M$^{-1}$ s$^{-1}$) |
| --- | --- | --- |
| OP Pesticide Substrate |  |  |
| Paraoxon | 15000$^a$ | $1.3 \times 10^8$ |
| OP CWA Substrates |  |  |
| Sarin | 56$^b$ | $8 \times 10^4$ |
| Soman | 5$^b$ | $1 \times 10^4$ |
| VX | 0.3$^b$ | $7.5 \times 10^2$ |
| R-VX | 0.5$^c$ | 105 |
| Tabun* | 77$^d$ | $7.6 \times 10^5$ |

*Wild-type $Zn^{2+}$ OPH was used in obtaining these kinetic parameters;
$^a$diSioudi, B. et al., 1999a;
$^b$Kolakoski, J. E. et al., 1997;
$^c$Rastogi, V. K. et al., 1997;
$^d$Raveh, L. et al., 1992.

The phosphoryl center of OP compounds is chiral, and *Pseudomonas* OPH preferentially binds and/or cleaves $S_p$ enantiomers over $R_p$ enantiomers of the chiral phosphorus in various substrates by a ratio of about 10:1 to about 90:1 (Chen-Goodspeed, M. et al., 2001a; Hong, S.-B. and Raushel, F. M., 1999a; Hong, S.-B. and Raushel, F. M., 1999b). CWAs such as VX, sarin, and soman are usually prepared and used as a mixture of stereoisomers of varying toxicity, with VX and sarin having two enantiomers each, with the chiral center around the phosphorus of the cleavable bond. Soman possesses four enantiomers, with one chiral center based on the phosphorus and an additional chiral center based on a pinacolyl moeity [In "Chemical Warfare Agents: Toxicity at Low Levels" (Satu M. Somani and James A. Romano, Jr., Eds.) pp 26-29, 2001; Li, W.-S. et al., 2001; Yang, Y.-C. et al., 1992; Benshop, H. P. et al., 1988]. The $S_p$ enantiomer of sarin is about $10^4$ times faster in inactivating acetylcholinesterase than the $R_p$ enantiomer (Benschop, H. P. and De Jong, L. P. A. 1988), while the two $S_p$ enantiomers of soman is about $10^5$ times faster in inactivating acetylcholinesterase than the $R_P$ enantiomers (Li, W.-S. et al., 2001; Benschop, H. P. et al., 1984). Wild-type organophosphorus hydrolase seems to have greater specificity for the less toxic enantiomers of sarin and soman. OPH is about 9-fold faster cleaving an analog of the $R_P$ enantiomer of sarin relative to an analog of the $S_p$ enantiomer, and about 10-fold faster in cleaving analogs of the $R_c$ enantiomers of soman relative to analogs of the $S_c$ enantiomers (Li, W.-S. et al., 2001).

b. Paraoxonase

Human paraoxonase (EC 3.1.8.1), is a calcium dependent protein, and is also known as an "arylesterase" or aryl-ester hydrolase" (Josse, D. et al., 1999; Vitarius, J. A. and Sultanos, L. G., 1995). Examples of the human paraoxonase ("HPON1") gene and gene products can be accessed at (Genbank accession no. M63012; Entrez databank no. AAB59538) (Hassett, C. et al., 1991).

c. Carboxylases

It is contemplated that a carboxylase gene isolated from an animal may be used as an organophosphate hydrolase in the present invention. As used herein, a "carboxylase" or "ali-esterase" (EC 3.1.1.1) is an enzyme that hydrolytically cleaves carboxylic esters (e.g., C-0 bonds). As is well known to those of ordinary skill in the art, most genes in eukaryotic organisms have multiple alleles which comprise variant nucleotide and/or expressed protein sequences for a particular gene. Certain insect species have been identified with reduced carboxylase activity and enhanced resistance to OP compounds such as malathion or diazinon. Examples of insect species include *Plodia interpunctella*, *Chrysomya putoria*, *Lucilia cuprina*, and *Musca domestica*. In particular, an allele of a carboxylase gene possessing organophosphate hydrolase (EC 3.1.8.1) activity is thought to be responsible for OP compound resistance. Examples of such carboxylase genes include alleles isolated from *Lucilia cuprina* (Genbank accession no. U56636; Entrez databank no. AAB67728), *Musca domestica* (Genbank accession no. AF133341; Entrez databank no. AAD29685), or a combination thereof (Claudianos, C. et al., 1999; Campbell, P. M. et al., 1998; Newcomb, R. D. et al., 1997). Additionally, carboxylases or carbamoyl lyases are useful against the carbamate nerve agents, and are specifically contemplated for use in biomolecule composition of the present invention for use against such agents.

d. OPAAs, Prolidases, Aminopeptideases and PepQ

Organophosphorus acid anhydrolases (E.C.3.1.8.2), known as "OPAAs," have been isolated from microorganisms and identified as enzymes that detoxify OP compounds (Serdar, C. M. and Gibson, D. T., 1985; Mulbry, W. W. et al., 1986; DeFrank, J. J. and Cheng, T.-C., 1991). The better-characterized OPAAs have been isolated from *Altermonas* species, such as *Alteromonas* sp JD6.5, *Alteromonas haloplanktis* and *Altermonas undina* (ATCC 29660) (Cheng, T.-C. et al., 1996; Cheng, T.-C. et al., 1997; Cheng, T. C. et al., 1999; Cheng, T.-C. et al., 1993). Examples of OPAA genes and gene products that may be used include the *Alteromonas* sp JD6.5 opaA gene, (GeneBank accession no. U29240; Entrez databank no. AAB05590); the *Alteromonas haloplanktis* prolidase gene (GeneBank accession no. U56398; Entrez databank AAA99824; ATCC 23821); or a combination thereof (Cheng, T. C. et al., 1996; Cheng, T.-C. et al., 1997). The wild-type encoded OPAA from *Alteromonas* sp JD6.5 is 517 amino acids, while the wild-type encoded OPAA from *Alteromonas haloplanktis* is 440 amino acids (Cheng, T. C. et al., 1996; Cheng, T.-C. et al., 1997).

The *Alteromonas* OPAAs accelerates the hydrolysis of phosphotriesters and phosphofluoridates, including cyclosarin, sarin and soman (Table 4).

TABLE 4

Catalytic Activity of Wild-Type OPAAs

| | $k_{cat}$ ($s^{-1}$) per species OPAA per OP Substrate | | |
|---|---|---|---|
| | A. sp JD6.5 | A. haloplanktis | A. undina |
| OP Compound Substrate | | | |
| DFP | 1650[a] | 575[a] | 1239[a] |
| OP CWA Substrates | | | |
| Sarin | 611[a] | 257[a] | 376[a] |
| Cyclosarin | 1650[a] | 269[a] | 1586[a] |
| Soman | 3145[a] | 1389[a] | 2496[a] |
| Tabun | 85[a] | 113[a] | 292[a] |

[a]Cheng, T. C. et al., 1999

Similar to OPH, OPAA from *Alteromonas* sp JD6.5 ("OPAA-2") has a general binding and cleavage preference up to 112:1 for the $S_p$ enantiomers of various p-nitrophenyl phosphotriesters (Hill, C. M. et al., 2000). Additionally, OPAA from *Alteromonas* sp JD6.5 is over 2 fold faster at cleaving an $S_p$ enantiomer of a sarin analog, and over 15-fold faster in cleaving analogs of the $R_c$ enantiomers of soman relative to analogs of the $S_c$ enantiomers (Hill, C. M. et al., 2001).

Additionally, a prolidase ("imidodipeptidase," "proline dipeptidase," "peptidase D," "g-peptidase"), PepQ and/or aminopeptidase P gene or gene product with OPAA activity, or a functional equivalent thereof may be used in the present invention. OPAAs possess sequence and structural similarity to human prolidase, *Escherichia coli* aminopeptidase P and *Escherichia coli* PepQ (Cheng, T.-C. et al., 1997; Cheng, T.-C. et al., 1996). A prolidase or a PepQ protein (E.C. 3.4.13.9) hydrolyzes a C—N bond of a dipeptide with a prolyl residue at the carboxyl-terminus, and OPAAs are also classified as prolidases. An aminopeptidase P (EC 3.4.11.9) hydrolyzes the C—N amino bond of a proline at the penultimate position from the amino terminus of an amino acid sequence. Partly purified human and porcine prolidase demonstrated the ability to cleave DFP and G-type nerve agents (Cheng, T.-C. et. al., 1997). Examples of prolidase genes and gene products include the *Mus musculus* prolidase gene (GeneBank accession no. D82983; Entrez databank no. BAB11685); the *Homo sapien* prolidase gene (GeneBank accession no. J04605; Entrez databank AAA60064); the *Lactobacillus helveticus* prolidase ("PepQ") gene (GeneBank accession no. AF012084; Entrez databank AAC24966); the *Escherichia coli* prolidase ("pepQ") gene (GeneBank accession no. X54687; Entrez databank CAA38501); the *Escherichia coli* aminopeptidase P ("pepP") gene (GeneBank accession no. D00398; Entrez databank BAA00299; Protein Data Bank entries 1A16, 1AZ9, 1JAW and 1M35); or a combination thereof (Ishii, T. et al., 1996; Endo, F. et al., 1989; Nakahigashi, K. and Inokuchi, H., 1990; Yoshimoto, T. et al., 1989).

e. Squid-Type DFPases

As used herein, a "squid-type DFPase" (EC 3.1.8.2) refers to an enzyme that catalyzes the cleavage of both DFP and soman, and is isolated from organisms of the *Loligo* genus. Generally, a squid-type DFPase cleaves DFP at a faster rate than soman. Squid-type DFPases include, for example, a DFPase from *Loligo vulgaris*, *Loligo pealei*, *Loligo opal-*

*escens*, or a combination thereof (Hoskin, F. C. G. et al., 1984; Hoskin, F. C. G. et al., 1993; Garden, J. M. et al., 1975).

A well-characterized example of a squid-type DFPase includes the DFPase that has been isolated from the optical ganglion of *Loligo vulgaris* (Hoskin, F. C. G. et al., 1984). This squid-type DFPase cleaves a variety of OP compounds, including DFP, sarin, cyclosarin, soman, and tabun (Hartleib, J. and Ruterjans, H., 2001a). The gene encoding this squid-type DFP has been isolated, and can be accessed at GeneBank accession no. AX018860 (International patent publication: WO 9943791-A). Further, this enzyme's X-ray crystal structure has been determined (Protein Data Bank entry 1E1A) (Koepke, J. et al., 2002; Scharff, E. I. et al., 2001). This squid-type DFPase binds two $Ca^{2+}$ ions, which are important in catalytic activity and enzyme stability (Hartleib, J. et al., 2001). Both the DFPase from *Loligo vulgaris* and *Loligo pealei* are susceptible to proteolytic cleavage into a 26-kDa and 16 kDa fragments, and the fragments from *Loligo vulgaris* are capable of forming active enzyme when associated together (Hartleib, J. and Ruterjans, H., 2001a).

f. Mazur-Type DFPases

As used herein, a "Mazur-type DFPase" (EC 3.1.8.2) refers to an enzyme that catalyzes the cleavage of both DFP and soman. Generally, Mazur-type DFPases cleaves soman at a faster rate than DFP. Examples of a Mazur-type DFPases include the DFPase isolated from mouse liver (Billecke, S. S. et al., 1999), which may be the same as the DFPase known as SMP-30 (Fujita, T. et al., 1996; Billecke, S. S. et al., 1999; Genebank accession no. U28937; Entrez databank AAC52721); a DFPase isolated from rat liver (Little, J. S. et al., 1989); a DFPase isolated from hog kidney; a DFPase isolated from *Bacillus stearothermophilus* strain OT, a DFPase isolated from *Escherichia coli* (ATCC25922) (Hoskin, F. C. G. et al., 1993; Hoskin, F. C. G, 1985); or a combination thereof.

g. Other Phosphoric Triester Hydrolases

It is contemplated that any phosphoric triester hydrolase that is known in the art may be used in preferred embodiments of the present invention. An example of an additional phosphoric triester hydrolase includes the product of the gene, mpd, (GenBank accession number AF338729; Entrez databank AAK14390) isolated from *Plesiomonas* sp. strain M6 (Zhongli, C. et al., 2001). Other examples include the phosphoric triester hydrolase identified in a *Xanthomonas* sp. (Tchelet, R. et al., 1993); *Tetrahymena* (Landis, W. G. et al., 1987); certain plants such as *Myriophyllum aquaticum, Spirodela origorrhiza* L, *Elodea Canadensis* and *Zea mays* (Gao, J. et al., 2000; Edwards, R. and Owen, W. J., 1988); and in hen liver and brain (Diaz-Alejo, N. et al., 1998). Additional, cholinesterases (e.g., an acetyl cholinesterase) with OP degrading activity have been identified in insects resistant OP pesticides (see, for example, Baxter, G. D. et al., 1998; Baxter, G. D. et al., 2002; Rodrigo, L., et al., 1997; Vontas, J. G., et al., 2002; Walsh, S. B., et al., 2001; Zhu, K. Y., et al., 1995), and are contemplate for use a bimolecular composition of the present invention.

2. Functional Equivalents of Wild-Type Enzymes

It is possible to optimize a proteinaceous molecule with a defined amino acid sequence and/or length for one or more properties. An alteration in a desirable property is possible because such molecules can be manipulated, for example, by chemical modification, as described herein or as would be known to one of ordinary skill in the art, in light of the present disclosures. As used herein "alter" or "alteration" may result in an increase or a decrease in the measured value for a particular property. As used herein a "property," in the context of an proteinaceous molecule, includes, but is not limited to, a ligand binding property, a catalytic property, a stability property, a property related to environmental safety, or a combination thereof. Examples of a catalytic property that may be altered include a kinetic parameter, such as $K_m$, a catalytic rate ($k_{cat}$) for a substrate, an enzyme's specificity for a substrate ($k_{cat}/K_m$), or a combination thereof. Examples of a stability property that may be altered include thermal stability, half-life of activity, stability after exposure to a weathering condition, or a combination thereof. Examples of a property related to environmental safety include an alteration in toxicity, antigenicity, bio-degradability, or a combination thereof. However, as would be readily apparent to one of ordinary skill in the art, an alteration to increase an enzyme's catalytic rate for a substrate, an enzyme's specificity for a substrate, a proteinaceous molecule's thermal stability, a proteinaceous molecule's half-life of activity, or a proteinaceous molecule's stability after exposure to a weathering condition may be preferred for some applications, while a decrease in toxicity and/or antigenicity for a proteinaceous molecule may be preferred in additional applications. An enzyme comprising a chemical modification that function as an enzyme of the present invention is a "functional equivalent" to, and "in accordance" with, an un-modified enzyme.

It is also understood by those of skill in the art that there is a limit to the number of chemical modifications that can be made to an enzyme of the present invention before a preferred property is undesirably altered. However, in light of the disclosures herein of assays for determining whether a composition possesses one or more desirable properties, including, for example, a preferred enzymatic activity, a stability property, etc., and that which is known in the art regarding such assays, it is well within the ability of one of ordinary skill in the art to determine whether a given chemical modification to an enzyme of the present invention produces a molecule that still possesses a suitable set of properties for use in a particular application. In certain aspects, a functional equivalent enzyme comprising a plurality of different chemical modifications can be produced in accordance with the present invention.

It is particularly contemplated that a functional equivalent enzyme comprising a structural analog and/or sequence analog may possess an enhanced desirable property and/or a reduced undesirable property, in comparison to the enzyme upon which it is based. All such functional equivalent enzymes described herein, or as would be known to one of ordinary skill in the art in light of the present disclosures, are considered part of the present invention. As used herein, a "structural analog" refers to one or more chemical modifications to the peptide backbone or non-side chain chemical moieties of a proteinaceous molecule. In certain aspects, a subcomponent of an enzyme such as an apo-enzyme, a prosthetic group, a co-factor, or a combination thereof, may be modified to produce a functional equivalent structural analog. In particular facets, such an enzyme sub-component that does not comprise a proteinaceous molecule may be altered to produce a functional equivalent structural analog of an enzyme when combined with the other sub-components. As used herein, a "sequence analog" refers to one or more chemical modifications to the side chain chemical moieties, also known herein as a "residue" of one or more amino acids that define a proteinaceous molecule's sequence. Often such a "sequence analog" comprises an amino acid substitution, which is generally produced by recombinant expression of a nucleic acid comprising a genetic mutation to produce a mutation in the expressed amino acid sequence.

As used herein, an "amino acid" may be a common or uncommon amino acid. The common amino acids include: alanine (Ala, A); arginine (Arg, R); aspartic acid (a.k.a. aspartate; Asp, D); asparagine (Asn, N); cysteine (Cys, C); glutamic acid (a.k.a. glutamate; Glu, E); glutamine (Gln, Q); glycine (Gly, G); histidine (His, H); isoleucine (Ile, I); leucine (Leu, L); lysine (Lys, K); methionine (Met, M); phenylalanine (Phe, F); proline (Pro, P); serine (Ser, S); threonine (Thr, T); tryptophan (Trp, W); tyrosine (Tyr, Y); and valine (Val, V). Common amino acids are often biologically produced in the biological synthesis of a peptide or a polypeptide. An uncommon amino acid refers to an analog of a common amino acid, as well as a synthetic amino acid whose side chain is chemically unrelated to the side chains of the common amino acids. Various uncommon amino acids are well known to those of ordinary skill in the art though it is contemplated that in general embodiments, an enzyme of the present invention will be biologically produced, and thus lack or possess relatively few uncommon amino acids prior to any subsequent non-mutation based chemical modifications.

As is well known in the art, the side chains of amino acids comprise moieties with specific chemical and physical properties. Certain side chains contribute to a ligand binding property, a catalytic property, a stability property, a property related to environmental safety, or a combination thereof. For example, cysteines can form covalent bonds between different parts of a contiguous amino acid sequence, or between non-contiguous amino acid sequences to confer enhanced stability to a secondary, tertiary or quaternary structure. In an additional example, the presence of hydrophobic or hydrophilic side chains exposed to the outer environment can alter the hydrophobicity or hydrophilicity of part of a proteinaceous sequence such as in the case of a transmembrane domain that is embedded in a lipid layer of a membrane. In another example, hydrophilic side chains may be exposed to the environment surrounding a proteinaceous molecule, which can enhance the overall solubility of a proteinaceous molecule in a polar liquid, such as water or a liquid component of a coating. In a further example, various acidic, basic, hydrophobic, hydrophilic, and/or aromatic side chains present at or near a binding site of a proteinaceous structure can affect the affinity for a proteinaceous sequence for binding a ligand and/or a substrate, based on the covalent, ionic, Van der Waal forces, hydrogen bond, hydrophilic, hydrophobic, and/or aromatic interactions at a binding site. Such interactions by residues at or near an active site also contribute to a chemical reaction that occurs at the active site of an enzyme to produce enzymatic activity upon a substrate. As used herein, a residue is "at or near" another residue or group of residues when it is within 15 Å, 14 Å, 13 Å, 12 Å, 11 Å, 10 Å, 9 Å, 8 Å, 7 Å, 6 Å, 5 Å, 4 Å, 3 Å, 2 Å, or 1 Å the residue or group of residues such as residues identified as contributing to the active site and/or binding site.

Identification of an amino acid whose chemical modification would likely change a desirable property of a proteinaceous molecule can be accomplished using such methods as a chemical reaction, mutation, X-ray crystallography, nuclear magnetic resonance ("NMR"), computer based modeling or a combination thereof. Selection of an amino acid on the basis of such information can then be used in the rational design of a mutant proteinaceous sequence that would possess an altered desired property. Preferred alterations include those that alter enzymatic activity to produce a functional equivalent of an enzyme.

For example, many residues of a proteinaceous molecule that contribute to the properties of a proteinaceous molecule comprise chemically reactive moieties. These residues are often susceptible to chemical reactions that can inhibit their ability to contribute to a desirable property of the proteinaceous molecule. Thus, a chemical reaction can be used to identify one or more amino acids comprised within the proteinaceous molecule that may contribute to a desirable property. The identified amino acids then can be subject to modifications such as amino acid substitutions to produce a functional equivalent. Examples of amino acids that can be so chemically reacted include Arg, which can be reacted with butanedione; Arg and/or Lys, which can be reacted with phenylglyoxal; Asp and/or Glu, which can be reacted with carbodiimide and HCl; Asp and/or Glu, which can be reacted with N-ethyl-5-phenylisoxazolium-3'-sulfonate ("Woodward's reagent K"); Asp and/or Glu, which can be reacted with 1,3-dicyclohexyl carbodiimide; Asp and/or Glu, which can be reacted with 1-ethyl-3-(3-dimethylaminopropyl)carbodiimide ("EDO"); Cys, which can be reacted with p-hydroxy mercuribenzoate; Cys, which can be reacted with dithiobisnitrobenzoate ("DTNB"); Cys, which can be reacted with iodoacetamide; His, which can be reacted with diethylpyrocarbonate ("DEPC"); His, which can be reacted with diazobenzenesulfonic acid ("DBS"); His, which can be reacted with 3,7-bis(dimethylamino)phenothiazin-5-ium chloride ("methylene blue"); Lys, which can be reacted with dimethylsuberimidate; Lys and/or Arg, which can be reacted with 2,4-dinitrofluorobenzene; Lys and/or Arg, which can be reacted with trinitrobenzene sulfonic acid ("TNBS"); Trp, which can be reacted with 2-hydroxy-5-nitrobenzyl bromide 1-ethyl-3(3-dimethylaminopropyl); Trp, which can be reacted with 2-acetoxy-5-nitrobenzyl chloride; Trp, which can be reacted with N-bromosucinimide; Tyr, which can be reacted with N-acetylimidazole ("NAI"); or a combination thereof (Hartleib, J. and Ruterjans, H., 2001b; Josse, D. et al., 1999; Josse, D. et al., 2001).

In an additional example, the secondary, tertiary and/or quaternary structure of a proteinaceous molecule may be modeled using techniques known in the art, including X-ray crystallography, nuclear magnetic resonance, computer based modeling, or a combination thereof to aid in the identification of active-site, binding site, and other residues for the design and production of a mutant form of an enzyme (Bugg, C. E. et al., 1993; Cohen, A. A. and Shatzmiller, S. E., 1993; Hruby, V. J., 1993; Moore, G. J., 1994; Dean, P. M., 1994; Wiley, R. A. and Rich, D. H., 1993). The secondary, tertiary and/or quaternary structures of a proteinaceous molecule may be directly determined by techniques such as X-ray crystallography and/or nuclear magnetic resonance to identify amino acids most likely affect one or more desirable properties. Additionally, many primary, secondary, tertiary, and/or quaternary structures of proteinaceous molecules can be obtained using a public computerized database. An example of such a databank that may be used for this purpose is the Protein Data Bank (PDB), which is an international repository of the 3-dimensional structures of many biological macromolecules.

Computer modeling can be used to identify amino acids most likely to affect one or more desirable properties. Often, a structurally related proteinaceous molecule comprises primary, secondary, tertiary and/or quaternary structures that are evolutionarily conserved in the wild-type protein sequences of various organisms. As would be known to those of ordinary skill in the art, the secondary, tertiary and/or quaternary structure of a proteinaceous molecule can be modeled using a computer to overlay the proteinaceous molecule's amino acid sequence, which is also known as the "primary structure," onto the computer model of a described primary, secondary, tertiary, and/or quaternary structure of another, structurally related proteinaceous molecule. Often the amino acids that may participate in an active site, a binding site, a transmembrane domain, the general hydrophobicity and/or hydrophilicity of a proteinaceous molecule, the general positive and/or negative charge of a proteinaceous molecule, etc, may be identified by such comparative computer modeling.

In embodiments wherein an amino acid of particular interest have been identified using such techniques, functional equivalents may be created using mutations that substitute a different amino acid for the identified amino acid of interest. Examples of substitutions of an amino acid side chain to produce a "functional equivalent" proteinaceous molecule are also known in the art, and may involve a conservative side chain substitution a non-conservative side chain substitution, or a combination thereof, to rationally alter a property of a proteinaceous molecule. Examples of conservative side chain substitutions include, when applicable, replacing an amino acid side chain with one similar in charge (e.g., an arginine, a histidine, a lysine); similar in hydropathic index; similar in hydrophilicity; similar in hydrophobicity; similar in shape (e.g., a phenylalanine, a tryptophan, a tyrosine); similar in size (e.g., an alanine, a glycine, a serine); similar in chemical type (e.g., acidic side chains, aromatic side chains, basic side chains); or a combination thereof. Conversely, when a change to produce a non-conservative substitution is contemplated to alter a property of proteinaceous molecule, and still produce a "functional equivalent" proteinaceous molecule, these guidelines can be used to select an amino acid whose side-chains relatively non-similar in charge, hydropathic index, hydrophilicity, hydrophobicity, shape, size, chemical type, or a combination thereof. Various amino acids have been given a numeric quantity based on the characteristics of charge and hydrophobicity, called the hydropathic index (Kyte, J. and Doolittle, R. F. 1982), which can be used as a criterion for a substitution. The hydropathic index of the common amino acids are: Arg (−4.5); Lys (−3.9); Asn (−3.5); Asp (−3.5); Gln (−3.5); Glu (−3.5); His (−3.2); Pro (−1.6); Tyr (−1.3); Trp (−0.9); Ser (−0.8); Thr (−0.7); Gly (−0.4); Ala (+1.8); Met (+1.9); Cys (+2.5); Phe (+2.8); Leu (+3.8); Val (+4.2); and Ile (+4.5). Additionally, a value has also been given to various amino acids based on hydrophilicity, which can also be used as a criterion for substitution (U.S. Pat. No. 4,554,101). The hydrophilicity values for the common amino acids are: Trp (−3.4); Phe (−2.5); Tyr (−2.3); Ile (−1.8); Leu (−1.8); Val (−1.5); Met (−1.3); Cys (−1.0); Ala (−0.5); His (−0.5); Pro (−0.5+/−0.1); Thr (−0.4); Gly (0); Asn (+0.2); Gln (+0.2); Ser (+0.3); Asp (+3.0+/−0.1); Glu (+3.0+/−0.1); Arg (+3.0); and Lys (+3.0). In aspects wherein an amino acid is being conservatively substituted for an amino acid whose hydropathic index or hydrophilic value is similar, the difference between the respective index and/or value is preferably within +/−2, more preferably within +/−1, and most preferably within +/−0.5. In aspects wherein an amino acid is being non-conservatively substituted for an amino acid whose hydropathic index or hydrophilic value is similar, the difference between the respective index and/or value is preferably greater than +/−0.5, more preferably greater than +/−1, and most preferably greater than +/−2.

In certain embodiments, a functional equivalent may be produced by a non-mutation based chemical modification to an amino acid, a peptide or a polypeptide. Examples of chemical modifications include, when applicable, a hydroxylation of a proline or a lysine; a phosphorylation of a hydroxyl group of a serine and/or a threonine; a methylation of an alpha-amino group of a lysine, an arginine and/or a histidine (Creighton, T. E., 1983); adding a detectable label such as a fluorescein isothiocyanate compound ("FITC") to a lysine side chain and/or a terminal amine (Rogers, K. R. et al., 1999); covalent attachment of a poly ethylene glycol (Yang, Z. et al., 1995; Kim, C. et al., 1999; Yang, Z. et al., 1996; Mijs, M. et al., 1994); an acylatylation of an amino acid, particularly at the N-terminus; an amination of an amino acid, particularly at the C-terminus (Greene, T. W. and Wuts, P. G. M. "Productive Groups in Organic Synthesis," Second Edition, pp. 309-315, John Wiley & Sons, Inc., USA, 1991); a deamidation of an asparagine or a glutamine to an aspartic acid or glutamic acid, respectively; a derivation of an amino acid by a sugar moiety, a lipid, a phosphate, or a farnysyl group; an aggregation (e.g., a dimerization) of a plurality of proteinaceous molecules, whether of identical sequence or varying sequences; a cross-linking of a plurality of proteinaceous molecules of the present invention using a cross-linking agent [e.g., a 1,1-bis(diazoacetyl)-2-phenylethane; a glutaraldehyde; a N-hydroxysuccinimide ester; a 3,3'-dithiobis (succinimidyl-propionate); a bis-N-maleimido-1,8-octane]; an ionization of an amino acid into an acidic, basic or neutral salt form; an oxidation of an amino acid; or a combination thereof of any of the forgoing. Such modifications may produce a desirable alteration in a property of a proteinaceous molecule, as would be known to those of ordinary skill in the art. For example, it is contemplated that a N-terminal glycosylation may enhance a proteinaceous molecule's stability (Powell, M. F. et al., 1993). In an additional example, it is contemplated that substitution of a beta-amino acid isoserine for a serine may enhance the aminopeptidase resistance a proteinaceous molecule (Coller, B. S. et al., 1993).

A proteinaceous molecule for use in the present invention may comprise a proteinaceous molecule longer or shorter than the wild-type amino acid sequences specifically disclosed herein, or that would be known to those of ordinary skill in the art in light of the present disclosure. For example, an enzyme comprising longer or shorter sequences is encompassed as part of the present invention, insofar as it retains enzymatic activity. In some embodiments, a proteinaceous molecule for use in the present invention may comprise one or more peptide and/or polypeptide sequences. In certain embodiments, a modification to a proteinaceous molecule may add and/or subtract one or two amino acids from a peptide and/or polypeptide sequence. In other embodiments, a change to a proteinaceous molecule may add and/or remove one or more peptide and/or polypeptide sequences. Often a peptide or a polypeptide sequence may be added or removed to confer or remove a specific property from the proteinaceous molecule, and numerous examples of such modifications to a proteinaceous molecule are described herein, particularly in reference to fusion proteins. In particular, the native OPH of *Pseudomonas diminuta* is produced with a short amino acid sequence at its N-terminus that promotes the exportation of the protein through the cell membrane and is later cleaned. Thus, in certain embodiment, this signal sequence amino acid sequence is deleted by genetic modification in the DNA construction placed into *Escherichia coli* host cells in order to enhance its production.

As used herein, a "peptide" comprises a contiguous molecular sequence from 3 to 100 amino acids in length, including all intermediate ranges and combinations thereof. A sequence of a peptide may be 3 to 100 amino acids in length, including all intermediate ranges and combinations thereof. As used herein a "polypeptide" comprises a contiguous molecular sequence 101 amino acids or greater. Examples of a sequence length of a polypeptide include 101 to 10,000 amino acids, including all intermediate ranges and combinations thereof. As used herein a "protein" is a proteinaceous molecule comprising a contiguous molecular sequence three amino acids or greater in length, matching the length of a biologically produced proteinaceous molecule encoded by the genome of an organism.

It is recognized that removal of one or more amino acids from an enzyme's sequence may reduce or eliminate a detectable, desirable property such as enzymatic activity, and therefore would not be preferred. However, it is further contemplated that a longer sequence, particularly a proteinaceous molecule that consecutively or non-consecutively comprises or even repeats one or more enzymatic sequences disclosed herein, or as would be known to those of ordinary skill in the art in light of the present disclosure, would be encompassed within the present invention. Additionally, fusion proteins may be bioengineered to comprise a wild-type sequence and/or a functional equivalent of an enzyme sequence and an additional peptide or polypeptide sequence that confers a desirable property and/or function.

a. OPH Functional Equivalents

Using recombinant DNA technology, wild-type and mutant forms of the opd gene have been expressed, predominantly in *Escherichia coli*, for further characterization and analysis. Unless otherwise noted, the various OPH enzymes, whether wild-type or mutants, that act as functional equivalents were prepared using the OPH genes and encoded enzymes first isolated from *Pseudomonas diminuta* and *Flavobacterium* spp.

OPH normally binds two atoms of $Zn^{2+}$ per monomer when endogenously expressed. While binding $Zn^{2+}$, this enzyme is one of the most stable dimeric enzymes known, with a thermal temperature of melting ("$T_m$") of approximately 75° C. and a conformational stability of approximately 40 killocalorie per mole ("kcal/mol") (Grimsley, J. K. et al., 1997). However, structural analogs have been made wherein $Co^{2+}$, $Fe^{2+}$, $Cu^{2+}$, $Mn^{2+}$, $Cd^{2+}$, or $Ni^{2+}$ are bound instead to produce enzymes with altered stability and rates of activity (Omburo, G. A. et al., 1992). For example, $Co^{2+}$ substituted OPH does possess a reduced conformational stability (~22 kcal/mol). But this reduction in thermal stability is offset by the superior catalytic activity of $Co^{2+}$ substituted OPH in degrading various OP compounds. For example, five-fold or greater rates of detoxification of sarin, soman, and VX were measured for $Co^{2+}$ substituted OPH relative to OPH binding $Zn^{2+}$ (Kolakoski, J. E. et al., 1997). It is contemplated that structural analogs of an OPH sequence may be prepared comprising a $Zn^{2+}$, $Co^{2+}$, $Fe^{2+}$, $Cu^{2+}$, $Mn^{2+}$, $Cd^{2+}$, $Ni^{2+}$, or a combination thereof. Generally, changes in the bound metal can be achieved by using cell growth media during cell expression of the enzyme wherein the concentration of a metal present is defined, and/or removing the bound metal with a chelator (e.g., 1,10-phenanthroline; 8-hydroxyquinoline-5-sulfphonic acid; ethylenediaminetetraacetic acid) to produce an apoenzyme, followed by reconstitution of a catalytically active enzyme by contact with a selected metal (Omburo, G. A. et al., 1992; Watkins, L. M. et al., 1997a; Watkins, L. M. et al., 1997b). It is further contemplated that structural analogs of an OPH sequence may be prepared to comprise only one metal atom per monomer.

In an additional example, OPH structure analysis has been conducted using NMR (Omburo, G. A. et al., 1993). In a further example, the X-ray crystal structure for OPH has been determined (Benning, M. M. et al., 1994; Benning, M. M. et al., 1995; Vanhooke, J. L. et al., 1996), including the structure of the enzyme while binding a substrate, further identifying residues involved in substrate binding and catalytic activity (Benning, M. M. et al., 2000). From these structure evaluations, the amino acids His55, His57, His201, His230, Asp301, and the carbamylated lysine, Lys169, have been identified as coordinating the binding of the active site metal. Additionally, the positively charged amino acids His55, His57, His201, His230, His254, and His257 are counter-balanced by the negatively charged amino acids Asp232, Asp233, Asp235, Asp 253, Asp301, and the carbamylated lysine Lys169 at the active site area. A water molecule and amino acids His55, His57, Lys169, His201, His230, and Asp301 are thought to be involved in direct metal binding. The amino acid Asp301 is thought to aid a nucleophilic attack by a bound hydroxide upon the phosphorus to promote cleavage of an OP compound, while the amino acid His354 may aid the transfer of a proton from the active site to the surrounding liquid in the latter stages of the reaction (Raushel, F. M., 2002). The amino acids His254 and His257 are not thought to be direct metal binding amino acids, but may be residues that interact (e.g., a hydrogen bond, a Van der Waal interaction) with each other and other active site residues, such as residues that directly contact a substrate or bind a metal atom. In particular, amino acid His254 is thought to interact with the amino acids His230, Asp232, Asp233, and Asp301. Amino acid His257 is thought to be a participant in a hydrophobic substrate-binding pocket. The active site pocket comprises various hydrophobic amino acids, Trp131, Phe132, Leu271, Phe306, and Tyr309. These amino acids may aid the binding of hydrophobic OP compounds (Benning, M. M. et al., 1994; Benning, M. M. et al., 1995; Vanhooke, J. L. et al., 1996). Electrostatic interactions may occur between phosphoryl oxygen, when present, and the side chains of Trp131 and His201. Additionally, the side chains of amino acids Trp131, Phe132, and Phe306 are thought to be orientated toward the atom of the cleaved substrate's leaving group that was previously bonded to the phosphorus atom (Watkins, L. M. et al., 1997a).

Substrate binding subsites known as the small subsite, the large subsite, and the leaving group subsite have been identified (Benning, M. M. et al., 2000; Benning, M. M. et al., 1994; Benning, M. M. et al., 1995; Vanhooke, J. L. et al., 1996). The amino acids Gly60, Ile106, Leu303, and Ser308 are thought to comprise the small subsite. The amino acids Cys59 and Ser61 are near the small subsite, but with the side chains thought to be orientated away from the subsite. The amino acids His254, His257, Leu271, and Met317 are thought to comprise the large subsite. The amino acids Trp131, Phe132, Phe306, and Tyr309 are thought to comprise the leaving group subsite, though Leu271 is sometimes considered part of this subsite as well (Watkins, L. M. et al., 1997a). Comparison of this opd product with the encoded sequence of the opdA gene from *Agrobacterium radiobacter* P230 revealed that the large subsite possessed generally larger residues that affected activity, specifically the amino acids Arg254, Tyr257, and Phe271 (Horne, I. et al., 2002). Few electrostatic interactions are apparent from the X-ray crystal structure of the inhibitor bound by OPH, and it is thought that hydrophobic interactions and the size of the subsites affect substrate specificity, including steriospecificity for a stereoisomer, such as a specific enantiomer of an OP compound's chiral chemical moiety (Chen-Goodspeed, M. et al., 2001b).

Using the sequence and structural knowledge of OPH, numerous mutants of OPH comprising a sequence analog have been specifically produced to alter one or more properties relative to a substrate's cleavage rate ($k_{cat}$) and/or specificity ($k_{cat}/K_m$). Examples of OPH sequence analog mutants include H55C, H57C, C59A, G60A, S61A, I106A, I106G, W131A, W131F, W131K, F132A, F132H, F132Y, L136Y, L140Y, H201C, H230C, H254A, H254R, H254S, H257A, H257L, H257Y, L271A, L271Y, L303A, F306A, F306E, F306H, F306K, F306Y, S308A, S308G, Y309A, M317A, M317H, M317K, M317R, H55C/H57C, H55C/H201C, H55C/H230C, H57C/H201C, H57C/H230C, A80V/S365P, I106A/F132A, I106A/S308A, I106G/F132G, I106G/S308G, F132Y/F306H, F132H/F306H, F132H/F306Y, F132Y/F306Y, F132A/S308A, F132G/S308G, L182S/V310A, H201C/H230C, H254R/H257L, H55C/H57C/H201C, H55C/H57C/H230C, H55C/H201C/H230C, I106A/F132A/H257Y, I106A/F132A/H257W, I106G/F132G/S308G, L130M/H257Y/I274N, H257Y/I274N/S365P, H55C/H57C/H201C/H230C, I106G/F132G/H257Y/S308G, or A14T/A80V/L185R/H257Y/I274N (Li, W.-S. et al., 2001; Gopal, S. et al., 2000; Chen-Goodspeed, M. et al., 2001a; Chen-Goodspeed, M. et al., 2001b; Watkins, L. M. et al., 1997a; Watkins, L. M. et al., 1997b; diSioudi, B. et al., 1999; Cho, C. M.-H. et al., 2002; Shim, H. et al., 1996; Raushel, F. M., 2002; Wu, F. et al., 2000a; diSioudi, B. D. et al., 1999).

For example, the sequence and structural information has been used in production of mutants of OPH possessing cysteine substitutions at the metal binding histidines His55, His57, His201, and His230. OPH mutants H55C, H57C, H201C, H230C, H55C/H57C, H55C/H201C, H55C/H230C, H57C/H201C, H57C/H230C, H201C/H230C, H55C/H57C/H201C, H55C/H57C/H230C, H55C/H201C/H230C, H57C/H201C/H230C, and H55C/H57C/H201C/H230C were produced binding either $Zn^{2+}$; $Co^{2+}$ or $Cd^{2+}$. The H57C mutant had between 50% (i.e., binding $Cd^{2+}$, $Zn^{2+}$) and 200% (i.e., binding $Co^{2+}$) wild-type OPH activity for paraoxon cleavage. The H201C mutant had about 10% activity, the H230C mutant had less than 1% activity, and the H55C mutant bound only one atom of $Co^{2+}$ and possessed little detectable activity, but may still be useful if possessing a desirable property (e.g., enhanced stability) (Watkins, L. M., 1997b).

In an additional example, the sequence and structural information has been used in production of mutants of OPH possessing altered metal binding and/or bond-type cleavage properties. OPH mutants H254R, H257L, and H254R/H257L have been made to alter amino acids that are thought to interact with nearby metal-binding amino acids. These mutants also reduced the number of metal ions (i.e., $Co^{2+}$, $Zn^{2+}$) binding the enzyme dimer from four to two, while still retaining 5% to greater than 100% catalytic rates for the various substrates. These reduced metal mutants possess enhanced specificity for larger substrates such as NPPMP and demeton-S, and reduced specificity for the smaller substrate diisopropyl fluorophosphonate (diSioudi, B. et al., 1999). In a further example, the H254R mutant and the H257L mutant each demonstrated a greater than four-fold increase in catalytic activity and specificity against VX and its analog demeton S. The H257L mutant also demonstrated a five-fold enhanced specificity against soman and its analog NPPMP (diSioudi, B. D. et al., 1999).

In an example, specific mutants of OPH (a phosphotriesterase), were designed and produced to aid phosphodiester substrates to bind and be cleaved by OPH. These substrates either comprised a negative charge and/or a large amide moiety. A M317A mutant was created to enlarge the size of the large subsite, and M317H, M317K, and M317R mutants were created to incorporate a cationic group in the active site. The M317A mutant demonstrated a 200-fold cleavage rate enhancement in the presence of alkylamines, which were added to reduce the substrate's negative charge. The M317H, M317K, and M317R mutants demonstrated modest improvements in rate and/or specificity, including a 7-fold $k_{cat}/K_m$ improvement for the M317K mutant (Shim, H. et al., 1998).

In a further example, the W131K, F132Y, F132H, F306Y, F306H, F306K, F306E, F132H/F306H, F132Y/F306Y, F132Y/F306H, and F132H/F306Y mutants were made to add or change the side chain of active site residues to form a hydrogen bond and/or donate a hydrogen to a cleaved substrate's leaving group, to enhance the rate of cleavage for certain substrates, such as phosphofluoridates. The F132Y, F132H, F306Y, F306H, F132H/F306H, F132Y/F306Y, F132Y/F306H, and F132H/F306Y mutants all demonstrated enhanced enzymatic cleavage rates, of about three- to ten-fold improvement, against the phosphonofluoridate, diisopropyl fluorophosphonate (Watkins, L. M. et al., 1997a).

In an additional example, OPH mutants W131F, F132Y, L136Y, L140Y, L271Y and H257L were designed to modify the active site size and placement of amino acid side chains to refine the structure of binding subsites to specifically fit the binding of a VX substrate. The refinement of the active site structure produced a 33% increase in cleavage activity against VX in the L136Y mutant (Gopal, S. et al., 2000).

Various mutants of OPH have been made to alter the steriospecificity, and in some cases, the rate of reaction, by substitutions in substrate binding subsites. For example, the C59A, G60A, S61A, I106A, W131A, F132A, H254A, H257A, L271A, L303A, F306A, S308A, Y309A, and M317A mutants of OPH have been produced to alter the size of various amino acids associated with the small subsite, the large subsite and the leaving group subsite, in order to alter enzyme activity and selectivity, including sterioselectivity, for various OP compounds. The G60A mutant reduced the size of the small subsite, and decreased both rate ($k_{cat}$) and specificity ($k_{cat}/K_a$) for $R_p$-enantiomers, thereby enhancing the overall specificity for some $S_p$-enantiomers to over 11,000:1. Mutants I106A and S308A, which enlarged the size of the small subsite, as well as mutant F132A, which enlarged the leaving group subsite, all increased the reaction rates for $R_p$-enantiomers and reduced the specificity for $S_p$-enantiomers (Chen-Goodspeed, M. et al., 2001a).

Additional mutants I106A/F132A, I106A/S308A, F132A/S308A, I106G, F132G, S308G, I106G/F132G, I106G/S308G, F132G/S308G, and I106G/F132G/S308G were produced to further enlarge the small subsite and leaving group subsite. These OPH mutants demonstrated enhanced selectivity for $R_p$-enantiomers. Mutants H254Y, H254F, H257Y, H257F, H257W, H257L, L271Y, L271F, L271W, M317Y, M317F, and M317W were produced to shrink the large subsite, with the H257Y mutant, for example, demonstrating a reduced selectivity for $S_p$-enantiomers (Chen-Goodspeed, M. et al., 2001b). Further mutants I106A/H257Y, F132A/H257Y, I106A/F132A/H257Y, I106A/H257Y/S308A, I106A/F132A/H257W, F132A/H257Y/S308A, I106G/H257Y, F132G/H257Y, I106G/F132G/H257Y, I106G/H257Y/S308G, and I106G/F132G/H257Y/S308G were made to simultaneously enlarge the small subsite and shrink the large subsite. Mutants such as H257Y, I106A/H257Y, I106G, I106A/F132A, and I106G/

F132G/S308G were effective in altering steriospecificity for $S_p{:}R_p$ enantiomer ratios of some substrates to less than 3:1 ratios. Mutants including F132A/H257Y, I106A/F132A/H257W, I106G/F132G/H257Y, and I106G/F132G/H257Y/S308G demonstrated a reversal of selectivity for $S_p{:}R_p$ enantiomer ratios of some substrates to ratios from 3.6:1 to 460:1. In some cases, such a change in steriospecificity was produced by enhancing the rate of catalysis of a less preferred $R_p$ enantiomer with little change on the rate of $S_p$ enantiomer cleavage (Chen-Goodspeed, M. et al., 2001 b; Wu, F. et al., 2000a).

Such alterations in sterioselectivity can enhance OPH performance against a specific OP compound that is a preferred target of detoxification, including a CWA. Enlargement of the small subsite by mutations that substitute the Ile106 and Phe132 residues with the less bulky amino acid alanine and/or reduction of the large subsite by a mutation that substitutes His257 with the bulkier amino acid phenylalanine increased catalytic rates for the $S_p$-isomer; and decreased the catalytic rates for the $R_p$-isomers of a sarin analog, thus resulting in a triple mutant, I106A/F132A/H257Y, with a reversed sterioselectivity such as a $S_p{:}R_p$ preference of 30:1 for the isomers of the sarin analog. A mutant of OPH designated G60A has also been created with enhanced steriospecificity relative to specific analogs of enantiomers of sarin and soman (Li, W.-S. et al., 2001; Raushel, F. M., 2002). Of greater interest, these mutant forms of OPH have been directly assayed against sarin and soman nerve agents, and demonstrated enhanced detoxification rates for racemic mixtures of sarin or soman enantiomers. Wild-type OPH has a $k_{cat}$ for sarin of 56 $s^{-1}$, while the I106A/F132A/H257Y mutant has $k_{cat}$ for sarin of 1000 $s^{-1}$. Additionally, wild-type OPH has a $k_{cat}$ for soman of 5 $s^{-1}$, while the G60A Mutant has $k_{cat}$ for soman of 10 $s^{-1}$ (Kolakoski, Jan E. et al. 1997; Li, W.-S. et al., 2001).

It is also possible to produce a mutant enzyme with an enhanced enzymatic property against a specific substrate by evolutionary selection rather than rational design. Such techniques can screen hundreds or thousands of mutants for enhanced cleavage rates against a specific substrate. The mutants identified may possess substitutions at amino acids that have not been identified as directly comprising the active site, or its binding subsites, using techniques such as NMR, X-ray crystallography and computer structure analysis, but still contribute to activity for one or more substrates. For example, selection of OPH mutants based upon enhanced cleavage of methyl parathion identified the A80V/S365P, L182S/V310A, I274N, H257Y, H257Y/I274N/S365P, L130M/H257Y/I274N, and A14T/A80V/L185R/H257Y/I274N mutants as having enhanced activity. Amino acids Ile274 and Val310 are within 10 Å of the active site, though not originally identified as part of the active site from X-ray and computer structure analysis. However, mutants with substitutions at these amino acids demonstrated improved activity, with mutants comprising the I274N and H257Y substitutions particularly active against methyl parathion. Additionally, the mutant, A14T/A80V/L185R/H257Y/I274N, further comprising a L185R substitution, was most active having a 25-fold improvement against methyl parathion (Cho, C. M.-H. et al., 2002).

In an example, a functional equivalent of OPH may be prepared that lacks the first 29-31 amino acids of the wild-type enzyme. The wild-type form of OPH endogenously or recombinantly expressed in *Pseudomonas* or *Flavobacterium* removes the first N-terminal 29 amino acids from the precursor protein to produce the mature, enzymatically active protein (Mulbry, W. and Karns, J., 1989; Serdar, C. M. et al., 1989). Recombinant expressed OPH in *Gliocladium virens* apparently removes part or all of this sequence (Dave, K. I. et al., 1994b). Recombinant expressed OPH in *Streptomyces lividans* primarily has the first 29 or 30 amino acids removed during processing, with a few percent of the functional equivalents having the first 31 amino acids removed (Rowland, S. S. et al., 1992). Recombinant expressed OPH in *Spodoptera frugiperda* cells has the first 30 amino acids removed during processing (Dave, K. I. et al., 1994a).

The 29 amino acid leader peptide sequence targets OPH enzyme to the cell membrane in *Escherichia coli*, and this sequence is partly or fully removed during cellular processing (Dave, K. I. et al., 1994a; Miller, C. E., 1992; Serdar, C. M. et al., 1989; Mulbry, W. and Karns, J., 1989). The association of OPH comprising the leader peptide sequence with the cell membrane in *Escherichia coli* expression systems seems to be relatively weak, as brief 15 second sonication releases most of the activity into the extracellular environment (Dave, K. I. et al., 1994a). For example, recombinant OPH often is expressed without this leader peptide sequence to enhance enzyme stability and expression efficiency in *Escherichia coli* (Serdar, C. M., et al. 1989). In another example, recombinant expression efficiency in *Pseudomonas putida* for OPH was improved by retaining this sequence, indicating that different species of bacteria may have varying preferences for a signal sequence (Walker, A. W. and Keasling, J. D., 2002). However, it is contemplated that one of ordinary skill in the art can easily modify the length of an enzymatic sequence to optimize expression or other properties in a particular organism, or select a cell with a relatively good ability to express a biomolecule, in light of the present disclosures and methods known in the art (see U.S. Pat. Nos. 6,469,145, 5,589,386 and 5,484,728)

In an example, recombinant OPH sequence-length mutants have been expressed wherein the first 33 amino acids of OPH have been removed, and a peptide sequence M-I-T-N-S added at the N-terminus (Omburo, G. A. et al., 1992; Mulbry, W. and Karns, J., 1989). Often removal of the 29 amino acid sequence is used when expressing mutants of OPH comprising one or more amino acid substitutions such as the C59A, G60A, S61A, I106A, W131A, F132A, H254A, H257A, L271A, L303A, F306A, S308A, Y309A, M317A, I106A/F132A, I106A/S308A, F132A/S308A, I106G, F132G, S308G, I106G/F132G, I106G/S308G, F132G/S308G, I106G/F132G/S308G, H254Y, H254F, H257Y, H257F, H257W, H257L, L271Y, L271W, M317Y, M317F, M317W, I106A/H257Y, F132A/H257Y, I106A/F132A/H257Y, I106A/H257Y/S308A, I106A/F132A/H257W, F132A/H257Y/S308A, I106G/H257Y, F132G/H257Y, I106G/F132G/H257Y, I106G/H257Y/S308G, and I106G/F132G/H257Y/S308G mutants (Chen-Goodspeed, M. et al., 2001a). In a further example, LacZ-OPH fusion protein mutants lacking the 29 amino acid leader peptide sequence and comprising an amino acid substitution mutant such as W131F, F132Y, L136Y, L140Y, H257L, L271L, L271Y, F306A, or F306Y have been recombinantly expressed (Gopal, S. et al., 2000).

In an additional example, OPH mutants that comprise additional amino acid sequences are also known in the art. An OPH fusion protein lacking the 29 amino acid leader sequence and possessing an additional C-terminal flag octapeptide sequence was expressed and localized in the cytoplasm of *Escherichia coli* (Wang, J. et al., 2001). In another example, nucleic acids encoding truncated versions of the ice nucleation protein ("InaV") from *Pseudomonas syringae* have been used to construct vectors that express OPH-InaV fusion proteins in *Escherichia coli*. The InaV sequences targeted and anchored the OPH-InaV fusion proteins to the cells' outer membrane (Shimazu, M. et al., 2001a; Wang, A. A. et al., 2002). In a further example, a vector encoding a similar fusion protein was expressed in *Moraxella* sp., and demonstrated a 70-fold improved OPH activity on the cell surface compared to *Escherichia coli* expression (Shimazu, M. et al., 2001b). In a further example, fusion proteins comprising the signal sequence and first nine amino acids of lipoprotein, a transmembrane domain of outer membrane protein A ("Lpp-OmpA"), and either a wild-type OPH sequence or an OPH truncation mutant lacking the first 29 amino acids has been expressed in *Escherichia coli*. These OPH-Lpp-OmpA fusion proteins were targeted and anchored to the *Escherichia coli* cell membrane, though the OPH truncation mutant had only 5% to 10% the activity of the wild-type OPH sequence (Richins, R. D. et al., 1997; Kaneva, I. et al., 1998). In one example, a fusion protein comprising N-terminus to C-terminus, a (His)6 polyhistidine tag, a green fluorescent protein ("GFP"), an enterokinase recognition site, and an OPH sequence lacking the 29 amino acid leader sequence has been expressed within *Escherichia coli* cells (Wu, C.-F. et al., 2000b, Wu, C.-F. et al., 2002). A similar fusion protein a (His)6 polyhistidine tag, an enterokinase recognition site, and an OPH sequence lacking the 29 amino acid leader sequence has also been expressed within *Escherichia coli* cells (Wu, C.-F. et al., 2002). Additionally, variations of these GFP-OPH fusion proteins have been expressed within *Escherichia coli* cells where an second enterokinase recognition site was placed at the C-terminus of the OPH gene fragment sequence, followed by a second OPH gene fragment sequence (Wu, C.-F. et al., 2001 b). The GFP sequence produced fluorescence that was proportional to both the quantity of the fusion protein, and the activity of the OPH sequence, providing a fluorescent assay of enzyme activity and stability in GFP-OPH fusion proteins (Wu, C.-F. et al., 2000b, Wu, C.-F. et al., 2002).

In a further example, a fusion protein comprising an elastin-like polypeptide ("ELP") sequence, a polyglycine linker sequence, and an OPH sequence was expressed in *Escherichia coli* (Shimazu, M. et al., 2002). In an additional example, a cellulose-binding domain at the N-terminus of an OPH fusion protein lacking the 29 amino acid leader sequence, and a similar fusion protein wherein OPH possessed the leader sequence, where both predominantly excreted into the external medium as soluble proteins by recombinant expression in *Escherichia coli* (Richins, R. D. et al., 2000).

b. Paraoxonase Functional Equivalents

Various chemical modifications to the amino acid residues of the recombinantly expressed human paraoxonase have been used to identify specific residues including tryptophans, histidines, aspartic acids, and glutamic acids as of importance to enzymatic activity for the cleavage of phenylacetate, paraoxon, chlorpyrifosoxon. and diazoxon. Additionally, comparison to conserved residues in human, mouse, rabbit, rat dog, chicken, and turkey paraoxonase enzymes was used to further identify amino acids for the production of specific mutants. Site-directed mutagenesis was used to alter the enzymatic activity of human paraoxonase through conservative and non-conservative substitutions, and thus clarify the specific amino acids of particular importance for enzymatic activity. Specific paraoxonase mutants include the sequence analogs E32A, E48A, E52A, D53A, D88A, D107A, H114N, D121A, H133N, H154N, H160N, W193A, W193F, W201A, W201F, H242N, H245N, H250N, W253A, W253F, D273A, W280A, W280F, H284N, or H347N.

The various paraoxonase mutants generally had different enzymatic properties. For example, W253A had a 2-fold greater $k_{cat}$; and W201F, W253A and W253F each had a 2 to 4 fold increase in $k_{cat}$, though W201F also had a lower substrate affinity. A non-conservative substitution mutant W280A had 1% wild-type paraoxonase activity, but the conservative substitution mutant W280F had similar activity as the wild-type paraoxonase (Josse, D. et al., 1999; Josse, D. et al., 2001).

c. Squid-Type DFPase Functional Equivalents

Various chemical modifications to the amino acid residues of the recombinantly expressed squid-type DFPase from *Loligo vulgaris* has been used to identify which specific types of residues of modified arginines, aspartates, cysteines, glutamates, histidines, lysines, and tyrosines, are important to enzymatic activity for the cleavage of DFP. Modification of histidines generally reduced enzyme activity, and site-directed mutagenesis was used to clarify which specific histidines are of importance for enzymatic activity. Specific squid-type DFPase mutants include the sequence analogs H181N, H224N, H274N, H219N, H248N, or H287N.

The H287N mutant lost about 96% activity, and is thought to act as a hydrogen acceptor in active site reactions. The H181N and H274N mutants lost between 15% and 19% activity, and are thought to help stabilize the enzyme. The H224N mutant gained about 14% activity, indicating that alterations to this residue may also affect activity (Hartleib, J. and Ruterjans, H., 2001b).

In a further example of squid-type DFPase functional equivalents, recombinant squid-type DFPase sequence-length mutants have been expressed wherein a (His)6 tag sequence and a thrombin cleavage site has been added to the squid-type DFPase (Hartleib, J. and Ruterjans, H., 2001a). In an additional example, a polypeptide comprising amino acids 1-148 of squid-type DFPase has been admixed with a polypeptide comprising amino acids 149-314 of squid-type DFPase to produce an active enzyme (Hartleib, J. and Ruterjans, H., 2001a).

3. Combinations of Biomolecules

It is contemplated that in various embodiments, a composition of the present invention may comprise one or more selected biomolecules, with an enzyme being a preferred biomolecule. It is contemplated that in specific embodiments, a composition of the present invention may comprise an endogenously expressed wild-type enzyme, a recombinant enzyme, or a combination thereof. In specific aspects, a recombinant enzyme comprises a wild-type enzyme, a functional equivalent enzyme, or a combination thereof. Numerous examples of enzymes with different properties are described herein, and any such enzyme as would be known to one of ordinary skill in the art is contemplated for inclusion in a composition of the present invention.

It is contemplated that a combination of biomolecules may be selected for inclusion in the biomolecule composition, coating and/or paint, to optimize one or more properties of such a composition of the present invention. Thus, a composition of the present invention may comprise 1 to 100 or more different selected biomolecules of interest, including all intermediate ranges and combinations thereof. For example, as various enzymes have differing binding properties, catalytic properties, stability properties, properties related to environmental safety, etc, one may select a combination of enzymes to confer the a more desirable range of properties to a composition of the present invention. In a specific example, it is contemplated that phosphoric triester hydrolases, with differing but desirable abilities to cleave the chiral centers of OP compounds, may be admixed to confer a more desirable range of catalytic properties to a composition of the present invention than would be achieved by the selection of a single phosphoric triester hydrolase.

C. Recombinantly Produced Enzymes

In certain aspects, an enzyme of the present invention may be biologically produced in cell, tissue and/or organism transformed with a genetic expression vector. As used herein, an "expression vector" refers to a carrier nucleic acid molecule, into which a nucleic acid sequence can be inserted, wherein the nucleic acid sequence is capable of being transcribed into a ribonucleic acid ("RNA") molecule after introduction into a cell. Usually an expression vector comprises deoxyribonucleic acid ("DNA"). As used herein, an "expression system" refers to an expression vector, and may further comprise additional reagents needed to promote insertion of a nucleic acid sequence, introduction into a cell, transcription and/or translation. As used herein, a "vector," refers to a carrier nucleic acid molecule into which a nucleic acid sequence can be inserted for introduction into a cell. Certain vectors are capable of replication of the vector and/or any inserted nucleic acid sequence in a cell. For example, a viral vector may be used in conjunction with either an eukaryotic or prokaryotic host cell, particularly one that is permissive for replication or expression of the vector. A cell that is capable of being transformed with a vector is known herein as a "host cell."

In general embodiments, the inserted nucleic acid sequence encodes for at least part of a gene product. In some embodiments wherein the nucleic acid sequence is transcribed into an RNA molecule, the RNA molecule is then translated into a proteinaceous molecule. As used herein, a "gene" refers to a nucleic acid sequence isolated from an organism, and/or man-made copies or mutants thereof, that comprises a nucleic acid sequence capable of being transcribed and/or translated in an organism. A "gene product" is the transcribed RNA and/or translated proteinaceous molecule from a gene. Often, only partial nucleic acid sequences of a gene, known herein as a "gene fragment," are used COME BACK to produce a part of the gene product. Many gene and gene fragment sequences are known in the art, and are both commercially available and/or publicly disclosed at a database such as Genbank. It is contemplated that a gene and/or a gene fragment can be used to recombinantly produce an enzyme for use in the present invention. It is further contemplated that a gene and/or a gene fragment can be use in construction of a fusion protein comprising an enzyme, for use in the present invention.

In certain embodiments, a nucleic acid sequence such as a nucleic acid sequence encoding an enzyme, or any other desired RNA or proteinaceous molecule (as well as a nucleic acid sequence comprising a promoter, a ribosome binding site, an enhancer, a transcription terminator, an origin of replication, or other nucleic acid sequences described herein or would be known by one of ordinary skill in the art in light of the present disclosures) may be recombinantly produced or synthesized using any method or technique known to those of ordinary skill in the art in various combinations. [In "Molecular Cloning" (Sambrook, J., and Russell, D. W., Eds.) 3rd Edition, Cold Spring Harbor, N.Y.: Cold Spring Harbor Laboratory Press, 2001; In "Current Protocols in Molecular Biology" (Chanda, V. B. Ed.) John Wiley & Sons, 2002; In "Current Protocols in Cell Biology" (Morgan, K. Ed.) John Wiley & Sons, 2002; In "Current Protocols in Nucleic Acid Chemistry" (Harkins, E. W. Ed.) John Wiley & Sons, 2002; In "Current Protocols in Protein Science" (Taylor, G. Ed.) John Wiley & Sons, 2002; In "Current Protocols in Pharmacology" (Taylor, G. Ed.) John Wiley & Sons, 2002; In "Current Protocols in Cytometry" (Robinson, J. P. Ed.) John Wiley & Sons, 2002; In "Current Protocols in Immunology" (Coico, R. Ed.) John Wiley & Sons, 2002]. For example, a gene and/or a gene fragment encoding the enzyme of interest may be isolated and/or amplified through polymerase chain reaction ("PCR™") technology. Often such nucleic acid sequence is readily available from a public database and/or a commercial vendor, as previously described.

Nucleic acid sequences, called codons, encoding for each amino acid are well known in the art, and used to copy and/or mutate a nucleic acid sequence to produce a desired mutant in an expressed amino acid sequence. Codons comprise nucleotides such as adenine ("A"), cytosine ("C"), guanine ("G"), thymine ("T") and uracil ("U"). The common amino acids are generally encoded by the following codons: alanine is encoded by GCU, GCC, GCA, or GCG; arginine is encoded by CGU, CGC, CGA, CGG, AGA, or AGG; aspartic acid is encoded by GAU or GAC; asparagine is encoded by AAU or AAC; cysteine is encoded by UGU or UGC; glutamic acid is encoded by GAA or GAG; glutamine is encoded by CAA or CAG; glycine is encoded by GGU, GGC, GGA, or GGG; histidine is encoded by CAU or CAC; isoleucine is encoded by AUU, AUC, or AUA; leucine is encoded by UUA, UUG, CUU, CUC, CUA, or CUG; lysine is encoded by AAA or AAG; methionine is encoded by AUG; phenylalanine is encoded by UUU or UUC; proline is encoded by CCU, CCC, CCA, or CCG; serine is encoded by AGU, AGC, UCU, UCC, UCA, or UCG; threonine is encoded by ACU, ACC, ACA, or ACG; tryptophan is encoded by UGG; tyrosine is encoded by UAU or UAC; and valine is encoded by GUU, GUC, GUA, or GUG.

A mutation in a nucleic acid encoding a proteinaceous molecule may be introduced into the nucleic acid sequence through any technique known to one of ordinary skill in the art. As would be well understood by those of ordinary skill in the art, such a mutation may be bioengineered to a specific region of a nucleic acid comprising one or more codons using a technique such as site-directed mutagenesis or cassette mutagenesis. Numerous examples of phosphoric triester hydrolase mutants have been produced using site-directed mutagenesis or cassette mutagenesis, and are described herein.

It is contemplated that for recombinant expression, the choice of codons may be made to mimic the host cell's molecular biological activity, in order to optimize the efficiency of expression from an expression vector. For example, codons may be selected to match the preferred codons used by a host cell in expressing endogenous proteins. In some aspects, the codons selected may be chosen to approximate the G-C content of an expressed gene and/or a gene fragment in a host cell's genome, or the G-C content of the genome itself. In other aspects, a host cell may be genetically altered to recognize more efficiently use a variety of codons, such as *Escherichia coli* host cells that are dnaY gene positive (Brinkmann, U. et al., 1989).

1. General Expression Vector Components and Use

An expression vector may comprise specific nucleic acid sequences such as a promoter, a ribosome binding site, an enhancer, a transcription terminator, an origin of replication, or other nucleic acid sequence described herein or would be known by one of ordinary skill in the art in light of the present disclosures, in various combinations. A nucleic acid sequence can be "exogenous," which means that it is foreign to the cell into which the vector is being introduced or that the sequence is homologous to a sequence in the cell, but in a position within the host cell nucleic acid in which the sequence is ordinarily not found. An expression vector may have one or more nucleic acid sequences removed by restriction enzyme digestion, modified by mutagenesis, and/or replaced with another more appropriate nucleic acid sequence, for transcription and/or translation in a host cell suitable for the expression vector selected.

One of skill in the art can construct a vector through standard recombinant techniques, which are well known and routine in the art. Further, one of skill in the art would know how to express a vector to transcribe a nucleic acid sequence and/or translate its cognate proteinaceous molecule. One of skill in the art would further understand the conditions under which to incubate all of the above described host cells to maintain them and to permit replication of a vector. Also understood and known are techniques and conditions that would allow large-scale production of a vector, as well as production of a nucleic acid sequence encoded by a vector into an RNA molecule and/or translation of the RNA molecule into a cognate proteinaceous molecule.

In certain embodiments, a cell may express multiple gene and/or gene fragment products from the same vector, and/or express more than one vector. Often this occurs simply as part of the normal function of a multi-vector expression system. For example, one gene or gene fragment is often used to produce a repressor that suppresses the activity of a promoter that controls the expression of a gene or a gene fragment of interest. The repressor gene and the desired gene may be on different vectors. However, multiple gene, gene fragment and/or expression systems may be used to express an enzymatic sequence of interest and another gene or gene fragment that is desired for a particular function. In an example, recombinant *Pseudomonas putida* has co-expressed OPH from one vector, and the multigenes encoding the enzymes for converting p-nitrophenol to β-ketoadipate from a different vector. The expressed OPH catalyzed the cleavage of parathion to p-nitrophenol. The additionally expressed recombinant enzymes converted the p-nitrophenol, which is a moderately toxic compound, to β-ketoadipate, thereby detoxifying both an OP compound and the byproducts of its hydrolysis (Walker, A. W. and Keasling, J. D., 2002). In a further example, *Escherichia coli* cells expressed a cell surface targeted INPNC-OPH fusion protein from one vector to detoxify OP compounds, and co-expressed from a different vector a cell surface targeted Lpp-OmpA-cellulose binding domain fusion protein to immobilize the cell to a cellulose support (Wang, A. A. et al., 2002). In an additional example, a vector co-expressed an antisense RNA sequence to the transcribed stress response gene $\sigma^{32}$ and OPH in *Escherichia coli*. The antisense $\sigma^{32}$ RNA was used to reduce the cell's stress response, including proteolytic damage, to an expressed recombinant proteinaceous molecule. A six-fold enhanced specific activity of expressed OPH enzyme was seen (Srivastava, R. et al., 2000). In a further example, multiple OPH fusion proteins were expressed from the same vector using the same promoter but separate ribosome binding sites (Wu, C.-F. et al., 2001b).

As is well known to those of skill in the art, an expression vector generally comprises a plurality of functional nucleic acid sequences that either comprise a nucleic acid sequence with a molecular biological function in a host cell, such as a promoter, an enhancer, a ribosome binding site, a transcription terminator, etc, and/or encode a proteinaceous sequence, such as a leader peptide, a polypeptide sequence with enzymatic activity, a peptide or polypeptide with a binding property, etc. A nucleic acid sequence may comprise a "control sequence," which refers to a nucleic acid sequence necessary for the transcription and possibly translation of an operatively linked coding sequence in a particular host cell. As used herein, an "operatively linked" or "operatively positioned" nucleic acid sequence refers to the placement of one nucleic acid sequence into a functional relationship with another nucleic acid sequence. Vectors and expression vectors may further comprise one or more nucleic acid sequences that serve other functions as well and are described herein.

The various functional nucleic acid sequences that comprise an expression vector are operatively linked so to position the different nucleic acid sequences for optimal function in a host cell. In certain cases, the functional nucleic acid sequences may be contiguous such as placement of a nucleic acid sequence encoding a leader peptide sequence in correct amino acid frame with a nucleic acid sequence encoding a polypeptide comprising a polypeptide sequence with enzymatic activity. In other cases, the functional nucleic acid sequences may be non-contiguous such as placing a nucleic acid sequence comprising an enhancer distal to a nucleic acid sequence comprising such sequences as a promoter, a encoded proteinaceous molecule, a transcription termination sequence, etc. One or more nucleic acid sequences may be operatively linked using methods well known in the art, particularly ligation at restriction sites that may pre-exist in a nucleic acid sequence or be added through mutagenesis.

A "promoter" is a control sequence that is a region of a nucleic acid sequence at which initiation and rate of transcription are controlled. In the context of a nucleic acid sequence comprising a promoter and an additional nucleic acid sequence, particularly one encoding a gene or gene fragment's product, the phrases "operatively linked," "operatively positioned," "under control," and "under transcriptional control" mean that a promoter is in a correct functional location and/or orientation in relation to the additional nucleic acid sequence to control transcriptional initiation and/or expression of the additional nucleic acid sequence. A promoter may contain genetic elements at which regulatory proteins and molecules may bind such as RNA polymerase and other transcription factors. A promoter employed may be constitutive, tissue-specific, inducible, and/or useful under the appropriate conditions to direct high level expression of the introduced nucleic acid sequence, such as is advantageous in the large-scale production of a recombinant proteinaceous molecule. Examples of a promoter include a lac, a tac, an amp, a heat shock promoter of a P-element of *Drosophila*, a baculovirus polyhedron gene promoter, or a combination thereof. In a specific example, the nucleic acids encoding OPH have been expressed using the polyhedron promoter of a baculoviral expression vector (Dumas, D. P. et al., 1990). In a further example, a *Cochliobolus heterostrophus* promoter, prom1, has been used to express a nucleic acid encoding OPH (Dave, K. I. et al., 1994b).

The promoter may be endogenous or heterologous. An "endogenous promoter" comprises one naturally associated with a gene or sequence, as may be obtained by isolating the 5' non-coding sequences located upstream of the coding segment and/or exon. Alternatively, certain advantages will be gained by positioning the coding nucleic acid sequence under the control of a "heterologous promoter" or "recombinant promoter," which refers to a promoter that is not normally associated with a nucleic acid sequence in its natural environment.

A specific initiation signal also may be required for efficient translation of a coding sequence by the host cell. Such a signal may include an ATG initiation codon ("start codon") and/or an adjacent sequence. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signal and/or an initiation codon can be either natural or synthetic. The efficiency of expression may be enhanced by the inclusion of an appropriate transcription enhancer.

A promoter may or may not be used in conjunction with an "enhancer," which refers to a cis-acting regulatory sequence involved in the transcriptional activation of a nucleic acid sequence. An enhancer may be one naturally associated with a nucleic acid sequence, located either downstream or upstream of that sequence. A recombinant or heterologous enhancer refers also to an enhancer not normally associated with a nucleic acid sequence in its natural environment. Such a promoter and/or enhancer may include a promoter and/or enhancer of another gene, a promoter and/or enhancer isolated from any other prokaryotic, viral, or eukaryotic cell, a promoter and/or enhancer not "naturally occurring," i.e., a promoter and/or enhancer comprising different elements of different transcriptional regulatory regions, and/or mutations that alter expression. In addition to producing a nucleic acid sequence comprising a promoter and/or enhancer synthetically, a sequence may be produced using recombinant cloning and/or nucleic acid amplification technology, including PCR™, in connection with the compositions disclosed herein (U.S. Pat. Nos. 4,683,202, 5,928, 906).

It will be important to employ a promoter and/or enhancer that effectively directs the expression of the nucleic acid sequence in the cell type, chosen for expression. Those of skill in the art of molecular biology generally know the use of promoters, enhancers, and cell type combinations for expression. Furthermore, it is contemplated the control sequences that direct transcription and/or expression of sequences within non-nuclear organelles, including eukaryotic organelles such as mitochondria, chloroplasts, and the like, can be employed as well.

Vectors can include a multiple cloning site ("MCS"), which is a nucleic acid region that contains multiple restriction enzyme sites, any of which can be used in conjunction with standard recombinant technology to digest the vector. "Restriction enzyme digestion" refers to catalytic cleavage of a nucleic acid molecule with an enzyme which functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable an exogenous nucleic acid sequence to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

A "fusion protein," as used herein, is an expressed contiguous amino acid sequence comprising a proteinaceous molecule of interest and one or more additional peptide or polypeptide sequences. The additional peptide or polypeptide sequence generally provides an useful additional property to the fusion protein, including but not limited to, targeting the fusion protein to a particular location within or external to the host cell (e.g., a signal peptide); promoting the ease of purification and/or detection of the fusion protein (e.g., a tag, a fusion partner); promoting the ease of removal of one or more additional sequences from the peptide or polypeptide of interest (e.g., a protease cleavage site); and separating one or more sequences of the fusion protein to allow optimal activity or function of the sequence(s) (e.g., a linker sequence).

As used herein a "tag" is a peptide sequence operatively associated to the sequence of another peptide or polypeptide sequence. Examples of a tag include a His-tag, a strep-tag, a flag-tag, a T7-tag, a S-tag, a HSV-tag, a polyarginine-tag, a polycysteine-tag, a polyaspartic acid-tag, a polyphenylalanine-tag, or a combination thereof. A His-tag is 6 or 10 amino acids in length, and can be incorporated at the N-terminus, C-terminus or within an amino acid sequence for use in detection and purification. A His tag binds affinity columns comprising nickel, and is eluted using low pH conditions or with imidazole as a competitor (Unger, T. F., 1997). A strep-tag is 10 amino acids in length, and can be incorporated at the C-terminus. A strep-tag binds streptavidin or affinity resins that comprise streptavidin. A flag-tag is 8 amino acids in length, and can be incorporated at the N-terminus or C-terminus of an amino acid sequence for use in purification. A T7-tag is 11 or 16 amino acids in length, and can be incorporated at the N-terminus or within an amino acid sequence for use in purification. A S-tag is 15 amino acids in length, and can be incorporated at the N-terminus, C-terminus or within an amino acid sequence for use in detection and purification. A HSV-tag is 11 amino acids in length, and can be incorporated at the C-terminus of an amino acid sequence for use in purification. The HSV tag binds an anti-HSV antibody in purification procedures (Unger, T. F., 1997). A polyarginine-tag is 5 to 15 amino acids in length, and can be incorporated at the C-terminus of an amino acid sequence for use in purification. A polycysteine-tag, is 4 amino acids in length, and can be incorporated at the N-terminus of an amino acid sequence for use in purification. A polyaspartic acid-tag can be 5 to 16 amino acids in length, and can be incorporated at the C-terminus of an amino acid sequence for use in purification. A polyphenylalanine-tag is 11 amino acids in length, and can be incorporated at the N-terminus of an amino acid sequence for use in purification.

In one example, a (His)6 tag sequence has been used to purify fusion proteins comprising GFP-OPH or OPH using immobilized metal affinity chromatography ("IMAC") (Wu, C.-F. et al., 2000b; Wu, C.-F. et al., 2002). In a further example, a (His)6 tag sequence followed by a thrombin cleavage site has been used to purify fusion proteins comprising squid-type DFPase using IMAC (Hartleib, J. and Ruterjans, H., 2001a). In a further example, an OPH fusion protein comprising a C-terminal flag has been expressed (Wang, J. et al., 2001).

As used herein a "fusion partner" is a polypeptide that is operatively associated to the sequence of another peptide or polypeptide of interest. Properties that a fusion partner can confer to a fusion protein include, but are not limited to, enhanced expression, enhanced solubility, ease of detection, and/or ease of purification of a fusion protein. Examples of a fusion partner include a thioredoxin, a cellulose-binding domain, a calmodulin binding domain, an avidin, a protein A, a protein G, a glutathione-S-transferase, a chitin-binding domain, an ELP, a maltose-binding domain, or a combination thereof. Thioredoxin can be incorporated at the N-terminus or C-terminus of an amino acid sequence for use in purification. A cellulose-binding domain binds a variety of resins comprising cellulose or chitin (Unger, T. F., 1997). A calmodulin-binding domain binds affinity resins comprising calmodulin in the presence of calcium, and allows elution of the fusion protein in the presence of ethylene glycol tetra acetic acid ("EGTA") (Unger, T. F., 1997). Avidin is useful in purification or detection. A protein A or a protein G binds a variety of anti-bodies for ease of purification. Protein A is generally bound to an IgG sepharose resin (Unger, T. F., 1997). Streptavidin is useful in purification or detection. Glutathione-S-transferase can be incorporated at the N-terminus of an amino acid sequence for use in detection or purification. Glutathione-S-transferase binds affinity resins comprising glutathione (Unger, T. F., 1997). An elastin-like polypeptide comprises repeating sequences (e.g., 78 repeats) which reversibly converts itself, and thus the fusion protein, from an aqueous soluble polypeptide to an insoluble polypeptide above an empirically determined transition temperature. The transition temperature is affected by the number of repeats, and can be determined spectrographically using techniques known in the art, including measurements at 655 nano meters ("nm") over a 4° C. to 80° C. range (Urry, D. W. 1992; Shimazu, M. et al., 2002). A chitin-binding domain preferable comprises an intein cleavage site sequence, and can be incorporated at the C-terminus for purification. The chitin-binding domain binds affinity resins comprising chitin, and an intein cleavage site sequence allows the self-cleavage in the presence of thiols at reduced temperature to release the peptide or polypeptide sequence of interest (Unger, T. F., 1997). A maltose-binding domain can be incorporated at the N-terminus or C-terminus of an amino acid sequence for use in detection or purification. A maltose-binding domain sequence usually further comprises a ten amino acid poly asparagine sequence between the maltose binding domain and the sequence of interest to aid the maltose-binding domain in binding affinity resins comprising amylose (Unger, T. F., 1997).

In an example, a fusion protein comprising an elastin-like polypeptide sequence and an OPH sequence has been expressed (Shimazu, M. et al., 2002). In a further example, a cellulose-binding domain-OPH fusion protein has also been recombinantly expressed (Richins, R. D. et al., 2000). In an additional example, a maltose binding protein-E3 carboxylesterase fusion protein has been recombinantly expressed (Claudianos, C. et al., 1999)

A protease cleavage site promotes proteolytic removal of the fusion partner from the peptide or polypeptide of interest. Often, a fusion protein is bound to an affinity resin, and cleavage at the cleavage site promotes the ease of purification of a peptide or polypeptide of interest with most or all of the tag or fusion partner sequence removed (Unger, T. F., 1997). Protease cleavage sites are well known in the art, and examples of protease cleavage sites include the factor Xa cleavage site, which is four amino acids in length; the enterokinase cleavage site, which is five amino acids in length; the thrombin cleavage site, which is six amino acids in length; the rTEV protease cleavage site, which is seven amino acids in length; the 3C human rhino virus protease, which is eight amino acids in length; and the PreScission™ cleavage site, which is eight amino acids in length. In an example, an enterokinase recognition site was used to separate an OPH sequence from a fusion partner (Wu, C.-F. et al., 2000b; Wu, C.-F. et al., 2001b).

In an eukaryotic expression system (e.g., a fungal expression system), the "terminator region" or "terminator" may also comprise a specific DNA sequence that permits site-specific cleavage of the new transcript so as to expose a polyadenylation site. This signals a specialized endogenous polymerase to add a stretch of adenosine nucleotides ("polyA") of about 200 in number to the 3' end of the transcript. RNA molecules modified with this polyA tail appear to more stable and are translated more efficiently. Thus, in other embodiments involving an eukaryote, it is preferred that that terminator comprises a signal for the cleavage of the RNA, and it is more preferred that the terminator signal promote polyadenylation of the message. The terminator and/or polyadenylation site elements can serve to enhance message levels and/or to minimize read through from the cassette into other sequences.

A terminator contemplated for use in the invention include any known terminator of transcription described herein or known to one of ordinary skill in the art, including but not limited to, for example, a termination sequence of a gene, such as for example, a bovine growth hormone terminator or a viral termination sequence, such as for example a SV40 terminator. In certain embodiments, the termination signal may be a lack of transcribable or translatable sequence, such as due to a sequence truncation. In one example, a trpC terminator from *Aspergillus nidulans* has been used in the expression of recombinant OPH (Dave, K. I. et al., 1994b).

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

In order to propagate a vector in a host cell, it may contain one or more origins of replication sites ("ori"), which is a specific nucleic acid sequence at which replication is initiated. Alternatively an autonomously replicating sequence ("ARS") can be employed if the host cell is yeast.

Various types of prokaryotic and/or eukaryotic expression vectors are known in the art. Examples of types of expression vectors include a bacterial artificial chromosome ("BAC"), a cosmid, a plasmid [e.g., a pMB1/colE1 derived plasmid such as pBR322, pUC18; a Ti plasmid of *Agrobacterium tumefaciens* derived vector (Rogers, S. G. et al., 1987)], a virus (e.g., a bacteriophage such as a bacteriophage M13, an animal virus, a plant virus), or a yeast artificial chromosome ("YAC"). Some vectors, known herein as "shuttle vectors" may employ control sequences that allow it to be replicated and/or expressed in both prokaryotic and eukaryotic cells [e.g., a wheat dwarf virus ("WDV") pW1-11 or pW1-GUS shuttle vector (Ugaki, M. et al., 1991)]. An expression vector operatively linked to a nucleic acid sequence encoding an enzymatic sequence of the present invention may be constructed using techniques known to those of skill in the art in light of the present disclosures [In "Molecular Cloning" (Sambrook, J., and Russell, D. W., Eds.) 3rd Edition, Cold Spring Harbor, N.Y.: Cold Spring Harbor Laboratory Press, 2001; In "Current Protocols in Molecular Biology" (Chanda, V. B. Ed.) John Wiley & Sons, 2002; In "Current Protocols in Nucleic Acid Chemistry" (Harkins, E. W. Ed.) John Wiley & Sons, 2002; In "Current Protocols in Protein Science" (Taylor, G. Ed.) John Wiley & Sons, 2002; In "Current Protocols in Cell Biology" (Morgan, K. Ed.) John Wiley & Sons, 2002].

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are widely available, including those provide by commercial vendors, as would be known to those of skill in the art. For example, an insect cell/baculovirus system can produce a high level of protein expression of a heterologous nucleic acid sequence, such as described in U.S. Pat. Nos. 5,871,986, 4,879,236, both incorporated herein by reference, and which can be bought, for example, under the name MAXBAC® 2.0 from INVITROGEN® and BACPACK™ BACULOVIRUS EXPRESSION SYSTEM FROM CLONTECH®. In an addition example of an expression system include STRATAGENE®'S COMPLETE CONTROL™ Inducible Mammalian Expression System, which involves a synthetic ecdysone-inducible receptor, or its pET Expression System, an *Escherichia coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. In a specific example, E3 carboxylesterase enzymatic sequences and phosphoric triester hydrolase functional equivalents have been recombinantly expressed in a BACPACK™ Baculovirus Expression System From CLONTECH® (Newcomb, R. D. et al., 1997; Campbell, P. M. et al., 1998). In certain embodiments, a biomolecule may be expressed in a plant cell (e.g., a corn cell), using techniques such as those described in U.S. Pat. Nos. 6,504, 085, 6,136,320, 6,087,558, 6,034,298, 5,914,123, and 5,804, 694.

2. Prokaryotic Expression Vectors and Use

In preferred embodiments, a prokaryote such as a bacterium comprises a host cell. In specific aspects, the bacterium host cell comprises a Gram-negative bacterium cell. Various prokaryotic host cells have been used in the art with expression vectors, and it is contemplated that any prokaryotic host cell known in the art may be used to express a peptide or polypeptide comprising an enzyme sequence of the present invention.

An expression vector for use in prokaryotic cells generally comprises nucleic acid sequences such as, a promoter, a ribosome binding site (e.g., a Shine-Delgarno sequence), a start codon, a multiple cloning site, a fusion partner, a protease cleavage site, a stop codon, a transcription terminator, an origin of replication, a repressor, and/or any other additional nucleic acid sequence that would be used in such an expression vector, as would be known to one of ordinary skill in the art [Makrides, S. C., 1996; Hannig, G. and Makrides, S. C., 1998; Stevens, R. C., 2000; In "Molecular Cloning" (Sambrook, J., and Russell, D. W., Eds.) 3rd Edition, Cold Spring Harbor, N.Y.: Cold Spring Harbor Laboratory Press, 2001; In "Current Protocols in Molecular Biology" (Chanda, V. B. Ed.) John Wiley & Sons, 2002; In "Current Protocols in Nucleic Acid Chemistry" (Harkins, E. W. Ed.) John Wiley & Sons, 2002; In "Current Protocols in Protein Science" (Taylor, G. Ed.) John Wiley & Sons, 2002; In "Current Protocols in Cell Biology" (Morgan, K. Ed.) John Wiley & Sons, 2002].

A promoter generally is positioned 10 to 100 nucleotides 5' to a nucleic acid sequence comprising a ribosome binding site. Examples of promoters that have been used in a prokaryotic cell includes a T5 promoter, a lac promoter, a tac promoter, a trc promoter, an araBAD promoter, a $P_L$ promoter, a T7 promoter, a T7-lac operator promoter, and variations thereof. The T5 promoter is regulated by the lactose operator. A lac promoter (e.g., a lac promoter, a lacUV5 promoter), a tac promoter (e.g., a tacI promoter, a tacII promoter), a T7-lac operator promoter or a trc promoter are each suppressed by a lacI repressor, a more effective $lacI^Q$ repressor or an even stronger $lacI^{Q1}$ repressor (Glascock, C. B. and Weickert, M. J., 1998).

Isopropyl-β-D-thiogalactoside ("IPTG") is used to induce lac, tac, T7-lac operator and trc promoters. An araBAD promoter is suppressed by an araC repressor, and is induced by 1-arabinose. A $P_L$ promoter or a T7 promoter are each suppressed by a λcIts857 repressor, and induced by a temperature of 42° C. Nalidixic acid may be used to induce a $P_L$ promoter.

In an example, recombinant amino acid substitution mutants of OPH have been expressed in *Escherichia coli* using a lac promoter induced by IPTG (Watkins, L. M. et al., 1997b). In another example, recombinant wild type and a signal sequence truncation mutant of OPH was expressed in *Pseudomonas putida* under control of a lactac and tac promoters (Walker, A. W. and Keasling, J. D., 2002). In a further example, an OPH-Lpp-OmpA fusion protein has been expressed in *Escherichia coli* strains JM105 and XL1-Blue using a constitutive lpp-lac promoter or a tac promoter induced by IPTG and controlled by a $lacI^Q$ repressor (Richins, R. D. et al., 1997; Kaneva, I. et al., 1998; Mulchandani, A. et al., 1999b). In an additional example, a cellulose-binding domain-OPH fusion protein has also been recombinantly expressed under the control of a T7 promoter (Richins, R. D. et al., 2000). In a further example, recombinant *Altermonas* sp. JD6.5 OPAA has been expressed under the control of a trc promoter in *Escherichia coli* (Cheng, T.-C. et al., 1999). In an additional example, a (His)6 tag sequence-thrombin cleavage site-squid-type DFPase has been expressed using a Ptac promoter in *Escherichia coli* (Hartleib, J. and Ruterjans, H., 2001a).

A ribosome binding site is important for transcription initiation, and is usually positioned 4 to 14 nucleotides 5' from the start codon. A start codon signals initiation of transcription. A multiple cloning site comprises restriction sites for incorporation of a nucleic acid sequence encoding a peptide or polypeptide of interest.

A stop codon signals translation termination. The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels. A transcription terminator signals the end or transcription and often enhances mRNA stability. Examples of a transcription terminator include a rrnB T1 or a rrnB T2 transcription terminator (Unger, T. F., 1997). An origin of replication regulates the number of expression vector copies maintained in a transformed host cell.

A selectable marker usually provides a transformed cell resistance to an antibiotic. Examples of a selectable marker used in a prokaryotic expression vector include a β-lactamase, which provides resistance to antibiotic such as an ampicillin or a carbenicillin; a tet gene product, which provides resistance to a tetracycline, or a Km gene product, which provides resistance to a kanamycin. A repressor regulatory gene suppresses transcription from the promoter. Examples of repressor regulatory genes include the lacI, lacI$^q$, or lacI$^{Q1}$ repressors (Glascock, C. B. and Weickert, M. J., 1998). Often, the host cell's genome, or additional nucleic acid vector co-transfected into the host cell, may comprise one or more of these nucleic acid sequences, such as, for example, a repressor.

It is contemplated that an expression vector for a prokaryotic host cell will comprise a nucleic acid sequence that encodes a periplasmic space signal peptide. In preferred aspects, this nucleic acid sequence will be operatively linked to a nucleic acid sequence comprising an enzymatic peptide or polypeptide of the present invention, wherein the periplasmic space signal peptide directs the expressed fusion protein to be translocated into a prokaryotic host cell's periplasmic space. Fusion proteins secreted in the periplasmic space may be obtained through simplified purification protocols compared to non-secreted fusion proteins. A periplasmic space signal peptide are usually operatively linked at or near the N-terminus of an expressed fusion protein. Examples of a periplasmic space signal peptide include the *Escherichia coli* ompA, ompT, and maleI leader peptide sequences and the T7 caspid protein leader peptide sequence (Unger, T. F., 1997).

Mutated and/or recombinantly altered bacterium that release a peptide or polypeptide comprising an enzyme sequence of the present invention into the environment may be particularly advantageous for purification and/or contact of enzyme with a target chemical substrate. It is contemplated that a strain of bacteria, such as, for example, a bacteriocin-release protein mutant strain of *Escherichia coli*, may be used to promote release of expressed proteins targeted to the periplasm into the extracellular environment (Van der Wal, F. J. et al., 1998). In other aspects, it is contemplated that a bacterium may be transfected with an expression vector that produces a gene and/or a gene fragment product that promotes the release of a protenaceous molecule of interest from the periplasm into the extracellular environment. For example, a plasmid encoding the third topological domain of TolA has been described as promoting the release of endogenous and recombinantly expressed proteins from the periplasm (Wan, E. W. and Baneyx, F., 1998).

D. Host Cells

Many host cells from various cell types and organisms are available and would be known to one of skill in the art. As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene and/or gene fragment encoded by a vector. A host cell can, and has been, used as a recipient for vectors. A host cell may be "transfected" or "transformed," which refers to a process by which exogenous nucleic acid sequence is transferred or introduced into the host cell. A transformed cell includes the primary subject cell and its progeny. Techniques for transforming a cell are extremely well known in the art, and include, for example calcium phosphate precipitation, cell sonication, diethylaminoethanol ("DEAE")-dextran, direct microinjection, DNA-loaded liposomes, electroporation, gene bombardment using high velocity microprojectiles, receptor-mediated transfection, viral-mediated transfection, or a combination thereof [In "Molecular Cloning" (Sambrook, J., and Russell, D. W., Eds.) 3rd Edition, Cold Spring Harbor, N.Y.: Cold Spring Harbor Laboratory Press, 2001; In "Current Protocols in Molecular Biology" (Chanda, V. B. Ed.) John Wiley & Sons, 2002].

Once a suitable expression vector is transformed into a cell, the cell may be grown in an appropriate environment, and in some cases, used to produce a tissue or whole multicellular organism. As used herein, the terms "engineered" and "recombinant" cells or host cells are intended to refer to a cell into which an exogenous nucleic acid sequence has been introduced. Therefore, engineered cells are distinguishable from naturally occurring cells that do not contain a recombinantly introduced exogenous nucleic acid sequence. Engineered cells are thus cells having a nucleic acid sequence introduced through the hand of man. Recombinant cells include those having an introduced cDNA or genomic gene and/or a gene fragment positioned adjacent to a promoter not naturally associated with the particular introduced nucleic acid sequence, a gene, and/or a gene fragment. An enzyme or proteinaceous molecule produced from the introduced gene and/or gene fragment is referred to as a recombinant enzyme or recombinant proteinaceous molecule, respectively. All tissues, offspring, progeny or descendants of such a cell, tissue, and/or organism that comprise the transformed nucleic acid sequence thereof are considered part of the present invention.

Though it is possible to purify an expressed enzyme from cellular material, the discovery disclosed herein of the properties of an enzyme composition comprising, in preferred embodiments, an enzyme expressed and retained, whether naturally or through recombinant expression, within a cell. In preferred embodiments, an enzyme is produced using recombinant nucleic acid expression systems in the cell. Cells are known herein based on the type of enzyme expressed within the cell, whether endogenous or recombinant, so that, for example, a cell expressing an enzyme of interest would be known as an enzyme$^+$ cell, a cell expressing a phosphoric triester hydrolase would be known herein as a "phosphoric triester hydrolase$^+$ cell," etc. Additional examples of such nomenclature include an aryldialkylphosphatase$^+$ cell, an OPH$^+$ cell, an OPAA$^+$ cell, a human paraoxonase$^+$ cell, a carboxylase$^+$ cell, a prolidase$^+$ cell, an aminopeptidases$^+$ cell, a PepQ$^+$ cell, a mpd product$^+$ cell, a "B" esterase$^+$ cell, an acetycholinesterase$^+$ cell, a butyrylcholinesterase$^+$ cell, diisopropyl-fluorophosphatase$^+$ cell, Mazur-type DFPase$^+$ cell, or a squid-type DFPase$^+$ cell, respectively denoting cells that comprise, an aryldialkylphosphatase, an OPH, a OPAA, a human paraoxonase, a carboxylase, a prolidase, an aminopeptidease, a PepQ, a mpd product, a "B" esterase, an acetycholinesterase, a butyrylcholinesterase, a diisopropyl-fluorophosphatase, a Mazur-type DFPase, or a squid-type DFPase, etc.

In preferred embodiments, an enzyme$^+$ cell comprises a bacterial cell, a yeast cell, an insect cell, a plant cell, or a combination thereof. In preferred aspects, the cell comprises a cell wall. Contemplated enzyme$^+$ cells that comprise cell walls include, but are not limited to, a bacterial cell, a fungal cell, a plant cell, or a combination thereof. In preferred facets, a microorganism comprises the enzyme$^+$ cell. Examples of contemplated microorganisms include a bacterium, a fungus, or a combination thereof. Examples of a bacterial host cell that have been used with expression vectors include an *Aspergillus niger*, a *Bacillus* (e.g., *B.* amyloliquefaciens, B. brevis, B. licheniformis, B. subtilis), an *Escherichia coli*, a *Kluyveromyces lactis*, a *Moraxella* sp., a *Pseudomonas* (e.g., *fluorescens, putida*), *Flavobacterium* cell, a *Plesiomonas* cell, an *Alteromonas* cell, or a combination thereof. Examples of a yeast cell include a *Streptomyces lividans* cell, a *Gliocladium virens* cell, a *Saccharomyces* cell, or a combination thereof.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection, which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Examples of a bacterial cell used as a host cell for vector replication and/or expression include DH5a, JM109, and KC8, as well as a number of commercially available bacterial hosts such as Novablue™ *Escherichia coli* cells (NOVAGENE®), SURE® Competent Cells and SOLOPACK™ Gold Cells (STRATAGENE®). However, *Escherichia coli* cells have been the most common cell types used to express both wild type and mutant forms of OPH (Dumas, D. P. et al., 1989a; Dave, K. I. et al., 1993; Lai, K. et al., 1994; Wu, C.-F. et al., 2001a). In an example, the OPH I106A/F132A/H257Y and G60A mutants have been expressed in *Escherichia coli* BL-21 host cells (Kuo, J. M. and Raushel, F. M., 1994; Li, W.-S. et al., 2001). In a further example, maltose-binding domain-E3 carboxylesterase and phosphoric triester hydrolase functional equivalents have been expressed in *Escherichia coli* TB1 cells (Claudianos, C. et al., 1999). In another example, the OPH mutants designated W131F, F132Y, L136Y, L140Y, H257L, L271Y, F306A, and F306Y each have been expressed in Novablue™ *Escherichia coli* cells (Gopal, S. et al., 2000). In an addition example, OPAA from *Alteromonas* sp JD6.5 has been recombinantly expressed in *Escherichia coli* cells (Hill, C. M., 2000). In a further example, recombinant *Altermonas* sp. JD6.5 OPAA has been expressed in *Escherichia coli* (Cheng, T.-C. et al., 1999). In a further example, the mpd gene has been recombinantly expressed in *Escherichia coli*, and the encoded enzyme demonstrated methyl parathion degradation activity (Zhongli, C. et al., 2001). In an additional example, a recombinant squid-type DFPase fusion protein has been expressed *Escherichia coli* BL-21 cells (Hartleib, J. and Ruterjans, H., 2001a). Alternatively, bacterial cells such as *Escherichia coli* LE392 could be used as host cells for phage viruses. Of course, one of skill in the art may select a bacterium species to express a proteinaceous molecule due to a particular desirable property. In an example, *Moraxella* sp. that degrades p-nitrophenol, a toxic cleavage product of parathion and methyl parathion, has been used to recombinantly express an OPH-InaV fusion protein. The resulting recombinant bacterial degrades both toxic OP compounds and their cleavage byproduct (Shimazu, M. et al., 2001b).

Examples of eukaryotic host cells for replication and/or expression of a vector include yeast cells HeLa, NIH3T3, Jurkat, 293, Cos, CHO, Saos, and PC12. In an example, OPH has been expressed in the host yeast cells of *Streptomyces lividans* (Steiert, J. G. et al., 1989). In another example, OPH has been expressed in host insect cells, including *Spodoptera frugiperda* sf9 cells (Dumas, D. P. et al., 1989b; Dumas, D. P. et al., 1990). In a further example, OPH has been expressed in the cells of *Drosophila melanogaster* (Phillips, J. P. et al., 1990). In an additional example, OPH has been expressed in the fungus *Gliocladium virens* (Dave, K. I. et al., 1994b). In a further example, the gene for human paraoxonase, PON1, has been recombinantly expressed in human embryonic kidney cells (Josse, D. et al., 2001; Josse, D. et al., 1999). In a further example, E3 carboxylesterase and phosphoric triester hydrolase functional equivalents have been expressed in host insect *Spodoptera frugiperda* sf9 cells (Campbell, P. M. et al., 1998; Newcomb, R. D. et al., 1997). In an additional example, a phosphoric triester hydrolase functional equivalent of a butyrylcholinesterase has been expressed in Chinese hamster ovary ("CHO") cells (Lockridge, O. et al., 1997). In certain embodiments, an eukaryotic cell that may be selected for expression is a plant cell, such as, for example, a corn cell.

E. Production of Expressed Proteinaceous Molecules

It is contemplated that any size flask or fermentor may be used to grow a tissue or organism that can express a recombinant proteinaceous molecule of the present invention. In certain embodiments, bulk production of compositions with enzymatic sequences is contemplated.

In an example, a fusion protein comprising, N-terminus to C-terminus, a (His)6 polyhistidine tag, a green fluorescent protein ("GFP"), an enterokinase recognition site, and a OPH lacking the 29 amino acid leader sequence, has been expressed in *Escherichia coli*. The GFP sequence produced fluorescence that was proportional both the quantity of the fusion protein, and the activity of the OPH sequence. The fusion protein was more soluble than OPH expressed without the added sequences, and was expressed within the cells (Wu, C.-F. et al., 2000b; Wu, C.-F. et al., 2001a).

It is contemplated that the temperature selected may influence the rate and/or quality of recombinant enzyme production. It is contemplated that in some embodiments, expression of an enzyme may be conducted at 4° C. to 50° C., including all intermediate ranges and combinations thereof. Such combinations may include a shift from one temperature (e.g., 37° C.) to another temperature (e.g., 30° C.) during the induction of the expression of proteinaceous molecule. For example, both eukaryotic and prokaryotic expression of OPH may be conducted at temperatures 30° C., which has increased the production of enzymatically active OPH by reducing protein misfolding and inclusion body formation in some instances (Chen-Goodspeed, M. et al., 2001b; Wang, J. et al., 2001; Omburo, G. A. et al., 1992; Rowland, S. S. et al., 1991). In an additional example, prokaryotic expression of recombinant squid-type DFPase fusion protein at 30° C. also enhanced yields of active enzyme (Hartleib, J. and Ruterjans, H., 2001a). It is contemplated that fed batch growth conditions at 30° C., in a minimal media, using glycerol as a carbon source, will be suitable for expression of various enzymes.

F. Processing of Expressed Proteinaceous Molecules

After production of a biomolecule by a living cell, the composition comprising the biomolecule may undergo one or more processing steps to prepare a biomolecule composition of the present invention. Examples of such steps include permeabilizing, disrupting, sterilizing, concentrating, drying, resuspending, or a combination thereof. Various embodiments of a biomolecule composition of the present invention are contemplated after one or more such processing steps. However, it is further contemplated that each processing step will increase economic costs and/or reduce total biomolecule yield, so that embodiments comprising fewer steps are preferred. It is further contemplated that the order of steps may be varied and still produce a biomolecule composition of the present invention.

In certain embodiments, a biomolecule composition of the present invention may comprise various cellular components (e.g., cell wall material, cell membrane material, nucleic acids, sugars, polysacharrides, peptides, polypeptides, proteins, lipids, etc). Such a biomolecule composition of the present invention is known herein as a "crude cell preparation". A "a crude cell preparation comprises the biomolecule within or otherwise in contact with a cell and/or cellular debris. In certain aspects, it is contemplated that the total content of desired biomolecule (e.g., an active biomolecule) may range from 0.0001% to 99.9999% of a crude cell preparation, including all intermediate ranges and combinations thereof, by volume or dry weight, depending upon factors such as expression efficiency of the biomolecule in the cell and the amount of processing and/or purification steps. A higher content of desired biomolecule in the biomolecular composition is preferred. But, in certain embodiments, it is also preferred that the biomolecule composition comprise cellular components, particularly cell wall and/or cell membrane material, to provide material that may be protective to the biomolecule, enhances the particulate nature of the biomolecule composition, or a combination thereof. Thus, the biomolecule composition may comprise 0.0001% to 99.9999% of cellular components, including all intermediate ranges and combinations thereof, by volume or dry weight. However, in certain embodiments, lower ranges of cellular components is preferred, as the biomolecular composition would therefore comprise a greater percentage of a desired biomolecule.

In embodiments wherein the cellular material is derived from a microorganism, such as through expression of the biomolecule by a microorganism, the biomolecular composition is known herein as a "microorganism based particulate material". The association of a biomolecule with a cell or cellular material is generally produced through endogenous expression, expression due to recombinant engineering, or a combination thereof. In preferred embodiments, a crude cell preparation comprises a biomolecule partly or whole encapsulated by a cell membrane and/or cell wall, whether naturally so and/or through recombinant engineering. Such a biomolecule (e.g., the active biomolecule) encapsulated within or as a part of a cell wall and/or cell membrane is referred to herein as a "whole cell material" or "whole cell particulate material".

It is contemplated that a biomolecule prepared as a crude cell preparation may have greater stability than a preparation wherein the biomolecule has been substantially separated from a cell membrane and/or cell wall. It is further contemplated that a biomolecule prepared as a crude cell preparation, wherein the biomolecule is localized between the cell wall and cell membrane and/or within the cell so that the cell wall separates the biomolecule from the extracellular environment, may have greater stability than a preparation wherein the biomolecule has been substantially separated from a cell membrane and/or cell wall.

Additionally, it is contemplated that a biomolecule composition of the present invention may be encapsulated using a microencapsulation technique as would be known to one of ordinary skill in the art. Such encapsulation may enhance or confer the particulate nature of the biomolecule composition, provide protection to the biomolecule, increase the average particle size to a desired range, allow release of the biomolecule from the encapsulating material, alter surface charge, hydrophobicity, hydrophilicity, solubility and/or disperability of the particulate material, or a combination thereof. Examples of microencapsulation (e.g., microsphere) compositions and techniques are described in Wang, H. T. et al., *J. of Controlled Release* 17:23-25, 1991; and U.S. Pat. Nos. 4,324,683, 4,839,046, 4,988,623, 5,026,650, 5,153,131, 6,485,983, 5,627,021 and 6,020,312).

1. Cell Permeabilization/Disruption

In preferred aspects, a biomolecular composition of the present invention comprises a crude cell preparation wherein the cell membrane and/or cell wall has been altered through a permeabilizating process, a disruption process, or a combination thereof. An example of such an altered crude cellular preparation includes disrupted cells, permeabilized cells, or a combination thereof. As used herein, a "disrupted cell" is a crude cell preparation wherein the cell membrane and/or cell wall has been altered through a disruption process. As used herein, a "permeabilized cell" is a crude cell preparation wherein the cell membrane and/or cell wall has been altered through a permeabilizating process. It is contemplated that a biomolecule composition of the present invention prepared as a crude cellular preparation may have greater stability than a preparation wherein the biomolecule has been substantially purified from the cell wall and/or membrane.

A processing step may comprise a permeabilizing step, wherein a cell is contacted with a permeabilizing agent such as dimethyl sulfoxide ("DMSO"), ethylenediaminetetraacetic acid ("EDTA"), tributyl phosphate, or a combination thereof. A permeabilizing step may increase the mass transport of a substrate into the interior of a cell, where an enzyme localized inside the cell can catalyze a chemical reaction with the substrate. (Martinez, M. B. et al., 1996; Martinez, M. B. et al., 2001; Hung, S.-C. and Liao, J. C., 1996). Cell permeabilizing using EDTA (Leduc, M. et al., 1985).

OP compound degradation rate has been limited by OPH intracellularly expressed in whole cells (Elashvili, I. and DeFrank, J. J., 1996; Elashvili, I. et al., 1998; Hung, S.-C. and Liao, J. C., 1996; Richins, R. et al., 1997). However, it is contemplated that a composition of the present invention comprising a whole cell particulate material will provide protection from diffusion of compounds that may damage a biomolecule, while allowing sufficient permeability to allow biomolecule function.

In some embodiments, a processing step comprises disrupting a cell. A cell may be disrupted by any method known in the art, including, for example, a chemical method, a mechanical method, a biological method, or a combination thereof. Examples of a chemical cell disruption method include suspension in a solvent for certain cellular components. In specific facets, such a solvent may comprise an organic solvent (e.g., acetone), a volatile solvent, or a combination thereof. In a particular facet, a cell be disrupted by acetone (Wild, J. R. et al., 1986; Albizo, J. M. and White, W. E., 1986). In certain preferred facets, the cells are disrupted in a volatile solvent for ease in evaporation. Examples of a mechanical cell disruption method include pressure (e.g., processing through a French press), sonication, mechanical shearing, or a combination thereof. An example of a pressure cell disruption method includes processing through a French press. Examples of a biological cell disruption method include contacting the cell with one or more enzymes (e.g., lysozyme) that weaken, damage, and/or permeabilize a cell membrane, cell wall or combination thereof. Biological material comprising a proteinaceous molecule of the present invention may be homogenized, sheared, undergo one or more freeze thaw cycles, be subjected to enzymatic and/chemical digestion of cellular materials (e.g., cell walls, sugars, etc), undergo extraction with organic or aqueous solvents, etc, to weaken interactions between the proteinaceous molecule and other cellular materials and/or partly purify the proteinaceous molecule. A processing step may comprise sonicating a composition comprising an enzyme. Other dissepting and drying will be done by freezedrying with or without a cryoprotector (typically a sugar).

2. Sterilization

A processing step may comprise sterilizing an enzyme composition of the present invention. Sterilizing kills living matter, and may be desirable as continued post expression growth of a host cell and/or a contaminating organism may detrimentally affect the composition. For example, one or more properties of a coating may be undesirably altered by the presence of a living organism. Additionally, sterilizing reduces the ability of a living recombinant organism to be introduced into the environment, when such an event is not desired. Sterilizing may be accomplished by any method known in the art. Examples of sterilizing may include contacting the living matter with a toxin, irradiating the living matter, heating the living matter above 100° C., or a combination thereof. It is preferred that sterilizing comprises irradiating the living matter, as radiation generally does not leave a toxic residue, and is not contemplated to detrimentally affect the enzymes stability such as that which might occur during heating. Examples of radiation include infrared ("IR") radiation, ionizing radiation, microwave radiation, ultra-violet ("UV") radiation, particle radiation, or a combination thereof. Particle radiation, UV radiation and/or ionizing radiation are preferred, and particle radiation is particularly preferred. Examples of particle radiation include alpha radiation, electron beam/beta radiation, neutron radiation, proton radiation, or a combination thereof.

3. Concentrating a Biomolecule Composition

A processing step may comprise concentrating a biomolecule composition of the present invention. As used herein, "concentrating" refers to any process wherein the volume of a composition is reduced. Often, undesired components that comprise the excess volume are removed, the desired composition is localized to a reduced volume, or a combination thereof.

For example, it is contemplated that a concentrating step may be used to reduce the amount of a growth and/or expression medium component from a composition of the present invention. It is contemplated that nutrients, salts and other chemicals that comprise a biological growth and/or expression medium may be unnecessary and/or unsuitable in a composition of the present invention, and reducing the amount of such compounds is preferred. A growth medium may promote undesirable microorganism growth in a composition of the present invention, while salts or other chemicals may undesirably alter the formulation of a coating.

Concentrating a biomolecule composition may be by any method known in the art, including, for example, filtrating, a gravitational force, a gravimetric force, or a combination thereof. An example of a gravitational force is normal gravity. An example of a gravimetric force is the force exerted during centrifugation. Often a gravitational or gravimetric force is used to concentrate a composition comprising the desired biomolecule from undesired components that are retained in the volume of a liquid medium. After cells are localized to the bottom of a centrifugation devise, the media may be removed via such techniques as decanting, aspiration, etc.

4. Drying a Biomolecule Composition

In additional embodiments, the disrupted cells and/or cell debris are dried, ground and/or milled to a powder. In specific facets, the cells added to the paint comprise disrupted cells, cell debris, and/or powder. The powder may be Preferrably stored at room temperature without need for desiccation.

5. Resuspending Biomolecule Composition

A purification step may comprise resuspending a precipitated composition comprising an enzyme from cell debris.

The invention provides, in certain preferred embodiments, a composition comprising a coating and an enzyme prepared by the following steps: obtaining a culture of cells that express the enzyme; concentrating the cells and removing the culture media; disrupting the cell structure; drying the cells; and adding the cells to the coating. In some aspects, the composition is prepared by the additional step of suspending the disrupted cells in a solvent prior to adding the cells to the coating.

In certain aspects, the composition is prepared by adding the cell culture powder to glycerol, admixing with glycerol and/or suspending in glycerol. In other facets, the glycerol is at a concentration of about 50%. In specific facets, the cell culture powder comprised in glycerol at a concentration of about 3 mg of the milled powder to 3 ml of 50% glycerol. In certain facets, the composition is prepared by adding the powder comprised in glycerol to the paint at a concentration of about 3 ml glycerol comprising powder to 100 ml of paint. The powder may also be added to a liquid component such as glycerol prior to addition to the paint. The numbers are exemplary only and do not limit the use of the invention. The concentration was chosen merely to be compatible with the amount of substance that can be added to one example of paint without affecting the integrity of the paint itself. Any compatible amount may used within the scope of the present invention.

6. Temperatures

It is contemplated that in some embodiments, processing of an enzyme composition may be conducted at 4° C. to 50° C., including all intermediate ranges and combinations thereof. In preferred embodiments, a processing step may comprise maintaining a composition comprising an enzyme at a temperature less than the optimum temperature for the activity of a living organism and/or enzyme that may detrimentally affect an enzyme of the present invention. Often 37° C. is the maximum temperature for the processing of a eukaryotic biomolecule (e.g., an enzyme). Thus temperatures less than 37° C. are preferred, temperatures less than 30° C. are more preferred, temperatures less than 20° C. even more preferred, temperatures less than 10° C. are particularly preferred, and temperatures of 4° C. more preferred.

7. Other Processing Steps

In other embodiments, a proteinaceous molecule of the present invention may be a purified a proteinaceous molecule. A "purified proteinaceous molecule" as used herein refers to any proteinaceous molecule of the present invention removed in any degree from other extraneous materials (e.g., cellular material, nutrient or culture medium used in growth and/or expression, etc). In certain aspects, removal of other extraneous material may produce a purified proteinaceous molecule of the present invention wherein its concentration has been enhanced 2- to 10,000-fold or more, including all intermediate ranges and combinations thereof, from its original concentration in a material (e.g., a recombinant cell, a nutrient or culture medium, etc). In other embodiments, a purified proteinaceous molecule of the present invention may comprise 0.001% to 100%, including all intermediate ranges and combinations thereof of a composition comprising a proteinaceous molecule of the present invention. The degree or fold of purification may be determined using any method known to those of skill in the art or described herein. For example, it is contemplated that techniques such as measuring specific activity of a fraction by an assay described herein, relative to the specific activity of the source material, or fraction at an earlier step in purification, may be used.

Techniques for preparation of a proteinaceous molecule of the present invention are described herein. However, it is contemplated that one or more additional methods for purification of biologically produced molecule(s) that are known in the art or described herein may be applied to obtain a purified proteinaceous molecule of the present invention [Azzoni, A. R. et al., 2002; In "Current Protocols in Molecular Biology" (Chanda, V. B. Ed.) John Wiley & Sons, 2002; In "Current Protocols in Nucleic Acid Chemistry" (Harkins, E. W. Ed.) John Wiley & Sons, 2002; In "Current Protocols in Protein Science" (Taylor, G. Ed.) John Wiley & Sons, 2002; In "Current Protocols in Cell Biology" (Morgan, K. Ed.) John Wiley & Sons, 2002; In "Current Protocols in Pharmacology" (Taylor, G. Ed.) John Wiley & Sons, 2002; In "Current Protocols in Cytometry" (Robinson, J. P. Ed.) John Wiley & Sons, 2002; In "Current Protocols in Immunology" (Coico, R. Ed.) John Wiley & Sons, 2002]. A biological material comprising a proteinaceous molecule of the present invention may be homogenized, sheared, undergo one or more freeze thaw cycles, be subjected to enzymatic and/chemical digestion of cellular materials (e.g., cell walls, sugars, etc), undergo extraction with organic or aqueous solvents, etc, to weaken interactions between the proteinaceous molecule and other cellular materials and/or partly purify the proteinaceous molecule. A processing step may comprise sonicating a composition comprising an enzyme.

Cellular materials may be further fractionated to separate a proteinaceous molecule of the present invention from other cellular components using chromatographic e.g., affinity chromatography (e.g., antibody affinity chromatography, lectin affinity chromatography), fast protein liquid chromatography, high performance liquid chromatography "HPLC"), ion-exchange chromatography, exclusion chromatography; or electrophoretic (e.g., polyacrylamide gel electrophoresis, isoelectric focusing) methods. It is contemplated that a proteinaceous molecule of the present invention may be precipitated using antibodies, salts, heat denaturation, centrifugation and the like. A purification step may comprise dialyzing a composition comprising an enzyme from cell debris.

For example, the molecular weight of a proteinaceous molecule can be calculated when the sequence is known, or estimated when the approximate sequence and/or length is known. SDS-PAGE and staining (e.g., Coomassie Blue) has been commonly used to determine the success of recombinant expression and/or purification of OPH, as described (Kolakowski, J. E. et al., 1997; Lai, K. et al., 1994).

In certain embodiments, an enzyme may be in the form of a crystal. In other aspects, one or more enzyme crystals may be cross-linked for from an crosslinked enzyme crystal ("CLEC") (Hoskin, F. C. G. et al., 1999).

G. Coatings

In preferred embodiments, a coating comprises a biomolecule composition of the present invention. A coating ("coat," "surface coat," "surface coating") is "a liquid, liquefiable or mastic composition that is converted to a solid protective, decorative, or functional adherent film after application as a thin layer" ("Paint and Coating Testing Manual, Fourteenth Edition of the Gardner-Sward Handbook" (Koleske, J. V. Ed.), p. 696, 1995; and in "ASTM Book of Standards, Volume 06.01, Paint—Tests for Chemical, Physical, and Optical Properties; Appearance," D16-00, 2002). Additionally, a thin layer is 5 um to 1500 um thick, including all intermediate ranges and combinations thereof. However, in most embodiments, it is contemplated that a coating will form a thin layer 15 um to 150 um thick, including all intermediate ranges and combinations thereof. Examples of a coating of the present invention include a clear coating or a paint.

A surface is the outer layer of any solid object. As would be known to those of ordinary skill in the art, the term "substrate," in the context of a coating, is synonymous with the term "surface." However, as "substrate" has a different meaning to those of skill in arts of enzymology and coatings, the term "surface" will be preferentially used herein for clarity. A surface wherein a coating has been applied, whether or not film formation has occurred, is known herein as a "coated surface."

As is known to those of ordinary skill in the art, a coating generally comprises one or more materials that contribute to the properties of the coating, the ability of a coating to be applied to a surface, the ability of the coating to undergo film formation, and/or the properties of the produced film. Examples of such coating components include a binder, a liquid component, a colorizing agent, an additive, or a combination thereof, and such materials are contemplated for used in a coating of the present invention. A coating typically comprises a material often referred to as a "binder," which is the primary material in a coating capable of film formation. Often the binder is the coating component that dominates conferring a physical and/or chemical property to a coating and/or film. Examples of properties of a binder typically affects include chemical reactivity, minimum film formation temperature, minimum $T_g$, volume fraction solids, a rheological property (e.g., viscosity), film moisture resistance, film UV resistance, film heat resistance, film weathering resistance, adherence, film hardness, film flexibility, or a combination thereof. Consequently, different categories of coatings may be identified herein by the binder used in the coating. For example, a binder may be an oil, a chlorinated rubber, or an acrylic, and examples of a coating comprising such binders include an oil coating, a chlorinated rubber-topcoat, an acrylic-lacquer, etc.

In most embodiments, a coating will comprise a liquid component (e.g., a solvent, a diluent, a thinner), which often confers and/or alters the coating's rheological properties (e.g., viscosity) to ease the application of the coating to a surface. In some embodiments, a coating will comprise a colorizing agent (e.g., a pigment), which usually functions to alter an optical property of a coating and/or film. In certain preferred embodiments, a microorganism based particulate material of the present invention is a colorizing agent. In particularly preferred embodiments, a colorizing agent comprising a microorganism based particulate material of the present invention is an extender, a pigment, or a combination thereof. In other preferred embodiments, a coating comprises a colorizing agent that comprises a microorganism based particulate material of the present invention. A coating will often comprise an additive which is a composition incorporated into a coating to reduce and/or prevent the development of a physical, chemical, and/or aesthetic defect in the coating and/or film; confer some addition desired property to a coating and/or film; or a combination thereof.

Examples of an additive include an accelerator, an adhesion promoter, an antioxidant, an antiskinning agent, a coalescing agent, a defoamer, a dispersant, a drier, an emulsifier, a fire retardant, a flow control agent, a gloss aid, a leveling agent, a marproofing agent, a slip agent, a thickener, a UV stabilizer, a viscosity control agent, a wetting agent, or a combination thereof. In certain preferred embodiments, a microorganism based particulate material of the present invention is an additive. In particularly preferred embodiments, an additive comprising a microorganism based particulate material of the present invention comprises a viscosity control agent, a dispersant, or a combination thereof. In other preferred embodiments, a coating comprises an additive that comprises a microorganism based particulate material of the present invention. A contaminant is a material that is unintentionally added to a coating, and may be volatile and/or non-volatile component of a coating and/or film. As would be known to those of ordinary skill in the art, a coating component may be categorized as possessing more than one defining characteristic, and thereby simultaneously functioning in a coating composition as a combination of a binder, a liquid component, a colorizing agent, and/or additive. Different coating compositions are described herein as examples of coatings with varying sets of properties.

In certain embodiments, a coating may be stored in a container ("pot") prior to application. In certain aspects, the coating is a multi-pack coating which is a coating wherein different components are stored in a plurality of containers. Typically, this is done to reduce film formation during storage for certain types of coatings. The components are admixed prior to and/or during application. However, in certain embodiments, it is specifically contemplated that a coating comprising a microorganism based particulate material of the present invention is a multi-pack coating. In specific aspects, the coating is a two-pack coating, three-pack coating, four-pack coating, five-pack coating, or more wherein the coating components are stored in separate containers. In certain aspects, 0.001% to 100%, including all intermediate ranges and combinations thereof, of the microorganism based particulate material is stored in a separate container from a coating component. It is contemplated that separate storage may reduce undesirable microorganism growth in the coating component, damage to the microorganism-based particulate material of the present invention by the coating component, increase the storage life ("pot life") of a coating, reduce the amount of a preservative in a coating, or a combination thereof. In certain facets, it is contemplated that the coating components of a container holding the microorganism based particulate material of the present invention may further include a coating component such as a preservative, a wetting agent, a dispersing agent, a liquid component, a rheological modifier, or a combination thereof. It is contemplated that a preservative may reduce undesirable growth of a microorganism, whether the microorganism is derived from the microorganism based particulate material of the present invention or a contaminating microorganism. It is contemplated that a wetting agent, a dispersing agent, a liquid component, a rheological modifier, or a combination thereof, may promote ease of admixing of coating components in a multi-pack coating. In certain aspects, a three-pack coating or four-pack coating may be used, wherein the first container and the second container contain coating components separated to reduced film formation during storage, and a third container comprises 0.001% to 100%, including all intermediate ranges and combinations thereof, of the microorganism based particulate material. In certain facets, a multi-pack coating may be used to separate two or more preparations of the microorganism based particulate material of the present invention such as to reduce damage by different species of microorganisms to each other during storage.

A coating may be applied to a surface using any technique known in the art. A in the context of a coating, "application," "apply," or "applying" is the process of transferring of a coating to a surface to produce a layer of coating upon the surface. As known herein, an "applicator" is a devise that is used to apply the coating to a surface. Examples of an applicator include a brush, a roller, a pad, a rag, a spray applicator, etc. Application techniques that are contemplated as suitable for a user of the present invention of little or no particular skill include, for example, dipping, pouring, siphoning, brushing, rolling, padding, ragging, spraying, etc. Certain types of coatings may be applied using techniques contemplated as more suitable for a skilled artisan such as anodizing, electroplating, and/or laminating of a polymer film onto a surface.

In certain embodiments, the layer of coating undergoes film formation ("curing," "cure"), which is the physical and/or chemical change of a coating to a solid that is a preferred solid when in the form of a layer upon the surface. In certain aspects, a coating may be prepared, applied and cured at an ambient condition, a baking condition, or a combination thereof. An ambient condition is a temperature range between −10° C. to 40° C., including all intermediate ranges and combinations thereof. As used herein, a "baking condition" or "baking" is contacting a coating with a temperature above 40° C. and/or raising the temperature of a coating above 40° C., typically to promote film formation. Examples of baking the coating include contacting a coating and/or raising the temperature of coating to 40° C. to 300° C., or more, including all intermediate ranges and combinations thereof. Various coatings described herein or as would be known to one of ordinary skill in the art may be applied and/or cured at ambient conditions, baking conditions, or a combination thereof.

It is contemplated that in general embodiments, a coating comprising a microorganism based particulate material of the present invention may be prepared, applied and cured at any temperature range described herein or would be known to one of ordinary skill in the art in light of the present disclosures. An example of such a temperature range is −100° C. to 300° C., or more, including all intermediate ranges and combinations thereof. However, a microorganism based particulate material may further comprise a desired biomolecule (e.g., a colorant, an enzyme), whether endogenously or recombinantly produced, that may have a reduced tolerance to temperature. It is contemplated that the preferred temperature that can be tolerated by a biomolecule will vary depending on the specific biomolecule used in a coating, and will generally be within the range of temperatures tolerated by the living organism from which the biomolecule was derived. For example, it is preferred for a coating comprising a microorganism based particulate material of the present invention, wherein the microorganism based material comprises an desired enzyme, that the coating is prepared, applied and cured at −100° C. to 110° C., including all intermediate ranges and combinations thereof. For example, it is contemplated that a temperature of −100° C. to 40° C. including all intermediate ranges and combinations thereof, will be suitable for many enzymes (e.g., a wild-type sequence and/or a functional equivalent) derived from an eukaryote, while temperatures up to, for example −100° C. to 50° C. including all intermediate ranges and combinations thereof, may be tolerated by enzymes derived from many prokaryotes.

The type of film formation that a coating may undergo depends upon the coating components. A coating may comprise, for example, volatile coating components, non-volatile coating components, or a combination thereof. In certain aspects, the physical process of film formation comprises loss of 1% to 100%, including all intermediate ranges and combinations thereof, of a volatile coating component. In general embodiments, a volatile component is lost by evaporation. In certain aspects, loss of a volatile coating component during film formation reaction is promoted by baking the coating. Examples of volatile coating components include a coalescing agent, a solvent, a thinner, a diluent, or a combination thereof. A non-volatile component of the coating remains upon the surface. In specific aspects, the non-volatile component forms a film. Examples of non-volatile coating components include a binder, a colorizing agent, a plasticizer, a coating additive, or a combination thereof. In specific aspects, a coating component may undergo a chemical change to form a film. In general embodiments, a binder undergoes a cross-linking (e.g., polymerization) reaction to produce a film. In general embodiments, a chemical film formation reaction occurs spontaneously under ambient conditions. In other aspects, a chemical film formation reaction is promoted by irradiating the coating, heating the coat, or a combination thereof. In some embodiments, irradiating the coating comprises exposing the coating to electromagnetic radiation, particle radiation, or a combination thereof. Examples of electromagnetic radiation used to irradiate a coating include UV radiation, infrared radiation, or a combination thereof. Examples of particle radiation used to irradiate a coating include electron-beam radiation. Often irradiating the coating induces an oxidative and/or free radical chemical reaction that crosslinks of one or more coating components.

However, in some alternate embodiments, it is contemplated that a coating undergoes a reduced amount of film formation than such a solid film is not produced, or does not undergo film formation to a measurable extent during the period of time it is used on a surface. Such a coating is referred to herein as a "non-film forming coating." Such a non-film forming coating may be prepared, for example, by increasing the non-volatile component in a thermoplastic coating (e.g., increasing plasticizer content in a liquid component), reducing the amount of a coating component that contributes to the film formation chemical reaction (e.g., a binder, a catalyst), reducing the contact with an external a curing agent (e.g., radiation, baking), selection of a non-film formation binder produced from components that lack crosslinking moieties, selection of a non-film formation binder that lack sufficient size to undergo thermoplastic film formation, or a combination thereof. As used herein, a "non-film formation binder" refers to a molecule that is chemically similar to a binder, but lacks sufficient size and/or crosslinking moiety to undergo film formation. For example, a coating may be prepared by selection of an oil-based binder that lacks sufficient double bonds to undergo sufficient crosslinking reactions to produce a film. In another example, a non-film formation binder may be selected that lacks sufficient crosslinking moieties such as an epoxide, an isocyanate, a hydroxyl, a carboxyl, an amine, an amide, a silicon moiety, etc., to produce a film by thermosetting. Such a non-film formation binder may be prepared by chemical modification of a binder, such as, for example, a crosslinking reaction with a small molecule (e.g., less than 1 kDa) that comprises a moiety capable of reaction with a binder's crosslinking moiety, to produce a chemically blocked binder moiety that is inert to a further crosslinking reaction. In another example, a thermoplastic binder typically comprises a molecule 29 kDa to 1000 kDa or more in size. Film formation may be reduced or prevented by selection of a like molecule that is too small to effectively undergo thermoplastic film formation. An example would be selection of a non-film formation binder molecule between 1 kDa to 29 kDa in molecular weight, including all intermediate ranges and combinations thereof.

In other alternative embodiments, a coating may undergo film formation, but produce a film whose properties makes it more suited for a temporary use. Such a temporary film will generally possess a poor and/or low rating for a property that would confer longevity in use. For example, a film with a poor scrub resistance, a poor solvent resistance, a poor water resistance, a poor weathering property (e.g., UV resistance), a poor adhesion property, or a combination thereof, may be selected as a temporary film. In one aspect, a film may have poor adhesion for a surface, allowing ease of removal by stripping and/or peeling. In another example, a film may have a poor resistance to an environmental factor, and subsequently fail (e.g., crack, peel, chalk, etc.) to remain a viable film upon the surface. For example, a film that undergoes chalking is specifically contemplated. Chalking is the erosion a coating, typically by degradation of the binder due to various environmental forces (e.g., UV irradiation). It is contemplated that in some embodiments, chalking may be desirable, to expose remove a contaminant from the surface of a film and/or expose a component of the film (e.g., a biomolecular composition of the present invention) to the surface of the coating. A self-cleaning coating is a film with a desirable chalking property. It is further contemplated that in many aspects the layer of non-film forming coating, a temporary film and/or a self-cleaning film may be removed from a surface with ease. In such embodiments, a non-film forming coating, a temporary film, a self-cleaning film, or a combination thereof would be more suitable for a temporary use upon a surface, due to the ability to be applied as a layer and easily removed when its presence is no longer desired. In these embodiments, it is contemplated that the non-film forming coating, the temporary film, the self-cleaning film, or a combination thereof, is desired for a use upon a surface that lasts a temporary period of time, such as, for example, 1 to 60 seconds, 1 to 24 hours, 1 to 7 days, 1 to 10 weeks, 1 to 6 months, including all intermediate ranges and combinations thereof, respectively.

In some embodiments, a plurality of coating layers, known herein as a "multicoat system" ("multicoating system"), may be applied upon a surface. The coating selected for use in a specific layer may differ from an additional layer of the multicoat system. This selection of coatings with differing components and/or properties is typically done to sequentially confer, in a desired pattern, the properties of differing coatings to a coated surface and/or multicoat system. Examples of a coating that may be selected for use, either alone or in a multicoat system, include a sealer, a water repellent, a primer, an undercoat, a topcoat, or a combination thereof. A sealer is coating applied to a surface to reduce or prevent absorption by the surface of a subsequent coating layer and/or a coating component thereof, and/or to prevent damage to the subsequent coating layer by the surface. A water repellant is a coating applied to a surface to repel water. A primer is a coating that is applied to increase adhesion between the surface and a subsequent layer. In typical embodiments a primer-coating, a sealer-coating, a water repellent-coating, or a combination thereof is applied to porous surface. Examples of a porous surface include drywall, wood, plaster, masonry, damaged and/or degraded metal, corroded metal, or a combination thereof. In certain aspects, the porous surface is not coated or lacks a film prior to application of a primer, sealer, water repellent, or combination thereof. An undercoat is a coating applied to surface to provide a smooth surface for a subsequent coat. A topcoat ("finish") is a coating applied to a surface for a protective and/or decorative purpose. Of course, a sealer, water repellent, primer, undercoat, and/or topcoat may possess additional protective, decorative, and/or functional properties. Additionally, the surface a sealer, water repellent, primer, undercoat, and/or topcoat are applied to may be a coated surface such as a coating and/or film of a layer of the a multicoat system. In certain embodiments, a multicoat system may comprise any combination of a sealer, water repellent, primer, undercoat, and/or topcoat. For example, a multicoat system may comprise any of the following combinations: a sealer, a primer and a topcoat; a primer and topcoat; a water repellent, a primer, undercoat, and topcoat; an undercoat and topcoat; a sealer, an undercoat, and a topcoat; a sealer and topcoat; a water repellent and topcoat, etc. In particular aspects, a coating layer may comprise properties that would be a combination of those associated with different coating types such as a sealer, water repellent, primer, undercoat, and/or topcoat. In such instances, such a combination coating and/or film is designated by a backslash "/" separating the individual coating designations encompassed by the layer. Examples of such a coating layer comprising a plurality of functions include a sealer/primer coating, a sealer/primer/undercoat coating, a sealer/undercoat coating, a primer/undercoat coating, a water repellant/primer coating, an undercoat/topcoat coating, a primer/topcoat coating, a primer/undercoat/topcoat coating, etc. In embodiments wherein the coated surface comprises a particular type of coating, then the coated surface may be known herein by the type of coating such as a "painted surface," a "clear coated surface," a "lacquered surface," a "varnished surface," a "water repellant/primered surface," an "primer/undercoat-topcoated surface," etc.

In specific aspects, a multicoat system may comprise a plurality of layers of the same type, such as, for example, 1 to 10 layers, including all intermediate ranges and combinations thereof, of a sealer, water repellent, primer, undercoat, topcoat, or any combination thereof. In specific facets, a multicoat system comprises a plurality of layers of the same coating type, such as, for example, 1 to 10 layers, including all intermediate ranges and combinations thereof, of a sealer, water repellent, primer, undercoat, or topcoat. In embodiment where a coating does not comprise a multicoat system, but a single layer of coating applied to a surface, such a layer, regardless of typical function in a multicoat system, is regarded herein as a topcoat.

1. Paints

A paint is a "pigmented liquid, liquefiable or mastic composition designed for application to a substrate in a thin layer which is converted to an opaque solid film after application. Used for protection, decoration or identification, or to serve some functional purpose such as the filling or concealing of surface irregularities, the modification of light and heat radiation characteristics, etc." ["Paint and Coating Testing Manual, Fourteenth Edition of the Gardner-Sward Handbook" (Koleske, J. V. Ed.), p. 696, 1995]. However, as certain coatings disclosed herein are non-film forming coatings, this definition is modified herein to encompass a coating with the same properties of a film forming paint, with the exception that it does not produce a solid film. In particular embodiments, a non-film forming paint possesses a hiding power sufficient to concealing surface feature comparable to an opaque film.

Hiding power is the ability of a coating and/or film to prevent light from being reflected from a surface, particularly to convey the surface's visual pattern. Opacity is the hiding power of a film. An example of hiding power would be the ability of a paint-coating to visually block the appearance of grain and color of a wooden surface, as opposed to a clear varnish-coating allowing the relatively unobstructed appearance of wood to pass through the coating. Standard techniques for determining the hiding power of a coating and/or film (e.g., paint, a powder coating) are described, for example, in "ASTM Book of Standards, Volume 06.01, Paint—Tests for Chemical, Physical, and Optical Properties; Appearance," E284-02b, D344-97, D2805-96a, D2745-00 and D6762-02a 2002; "ASTM Book of Standards, Volume 06.02, Paint—Products and Applications; Protective Coatings; Pipeline Coatings," D5007-99, D5150-92 and D6441-99, 2002; and "Paint and Coating Testing Manual, Fourteenth Edition of the Gardner-Sward Handbook" (Koleske, J. V. Ed.), pp. 481-506, 1995.

2. Clear-Coatings

A clear-coating is a coating that is not opaque and/or does not produce an opaque solid film after application. A clear-coating and/or film may be transparent or semi-transparent (e.g., translucent). A clear-coating may be colored or non-colored. In certain embodiments, reducing the content of a pigment in a paint composition may produce a clear-coating. Additionally, a clear-coating may comprise a lacquer, a varnish, a shellac, a stain, a water repellent coating, or a combination thereof. Though some opaque coatings are referred to in the art as a lacquer, a varnish, a shellac, or a water repellent coating, all such opaque coatings are considered as paints herein (e.g., a lacquer-paint, a varnish-paint, a shellac-paint, a water repellent paint).

a. Varnishes

A varnish is a thermosetting coating that converts to a transparent or translucent solid film after application. In general embodiments, a varnish is a wood-coating. A varnish comprises an oil and a dissolved binder. In general embodiments, the oil comprises a drying oil, wherein the drying oil functions as an additional binder. In other embodiments, the binder is solid at room temperature prior to dissolving into the oil and/or an additional liquid component of the varnish. Examples of a dissolvable binder include resins obtained from a natural source (e.g., a Congo resin, a copal resin, a damar resin, a kauri resin), a synthetic resin, or a combination thereof. In specific aspects, the additional liquid component comprises a solvent such as a hydrocarbon solvent. In some facets, the solvent is added to reduce viscosity of the varnish. A varnish may further comprise a coloring agent, including a pigment, for such purposes as conferring or altering a color, gloss, sheen, or a combination thereof. A varnish undergoes thermosetting film formation by oxidative cross-linking. In certain aspects, a varnish may additionally undergo film-formation by evaporation of a volatile component. The dissolved binder generally functions to shorten the time to film-formation relative to certain measures (e.g., dryness, hardness), though the final cross-linking reaction time may not be significantly or measurably shortened. Standards for determining a varnish-coating and/or film's properties are described in, for example, "ASTM Book of Standards, Volume 06.03, Paint—Pigments, Drying Oils, Polymers, Resins, Naval Stores, Cellulosic Esters, and Ink Vehicles," D154-85, 2002.

b. Lacquers

A lacquer is a thermoplastic, solvent-borne coating that converts to a transparent or translucent solid film after application. In general embodiments, a lacquer is a wood-coating. A lacquer-coating comprises a thermoplastic binder dissolved in a liquid component comprising an active solvent. Examples of a thermoplastic binder include a cellulosic binder (e.g., nitrocellulose, cellulose acetate), a synthetic resin (e.g., an acrylic), or a combination thereof. In certain aspects, a liquid component comprises an active solvent, a latent solvent, diluent, a thinner, or a combination thereof. In certain embodiments, a lacquer is nonaqueous dispersion ("NAD") lacquer, wherein the content of solvent is not sufficient to fully dissolve the thermoplastic binder. In certain aspects, a lacquer may comprise an additional binder (e.g., an alkyd), a colorant, a plasticizer, or a combination thereof. Film formation of a lacquer occurs by loss of the volatile components, typically through evaporation.

Standards for a lacquer-coating and/or film's composition (e.g., a lacquer, a pigmented-lacquer, a nitrocellulose lacquer, a nitrocellulose-alkyd lacquer), physical and/or chemical properties (e.g., heat and cold resistance, hardness, film-formation time, stain resistance, particulate material dispersion), and procedures for testing a lacquer's composition/properties, are described in, for example, in "ASTM Book of Standards, Volume 06.02, Paint—Products and Applications; Protective Coatings; Pipeline Coatings," D333-01, D2337-01, D3133-01, D365-01, D2091-96, D2198-02, D2199-82, D2571-95 and D2338-02, 2002.

c. Shellacs

A shellac is similar to a lacquer, but the binder does not comprise a nitrocellulose binder, and the binder is soluble in alcohol, and the binder is obtained from a natural source. A preferred binder comprises *Laciffer lacca* beetle secretion. In general embodiments, a shellac comprises a liquid component (e.g., alcohol). In specific aspects, the additional liquid component comprises a solvent. In some facets, the liquid component is added to reduce viscosity of the varnish. In other embodiments, a shellac undergoes rapid film formation. Standards for a shellac-coating and/or film's composition and properties are described in, for example, "ASTM Book of Standards, Volume 06.03, Paint—Pigments, Drying Oils, Polymers, Resins, Naval Stores, Cellulosic Esters, and Ink Vehicles," D29-98 and D360-89, 2002.

d. Stains

A stain a clear or semitransparent coating formulated to change the color of surface. In general embodiments, a stain is a wood-coating designed to color or protect a wood surface but not conceal the grain pattern or texture. A stain comprises a binder such as an oil, an alkyd, or a combination thereof. Often a stain comprises a low solid content. A low solids content for a wood stain is less than 20% volume of solids. The low solid content of a stain promotes the ability of the coating to penetrate the material of the wooden surface. This property is often used to, for example, to promote the incorporation of a fungicide that may be comprised within the stain into the wood. In certain alternative aspects, a stain comprises a high solids content stain, wherein the solid content is 20% or greater, may be used on a surface to produce a film possessing the property of little or no flaking. In other alternative aspects, a water-borne stain may be used such as a stain comprising a water-borne alkyd. A stain typically further comprises a liquid component (e.g., a solvent), a fungicide, a pigment, or a combination thereof. In other aspects, a stain comprises a water repellent hydrophobic compound so it functions as a water repellent-coating ("stain/water repellent-coating"). Examples of a water repellent hydrophobic compound a stain may comprise include a silicone oil, a wax, or a combination thereof. Examples of a fungicide include a copper soap, a zinc soap, or a combination thereof. Examples of a pigment include a pigment that is similar in color to wood. Examples of such pigments include a red pigment (e.g., a red iron oxide) a yellow pigment (e.g., a yellow iron oxide), or a combination thereof. Standards procedures for testing a stain's (e.g., an exterior stain) properties, are described in, for example, in "ASTM Book of Standards, Volume 06.02, Paint—Products and Applications; Protective Coatings; Pipeline Coatings," D6763-02, 2002.

e. Water Repellent-Coatings

A water repellent-coating is a coating that comprises hydrophobic compounds that repel water. A water repellent-coating is typically applied to a surface susceptible to water damage, such as metal, masonry, wood, or a combination thereof. A water repellent-coating typically comprises a hydrophobic compound and a liquid component. In specific embodiments, a water repellent-coating comprises 1% to 65% hydrophobic compound, including all intermediate ranges and combinations thereof. Examples of a hydrophobic compound that may be selected include an acrylic, a siliconate, a metal-searate, a silane, a siloxane, a parafinnic wax, or a combination thereof. A water repellent may be a water-borne coating, or a solvent-borne coating. A solvent-borne water repellent-coating typically comprises a solvent that dissolves the hydrophobic compound. Examples of solvents include an aliphatic, an aromatic, a chlorinated solvent, or a combination thereof.

In certain embodiments, a water repellent-coating, undergoes film formation, penetrates pores, or a combination thereof. In certain aspects, an acrylic-coating, a silicone-coating, or a combination thereof, undergoes film formation. In other aspects, a metal-searate, a silane, a siloxane, a parafinnic wax, or a combination thereof, penetrates pores in a surface. In some facets, a water repellent-coating (e.g., a silane, a siloxane) covalently bonds to a surface and/or pore (e.g., masonry). Standards for a water repellent-coating and/or film's composition and properties are described in, for example, "ASTM Book of Standards, Volume 06.02, Paint—Products and Applications; Protective Coatings; Pipeline Coatings," D2921-98, 2002; and in "Paint and Coating Testing Manual, Fourteenth Edition of the Gardner-Sward Handbook," (Koleske, J. V. Ed.), pp. 748-750, 1995. Alternatively, standards for a sealer-coating (e.g., a floor sealer) and/or film's composition and properties are described in, for example, "ASTM Book of Standards, Volume 06.02, Paint—Products and Applications; Protective Coatings; Pipeline Coatings," D1546-96, 2002;

3. Coating Categories by Use

In light of the present disclosures, one of ordinary skill in the art may prepare and apply a coating of the present invention to any surface. However, it is preferred that the coating components and methods described herein are selected for a particular application to provide a coating and/or film with properties best suited for a particular use. For example, a coating used in an external environment would preferably comprise a coating component of superior UV resistance than a coating used in interior environment. In another example, a film used upon a surface of a washing machine would preferably comprise a component that confers superior moisture resistance than a component of a film for use upon a ceiling surface. In a further example, a coating applied to the surface of an assembly line manufactured product would preferably comprise components suitable for application by a spray applicator. Various properties of coating components are described herein to provide guidance to the selection of specific coating compositions with a suitable set of properties for a particular use.

A coating of the present invention may be classified by its preferred end use, including, for example, as an architectural coating, an industrial coating, a specification coating, or a combination thereof. An architectural coating is "an organic coating intended for on-site application to interior or exterior surfaces of residential, commercial, institutional, or industrial buildings, in contrast to industrial coatings. They are protective and decorative finishes applied at ambient conditions" ["Paint and Coating Testing Manual, Fourteenth Edition of the Gardner-Sward Handbook" (Koleske, J. V. Ed.), p. 686, 1995)] An industrial coating is a coating applied in a factory setting, typically for a protective and/or aesthetic purpose. A specification coating ("specification finish coating") is a coating formulated to a "precise statement of a set of requirements to be satisfied by a material, produce, system, or service that indicates the procedures for determining whether each of the requirements are satisfied" ["Paint and Coating Testing Manual, Fourteenth Edition of the Gardner-Sward Handbook" (Koleske, J. V. Ed.), p. 891, 1995]. Often, a coating may be categorized as a combination of an architectural coating, an industrial coating, and/or a specification coating. For example, a coating for the metal surfaces of ships may be classified as specification coating, as specific criteria of water resistance and corrosion resistance are required in the film, but typically such a coating can be classified as an industrial coating, since it would typically be applied in a factory. Various examples of an architectural coating, an industrial coating and/or a specification coating and coating components are described herein. Additionally, architectural coatings, industrial coatings, specification coatings are known to those of ordinary skill in the art, and are described, for example, in "Paint and Surface Coatings: Theory and Practice" $2^{nd}$ Edition, pp. 190-192, 1999; in "Paints, Coatings and Solvents" $2^{nd}$ Edition, pp. 330-410, 1998; in "Organic Coatings: Science and Technology, Volume 1: Film Formation, Components, and Appearance" $2^{nd}$ Edition, pp. 138 and 317-318.

a. Architectural Coatings

An architectural coating ("trade sale coating," "building coating," "decorative coating," "house coating") is a coating suitable to coat surface materials commonly found as part of buildings and/or associated objects (e.g., furniture). Examples of a surface an architectural coating is typically applied to include, a plaster surface, a wood surface, a metal surface, a composite particle board surface, a plastic surface, a coated surface (e.g., a painted surface), a masonry surface, a floor, a wall, a ceiling, a roof, or a combination thereof. Additionally, an architectural coating may be applied to an interior surface, an exterior surface, or a combination thereof. An interior coating generally possesses properties such as minimal odor (e.g., no odor, very low VOC), good blocking resistance, print resistance, good washability (e.g., wet abrasion resistance), or a combination thereof. An exterior coating typically is selected to possess good weathering properties. Examples of coating type commonly used as an architectural coating include an acrylic-coating, an alkyd-coating, a vinyl-coating, a urethane-coating, or a combination thereof. In certain aspects, a urethane-coating is applied to a piece of furniture. In other facets, an epoxy-coating, a urethane-coating, or a combination thereof, is applied to a floor. In some embodiments, an architectural coating is a multicoat system. In certain aspects, an architectural coating is a high performance architectural coating ("HIPAC"). A HIPAC is architectural coatings that produce a film with a combination of good abrasion resistance, staining resistance, chemical resistance, detergent resistance, and mildew resistance. Examples of binders suitable for producing a HIPAC include a two-pack epoxide or urethane, or a moisture cured urethane. In general embodiments, an architectural coating comprises a liquid component, an additive, or a combination thereof. In certain aspects, an architectural coating is a water-borne coating or a solvent-borne coating. In other aspects, an architectural coating comprises a pigment. In preferred aspects, such an architectural coating is formulated to comprise a reduced amount or lack a toxic coating component. Examples of a toxic coating component include a heavy metal (e.g., lead), formaldehyde, a nonyl phenol ethoxylate surfactant, a crystalline silicate, or a combination thereof.

In certain embodiments, a water-borne coating has a density of 1.20 kg/L to 1.50 kg/L, including all intermediate ranges and combinations thereof. In other embodiments, a solvent-borne coating has a density of 0.90 kg/L to 1.2 kg/L, including all intermediate ranges and combinations thereof. The density of a coating can be empirically determined, for example, as described in "ASTM Book of Standards, Volume 06.01, Paint—Tests for Chemical, Physical, and Optical Properties; Appearance," D1475-98, 2002. In certain embodiments, the course particle content of an architectural coating, by weight, is 0.5% or less. The coarse particle (e.g., coarse contaminants, pigment agglomerates) content of a coating can be empirically determined, for example, as described in "ASTM Book of Standards, Volume 06.03, Paint—Pigments, Drying Oils, Polymers, Resins, Naval Stores, Cellulosic Esters, and Ink Vehicles," D185-84, 2002. In some embodiments, the viscosity for an architectural coating at relatively low shear rates used during typical application, in Krebs Units ("Ku"), is 72 Ku to 95 Ku, including all intermediate ranges and combinations thereof.

In typical use, an architectural coating is often stored in a container for months or even years prior to first use, and/or between different uses. In many embodiments, it will be preferred that a building coating will retain a desirable set properties of a coating, film formation, film, or a combination thereof, for a period of 12 months or greater in a container at ambient conditions. Properties that are preferred for storage include settling resistance, skinning resistance, coagulation resistance, viscosity alteration resistance, or a combination thereof. Storage properties can be empirically determined for a coating (e.g., an architectural coating) as described, for example, in "ASTM Book of Standards, Volume 06.02, Paint—Products and Applications; Protective Coatings; Pipeline Coatings," D869-85 and D1849-95, 2002.

It is preferred that application and/or film formation of an architectural coating occurs at ambient conditions to provide ease of use to a casual user of the coating, as well as reduce potential damage to the target surface and the surrounding environment (e.g., unprotected people and objects). In general embodiments, it is preferred that an architectural coating does not undergo film formation by a temperature greater than 40° C. to reduce possible heat and fire damage. In other embodiments, it is preferred that an architectural coating is suitable to be applied by using hand-held applicator. Hand-held applicators are generally can be used without difficulty by most users of a coating, and examples include a brush, a roller, a sprayer (e.g., a spray can), or a combination thereof.

Specific procedures for determining the suitability of a coating and/or film for use as an architectural coating (e.g., a water-borne coating, a solvent-borne coating, an interior coating, an exterior paint, a latex paint), and specific assays for properties typically desired in an architectural coating (e.g., blocking resistance, hiding power, print resistance, washability, weatherability, corrosion resistance) have been described, for example, in "ASTM Book of Standards, Volume 06.02, Paint—Products and Applications; Protective Coatings; Pipeline Coatings," D5324-98, D5146-98, D3730-98, D1848-88, D5150-92, D2064-91, D4946-89, D6583-00, D3258-00, and D3450-00, 2002; "ASTM Book of Standards, Volume 06.01, Paint—Tests for Chemical, Physical, and Optical Properties; Appearance," D660-93, D4214-98, D772-86, D662-93, and D661-93, 2002; and in "Paint and Coating Testing Manual, Fourteenth Edition of the Gardner-Sward Handbook" (Koleske, J. V. Ed.), pp. 696-705, 1995.

(1) Wood Coatings

As is well known to those of ordinary skill in the art, a wood coating is often selected to protect the wood from damage, as well as aesthetic purposes. For example, wood is susceptible to damage from bacteria and fungi. Examples of fungi that damage wood include *Aureobasidium pullulans*, and *Ascomycotina, Deutermycotina, Basidiomycetes, Coniophora puteana, Serpula lacrymans*, and *Dacrymyces stillatus*. It is preferred that a wooden surface is impregnated with a preservative such as a fungicide, prior to application of a coating of the present invention. However, most wood that is contemplated as a surface for a coating of the present invention is provided this way from wood suppliers. Specific procedures for determining the presence of a preservative and/or water repellent in wood have been described, for example, in "ASTM Book of Standards, Volume 06.02, Paint—Products and Applications; Protective Coatings; Pipeline Coatings," D2921-98, 2002.

Typically, wood surfaces are coated with a paint, a varnish, a stain, or a combination thereof. Often, the choice of coating is based on the ability of a coating to protect the wood from damage by moisture. Generally, a paint, a varnish, and a stain generally have progressively greater permeability to moisture, and moisture penetration of a wooden surface can which can lead to undesirable alterations in wood structure (e.g., splitting); undesirable alteration in piece of wood's dimension ("dimensional movement") such as shrinking, swelling, and/or warping; promote the growth of a microorganism such as fungi (e.g., wet rot, dry rot); or a combination thereof. Additionally, UV light irradiation damages a wood surface by depolymerizing lignin comprised in the wood. It is preferred that in embodiments wherein a wood surface is irradiated by UV light (e.g., sunlight), the wood coating comprises a UV protective agent such as a pigment that absorbs UV light. An example of a UV absorbing pigment includes a transparent iron oxide.

A preferred paint for use on a wood surface comprises an oil-paint, an alkyd-paint, or a combination thereof. A preferred alkyd-paint for use on a wood surface comprises a solvent-borne paint. A preferred paint system comprises a combination of a primer, an undercoat, and a topcoat. A film produced by a paint is often moisture impermeable. A film produced by paint upon a wooden surface may crack, flake, trap moisture that can encourage wood decay, be expensive to repair, or a combination thereof.

(2) Masonry Coatings

Masonry coatings refer to coatings used on a masonry surface, such as, for example, stone, brick, tile, cement-based materials (e.g., concrete, mortar), or a combination thereof. In general embodiments, a masonry coating is selected to confer resistance to water (e.g., salt water), resistance to acid conditions, alteration of appearance (e.g., color, brightness), or a combination thereof. Typically, a masonry coating comprises a multicoat system. In specific embodiments, a masonry multicoat system comprises a primer, a topcoat, or a combination thereof. Examples of a masonry primer include a rubber primer (e.g., a styrene-butadiene copolymer primer). In certain embodiments, a topcoat comprises a water-borne coating or a solvent borne coating. Examples of a water-borne coating that may be selected for a masonry topcoat include a latex coating, a water reducible polyvinyl acetate-coating, or a combination thereof. In certain aspects, a solvent-borne topcoat comprises a thermoplastic coating, a thermosetting coating, or a combination thereof. Examples of a thermosetting coating include an oil, an alkyd, a urethane, an epoxy, or a combination thereof. In certain aspects, a thermosetting coating is a multi-pack coating, such as, for example, an epoxy, a urethane, or a combination thereof. In specific aspects, a thermosetting coating undergoes film formation at ambient conditions. In other aspects, a thermosetting coating undergoes film formation at film formation at an elevated temperature such as a baking alkyd, a baking acrylic, a baking urethane, or a combination thereof. Examples of a thermoplastic coating include an acrylic, cellulosic, a rubber-derivative, a vinyl, or a combination thereof. In specific aspects, a thermoplastic coating is a lacquer.

A masonry surface that is basic in pH, such as, for example, cement-based material and/or a calcareous stone (e.g., marble, limestone) may be damaging to certain coatings. Specific procedures for determining the pH of a masonry surface have been described, for example, in "ASTM Book of Standards, Volume 06.02, Paint—Products and Applications; Protective Coatings; Pipeline Coatings," D4262, 2002. Due to porosity and/or contact with an external environment, a masonry surface often accumulates dirt and other loose surface contaminants, which are preferably removed prior to application of a coating. Specific procedures for preparative cleaning (e.g., abrading, acid etching) of a masonry surface (e.g., sandstone, clay brick, concrete) have been described, for example, in "ASTM Book of Standards, Volume 06.02, Paint—Products and Applications; Protective Coatings; Pipeline Coatings," D4259-88, D4260-88D, 5107-90, D5703-95, D4261-83, and D4258-83, 2002. In certain embodiments, moisture at or near a masonry surface may be undesirable during application of a coating (e.g., a solvent-borne coating). Specific procedures for determining the presence of such moisture upon a masonry surface have been described, for example, in "ASTM Book of Standards, Volume 06.02, Paint—Products and Applications; Protective Coatings; Pipeline Coatings," D4263-83, 2002. Specific procedures for determining the suitability of a coating and/or film, particularly in conferring water resistance to a masonry surface, have been described, for example, in "ASTM Book of Standards, Volume 06.02, Paint—Products and Applications; Protective Coatings; Pipeline Coatings," D6237-98, D4787-93, D5860-95, D6489-99, D6490-99, and D6532-00, 2002. Additional procedures for determining the suitability of a coating and/or film for use as a masonry coating have been described, for example, in "Paint and Coating Testing Manual, Fourteenth Edition of the Gardner-Sward Handbook," (Koleske, J. V. Ed.), pp. 725-730, 1995.

(3) Artist's Coatings

Artist coatings refer to a coating used by artists for a decorative purpose. Often, an artist's coating (e.g., paint) is selected for durability for decades or centuries at ambient conditions, usually indoors. Coatings such as an alkyd coating, an oil coating, an oleoresinous coating, an emulsion (e.g., acrylic emulsion) coating, or a combination thereof, are typically selected for use as an artist's coating. Specific standards for physical properties, chemical properties, and/or procedures for determining the suitability (e.g., lightfastness) of a coating and/or film for use as an artist's coating have been described, for example, in "ASTM Book of Standards, Volume 06.02, Paint—Products and Applications; Protective Coatings; Pipeline Coatings," D4236-94, D5724-99, D4302-99, D4303-99, D4941-89, D5067-99, D5098-99, D5383-02, D5398-97, D5517-00, and D6801-02a, 2002; and in "Paint and Coating Testing Manual, Fourteenth Edition of the Gardner-Sward Handbook," (Koleske, J. V. Ed.), pp. 706-710, 1995.

b. Industrial Coatings

An industrial coating is a coating applied to a surface of a manufactured product in a factory setting. An industrial coating typically undergoes film formation to produce a film with a protective and/or aesthetic purpose. Industrial coatings share some similarities to an architectural coating, such as comprising similar coating components, being applied to the same material types of surfaces, being applied to an interior surface, being applied to an exterior surface, or a combination thereof. Examples of coating types that are commonly used for an industrial coating include an epoxy-coating, a urethane-coating, alkyd-coating, a vinyl-coating, chlorinated rubber-coating, or a combination thereof. Examples of a surface commonly coated by an industrial coating include metal (e.g., aluminum, zinc, copper, an alloy, etc); glass; plastic; cement; wood; paper; or a combination thereof. An industrial coating may be storage stable for 12 months or more, applied at ambient conditions, applied using a hand-held applicator, undergo film formation at ambient conditions, or a combination thereof.

However, an industrial coating often does not meet one or more of these characteristics previously described as preferred for an architectural coating. For example, an industrial coating may have a storage stability of only days, weeks, or months, as due to a more rapid use rate in coating factory prepared items. An industrial coating may be applied and/or undergo film formation at baking conditions. An industrial coating may be applied using techniques such as, for example, spraying by a robot, anodizing, electroplating, and/or laminating of a coating and/or film onto a surface. In some embodiments, an industrial coating undergoes film formation by irradiating the coating with non-visible light electromagnetic radiation and/or particle radiation such as UV radiation, infrared radiation, electron-beam radiation, or a combination thereof.

In certain embodiments, an industrial coating comprises an industrial maintenance coating, which is a coating that produces a protective film with excellent heat resistance (e.g., 121° C. or greater), solvent resistance (e.g., an industrial solvent, an industrial cleanser), water resistance (e.g., salt water, acidic water, alkali water), corrosion resistance, abrasion resistance (e.g., mechanical produced wear), or a combination thereof. An example of an industrial maintenance coating includes a high-temperature industrial maintenance coating, which is applied to a surface intermittently or continuously contacted with a temperature of 204° C. or greater. An additional example of an industrial maintenance coating is an industrial maintenance anti-graffiti coating, which is a two-pack clear coating applied to an exterior surface that is intermittently contacted with a solvent and abrasion. Examples of coating types that are commonly used for an industrial maintenance coating include an epoxy-coating, a urethane-coating, alkyd-coating, a vinyl-coating, chlorinated rubber-coating, or a combination thereof.

Industrial coatings (e.g., coil coatings) and their use are well known to those of ordinary skill in the art (see, for example, in "Paint and surface coatings: Theory and Practice," $2^{nd}$ Edition, pp. 502-528, 1999; in "Paints, Coatings and Solvents," $2^{nd}$ Edition, pp. 330-410, 1998; in "Organic Coatings: Science and Technology, Volume 1: Film Formation, Components, and Appearance," $2^{nd}$ Edition, pp. 138, 317-318). Standard procedures for determining the properties of an industrial coating (e.g., an industrial wood coating, an industrial water-reducible coating) have been described, for example, in "ASTM Book of Standards, Volume 06.02, Paint—Products and Applications; Protective Coatings; Pipeline Coatings," D4712-87a, D6577-00a, D2336-99, D3023-98, D3794-00, D4147-99, and D5795-95, 2002.

(1) Automotive Coatings

Automotive coatings refer to coatings used on automotive vehicles, particularly those for civilian use. The manufacturers of a vehicle typically require that a coating conform to specific properties of weatherability (e.g., UV resistance) and/or appearance. Typically, an automotive coating comprises a multicoat system. In specific embodiments, an automotive multicoat system comprises a primer, a topcoat, or a combination thereof. Examples of an automotive primer include a nonweatherable primer, which lack sufficient UV resistance for single layer use, or a weatherable primer, which possesses sufficient UV resistance to be used without an additional layer. Examples of a topcoat include an interior topcoat, an exterior topcoat, or a combination thereof.

Examples of a nonweatherable automotive primer include a primer applied by electrodeposition, a conductive ("electrostatic") primer, or a nonconductive primer. In certain embodiments, a primer is applied by electrodeposition, wherein a metal surface is immersed in a primer, and electrical current promotes application of a primer component (e.g., a binder) to the surface. An example of a metal primer suitable for electrodeposition application includes a primer comprising an epoxy binder comprising an amino moiety, a blocked isocyanate urethane binder, and a 75% to 95% aqueous liquid component. In other embodiments, a primer is a conductive primer, which allows additional coating layers to be applied using electrostatic techniques. A conductive primer typically is applied to a plastic surface, including a flexible plastic surface or a nonflexible plastic surface. Such primers vary in their respective flexibility property to better suit use upon the surface. An example of a flexible plastic conductive primer includes a primer comprising polyester binder, a melamine binder and a conductive carbon black pigment. An example of a nonflexible plastic primer includes a primer that comprises an epoxy ester binder and/or an alkyd binder, a melamine binder and conductive carbon black pigment. In certain embodiments, a melamine binder may be partly or fully replaced with an aromatic isocyanate urethane binder, wherein the coating is a two-pack coating. A nonconductive primer is similar to a conductive primer, except the carbon-black pigment is absent or reduced in content. In certain embodiments, a nonconductive primer is a metal primer, a plastic primer, or a combination thereof. In specific aspects, the nonconductive primer comprises a pigment for colorizing purposes.

Examples of a weatherable automotive primer include a primer/topcoat or a conductive primer. An example of a primer/topcoat includes a flexible plastic primer, with suitable weathering properties (e.g., UV resistance) to function as a single layer topcoat. Examples of a flexible plastic primer include a primer comprising an acrylic and/or polyester binder and a melamine binder. In certain embodiments, a melamine binder may be partly or fully replaced with an aliphatic isocyanate urethane binder, wherein the coating is a two-pack coating. A weatherable conductive primer typically is similar to a weatherable primer/topcoat, including a conductive pigment. In specific aspects, a weatherable automotive primer comprises a pigment for colorizing purposes.

An interior automotive topcoat typically is applied to a metal surface, a plastic surface, a wood surface, or a combination thereof. In certain aspects, an interior automotive topcoat is part of a multicoat system further comprising a primer. Examples of an interior automotive topcoat include a coating comprising a urethane binder, an acrylic binder, or a combination thereof.

An exterior automotive topcoat is typically is applied to a metal surface, a plastic surface, or a combination thereof. In certain aspects, an exterior automotive topcoat is part of a multicoat system further comprising a primer, sealer, undercoat, or a combination thereof. In certain embodiments, an exterior automotive topcoat comprises a binder capable of thermosetting in combination with a melamine binder. Examples of such a thermosetting binder include an acrylic binder, an alkyd binder, a urethane binder, polyester binder, or a combination thereof. In certain embodiments, a melamine binder may be partly or fully replaced with an urethane binder, wherein the coating is a two-pack coating. In typical embodiments, an exterior automotive topcoat further comprises a light stabilizer, a UV absorber, or a combination thereof. In general aspects, an exterior automotive topcoat further comprises a pigment.

Specific procedures for determining the suitability of a coating (e.g., a nonconductive coating) and/or film for use as an automotive coating, including spray application suitability, coating VOC content and film properties (e.g., corrosion resistance, weathering) have been described, for example, in "ASTM Book of Standards, Volume 06.01, Paint—Tests for Chemical, Physical, and Optical Properties; Appearance," D5087-02, D6266-00, and D6675-01, 2002; and "ASTM Book of Standards, Volume 06.02, Paint—Products and Applications; Protective Coatings; Pipeline Coatings," D5066-91, D5009-02, D5162-01, and D6486-01, 2002; and in "Paint and Coating Testing Manual, Fourteenth Edition of the Gardner-Sward Handbook," (Koleske, J. V. Ed.), pp. 711-716, 1995.

(2) Can Coatings

Can coatings refer to coatings used on a container (e.g., an aluminum container, a steel container), for food, chemicals, or a combination thereof. The manufacturers of a can typically require that a coating conform to specific properties of corrosion resistance, inertness (e.g., to prevent flavor alterations in food, a chemical reaction with a container's contents, etc), appearance, durability, or a combination thereof. Typically, a can coating comprises an acrylic-coating, an alkyd-coating, an epoxy-coating, a phenolic-coating, a polyester-coating, a poly(vinyl chloride)-coating, or combination thereof. Though a can may be made of the same or similar material, different surfaces of a can may require coatings of differing properties of inertness, durability and/or appearance. For example, a coating for a surface of the interior of a can that contacts the container's contents may be selected for a chemical inertness property, a coating for a surface at the end of a can may be selected for a physical durability property, or a coating for a surface on the exterior of a can may be selected for an aesthetic property. To meet the varying can surface requirements, a can coating may comprise a multicoat system. In specific embodiments, a can multicoat system comprises a primer, a topcoat, or a combination thereof. In certain embodiments, an epoxy-coating, a poly(vinyl chloride-coating), or a combination thereof is selected as a primer for a surface at the end of a can. In other embodiments, an oleoresinous-coating, a phenolic-coating, or a combination thereof is selected as a primer for a surface in the interior of a can. In some aspects, a water-borne epoxy and acrylic-coating is selected as a topcoat for a surface of an interior of a can. In addition embodiments, an acrylic-coating, an alkyd-coating, a polyester-coating, or a combination thereof is selected as an exterior coating. In certain facets, a can coating (e.g., a primer, a topcoat) will further comprise an amino resin, a phenolic resin, or a combination thereof for cross-linking in a thermosetting film formation reaction. In certain embodiments, a can coating is applied to a surface by spray application. In other embodiments, a can coating undergoes film formation by UV irradiation. Specific procedures for determining the suitability of a coating and/or film for use as a can coating, have been described, for example, in "Paint and Coating Testing Manual, Fourteenth Edition of the Gardner-Sward Handbook," (Koleske, J. V. Ed.), pp. 717-724, 1995.

(3) Sealant Coatings

Sealant coatings refer to coatings used to fill a joint to reduce or prevent passage of a gas (e.g., air), water, a small material (e.g., dust), a temperature change, or a combination thereof. A sealant coating ("sealant") may be thought of as a coating that bridges by contact two or more surfaces. A joint is a gap or opening between two or more surfaces, which may or may not be of the same material type (e.g., metal, wood, glass, masonry, plastic, etc). In typical embodiments, a joint has a width, depth, breadth, or a combination thereof, of 0.64 mm to 5.10 mm, including all intermediate ranges and combinations thereof.

In certain embodiments, a sealant coating comprises an oil, a butyl, an acrylic, a blocked styrene, a polysulfide, a urethane, a silicone, or a combination thereof. A sealant may be a solvent-borne coating or a water-borne coating (e.g., a latex). In certain aspects, a sealant comprises a latex (e.g., an acrylic latex). In other embodiments, a sealant is selected for flexibility, as one or more of the joint surfaces may move during normal use. Examples of a flexible sealant include a silicone, a butyl, an acrylic, a blocked styrene, an acrylic latex, or a combination thereof. An oil sealant typically comprises a drying oil, an extender pigment, a thixotrope, and a drier. A solvent-borne butyl sealant typically comprises a polyisobytylene and/or a polybutene, an extender pigment (e.g., talc, calcium carbonate), a liquid component, and an additive (e.g., an adhesion promoter, an antioxidant, a thixotrope). A solvent-borne acrylic sealant typically comprises a polymethylacrylate (e.g., polyethyl, polybutyl), a colorant, a thixotrope, an additive, and a liquid component. A solvent-borne blocked styrene sealant typically comprises styrene, styrene-butadiene, isoprene, or a combination thereof, and a liquid component. A solvent-borne acrylic sealant, blocked styrene sealant, or a combination thereof typically is selected for aspects wherein UV resistance is desired. A urethane sealant may be a one-pack or two-pack coating. A solvent-borne one-pack urethane sealant typically comprises an urethane that comprises a hydroxyl moiety, a filler, a thixotrope, an additive, an adhesion promoter, and a liquid component. A solvent-borne two-pack urethane sealant typically comprises a polyether that comprises an isocyanate moiety in one-pack and a binder comprising a hydroxyl moiety in a second pack. A solvent-borne two-pack urethane sealant typically also comprises a filler, an adhesion promoter, an additive (e.g., a light stabilizer), or a combination thereof. In certain aspects, a solvent-borne urethane sealant is selected for a sealant with a good abrasion resistance. A polysulfide sealant may be a one-pack or two-pack coating. A solvent-borne one-pack polysulfide sealant typically comprises an urethane that comprises a hydroxyl moiety, a filler, a thixotrope, an additive, an adhesion promoter, and a liquid component. A solvent-borne two-pack polysulfide sealant typically comprises a first pack, which typically comprises a polysulfide, an opacifying pigment, a colorizer (e.g., a pigment), clay, a thixotrope (e.g., a mineral), and a liquid component; and a second pack, which typically comprises a curing agent (e.g., lead peroxide), an adhesion promoter, an extender pigment, and a light stabilizer. A silicone sealant typically comprises a polydimethyllsiloxane and a methyltriacetoxy silane, a methyltrimethoxysilane, a methyltricyclorhexylaminosilane, or a combination thereof. A water-borne acrylic latex sealant typically comprises a thermoplastic acrylic, a filler, a surfactant, a thixotrope, an additive, and a liquid component. Procedures for determining the suitability of a coating and/or film for use as an sealant coating have been described, for example, in "Paint and Coating Testing Manual, Fourteenth Edition of the Gardner-Sward Handbook," (Koleske, J. V. Ed.), pp. 735-740, 1995.

(4) Marine Coatings

A marine coating is a coating used on a surface that contacts water, or a surface that is part of a structure continually near water (e.g., a ship, a dock, an drilling platform for fossil fuels, etc). Typically, such surfaces comprise metal, such as aluminum, high tensile steel, mild steel, or a combination thereof. For embodiments wherein a surface contacts water, the type of marine coating is selected to resist fouling, corrosion, or a combination thereof. Fouling is an accumulation of aquatic organisms, including microorganisms, upon a marine surface. Fouling can damage a film, and as many marine coatings are formulated with a preservative, an anti-corrosion property (e.g., an anticorrosion pigment), or a combination thereof, as such damage often leads to corrosion of metal surfaces. Additionally, a marine coating may be selected to resist fire, such as a coating applied to a surface of a ship. Further properties that are often desirable for a marine coating include chemical resistance, impact resistance, abrasion resistance, friction resistance, acoustic camouflage, electromagnetic camouflage, or a combination thereof.

To achieve the various properties of a marine coating, often a multicoat system is used. For metal surfaces, a primer known as a blast primer is typically applied to the surface within seconds of blast cleaning. Examples of a blast primer include a polyvinyl butyral ("PVB") and phenolic resin coating, a two-pack epoxy coating, or a two-pack zinc and ethyl silicate coating. A marine metal surface undercoat or topcoat typically comprises an alkyd coating, a bitumen coating, a polyvinyl coating, or a combination thereof. Marine coatings and their use are well known to those of ordinary skill in the art (see, for example, in "Paint and Surface Coatings: Theory and Practice," $2^{nd}$ Edition, pp. 529-549, 1999; in "Paints, Coatings and Solvents," $2^{nd}$ Edition, pp. 252-258, 1998; in "Organic Coatings: Science and Technology, Volume 1: Film Formation, Components, and Appearance," $2^{nd}$ Edition, pp. 138, 317-318). Specific procedures for determining the purity/properties of a marine coating, anti-fouling coating, or coating component thereof (e.g., cuprous oxide, copper powder, organotin) under marine conditions (e.g., submergence, water based erosion, seawater biofouling resistance, barnacle adhesion resistance) and/or film have been described, for example, in "ASTM Book of Standards, Volume 06.02, Paint—Products and Applications; Protective Coatings; Pipeline Coatings," D3623-78a, D4938-89, D4939-89, D5108-90, D5479-94, D6442-99, D6632-01, D4940-98, and D5618-94, 2002; and "ASTM Book of Standards, Volume 06.03, Paint—Pigments, Drying Oils, Polymers, Resins, Naval Stores, Cellulosic Esters, and Ink Vehicles," D912-81 and D964-65, 2002.

c. Specification Coatings

It is contemplated that, in light of the present disclosures, a specification coating may be formulated by selection of coating components one of ordinary skill in the art to fulfill a set of requirements prescribed by a consumer. Examples a specification finish coating include a military specified coating, a Federal agency specified coating (e.g., Department of Transportation), a state specified coating, or a combination thereof. A specification coating such as a CARC, a camouflage coating, or a combination thereof would be preferred in certain embodiments for incorporation of a biomolecule composition of the present invention. A camouflage coating is a coating that is formulated with materials (e.g., pigments) that reduce the visible differences between the appearance of a coated surface from the surrounding environment. Often, as would be known to one of ordinary skill in the art, a camouflage coating is formulated to reduce the detection of an coated surface by devise that measures nonvisible light (e.g., infrared radiation). Various sources of specification coating requirements are described in, for example, "Paint and Coating Testing Manual, Fourteenth Edition of the Gardner-Sward Handbook," (Koleske, J. V. Ed.), pp. 891-893, 1995).

(1) Pipeline Coatings

An example of a specification coating is a pipeline (e.g., a metal pipeline) coating used to convey a fossil fuel. A pipeline coating must possess corrosion resistance, and an example of a pipeline coating includes a coal tar-coating, a polyethylene-coating, an epoxy powder-coating, or a combination thereof. A coal tar-coating may comprise, for example, a coal tar mastic-coating, a coal tar epoxide-coating, a coal tar urethane-coating, a coal tar enamel-coating, or a combination thereof. A coal tar mastic-coating typically comprises an extender, a vicosifier, or a combination thereof. In general aspects, a coal tar mastic-coating layer is 127 mm to 160 mm thick, including all intermediate ranges and combinations thereof. In embodiments wherein superior water resistance is desired, a coal tar epoxide-coating may be selected. In embodiments wherein rapid film formation is desired (e.g., pipeline repair), a coal tar urethane-coating may be selected. In embodiments wherein good water resistance, heat resistance up to 82° C., bacterial resistance, poor UV resistance, or a combination thereof, is suitable, a coal tar enamel may be selected. In embodiments wherein cathodic protection, physical durability, or a combination thereof is desired, an epoxide powder-coating may be selected. In certain embodiments, an electrostatic spray applicator may be used to apply the powder coating. In certain embodiments, a pipeline coating comprises a multicoat system. In specific aspects, a pipeline multicoat system comprises an epoxy powder primer, a two-pack epoxy primer, a chlorinated rubber primer, or a combination thereof and a polyethylene topcoat. Specific procedures for determining the suitability of a coating and/or film for use as a pipeline coating, including coating storage stability (e.g., settling) and film properties (e.g., abrasion resistance, water resistance, flexibility, weathering, film thickness, impact resistance, chemical resistance, cathodic disbonding resistance, heat resistance) have been described, for example, in "ASTM Book of Standards, Volume 06.02, Paint—Products and Applications; Protective Coatings; Pipeline Coatings,"

G6-88, G9-87, G10-83, G11-88, G12-83, G13-89, G20-88, G70-81, G8-96, G17-88, G18-88, G19-88, G42-96, G55-88, G62-87, G80-88, G95-87, and D6676-01e1, 2002; and in "Paint and Coating Testing Manual, Fourteenth Edition of the Gardner-Sward Handbook," (Koleske, J. V. Ed.), pp. 731-734, 1995.

(2) Traffic Marker Coatings

A traffic marker coating is a coating (e.g., a paint) used to very visibly conveys information on a surface usually subjected to weathering and abrasion (e.g., a pavement). A traffic marker coating may be a solvent-borne coating or a water-borne coating. Examples of a solvent-borne traffic marker coating include an alkyd, a chlorinated rubber, or a combination thereof. In certain aspects, a solvent-borne coating is applied by spray application. In some embodiments, a traffic marker coating is a two-pack coating, such as, for example, an epoxy-coating, a polyester-coating, or a combination thereof. In other embodiments, a traffic marker coating comprises a thermoplastic coating, a thermosetting coating, or a combination thereof. Examples of a combination thermoplastic/thermosetting coating include a solvent-borne alkyd and/or solvent-borne chlorinated rubber-coating. Examples of a thermoplastic coating include a maleic-modified glycerol ester-coating, a hydrocarbon-coating, or a combination thereof. In certain aspects, a thermoplastic coating comprises a liquid component, wherein the liquid component comprises a plasticizer, a pigment, and an additive (e.g., a glass bead).

Specific procedures for determining the suitability of a coating and/or film for use as a traffic marker paint, including coating storage stability (e.g., settling), glass bead properties (e.g., reflectance), film durability (e.g., adhesion, pigment retention, solvent resistance, fuel resistance) and particularly relevant film visual properties (e.g., retroreflectance, fluorescence) have been described, for example, in "ASTM Book of Standards, Volume 06.02, Paint—Products and Applications; Protective Coatings; Pipeline Coatings," D713-90, D868-85, D969-85, D1309-93, D2205-85, D2743-68, D2792-69, D4796-88, D4797-88, D1155-89, D1214-89, and D4960-89, 2002; in "ASTM Book of Standards, Volume 06.01, Paint—Tests for Chemical, Physical, and Optical Properties; Appearance," F923-00, E1501-99e1, E1696-02, E1709-00e1, E1710-97, E1743-96, E2176-01, E808-01, E809-02, E810-01, E811-95, D4061-94, E2177-01, E991-98, and E1247-92, 2002; and in "Paint and Coating Testing Manual, Fourteenth Edition of the Gardner-Sward Handbook," (Koleske, J. V. Ed.), pp. 741-747, 1995.

(3) Aircraft Coatings

An aircraft coating protects and/or decorates a surface (e.g., metal, plastic) of an aircraft. Typically, an aircraft coating is selected for excellent weathering properties, excellent heat and cold resistance (e.g., −54° C. to 177° C.), or a combination thereof. Specific procedures for determining the suitability of a coating and/or film for use as aircraft coating, are described in, for example, in "Paint and Coating Testing Manual, Fourteenth Edition of the Gardner-Sward Handbook," (Koleske, J. V. Ed.), pp. 683-695, 1995.

(4) Nuclear Power Plant Coatings

An additional example of a specification coating is a coating for a nuclear power plant, which generally must possess particular properties (e.g., gamma radiation resistance, chemical resistance), as described in "ASTM Book of Standards, Volume 06.02, Paint—Products and Applications; Protective Coatings; Pipeline Coatings," D5962-96, D5163-91, D5139-90, D5144-00, D4286-90, D3843-00, D3911-95, D3912-95, D4082-02, D4537-91, D5498-01, and D4538-95, 2002.

H. Coating Components

In addition to the disclosures herein, the preparation and/or chemical syntheses of coating components, other than the microbial-based particulate matter of the present invention disclosed herein, are well known to those ordinary skill in the art [see, for example, "Paint and Coating Testing Manual, Fourteenth Edition of the Gardner-Sward Handbook," (Koleske, J. V., Ed.) (1995); "Paint and Surface Coatings, Theory and Practice, Second Edition," (Lambourne, R. and Strivens, T. A., Eds.) (1999); Wicks, Jr., Z. W., Jones, F. N., Pappas, S. P. "Organic Coatings, Science and Technology, Volume 1: Film Formation, Components, and Appearance," (1992); Wicks, Jr., Z. W., Jones, F. N., Pappas, S. P. "Organic Coatings, Science and Technology, Volume 2: Applications, Properties and Performance," (1992); "Paints, Coatings and Solvents, Second, Completely Revised Edition," (Stoye, D. and Freitag, W., Eds.) (1998); "ASTM Book of Standards, Volume 06.01, Paint—Tests for Chemical, Physical, and Optical Properties; Appearance," (2002); "ASTM Book of Standards, Volume 06.02, Paint—Products and Applications; Protective Coatings; Pipeline Coatings," (2002); "ASTM Book of Standards, Volume 06.03, Paint—Pigments, Drying Oils, Polymers, Resins, Naval Stores, Cellulosic Esters, and Ink Vehicles," (2002); and "ASTM Book of Standards, Volume 06.04, Paint—Solvents; Aromatic Hydrocarbons," (2002)].

However, as would be known to one of ordinary skill in the art, coating components are typically obtained from commercial vendors, which is a preferred method of obtaining a coating component due to ease and reduced cost. As would be known to one of ordinary skill in the art, texts as, for example, Flick, E. W. "Handbook of Paint Raw Materials, Second Edition," 1989, describes over 4,000 coating components (e.g., an antifoamer, an antiskinning agent, a bactericide, a binder, a defoamer, a dispersant, a drier, an extender, a filler, a flame/fire retardant, a flatting agent, a fungicide, a latex emulsion, an oil, a pigment, a preservative, a resin, a rheological/viscosity control agent, a silicone additive, a surfactant, a titanium dioxide, etc) provided by commercial vendors; and Ash, M. and Ash, I. "Handbook of Paint and Coating Raw Materials, Second Edition," 1996, which describes over 18,000 coating components (e.g., an accelerator, an adhesion promoter, an antioxidant, an antiskinning agent, a binder, a coalescing agent, a defoamer, a diluent, a dispersant, a drier, an emulsifier, a fire retardant, a flow control agent, a gloss aid, a leveling agent, a marproofing agent, a pigment, a slip agent, a thickener, a UV stabilizer, viscosity control agent, a wetting agent, etc) provided by commercial vendors.

Specific commercial vendors are referred to herein as examples, and include Acima™ AG, Im Ochsensand, CH-9470 Buchs/SG; Air Products and Chemicals, Inc., 7201 Hamilton Boulevard, Allentown, Pa. 18195-1501; Avecia Inc., 1405 Foulk Road, PO Box 15457, Wilmington, Del. 19850-5457, U.S.A.; Bayer Corporation, 100 Bayer Rd., Pittsburgh, Pa. 15205-9741, U.S.A.; Buckman Laboratories, Inc., 1256 North McLean Blvd., Memphis, Tenn. 38108-0305, U.S.A.; BYK-Chemie GmbH, Abelstrasse 45, P.O. Box 100245, D-46462 Wesel, Germany; Ciba Specialty Chemicals, 540 White Plains Road, P.O. Box 2005, Tarrytown, N.Y. 10591-9005, U.S.A.; Clariant LSM (America) Inc., 200 Rodney Building, 3411 Silverside Road, Wilmington, Del. 19810 U.S.A.; Cognis Corporation, 5051 Estecreek Drive, Cincinnati, Ohio 45232-1446, U.S.A.; Condea Servo LLC., 4081 B Hadley Road, South Plainfield, N.J. 07080-1114, U.S.A.; Cray Valley Limited, Waterloo Works, Machen, Caerphilly CF83 8YN United Kingdom; Dexter Chemical L.L.C., 845 Edgewater Road Bronx, N.Y. 10474, U.S.A.; Dow Chemical Company, 2030 Dow Center, Midland, Mich. 48674 U.S.A.; Elementis Specialties, Inc., PO Box 700, 329 Wyckoffs Mill Road, Hightstown, N.J. 08520 U.S.A.; Goldschmidt Chemical Corp., 914 East Randolph Road PO Box 1299 Hopewell, Va. 23860 U.S.A.; Hercules Incorporated, 1313 North Market Street, Wilmington, Del. 19894-0001, U.S.A.; International Specialty Products, 1361 Alps Road, Wayne, N.J. 07470, U.S.A.; Octel-Starreon LLC USA, North American Headquarters, 8375 South Willow Street, Littleton, Colo. 80124, U.S.A.; Rohm and Haas Company, 100 Independence Mall West, Philadelphia, Pa. 19106-2399, U.S.A.; Solvay Advanced Functional Minerals, Via Varesina 2-4, I-21021 Angera (VA); Troy Corporation, 8 Vreeland Road, PO Box 955, Florham Park, N.J., 07932 U.S.A.; R. T. Vanderbilt Company, Inc., 30 Winfield Street, Norwalk, Conn. 06855, U.S.A; Union Carbide Chemicals and Plastics Co., Inc., 39 Old Ridgebury Road, Danbury, Conn. 06817-0001, U.S.A.

1. Binders

A binder ("polymer," "resin," "film former") is a molecule capable of film formation. Film formation is a physical and/or chemical change of a binder in a coating, wherein the change converts the coating into a film. Often, a binder converts into a film through a polymerization reaction, wherein a first binder molecule covalently bonds with at least a second binder molecule to form a larger molecule, known as a "polymer." As this process is repeated a plurality of times, the composition converts from a coating comprising a binder into a film comprising a polymer.

A binder may comprise a monomer, an oligomer, a polymer, or a combination thereof. A monomer is a single unit of a chemical species that can undergo a polymerization reaction. However, a binder itself is often a polymer, as such larger binder molecules are more suitable for formulation into a coating capable of both being easily applied to a surface and undergoing an additional polymerization reaction to produce a film. An oligomer comprises 2 to 25 polymerized monomers, including all intermediate ranges and combinations thereof.

A homopolymer is a polymer that comprises monomers of the same chemical species. A copolymer is a polymer that comprises monomers of at least two different chemical species. A linear polymer is an unbranched chain of monomers. A branched polymer is a branched ("forked") chain of monomers. A network ("cross-linked") polymer is a branched polymer wherein at least one branch forms an interconnecting covalent bond with at least one additional polymer molecule.

A thermoplastic binder and/or coating reversibly softens and/or liquefies when heated. Film formation for a thermoplastic coating generally comprises a physical process, typically the loss of the volatile (e.g., liquid) component from a coating. As a volatile component is removed, a solid film may be produced through entanglement of the binder molecules. In many aspects, a thermoplastic binder is generally a higher molecular mass than a comparable thermosetting binder. In many aspects, a thermoplastic film is often susceptible to damage by a volatile component that can be absorbed by the film, which can soften and/or physically expand the film. In certain facets, a thermoplastic film may be removed from a surface by use of a volatile component. However, in many aspects, damage to a thermoplastic film may be repaired by application of a thermoplastic coating into the damaged areas and subsequent film formation.

A thermosetting binder undergoes film formation by a chemical process, typically the cross-linking of a binder into a network polymer. In certain embodiments, a thermosetting binder does not possess significant thermoplastic properties.

The glass transition temperature is the temperature wherein the rate of increase of the volume of a binder or a film changes. Binders and films often do not convert from solid to liquid ("melt") at a specific temperature ("$T_m$"), but rather possess a specific glass transition temperature wherein there is an increase in the rate of volume expansion with increasing temperature. At temperatures above the glass transition temperature, a binder or film becomes increasingly rubbery in texture until it becomes a viscous liquid. In certain embodiments described herein, a binder, particularly a thermoplastic binder, may be selected by its glass transition temperature, which provides guidance to the temperature range of film formation, as well as thermal and/or heat resistance of a film. The lower the $T_g$, the "softer" the resin, and generally, the film produced from such a resin. A softer film typically possesses greater flexibility (e.g., crack resistance) and/or poorer resistance to dirt accumulation than a harder film.

In certain embodiments, a coating comprises a low molecular weight polymer, a high molecular weight polymer, or a combination thereof. Examples of a low molecular weight polymer include an alkyd, an amino resin, a chlorinated rubber, an epoxide resin, an oleoresinous binder, a phenolic resin, a urethane, a polyester, an urethane oil, or a combination thereof. Examples of a high molecular weight polymer include a latex, a nitrocellulose, a non-aqueous dispersion polymer ("NAS"), a solution acrylic, a solution vinyl, or a combination thereof. Examples of a latex include an acrylic, a polyvinyl acetate ("PVA"), a styrene/butadiene, or a combination thereof.

In addition to the disclosures herein, a binder, methods of binder preparation, commercial vendors of binder, and techniques for using an binder in a coating known to those of ordinary skill in the art may be applied in the practice of the present invention (see, for example, Flick, E. W. "Handbook of Paint Raw Materials, Second Edition," pp. 287-805 and 879-998, 1989; in "Paint and Coating Testing Manual, Fourteenth Edition of the Gardner-Sward Handbook," (Koleske, J. V. Ed.), pp. 23-29, 39-67, 74-84, 87, 268-285, 410, 539-540, 732, 735-736, 741, 770, 806-807, 845-849, and 859-861, 1995; in "Paint and Surface Coatings, Theory and Practice, Second Edition," (Lambourne, R. and Strivens, T. A., Eds.), pp. 2-3, 7-10, 21, 24-40, 40-54, 60-71, 76, 81-86, 352, 358, 381-394, 396, 398, 405, 433-448, 494-497, 500, 537-540, 700-702, and 734, 1999; Wicks, Jr., Z. W., Jones, F. N., Pappas, S. P. "Organic Coatings, Science and Technology, Volume 1: Film Formation, Components, and Appearance," pp. 39, 49-57, 62, 65-67, 67, 76-80, 83, 91, 104-118, 155, 168, 178, 182-183, 200, 202-203, 209, 214-216, 220 and 250, 162-186, 215-216 and 232, 59-60, 183-184, 133-143, 39, 144-161, 203, 219-220 and 239, 23, 110, 120-132, 122-130, 198, 202-203, 209 and 220, 60-62, 83-103, 164-167, 173, 177-178, 184-187, 195, 206, and 216-219, 1992; Wicks, Jr., Z. W., Jones, F. N., Pappas, S. P. "Organic Coatings, Science and Technology, Volume 2: Applications, Properties and Performance," pp. 13-14, 18-19, 26, 33-34, 36, 41, 57, 77, 92, 95, 116-119, 143-145, 156, 161-165, 179-180, 191-193, 197-203, 210-211, 213-214, 216, 219-222, 230-239, 260-263, 269-271, 276-284, 288-293, 301-307, 310, 315-316, 319-321, and 325-346, 1992; and in "Paints, Coatings and Solvents, Second, Completely Revised Edition," (Stoye, D. and Freitag, W., Eds.) pp. 5, 11-22, 37-50, 54-55, 72, 80-87, 96-98, 108, 126, and 136, 1998.

a. Oil-Based Binders

Certain binders, such as, for example, an oil (e.g., a drying oil), an alkyd, an oleoresinous binder, a fatty acid epoxide ester, or a combination thereof, are prepared and/or synthesized from an oil and/or a fatty acid, and undergo film formation by thermosetting oxidative cross-linking of fatty acids, and will be referred to herein as an "oil-based binder." These types of binders often possess similar properties (e.g., solubility, viscosity). An oil-based binder coating often further comprises a drier, an antiskinning agent, an alkylphenolic resin, a pigment, an extender, a liquid component (e.g., a solvent), or a combination thereof. A drier, such as a primary drier, secondary drier, or a combination thereof, may be selected to promote film formation. In certain facets, an oil-based binder coating may comprise an anti-skinning agent, which is typically used to control undesirable film-formation caused by a primary drier and/or oxidation. A liquid component may be selected, for example, to alter a rheological property (e.g., flow), wetting and/or dispersion of particulate material, or a combination thereof. In certain embodiments, a liquid component comprises a hydrocarbon. In particular embodiments, the hydrocarbon comprises an aliphatic hydrocarbon, an aromatic hydrocarbon (e.g., toluene, xylene), or a combination thereof. In some facets, the liquid component comprises, by weight, 5% to 20% of an oil-based binder coating, including all intermediate ranges and combinations thereof.

In alternative embodiments, an oil-based temporary coating (e.g, a non-film forming coating) may be produced, for example, by inclusion of an antioxidant, reduction of the amount of a drier, selection of a oil-based binder that comprises fewer or no double bonds, or a combination thereof.

An oil-based binder coating may be selected for embodiments wherein a relatively low viscosity is desired, such as, for example, application to a corroded metal surface, a porous surface (e.g., wood), or a combination thereof, due to the penetration power of a low viscosity coating. In certain facets, it is preferred that application of an oil-binder coating produces a layer is less than 25 µm on vertical surfaces and 40 µm on horizontal surfaces to reduce shrinkage, wrinkling. Additionally, in aspects wherein the profile of the wood surface is to be retained, a such a thin film thickness is preferred. In specific aspects, an oil-binder coating may be selected as a wood stains, a topcoat, or a combination thereof. In particular facets, a wood stain comprises an oil (e.g., linseed oil) coating, an alkyd, or a combination thereof. Often, wood coating comprises a lightstabilizer (e.g., UV absorber).

(1) Oils

An oil is a polyol esterified to at least one fatty acid. A polyol ("polyalcohol," "polyhydric alcohol") is an alcohol comprising more than one hydroxyl moiety per molecule. In certain embodiments, an oil comprises an acylglycerol esterified to one fatty acid ("monacylglycerol"), two fatty acids ("diacylglycerol"), or three fatty acids ("triacylglycerol," "triglyceride"). Typically, however, an oil will comprise a triacylglycerol. A fatty acid is an organic compound comprising a hydrocarbon chain that includes a terminal carboxyl moiety. A fatty acid may be unsaturated, monounsaturated, and polyunsaturated referring to whether the hydrocarbon chain possess no carbon double bonds, one carbon double bond, or a plurality of carbon double bonds (e.g., 2, 3, 4, 5, 6, 7, or 8 double bonds), respectively.

In typical use in a coating, a plurality of fatty acids forms covalent cross-linking bonds to produce a film in coatings comprising oil binders and/or other binders comprising a fatty acid. Usually oxidation through contact with atmospheric oxygen is used to promote film formation. Exposure to light also enhances film formation. The ability of an oil to undergo film formation by chemical cross-linking is related to the content of chemically reactive double bonds available in its fatty acids. Oils are generally a mixture of chemical species, comprising different combinations of fatty acids esterified to glycerol. The overall types and percentages of particular fatty acids that are comprised in oils affect the ability of the oil to be used as a binder. Oils can be classified as a drying oil, a semi-drying oil, or a non-drying oil depending upon the ability of the oil to cross-link into a dry film without additives (e.g., driers) at room temperature and atmospheric oxygen. A drying oil forms a dry film to touch upon cross-linking, a semi-drying oil forms a sticky ("tacky") film to touch upon cross-linking, while a non-drying oil does not produce a tacky or dry film upon cross-linking. In certain facets, it is contemplated that film-formation of a non-chemically modified oil-binder coating will typically take from 12 hours to 24 hours at room temperature, air, and lighting. Procedures for selection and testing of drying oils for a coating are described in, for example, "ASTM Book of Standards, Volume 06.03, Paint—Pigments, Drying Oils, Polymers, Resins, Naval Stores, Cellulosic Esters, and Ink Vehicles," D555-84, 2002.

Drying oils comprise at least one polyunsaturated fatty acid to promote cross-linking. Polyunsaturated fatty acids ("polyenoic fatty acids") include, but are not limited to, 7,10,13-hexadecatrienoic ("16:3 n-3"); linoleic ["9,12-octadecadienoic," "18:2(n-6)"]; γ-linolenic ["6,9,12-octadecatrienoic," "18:3(n-6)"]; a trienoic 20:3(n-9); dihomo-γ-linolenic ["8,11,14-eicosatrienoic," "20:3(n-6)"]; arachidonic ["5,8,11,14-eicosatetraenoic," "20:4(n-6)"]; a licanic, ("4-oxo 9c11t13t-18:3"); 7,10,13,16-docosatetraenoic ["22:4(n-6)"]; 4,7,10,13,16-docosapentaenoic ["22:5(n-6)"]; α-linolenic ["9,12,15-octadecatrienoic," "18:3(n-3)"]; stearidonic ["6,9,12,15-octadecatetraenoic," "18:4(n-3)"]; 8,11,14,17-eicosatetraenoic ["20:4(n-3)"]; 5,8,11,14,17-eicosapentaenoic ["EPA," "20:5(n-3)"]; 7,10,13,16,19-docosapentaenoic ["DPA," "22:5(n-3)"]; 4,7,10,13,16,19-docosahexaenoic ["DHA," "22:6(n-3)"]; 5,8,11-eicosatrienoic ["Mead acid," "20:3(n-9)"]; taxoleic ("all-cis-5,9-18:2"); pinolenic ("all-cis-5,9,12-18:3"); sciadonic ("all-cis-5,11,14-20:3"); dihomotaxoleic ("7,11-20:2"); cis-9, cis-15 octadecadienoic ("9, 15-18:2"); retinoic; or a combination thereof.

Drying oils can be further characterized as non-conjugated or conjugated drying oils depending upon whether their most abundant fatty acid comprises a polymethylene-interrupted double bond or a conjugated double bond, respectively. A polymethylene-interrupted double bond is two double bonds separated by two or more methylene moieties. A polymethylene-interrupted fatty acid is a fatty acid comprising such a configuration of double bonds. Examples of polymethylene-interrupted fatty acids include taxoleic, pinolenic, sciadonic, dihomotaxoleic, cis-9, cis-15 octadecadienoic, retinoic, or a combination thereof.

A conjugated double bond is a moiety wherein a single methylene moiety connects pair of carbon chain double bonds. A conjugated fatty acid is a fatty acid comprising such a pair of double bonds. A conjugated double bond is more prone to cross-linking reactions than non-conjugated double bonds. A conjugated diene fatty acid, a conjugated triene fatty acid or a conjugated tetraene fatty acid, possesses only two, three or four conjugated double bonds, respectively. An example of a common conjugated diene fatty acid is a conjugated linoleic. Examples of a conjugated triene fatty acid include an octadecatrienoic, a licanic, or a combination thereof. Examples of an octadecatrienoic acid include an α-eleostearic comprising the 9c, 11t, 13t isomer, a calendic comprising a 8t, 10t, 12c isomer, a catalpic comprising the 9c, 11t, 13c isomer, or a combination thereof. An example of a conjugated tetraene fatty acid is α-parinaric comprising the 9c, 11t, 13t, 15c isomer, and β-parinaric comprising the 9t, 11t, 13t, 15t isomer, or a combination thereof.

Oils for use in coatings are generally obtained from renewable biological sources, such as plants, fish or a combination thereof. Examples of plant oils commonly used in coatings or coating components include cottonseed oil, linseed oil, oiticica oil, safflower oil, soybean oil, sunflower oil, tall oil, rosin, tung oil, or a combination thereof. An example of a fish oil commonly used in coatings or coating components include caster oil. A colder environment generally promotes a higher polyunsaturated fatty acid content in an organism (e.g., sunflowers). Cottonseed oil comprises about 36% saturated fatty acids, 24% oleic, and 40% linoleic. Castor oil comprises about 3% saturated fatty acids, 7% oleic, 3% linoleic, and 87% ricinoleic ("12-hydroxy-9-octadecenoic"). Linseed oil comprises about 10% saturated fatty acids, 20% to 24% oleic ("cis-9-octadecenoic"), 14% to 19% linoleic, and 48% to 54% linolenic. Oiticica oil comprises about 16% saturated fatty acids, 6% oleic, and 78% licanic. Safflower oil comprises about 11% saturated fatty acids, 13% oleic, 75% linoleic, and 1% linolenic. Soybean oil comprises about 14% to 15% saturated fatty acids, 22% to 28% oleic, 52% to 55% linoleic, and 5% to 9% linolenic. Tall oil, which is a product of paper production and generally is not in the form of a triglyceride, often comprises about 3% saturated fatty acids, 30% to 35% oleic, 35% to 40% linoleic, 2% to 5% linolenic, and 10% to 15% of a combination of pinolenic and conjugated linoleic. Rosin is a combination of acidic compounds isolated during paper production, such as, for example, abietic acid, neoabietic acid, dihydroabietic acid, tetraabietic acid, isodextropimaric acid, dextropimaric acid, dehydroabietic acid, and levopimaric acid. Tung oil comprises about 5% saturated fatty acids, 8% oleic, 4% linoleic, 3% linolenic, and 80% α-elestearic. Standards for physical properties, chemical properties, and/or procedures for testing the purity/properties of various oils (e.g., caster, linseed, oiticica, safflower, soybean, sunflower, tall, tung, rosin, dehydrated caster, boiled linseed, a drying oil, a fish oil, a heat-bodied drying oil) for use in a coating are described, for example in "ASTM Book of Standards, Volume 06.03, Paint—Pigments, Drying Oils, Polymers, Resins, Naval Stores, Cellulosic Esters, and Ink Vehicles," D555-84, D960-02a, D961-86, D234-82, D601-87, D1392-92, D1462-92, D12-88, D1981-02, D5768-95, D3169-89, D260-86, D124-88, D803-02, D1541-97, D1358-86, D1950-86, D1951-86, D1952-86, D1954-86, D1958-86, D464-95, D465-01, D1959-97, D1960-86, D1962-85, D1964-85, D1965-87, D1966-69, D1967-86, D3725-78, D1466-86, D890-98, D1957-86, D1963-85, D5974-00, D1131-97, D1240-02, D889-99, D509-98, D269-97, D1065-96, and D804-02, 2002.

In certain embodiments, an oil comprises a chemically modified oil, which is an oil altered by a reaction thought to promote limited cross-linking. Generally, such a modified oil possesses an altered property, such as a higher viscosity, which may be more suitable for a particular coating application. Examples of a chemically modified oil include a bodied oil, a blown oil, a dimer acid, or a combination thereof. A bodied oil ("heat bodied oil," "stand oil") is produced, for example, by heating a nonconjugated oil (e.g., 320° C.) or a conjugated oil (e.g., 240° C.) in an chemically unreactive atmosphere to promote limited cross-linking. A blown oil is produced, for example, by passing air through a drying oil at, for example, 150° C. A dimer acid is produced, for example, by acid catalyzed dimerization or oligomerization of a polyunsaturated acid.

In certain embodiments, an oil comprises a synthetic conjugated oil, which is an oil altered by a reaction thought to produce a conjugated double bond in a fatty acid of the oil. Conjugated fatty acids have been produced from non-conjugated fatty acids by alkaline hydroxide catalyzed reactions. However, a synthetic conjugated oil is generally semi-drying in air catalyzed film formation at room temperature, and a coating comprising such an oil is typically cured by baking. Additionally richinoleic acid, which is prevalent in castor oil, can be dehydrogenated to produce a mixture of conjugated and non-conjugated fatty acids. Dehydrogenated castor oil comprises about 2% to 4% saturated fatty acids, 6% to 8% oleic, 48% to 50% linoleic, and 40% to 42% conjugated linoleic.

Certain other compounds comprising a fatty acid and polyol are classified herein as an oil for use as a binder such as a high ester oil, a maleated oil, or a combination thereof. A high ester oil comprises a polyol capable of comprising greater than three fatty acid esters per molecule and at least one fatty acid ester. However, a high ester oil comprising four or more fatty acid esters per molecule is preferred. Examples of such a polyol include a pentaerythritiol, a dipentaerythritiol, a tripentaerythritiol, or a styrene/allyl alcohol copolymer. These high ester oils generally form films more rapidly than acylglycerol based oil, as the opportunity for cross-linking reactions between fatty acids increases with the number of fatty acids attached to a single polyol. A maleated oil is an oil modified by a chemical reaction with maleic anhydride. Maleic acid and an unsaturated or polyunsaturated fatty acid react to produce a fatty acid with additional acid moieties. A maleated oil generally is more hydrophilic and/or has a faster film formation time than a comparative non-maleated oil.

(2) Alkyd Resins

In certain embodiments, a binder can comprise an alkyd resin. In general embodiments, an alkyd-coating may be selected as an architectural coating, a metal coating, a plastic coating, a wood coating, or a combination thereof. In certain aspects, an alkyd coating may be selected for use as a primer, an undercoat, a topcoat, or a combination thereof. In particular aspects, an alkyd coating comprises a pigment, an additive, or a combination thereof.

An alkyd resin comprises a polyester prepared from a polyol, a fatty acid, and a polybasic ("polyfunctional") organic acid or acid anhydride. An alkyd resin is generally produced by first preparing monoacylpolyol, which is a polyol esterified to one fatty acid. The monoacylpolyol is polymerized by ester linkages with a polybasic acid to produce an alkyd resin of desired viscosity in a solvent. Examples of a polyol include 1,3-butylene glycol; diethylene glycol; dipentaerythritol; ethylene glycol; glycerol; hexylene glycol; methyl glucoside; neopentyl glycol; pentaerythritol; pentanediol; propylene glycol; sorbitol; triethylene glycol; trimethylol ethane; trimethylol propane; trimethylpentanediol; or a combination thereof. In certain aspects, a polyol comprises ethylene glycol; glycerol; neopentyl glycol; pentaerythritol; trimethylpentanediol; or a combination thereof. Examples of a polybasic acid or an acid anhydride include adipic acid, azelaic acid, chlorendic anhydride, citric acid, fumaric acid, isophthalic acid, maleic anhydride, phthalic anhydride, sebacic acid, succinic acid, trimelletic anhydride, or a combination thereof. In certain aspects, a polybasic acid or an acid anhydride comprises isophthalic acid, maleic anhydride, phthalic anhydride, trimellitic anhydride, or a combination thereof. Examples of a fatty acid include abiatic, benzoic, caproic, caprylic, lauric, linoleic, linolenic, oleic, a tertiary-butyl benzoic acid, a fatty acid from an oil/fat (e.g., castor, coconut, cottonseed, tall, tallow), or a combination thereof. In certain aspects, a fatty acid comprises benzoic, a fatty acid from tall oil, or a combination thereof. In specific aspects, an oil is used in the reaction directly as a source of a fatty acid and/or a polyol. Examples of an oil include castor oil, coconut oil, corn oil, cottonseed oil, dehydrated castor oil, linseed oil, safflower oil, soybean oil, tung oil, walnut oil, sunflower oil, menhaden oil, palm oil, or a combination thereof. In some aspects, an oil comprises coconut oil, linseed oil, soybean oil, or a combination thereof.

In addition to the standards and analysis techniques previously described for an oil, standards for physical properties, chemical properties, and/or procedures for testing the purity/properties of various fatty acids (e.g., coconut, corn, cottonseed, dehydrated caster, linseed, soybean, tall oil fatty acids, rosin fatty acids) and a polyol (e.g., pentaerythritol, hexylene glycol, ethylene glycol, diethylene glycol, propylene glycol, dipropylene glycol) and acid anhydrides (e.g., phthalic anhydride, maleic anhydride) for use in an alkyd or other coating components are described, for example, in "ASTM Book of Standards, Volume 06.03, Paint—Pigments, Drying Oils, Polymers, Resins, Naval Stores, Cellulosic Esters, and Ink Vehicles," D1537-60, D1538-60, D1539-60, D1841-63, D1842-63, D1843-63, D5768-95, D1981-02, D1982-85, D1980-87, D804-02, D1957-86, D464-95, D465-01, D1963-85, D5974-00, D1466-86, D2800-92, D1585-96, D1467-89, and D1983-90, 2002; and in "ASTM Book of Standards, Volume 06.04, Paint—Solvents; Aromatic Hydrocarbons," D2403-96, D3504-96, D2930-94, D3366-95, D3438-99, D2195-00, D2636-01, D2693-02, D2694-91, D5164-91, D1257-90, and D1258-95, 2002. Further, the composition, properties and/or purity of an alkyd resin and/or a solution comprising an alkyd resin selected for use in a coating such as phthalic anhydride content, isophthalic acid content, unsaponifiable matter content, fatty acid content/identification, polyhydric alcohol content/identification, glycerol, ethylene glycol and/or pentaerythirol content, and silicon content can be empirically determined by procedures known to those of ordinary skill in the art (see, for example, "ASTM Book of Standards, Volume 06.03, Paint—Pigments, Drying Oils, Polymers, Resins, Naval Stores, Cellulosic Esters, and Ink Vehicles," D2689-88, D563-88, D2690-98, D2998-89, D1306-88, D1397-93, D1398-93, D2455-89, D1639-90, D1615-60, and D2456-91, 2002).

(i) Oil Length Alkyd Binders

In specific embodiments, an alkyd resin may be selected based on the materials used in its preparation, which typically affect the alkyd's properties. In general aspects, an alkyd resin is often classified and/or selected for use in a particular application by its oil content, as the oil content affects the alkyd resin properties. Oil content is the amount of oil relative to the solvent-free alkyd resin. Based on oil content, an alkyd resin may be classified as a very long oil alkyd resin, a long oil alkyd resin, a medium oil alkyd resin, or a short oil alkyd resin. Generally, the greater the oil content classification of an alkyd resin that is comprised in a coating, the greater the ease of brush application, the slower the rate of film formation, the greater the film's flexibility, the poorer the chemical resistance of the film, the poorer the retention of gloss in exterior environments, or a combination thereof. A short oil alkyd, a medium oil alkyd, a long oil alkyd, and a very long oil alkyd has an oil content range of 1% to 40%, 40% to 60%, 60% to 70%, and 70% to 85%, respectively, including all intermediate ranges and combinations thereof, respectively. In typical embodiments, a short oil alkyd, a medium oil alkyd, a long oil alkyd, and a very long oil alkyd resin and/or coating comprise 50%, 45% to 50%, 60% to 70%, or 85% to 100% nonvolatile component, respectively.

In certain embodiments, a short oil alkyd coating may be selected as an industrial coating. In certain aspects, a short oil alkyd is synthesized from an oil, wherein the oil comprises castor, dehydrated castor, coconut, linseed, soybean, tall, or a combination thereof. In some aspects, the oil of a short oil alkyd comprises a saturated fatty acid. Examples of a saturated fatty acid include, but are not limited to, caproic ("hexanoic," "6:0"); caprylic ("octanoic," "8:0"); lauric ("dodecanoic," "12:0"); or a combination thereof. In particular facets, a short oil alkyd coating comprises a solvent, wherein the solvent comprises an aromatic hydrocarbon, isobutanol, VMP naphtha, xylene, or a combination thereof. In other facets, the aromatic solvent comprises a high boiling aromatic solvent. In some aspects, a short oil alkyd is insoluble or poorly soluble in an aliphatic hydrocarbon. In further embodiments, a short oil alkyd coating undergoes film formation by baking.

In certain embodiments, a medium oil alkyd coating may be selected as a farm implement coating, a railway equipment coating, a maintenance coating, or a combination thereof. In certain aspects, a medium oil alkyd is synthesized from an oil, wherein the oil comprises linseed, safflower, soybean, sunflower, tall, or a combination thereof. In some aspects, the oil of a medium oil alkyd comprises a monounsaturated fatty acid (e.g., oleic acid). In particular facets, a medium oil alkyd coating comprises a solvent, wherein the solvent comprises an aliphatic hydrocarbon, an aromatic hydrocarbon, or a combination thereof.

In certain embodiments, a tall oil alkyd coating may be selected as an architectural coating, a maintenance coating, a primer, a topcoat, or a combination thereof. In certain aspects, a tall oil alkyd is synthesized from an oil, wherein the oil comprises linseed, safflower, soybean, sunflower, tall, or a combination thereof. In some aspects, the oil of a long oil alkyd comprises a polyunsaturated fatty acid. In particular facets, a tall oil alkyd coating comprises a solvent, wherein the solvent comprises an aliphatic hydrocarbon.

In certain embodiments, a very long oil alkyd coating may be selected as a latex architectural coating, a wood stain, or a combination thereof. In certain aspects, a very long oil alkyd is synthesized from an oil, wherein the oil comprises linseed, soybean, tall, or a combination thereof. In some aspects, the oil of a long oil alkyd comprises a polyunsaturated fatty acid. In particular facets, a very long oil alkyd coating comprises a solvent, wherein the solvent comprises an aliphatic hydrocarbon.

(ii) High Solid Alkyd Coatings

A high solid alkyd possesses a reduced viscosity, a lower average molecular weight, or a combination thereof. A high solid alkyd may be selected for embodiments wherein a reduced quantity liquid content (e.g., solvent) of a coating is desired. In some embodiments, a high solid alkyd coating comprises an enamel coating. In other aspects, a high solid long or very long oil alkyd coating comprises an architectural coating. In further aspects, a high solid medium oil alkyd coating comprises a transportation coating. In further aspects, a high solid short oil alkyd coating comprises an industrial coating. Additional, various chemical moieties may be incorporated in an alkyd to modify a property. Examples of such moieties include an acrylic, a benzoic acid, an epoxide, an isocyanate, a phenolic, a polyamide, a rosin, a silicon, a styrene (e.g., a paramethyl styrene), a vinyl toluene, or a combination thereof. In certain embodiments, a benzoic acid modified high solid alkyd coating comprises a coating for a tool. In other embodiments, a phenolic modified high solid alkyd coating comprises a primer. A silicone modified alkyd coating may be selected for improved weather resistance, heat resistance, or a combination thereof. In specific aspects, a silicone modified alkyd coating may comprise an additional binder capable of cross-linking with the silicone moiety (e.g., a melamine formaldehyde resin). In specific facets, a silicone modified alkyd coating may be selected as a coil coating, an architectural coating, a metal coating, an exterior coating, or a combination thereof. In certain facets, a high solid silicon-modified alkyd coating may substitute an oxygenated compound (e.g., a ketone, an ester) for an aromatic hydrocarbon liquid component. However, a high solid silicon-modified alkyd coating, to achieve cross-linking during film-formation, should comprise an additional binder capable of cross-linking. In further embodiments, a silicone modified high solid alkyd coating comprises a maintenance coating, a topcoat, or a combination thereof.

(iii) Uralkyd Coatings

An uralkyd binder ("uralkyd," "urethane alkyd," "urethane oil," "urethane modified alkyd") is an alkyd binder, with the modification that compound comprising plurality of diisocyanate moieties partly or fully replacing the dibasic acid (e.g., phthalic anhydride) in the synthesis reactions. Examples of an isocyanate comprising compounds include a 1,6-hexamethylene diisocyanate ("HDI"), a toluene diisocyanate ("TDI"), or a combination thereof. An uralkyd binder may be selected for embodiments wherein a superior abrasion resistance, superior resistance to hydrolysis, or a combination thereof, relative to an alkyd, is desired in a film. However, an uralkyd binder prepared using TDI often has greater viscosity in a coating, inferior color retention in a film, or a combination thereof, relative to an alkyd binder. Additionally, an uralkyd binder prepared using an aliphatic isocyanate generally possesses superior color retention to an uralkyd prepared from TDI. An uralkyd coating tends to undergo film formation faster than a comparable alkyd binder, due to a generally greater number of available conjugated double bonds, an increased $T_g$ in an uralkyd binder prepared using an aromatic isocyanate, or a combination thereof. A film comprising an uralkyd binder tends to develop a yellow to brown color. An uralkyd binder is often used in preparation of an architectural coating such as a varnish, an automotive refinish coating, or a combination thereof. Examples of a surface where an uralkyd coating may be applied include a furniture surface, a wood surface, or a floor surface.

(iv) Water-Borne Alkyd Coatings

In general embodiments, an alkyd coating is a solvent-borne coating.

However, an alkyd (e.g., a chemically modified alkyd) may be combined with a coupling solvent and water to produce a water-borne alkyd coating. Examples of a coupling solvent that may confer water reducibility to an alkyd resin includes ethylene glucol monobutyether, propylene glycol monoethylether, propylene glycol monopropylether, an alcohol whose carbon content is four carbon atoms (e.g., s-butanol), or a combination thereof. In certain embodiments, a water-borne long oil alkyd coating may be selected as a stain, an enamel, or a combination thereof. In other embodiments, a water-borne medium oil alkyd coating may be selected as an enamel, an industrial coating, or a combination thereof. In further facets, a water-borne medium oil alkyd coating may undergo film formation by air oxidation. In other embodiments, a water-borne short oil alkyd coating may be selected as an enamel, an industrial coating, or a combination thereof. In further facets, a water-borne short oil alkyd coating may undergo film formation by baking.

(3) Oleoresinous Binders

An oleoresinous binder is a type of binder prepared from heating a resin and an oil. Examples of a resin typically used in the preparation of an oleoresinous binder include resins obtained from a biological source (e.g., a wood resin, a bitumen resin); a fossil source (e.g., copal resin, a Kauri gum resin, a rosin resin, a shellac resin); a synthetic source (e.g., a rosin derivative resin, a phenolic resin, an epoxy resin); or a combination thereof. An example of an oil typically used in the preparation of an oleoresinous binder includes a vegetable oil, particularly an oil that is comprises a polyunsaturated fatty acid such as tung, linseed, or a combination thereof. The type of resin and oil used can identify an oleoresinous binder such as a copal-tung oleoresinous binder, a rosin-linseed oleoresinous binder, etc. An oleoresinous binder generally are used in clear varnishes such as a lacquer, as well as in applications as a primer, an undercoat, a marine coating, or a combination thereof. In addition to the standards and analysis techniques previously described for an oil, standards for physical properties, chemical properties, and/or procedures for testing the purity/properties (e.g., glass transition temperature, molecular weight, color stability) of a hydrocarbon resin (e.g., a synthetic source resin) for use in an oleoresinous binder or other coating component are described, for example, in "ASTM Book of Standards, Volume 06.03, Paint—Pigments, Drying Oils, Polymers, Resins, Naval Stores, Cellulosic Esters, and Ink Vehicles," E28-99, D6090-99, D6440-01, D6493-99, D6579-00, D6604-00, and D6605-00, 2002.

Similar to alkyd resins, oleoresinous binders can be categorized by oil length as a short oil or long oil oleoresinous binder, depending whether oil length is 1% to 67% or 67% to 99% oil, including all intermediate ranges and combinations thereof, respectively. Short oil oleoresinous binders generally dry fast and form relatively harder, less flexible films, and are used, for example, for floor varnishes. Long oil oleoresinous binders generally dry slower and form relatively more flexible films, and are used, for example, as an undercoat, exterior varnish, or combination thereof.

(4) Fatty Acid Epoxy Esters

In certain facets, an epoxy coating may be cured by fatty acid oxidation rather than epoxide moiety or hydroxyl moiety cross-linking reactions. A fatty acid epoxide ester resin is an ester of an epoxide resin and a fatty acid, which can be used to produce an ambient cure coating that undergoes film formation by oxidative reactions as an oil-based coating. In certain embodiments, an epoxy resin may be selected with an epoxy equivalent weight of 800 to 1000, including all intermediate ranges and combinations thereof. Short, medium, and long oil epoxide ester resins comprise 30% to 50%, 50% to 70%, or 70% to 90% fatty acid esterification, including all intermediate ranges and combinations thereof, respectively, with similar, though sometimes superior, properties relative to an analogous alkyd. An epoxide ester resin is inferior in chemical resistance than a film produced by an epoxy and a curing agent comprising an amine. An epoxy ester resin may be selected as a substitute for an alkyd, a marine coating, an industrial maintenance coating, a floor topcoat, or a combination thereof.

b. Polyester Resins

A polyester resin ("polyester," "oil-free alkyd") is a polyester chemical, other than an alkyd resin, capable as use as a binder. A polyester resin is chemically very similar to an alkyd, though the oil content is 0%. Consequently, a polyester-coating does not form cross-linking bonds by fatty acids oxidation during thermosetting film formation, but rather is combined with an additional binder to form a cross-linked film. The selection of a polyester and additional binder combination is generally determined by the polyester's crosslinkable moieties. For example, a hydroxy-terminated polyester is a polyester produced by an esterification reaction comprising a molar excess of a polyol, and may be crosslinked with a urethane, an amino resin, or a combination thereof. A hydroxy-terminated polyester's hydroxyl moiety may react with a urethane's isocyanate moiety such as at ambient conditions or low-bake conditions, while such a polyester generally undergoes film formation at baking temperatures with an amino resin. In another example, a "carboxylic acid-terminated polyester" is a polyester produced by an esterification reaction comprising an molar excess of a polycarboxylic acid, and may be crosslinked with a urethane, an amino resin, a 2-hydroxylakylamide, or a combination thereof.

In general embodiments, a polyester-coating possesses superior color retention, flexibility, hardness, weathering, or a combination thereof, relative to an alkyd-coating. In some embodiments, a polyester resin may be selected to produce a coating for a metal surface. Generally, a polyester-coating possesses a superior adhesion property on a metal surface than a thermosetting acrylic-coating. Often, a polyester-coating is a thermosetting coating, particularly in embodiments for use upon a metal surface. However, a polyester-coating generally comprises an ester linkage that is susceptible to hydrolysis, therefore, applications wherein such a polyester-coating contacts water is less preferred.

A polyester resin is generally prepared by an acid catalyzed esterification of a polyacid (e.g., a polycarboxylic acid, an aromatic polyacid) and a polyalcohol. A "polyacid" ("polybasic acid") is a chemical comprising more than one acid moiety. Typically, a polyacid used in the preparation of a polyester comprise two acidic moieties, such as, for example, an aromatic dibasic acid, an anhydride of an aromatic dibasic acid, an aliphatic dibasic acid, or a combination thereof. Usually, a polyester resin comprises a plurality of polycarboxylic acids and/or polyalcohols, and such a polyester resin is known herein as a "copolyester resin." Examples of polycarboxylic acids commonly used to prepare a polyester resin includes adipic acid ("AA"); azelic acid ("AZA"); dimerized fatty acid; dodecanoic acid; hexahydrophthalic anhydride ("HHPA"); isophthalic acid ("IPA"); phthalic anhydride ("PA"); sebacid acid; terephthalic acid; trimellitic anhydride; or a combination thereof. Examples of a polyalcohol commonly used to prepare a polyester resin include 1,2-propanediol; 1,4-butanediol; 1,4-cyclohexanedimethanol ("CHDM"); 1,6-hexanediol ("HD"); diethylene glycol; ethylene glycol; glycerol; neopentyl glycol ("NPG"); pentaerythitol ("PE"); trimethylolpropane ("TMP"); or a combination thereof. In certain embodiments, a polyester may be selected that has been synthesized by an acid catalyzed esterification reaction between a plurality of polyalcohols comprising two hydroxy moieties (a "diol"), a polyalcohol comprising three hydroxy moieties (a "triol"), and a dibasic acid. An example of a diol includes 1,4-cyclohexanedimethanol; 1,6-hexanediol; neopentyl glycol; or a combination thereof. An example of a triol includes trimethylolpropane. An example of a polyol comprising four hydroxy moieties (a "tetraol") includes pentaerythitol. In addition to the standards and analysis techniques previously described for an oil, an alkyd, a polyol, an acid anhydride standards for physical properties, chemical properties, and/or procedures for testing the purity/properties of an polyester are described, for example, in "ASTM Book of Standards, Volume 06.03, Paint—Pigments, Drying Oils, Polymers, Resins, Naval Stores, Cellulosic Esters, and Ink Vehicles," D2690-98 and D3733-93, 2002.

The selection of a polyacid and/or a polyalcohol often affects a property of the polyester resin, such as the resistance of the polyester resin to hydrolysis, and similarly the water resistance of a coating and/or film comprising such a polyester resin. In embodiments wherein a polyester-coating is desired with a superior water resistance property relative to other types of polyester-coatings, it is preferred that the coating comprises a polyester prepared with a polyol that is more difficult to esterify, and thus generally more difficult to hydrolyze. Examples of such polyols include neopentyl glycol, trimethylolpropane1,4-cyclohexanedimethanol, or a combination thereof.

In general embodiments, a polyester-coating is a solvent-borne coating. However, a polyester suitable for a water-borne coating is known to one of ordinary skill in the art. A water-borne polyester-coating generally comprises a polyester resin, wherein the acid number of the polyester resin is 40 to 60 including all intermediate ranges and combinations thereof, and wherein the acid moieties have been neutralized by an amine, and wherein the coating comprises liquid component that comprises a co-solvent. An additional water-borne binder (e.g., an amino resin) may be used to produce thermosetting film formation. In specific aspects, a water-borne polyester-coating produces a film of excellent hardness, gloss, flexibility, or a combination thereof.

In alternative embodiments, a polyester temporary coating (e.g, a non-film forming coating) may be produced, for example, by selection of a polyester that that comprises fewer or no crosslinkable moieties, selection of an addition binder that comprises fewer or no crosslinkable moieties, reducing the concentration of the polyester or additional binder, or a combination thereof.

c. Modified Cellulose Binders

In some embodiments, a chemically modified cellulose molecule ("modified cellulose," "cellulosic") may be used as a coating component (e.g., a binder). Cellulose is a polymer of anhydroglucose monomers that is insoluble in water and organic solvents. Various chemically modified forms of cellulose with enhanced solubility have been used as a coating component. Examples of chemically modified cellulose ("modified cellulose," "cellulosic") include a cellulose ester, a nitrocellulose, or a combination thereof. Examples of a cellulose ester include cellulose acetate ("CA"), cellulose butyrate, cellulose acetate butyrate ("CAB"), cellulose acetate propionate ("CAP"), a hydroxy ethyl cellulose, a carboxy methyl cellulose, cellulose acetobutyrate, ethyl cellulose, or a combination thereof. A cellulose ester coating typically produces films with excellent flame resistance, toughness, clarity, or a combination thereof. In certain embodiments, a cellulose ester coating is selected as a topcoat, a clear coating, a lacquer, or a combination thereof. A cellulose ester is often selected for embodiments wherein the coating comprises an automotive coating, a furniture coating, a wood surface coating, cable coating, or a combination thereof. A cellulose ester coating may be a thermoplastic coating, a thermosetting coating, or a combination thereof.

A cellulose ester may be selected by the properties associated with the degree and/or type of esterification. Typically, solubility in a liquid component and/or combinability with an addition binder is increased by partial esterification of an anhydroglucose's hydroxy moieties. For example, for a cellulose acetate butyrate, properties such as compatibility, diluent tolerance, flexibility (e.g., lower $T_g$), moisture resistance, solubility, or a combination thereof, increases with greater butyrate esterification. However, decreased hydroxyl content alters properties in a cellulose ester. For example, a cellulose acetate butyrate comprising a hydroxy content of 1% or below has limited solubility in most solvents, while a hydroxy content of 5% or greater allows solubility in many alcohols, and the increased number of hydroxy moieties allows a greater degree of crosslinking reactions with binders such as, for example, an amino binder, an acrylic binder, urethane binder, or a combination thereof. A cellulose acetate butyrate acrylic-coating may be selected as lacquers, an automotive coating, a coating comprising a metallic pigment (e.g., aluminum), or a combination thereof. A cellulose acetate butyrate acrylic-coating may comprise a liquid component that comprises greater amounts of an aromatic hydrocarbon solvent with the selection of a CAB with greater butyrate ester content. Though not a cellulosic, sucrose esters may be similarly used as cellulose ester, particularly CAB.

In some embodiments, in a cellulose ester comprising an acetyl ester (e.g., comprises cellulose acetate, cellulose acetate butyrate, cellulose acetate propionate), the acetyl content will range from 0.1% to 40.5% acetate, including all intermediate ranges and combinations thereof. In certain aspects, the acetyl content of a cellulose acetate, a cellulose acetate butyrate, or a cellulose acetate propionate will range from 39.0% to 40.5%, 1.0% to 30.0%, or 0.3% to 3.0%, respectively, including all intermediate ranges and combinations thereof, respectively. In many aspects, in a cellulose ester comprising a butyryl ester (e.g., cellulose acetate butyrate), the butyryl content will range from 15.0% to 55.0% butyryl, including all intermediate ranges and combinations thereof. In other aspects, in a cellulose ester comprising a propionyl ester (e.g., cellulose acetate propionate), the propionyl content will range from 40.0% to 47.0% propionyl, including all intermediate ranges and combinations thereof. In other embodiments, the hydroxyl content of a cellulose acetate, a cellulose acetate butyrate, or a cellulose acetate propionate will range from 0% to 5.0%, including all intermediate ranges and combinations thereof.

A nitrocellulose ("cellulose nitrate") resin comprises a cellulose molecule wherein a hydroxyl moiety has been nitrated. A nitrocellulose for use in a coating typically comprises an average of 2.15 to 2.25 nitrates per anhydroglucose monomer, and is soluble in an ester, a ketone, or a combination thereof. Additionally, nitrocellulose is soluble in a combination of a ketone, an ester, and an alcohol and/or hydrocarbon. A nitrocellulose may be selected as a lacquer, an automotive primer, automotive topcoat, a wood topcoat, or a combination thereof. Nitrocellulose coatings are typically a thermoplastic coating.

Standard procedures for determining physical and/or chemical properties (e.g., acetyl content, ash, apparent acetyl content, butyryl content, carbohydrate content, carboxyl content, color and haze, combined acetyl, free acidity, heat stability, hydroxyl content, intrinsic viscosity, solution viscosity, moisture content, propionyl content, sulfur content, sulfate content, metal content), of a cellulose and/or a modified cellulose (e.g., cellulose acetate, cellulose acetate propionate, cellulose acetate butyrate, methylcellulose, sodium carboxymethylcellulose, ethylcellulose, hydroxypropyl methylcellulose, hydroxyethylcellulose, hydroxypropylcellulose) have been described, for example, in "ASTM Book of Standards, Volume 06.03, Paint—Pigments, Drying Oils, Polymers, Resins, Naval Stores, Cellulosic Esters, and Ink Vehicles," D1695-96 D817-96, D871-96, D1347-72, D1439-97, D914-00, D2363-79, D2364-01, D5400-93, D1343-95, D1795-96, D2929-89, D3971-89, D4085-93, D1926-00, D4794-94, D3876-96, D3516-89, D5897-96, D5896-96, D6188-97, D1348-94, and D1696-95, 2002. Specific procedures for determining purity/properties of a nitrocellulose (e.g., nitrogen content) have been described, for example, in "ASTM Book of Standards, Volume 06.03, Paint—Pigments, Drying Oils, Polymers, Resins, Naval Stores, Cellulosic Esters, and Ink Vehicles," D301-95 and D4795-94, 2002.

In alternative embodiments, a modified cellulose temporary coating (e.g, a non-film forming coating) may be produced, for example, by selection of a modified cellulose that that comprises fewer or no crosslinkable moieties, selection of an addition binder that comprises fewer or no crosslinkable moieties, reducing the concentration of the modified cellulose or additional binder, or a combination thereof.

d. Polyamide and Amidoamine Binders

A polyamide ("fatty nitrogen compound," "fatty nitrogen product") is a reaction product of a polyamine and a dimerized and/or trimerized fatty acid. In typical embodiments, a polyamide is an oligomer. An amide resin comprises a terminal amine moiety capable of cross-linking with an epoxy moiety, and it is particularly preferred that a polyamide binder is combined with an epoxide binder. In other aspects, a polyamide may be considered an additive (e.g., a curing agent, a hardening agent, a coreactant) of an epoxide coating. A polyamine-epoxy coating may be used as an industrial coating (e.g., an industrial maintenance coating), a marine coating, or a combination thereof. A polyamide-epoxide coating may be applied to a surface such as, for example, wood, masonry, metal (e.g., steel), or a combination thereof. However, it is preferred that any surface is thoroughly cleaned prior to application to promote adhesion. Such surface preparation are well known to those of ordinary skill in the art, and include, for example, removal of rust, degraded film, grease, etc. A polyamide-epoxy coating typically is a solvent-borne coating. Examples of solvents for a polyamide include an alcohol, an aromatic hydrocarbon, a glycol ether, a ketone, or a combination thereof. In certain embodiments, a polyamide-epoxy coating may comprise a two-pack coating, wherein coating component(s) comprising the polyamide resin are stored in one container, and coating components comprising the epoxy resin are stored in a second container. Such a two-pack coating is admixed immediately before application, as the stoichiometric mix ratio of resin is formulated to promote a rapid cure. However, in other embodiments, a polyamide-epoxy coating may be a single container coating. Such a solvent-borne polyamine-epoxy coating may be formulated for a storage life of a year or more. An aluminum and or stainless steel container is suitable, though a carbon steel container may alter coating and/or film color. However, such a coating typically undergoes film formation in stages, wherein the liquid component is physically lost by evaporation while thermosetting produces a physically durable film in about 8 to 10 hours, a chemically resistant film in three to four days, and final cross-linking completed in about three weeks. In some embodiments, a polyamine-epoxy coating may undergo chalking upon exterior weathering.

Though a polyamide is prepared from a fatty acid, it is not classified as an oil-based binder herein due to the chemistry of film formation for polyamide binder. The dimerized ("dibasic") or trimerized fatty acid generally comprises a polyunsaturated fatty acid, a monounsaturated fatty acid, or a combination thereof. In certain aspects, the fatty acid is a linseed oil fatty acid, soybean oil fatty acid, tall oil fatty acid, or a combination thereof. In specific facets, the fatty acid is an 18-carbon fatty acid. However, to reduce the volatile organic compounds of solvent-borne coating, a polyamide binder may be partly or fully substituted, such as 0% to 100% substitution, including all intermediate ranges and combinations thereof, with an amidoamine binder. An amidomine binder differs from a polyamide binder by the use of a fatty acid rather than a dimerized fatty acid in the synthesis of the resin. The selection of the polyamine in the preparation of a polyamide can affect the properties of the polyamide. The polyamine may be linear (e.g., diethylenetriamine), branched or cyclic (e.g., aminoethylpiperazine). Standards for physical properties, chemical properties, and/or procedures for testing the purity/properties (e.g., amine value) of a polyamide and/or an amidoamine are described, for example, in "ASTM Book of Standards, Volume 06.03, Paint—Pigments, Drying Oils, Polymers, Resins, Naval Stores, Cellulosic Esters, and Ink Vehicles," D2071-87, D2073-92, D2082-92, D2072-92, D2074-92, D2075-92, D2076-92, D2077-92, D2078-86, D2079-92, D2080-92, D2081-92, and D2083-92, 2002.

In general embodiments, a polyamine comprises a polyethylene amine. A polyamide produced from diethylenetriamine can be prepared to comprise a varying amount, typically 35% to 85%, including all intermediate ranges and combinations thereof, of an imidazoline moiety. In other embodiments, the amount of amine moiety capable of cross-linking with an epoxy moiety may vary from 100 to 400 amine value, including all intermediate ranges and combinations thereof. However, the amine value is converted into units known as "active hydrogen equivalent weight," which varies from 550 to 140, including all intermediate ranges and combinations thereof, for comparison to the epoxy resins epoxide equivalent weight for determining the stoichiometric mix ratio of a polyamide-epoxy combination. The stoichiometric mix ratio affects coating and film properties. As the polyamide to epoxy stoichiometric mix ratio increases from a ratio of less than one to a ratio of greater than one, properties such as excellent impact resistance, excellent chemical resistance, or a combination thereof, decrease while film flexibility increases. Examples of polyamide to epoxy stoichiometric mix ratio include 2:1 to 1:2, including all intermediate ranges and combinations thereof.

In alternative embodiments, a polyamide and/or amidoamine temporary coating (e.g, a non-film forming coating) may be produced, for example, by selection of a polyamide and/or amidoamine that that comprises fewer or no cross-linkable moieties, selection of an addition binder that comprises fewer or no crosslinkable moieties, reducing the concentration of the polyamide and/or amidoamine or additional binder, selection of a stoichiometric ratio that is less suitable for crosslinking reactions, or a combination thereof.

e. Amino Resins

An amino resin ("amino binder," "aminoplast," "nitrogen resin") is a reaction product of formaldehyde, an alcohol and a nitrogen compound such as, for example, urea, melamine ("1:3:5 triamino triazine"), benzoguanamine, glucoluril, or a combination thereof. An amino resin may be used to a thermosetting coating. An amino resin comprises an alkoxymethyl moiety capable of cross-linking with a hydroxyl moiety of an additional binder such as an acrylic binder, an alkyd resin, a polyester binder, or a combination thereof, and it is preferred that an amino resin is combined with a binder that comprises a hydroxyl moiety in a coating. In aspects wherein the coating comprises an amino resin and an alkyd resin, it is preferred that the amino:alkyd resin ratio is 1:1 to 1:5, including all intermediate ranges and combinations thereof. An amino resin coating typically is a solvent-borne coating. Examples of solvents for an amino resin include an alcohol (e.g., butanol, isobutanol, methanol, isopropanol), a ketone, hydroxyl functional glycol ether, or a combination thereof. Additionally, an amino resin generally possesses limited solubility in a hydrocarbon (e.g., xylene), which may be added to a solvent-borne coating's liquid component. In certain aspects, an amino resin coating may be a water-borne coating, wherein water is a solvent for an amino resin comprising a plurality of methylol moieties. In other embodiments, a water-borne amino resin coating may comprise a water-reducible coating, particularly wherein the liquid component comprises a glycol ether, an alcohol, or a combination thereof. In certain embodiments, an amino coating comprises an acid catalyst.

An amino resin coating generally is cured by baking at a temperature of 82° C. and 204° C., including all intermediate ranges and combinations thereof. Baking generally promotes reactions between amino resins, though it does improve the reaction rate between an amino resin and an additional binder. It is preferred that in embodiments wherein the coating comprises an additional binder, the additional resin comprises less hydroxyl moieties and/or the amino resin is polar amino resin (e.g., a conventional amino resin) a when cured by baking than embodiments wherein an acid catalyst is used. An amino resin coating undergoes rapid film formation, typically lasting 30 seconds and 30 minutes, wherein a higher temperature and/or acid catalyst shortens film formation time. An amino resin prepared from urea is generally undergoes film formation faster than an amino resin prepared from melamine. However, an amino resin coating generally produces an alcohol (e.g., methanol, butanol) and formaldehyde during film formation as byproducts.

An amino resin for use in a coating may be classified by content of a liquid component (e.g., a solvent) as a high solids amino resin or a conventional amino resin. The liquid component is generally used to reduce the viscosity of the resin for coating preparation. A high solids amino resin comprises 80% to 100%, by weight, an amino resin, with the balance a liquid component. A high solids amino resin is are relatively less polar, less polymeric, lower in viscosity, or a combination thereof, relative to a conventional amino resin. The lower viscosity allows the use of little or no liquid component. Additionally, a high solids amino resin may be water-soluble and/or water reducible. A conventional amino resin comprises less than 80% amino resin, by weight, with the balance a liquid component. Properties of a high solids or conventional amino resin selected for use in a coating such as the amount of amino resin and liquid component, the amount of unreacted formaldehyde in the resin preparation, the viscosity of the resin, the ability of the resin to accept additional liquid component as a solvent, can be empirically determined by procedures known to those of ordinary skill in the art (see, for example, "ASTM Book of Standards, Volume 06.03, Paint—Pigments, Drying Oils, Polymers, Resins, Naval Stores, Cellulosic Esters, and Ink Vehicles," D4277-83, D1545-98, D1979-97, and D1198-93, 2002; and "ASTM Book of Standards, Volume 06.01, Paint—Tests for Chemical, Physical, and Optical Properties; Appearance," D2369-01e1, 2002).

In embodiments wherein an amino resin coating comprise an amino resin prepared from urea, the coating may be used as wood coating (e.g., furniture coating), an industrial coating (e.g., an appliance coating), an automotive primer, a clear coating, or a combination thereof. However, an amino resin film, wherein the resin was prepared from urea, generally produces a film with poor resistance to moisture, and is preferred as an internal coating and/or as part of a multicoat system. In certain embodiments, an amino resin prepared from melamine, generally produces films with good resistance to moisture, temperature, UV irradiation, or a combination thereof. A melamine-based amino coating may be applied to a metal surface. In specific aspects, such a melamine amino resin coating may be an automotive coating, a coil coating, a metal container coating, or a combination thereof. In embodiments wherein an amino resin coating comprise an amino resin prepared from benzoguanamine, the film produced generally possesses poor weathering resistance, good corrosion resistance, water resistance, detergent resistance, flexibility, hardness, or a combination thereof. A benzoguanamine amino resin may be used as an industrial coating, particularly for indoor applications (e.g., an appliance coating). In embodiments wherein an amino resin coating comprise an amino resin prepared from, glycoluril, a higher baking temperature and/or acid catalyst may be used during film formation, but less byproducts may be released. A glycoluril-based amino-coating typically produces a film with excellent corrosion resistance, humidity resistance, or a combination thereof. A glycoluril-based amino-coating may be selected as a metal coating.

In alternative embodiments, an amino resin temporary coating (e.g, a non-film forming coating) may be produced, for example, by selection of an amino resin that that comprises fewer or no crosslinkable moieties, selection of an addition binder that comprises fewer or no crosslinkable moieties, reducing the concentration of the amino resin and/or additional binder, selection of a binder ratio that is less suitable for crosslinking reactions, using a bake cured amino resin coating at temperatures less than is needed for curing (e.g., ambient conditions) or a combination thereof.

f. Urethane Binders

A urethane binder ("polyurethane binder," "urethane," "polyurethane") is a binder comprising prepared from compounds that comprise an isocyanate moiety. The urethane binder's urethane moiety can form intermolecular hydrogen bonds between urethane binder polymers, and these noncovalent bonds confer useful properties in a coating or film comprising an urethane binder. The hydrogen bonds can be broken by mechanical stress, but will reform, thereby conferring a property of abrasion resistance. Additionally, a urethane binder can form some hydrogen bonds with water, conferring a plasticizing property to the coating. In certain embodiments, a urethane binder comprises an isocyanate moiety. The isocyanate moiety is highly reactive (e.g., crosslinkable) with a moiety comprising a chemically reactive hydrogen. Examples of a chemically reactive hydrogen moiety include a hydroxyl moiety, an amine moiety, or a combination thereof. Examples of an additional binder include a polyol, an amine, an epoxide, silicone, vinyl, phenolic, or a combination thereof. In certain embodiments, a urethane coating is a thermosetting coating. In specific aspects, a urethane coating comprises a catalyst (e.g., dibutyltin dilaurate, stannous octoate, zinc octoate). In specific facets, the coating comprises 10 to 100 parts per million catalyst, including all intermediate ranges and combinations thereof. In some embodiments, such a coating will undergo film formation at ambient conditions or slightly greater temperatures. A binder comprising an isocyanate moiety is often selected to produce a coating with durability in an external environment. A urethane coating typically possesses good flexibility, toughness, abrasion resistance, chemical resistance, water resistance, or a combination thereof. An aliphatic urethane coating may be selected for the additional property of good lightfastness.

In general embodiments, a urethane binder may be selected based on the materials used in its preparation, which typically affect the urethane binder's properties. An example of a urethane binder includes an aromatic isocyanate urethane binder, an aliphatic isocyanate urethane binder, or a combination thereof. Aliphatic isocyanate urethane binders are often selected for embodiments wherein a superior exterior durability, color stability, good lightfastness, or a combination thereof relative to an aromatic isocyanate binder is desired. Examples of an aliphatic isocyanate urethane binder includes a hydrogenated bis(4-isocyanatophenyl)methane ("4,4'dicyclohexylmethane diisocyanate," "HMDI"), HDI, a combination of 2,2,4-trimethyl hexamethylene diisocyanate and 2,4,4-trimethyl hexamethylene diisocyanate ("TMHDI"), 1,4-cyclohexane diisocyanate ("CHDI"), isophorone diisocyanate ("3-isocyanatomethyl-3,5,5-trimethylcyclohexyl isocyanate," "IPDI"), or a combination thereof. In certain aspects, a HDI derived binder is prepared from excess HDI reacted with water, known as "HDI biuret." In certain aspects, a HDI derived binder may be prepared from a 1,6-hexamethylene diisocyanate isocyanurate, wherein such a HDI derived binder produces a coating with generally superior heat resistance and/or exterior durability is desired relative to other HDI derived binders. As would be known to one of ordinary skill in the art, standards for physical properties, chemical properties, and/or procedures for testing the purity/properties of urethane precursor components (e.g., toluene) and urethane resins (e.g., isocyanate moieties) for use in a coating are described, for example in "ASTM Book of Standards, Volume 06.04, Paint—Solvents; Aromatic Hydrocarbons," D5606-01, 2002; and "ASTM Book of Standards, Volume 06.03, Paint—Pigments, Drying Oils, Polymers, Resins, Naval Stores, Cellulosic Esters, and Ink Vehicles," D3432-89 and D2572-97, 2002.

In certain embodiments, a urethane coating comprises a urethane binder capable of a self-crosslinking reaction. An example is a moisture-cure urethane, which comprises an isocyanate moiety. Contact between an isocyanate moiety and a water molecule produces an amine moiety capable of bonding with an isocyanate moiety of another urethane binder molecule in a linear polymerization reaction. In certain aspects, a moisture cure urethane coating is baked at 100° C. to 140° C., including all intermediate ranges and combinations thereof, to promote crosslinking reactions between the linear polymers. In certain embodiments, a moisture-cure urethane coating is a solvent-borne coating. In specific aspects, a moisture-cure urethane coating comprises a dehydrator. In general aspects, moisture-cure urethane coating typically is a one-pack coating, prepared for storage of the coating in anhydrous conditions.

In certain embodiments, an urethane coating comprises a blocked isocyanate urethane binder, wherein the isocyanate moiety has been chemically modified by a hydrogen donor to be inert until contacted with a baking temperature. Such a blocked isocyanate urethane coating typically is a one-pack coating, as it is designed for stability at ambient conditions. Additionally, a blocked isocyanate urethane coating may be a powder coating.

In certain embodiments, a urethane coating comprises an additional binder. In certain embodiments, a urethane may be combined with a binder such as an amine, an epoxide, silicone, vinyl, phenolic, a polyol, or a combination thereof, wherein the binder comprises a reactive hydrogen moiety. In specific embodiments, selection of a second binder to crosslink with the urethane binder affects coating and/or film properties. In certain aspects, a coating comprising a urethane and an epoxide, vinyl, phenolic, or a combination thereof produces a film with good chemical resistance. In other aspects, a coating comprising a urethane and a silicone produces a coating with good thermal resistance. In some aspects, a coating comprises a urethane and a polyol. A primary hydroxyl moiety, secondary hydroxyl moiety, and tertiary hydroxyl moiety of a polyol are respectively the fastest, moderate, and slowest to react with a urethane. Steric hindrance from a neighboring moiety may slow the reaction with a hydroxyl moiety. In an additional example, use of a polyol may increase flexibility of a urethane coating. Often, a selected polyol has a molecular weight from 200 Da to 3000 Da, including all intermediate ranges and combinations thereof. Generally, a lower molecular weight polyol increases the hardness property, lowers the flexibility property, or a combination thereof, of a urethane polyol film. Examples of a polyol include a glycol, a triol (e.g., 1,4-butane-diol, diethylene glycol, trimethylolpropane), a tetraol, a polyester polyol, a polyether polyol, an acrylic polyol, a polylactone polyol, or a combination thereof. Examples of a polyether polyol include a poly (propylene oxide) homopolymer polyol, a poly (propylene oxide) and ethylene oxide copolymer polyol, or a combination thereof.

In certain embodiments, a urethane binder comprises a thermoplastic urethane binder. Typically, a thermoplastic urethane binder is from 40 kDa to 100 kDa, including all intermediate ranges and combinations thereof. In particular aspects, a thermoplastic urethane binder comprises little or no isocyanate moieties. In general aspects, a thermoplastic urethane coating is a solvent borne coating. In specific facets, a thermoplastic urethane coating is a lacquer, a high gloss coating, or a combination thereof.

In certain embodiments, a urethane binder is an urethane acrylate ("acrylated urethane") binder. An urethane acrylate binder generally comprises an acrylate moiety at an end of the polymeric binder. The acrylate moiety is typically part of an acrylate monomer, wherein the monomer comprises a hydroxyl moiety (e.g., a 2-hydroxy-ethyl acrylate). An urethane acrylate coating generally comprises another binder for crosslinking reactions. Examples of a suitable binder include a triacrylate (e.g., trimethylolpropane). A urethane acrylate coating generally also comprises a viscosifier, wherein the viscosifier reduces viscosity. Examples of such a viscosifier include an acrylate monomer, a N-vinyl pyrrolidone, or a combination thereof. A urethane acrylate coating is cured by irradiation. Examples of irradiation include UV light, electron beam, or a combination thereof. In embodiments wherein UV light is a curing agent, a urethane acrylate coating typically comprises a photoinitiator. Examples of a suitable initiator include 2,2,-diethoxyacetophenone, a combination of benzophenone and an amine synergist, or a combination thereof. In specific facets, an urethane acrylate coating is applied to a plastic surface. In other facets, an urethane acrylate coating floor coating, an electronic circuit board coating, or a combination thereof.

In alternative embodiments, a urethane temporary coating (e.g, a non-film forming coating) may be produced, for example, by selection of a urethane resin that that comprises fewer or no crosslinkable moieties, selection of an addition binder that comprises fewer or no crosslinkable moieties, reducing the concentration of the a urethane resin and/or additional binder, using a bake cured a urethane resin coating at temperatures less than is needed for curing (e.g., ambient conditions), selection of size range for a thermoplastic urethane resin coating that is less suitable for film formation (e.g., 1 kDa to 40 kDa), or a combination thereof.

(1) Water-Borne Urethanes

The previous discussion of urethane coatings focused on solvent-borne urethane coating. A water-borne urethane coating typically is comprises a water-dispersible urethane binder such as a cationic modified urethane binder and/or anionic modified urethane binder. A cationic modified urethane binder is a urethane binder chemically modified by an diol comprising an amine, such as, for example, diethanolamine, methyl diethanolamine, N,N-bis(hydroxyethyl)-α-aminopyridine, lysine, N-hydroxyethylpiperidine, or a combination thereof. An anionic modified urethane binder is a urethane binder chemically modified by an diol comprising a carboxylic acid such as dimethylolpropionic acid (2,2-bis (hydroxymethyl) propionic acid), dihydroxybenzoic acid, and/or a sulfonic acid (e.g., 2-hydroxymethyl-3-hydroxy-propanesulfonic acid), or a combination thereof.

(2) Urethane Powder Coatings

A urethane powder coating refers to a polyester and/or acrylic coating, wherein the binder has been modified to comprise a urethane moiety. Such a coating is typically a thermosetting, bake cured coating, an industrial coating (e.g., an appliance coating), or a combination thereof.

g. Phenolic Resins

A phenolic resin ("phenolic binder," "phenolic") is reaction product of a phenolic compound and an aldehyde. A preferred aldehyde is formaldehyde, and such a phenolic resin is known as a "phenolic formaldehyde resin" ("PF resin"). The properties of a phenolic resin are affected by the phenolic compound and reaction conditions used during synthesis. A resole resin ("resole phenolic") is prepared by a reaction of a molar excess of a phenolic compound with formaldehyde under alkaline conditions. A novolac resin ("novolac phenolic") is prepared by a reaction of a molar excess of formaldehyde with a phenolic compound under acidic conditions. Examples of phenolic compounds used in preparing a phenolic resin include phenol; orthocresol ("o-cresol"); metacresol, paracresol ("p-cresol"); a xylenol (e.g., 4-xylenol); bisphenol-A ["2,2-bis(4-hydroxylphenyl) propane"; "diphenylol propane"); p-phenylphenol; p-tert-butylphenol; p-tert-amylphenol; p-tert-octyl phenol; p-nonylphenol; or a combination thereof. As would be known to one of ordinary skill in the art, standards for physical properties, chemical properties, and/or procedures for testing the purity/properties of various compounds used in phenolic resins (e.g., bisphenol A, a phenol, a cresol, formaldehyde) for use in a coating are described, for example in "ASTM Book of Standards, Volume 06.04, Paint—Solvents; Aromatic Hydrocarbons," D6143-97, D3852-99, D4789-94, D2194-02, D2087-97, D2378-02, D2379-99, D2380-99, D1631-99, D6142-97, D4493-94, D4297-99, and D4961-99, 2002. As would be known to one of ordinary skill in the art, standards for physical properties, chemical properties, and/or procedures for testing the purity/properties of phenolic resins for use in a coating are described, for example in "ASTM Book of Standards, Volume 06.03, Paint—Pigments, Drying Oils, Polymers, Resins, Naval Stores, Cellulosic Esters, and Ink Vehicles," D1312-93, D4639-86, D4706-93, D4613-86 and D4640-86, 2002.

In alternative embodiments, a phenolic resin temporary coating (e.g, a non-film forming coating) may be produced, for example, by selection of a phenolic resin that that comprises fewer or no crosslinkable moieties, selection of an addition binder that comprises fewer or no crosslinkable moieties, reducing the concentration of the a phenolic resin and/or additional binder, using a bake cured a phenolic resin coating at temperatures less than is needed for curing (e.g., ambient conditions), or a combination thereof.

(1) Resole

A resole resin is the more commonly used PF resin. A solvent-borne phenolic formaldehyde coating typically comprises an alcohol, an ester, a glycol ether, a ketone, or a combination thereof, as a PF solvent. However, a phenolic resin prepared from phenolic compound comprising an alkyd moiety, such as, for example, p-tert-butylphenol p-tert-amylphenol p-tert-octyl phenol, or a combination thereof, typically has solubility in an aromatic compound and/or able to tolerate an aliphatic diluent. Often, a phenolic-resin coating comprises an additional binder such as an alkyd resin, an amino resin, a blown oil, an epoxy resin, a polyamide, a polyvinyl resin [e.g., poly(vinyl butyral)], or a combination thereof. An example of a phenolic-resin coating includes a varnish, an industrial coating, or a combination thereof. A phenolic resin-coating may be selected for embodiments wherein a film possessing solvent resistance, corrosion resistant, of a combination thereof, is desired. Examples of surfaces wherein such properties are often desirable include a surface of a metallic container (e.g., a can, a pipeline, a drum, a tank), a coil coating, or a combination thereof. In specific aspects, a phenolic coating produces a film 0.2 to 1.0 mil thick, including all intermediate ranges and combinations thereof. In specific aspects, coating comprising a phenolic-binder and additional binder undergoes thermosetting cross-linking reactions between the binders during film formation. In certain embodiments, a phenolic-resin coating undergoes cure by baking, such as, for example, 135° C. to 204° C., including all intermediate ranges and combinations thereof. In specific aspects, a baking cure time is one minute to four hours, with shorter cure times at high temperatures. A phenolic-resin film generally possesses excellent hardness property (e.g., glass-like), excellent resistance to solvents, water, acids, salt, electricity, heat resistance, as well as thermal resistance up to 370° C. for a period of minutes.

However, a phenolic-resin film is poorly resistant to alkali unless made from a coating that also comprised an epoxy binder. In certain embodiments, a phenolic-epoxy coating comprises a binder ratio of 15:85 to 50:50 phenolic binder: epoxy binder, including all intermediate ranges and combinations thereof. In certain aspects, a phenolic-epoxy coating possesses superior flexibility, toughness, or a combination thereof relative to a phenolic coating. In specific facets, a phenolic-epoxy coating is cured at 200° C. for 10 to 12 minutes.

In other aspects, a phenolic coating comprises a blown oil, an alkyd, or a combination thereof. In some aspects, such a coating comprises a phenolic resin prepared from p-tert-butylphenol p-tert-amylphenol p-tert-octyl phenol, or a combination thereof. In specific aspects, such a coating is applied to electrical coil, electrical equipment, or a combination thereof.

(2) Novolak

In other aspects, wherein a film is desired, it novolak coating may be used. However, a novolak resin is generally a non-film forming resin. In is particularly preferred that the coating comprise an epoxy resin. It is also preferred that the coating comprise a basic catalyst. A film produced from such a novolak-epoxy coating typically possesses good resistance to chemicals, water, heat, or a combination thereof. In specific facets, a novolak-epoxy coating may be a high solids coating, a powder coating, a pipeline coating, or a combination thereof.

A novolak resin prepared from phenolic compound comprising an alkyd moiety such as p-tert-butylphenol p-tert-amylphenol p-tert-octyl phenol, or a combination thereof, typically has solubility in an oil. Additionally, a PF resin may be modified by reaction with an oil to produce an oil modified PF resin, which is also oil soluble. An alkyd phenol-formaldehyde resin, an oil modified phenol-formaldehyde resin, is generally a non-film forming resin. A coating capable of producing a film may be formulated by combining such a resin with a drying oil, an alkyd, or a combination thereof. In specific aspects, an alkyd phenol-formaldehyde resin, an oil modified phenol-formaldehyde resin undergoes cross-linking with an oil and/or an alkyd. Such a coating may further comprise a liquid component (e.g., a solvent), a drier, a UV absorber, an anti-skinning agent, or a combination thereof. In certain facets, such a coating undergoes film formation under ambient conditions or by baking. In particular aspects, such a coating comprises a varnish, a wood coating, or a combination thereof. In specific facets, such a coating comprises a pigment.

h. Epoxy Resins

An epoxy resin ("epoxy binder," "epoxy") is a compound comprising an epoxide ("oxirane") moiety. An epoxide resin may be used in a thermosetting coating, thermoplastic coating, or a combination thereof. An epoxide coating typically is a solvent borne coating, though examples of a water-borne and powder epoxy coating are described herein. An epoxide coating generally possesses excellent properties of adhesion, corrosion resistance, chemical resistance, or a combination thereof. An epoxide coating may be selected for various surfaces, particularly a metal surface.

An epoxide resin (e.g., a bisphenol A epoxy resin) generally comprises one or two epoxide moieties per resin molecule. An epoxide resin may additionally comprise a monomer, oligomer, or polymer of repeating chemical units, each generally lacking an epoxide moiety, but comprising a hydroxy moiety. The number of monomer(s) present is expressed "n" value, wherein an average increase of one monomer per epoxide resin molecule increase the n value by one. The chemical and/or physical properties of an epoxide resin are affected by the n value. For example, as the n value increases, the chemical reactions selected for film formation in a thermosetting coating may become more dominated by reactions with the increasing numbers of hydroxyl moieties, and less dominated by the epoxide moieties. Often, an epoxide resin is classified by an epoxide equivalent weight, which is the grams of resin required to provide 1 M epoxide moiety equivalent. In certain embodiments, the epoxide equivalent weight is 182 to 3050, including all intermediate ranges and combinations thereof. Additionally, an epoxide resin may be used in a thermoplastic coating, particularly wherein the n value is greater than 25. In certain embodiments, an epoxide resin may possess an n value of 0 to 250, including all intermediate ranges and combinations thereof. As would be known to one of ordinary skill in the art, standards for physical properties, chemical properties, and/or procedures for testing the purity/properties of epoxy resins (e.g., epoxy moiety content) for use in a coating are described, for example in "ASTM Book of Standards, Volume 06.03, Paint—Pigments, Drying Oils, Polymers, Resins, Naval Stores, Cellulosic Esters, and Ink Vehicles," D4142-89, D1652-97, D1726-90, D1847-93, and D4301-84, 2002.

An epoxide moiety is chemically reactive with a variety of other moieties, such as, for example, an amine, a carboxyl, a hydroxyl or a phenol. An epoxide coating may comprise an additional binder capable of undergoing a cross-linking reaction with the epoxide during film formation. Various such additional binders are known to those of ordinary skill in the art, and are often referred to as a "curing agent" or "hardener." The selection of a curing agent and/or an epoxide can affect whether the coating undergoes film formation at ambient conditions or by baking.

In alternative embodiments, an epoxide resin temporary coating (e.g, a non-film forming coating) may be produced, for example, by selection of an epoxide resin that that comprises fewer or no crosslinkable moieties, selection of an addition binder that comprises fewer or no crosslinkable moieties, reducing the concentration of the an epoxide resin and/or additional binder, using a bake cured an epoxide resin at temperatures less than is needed for curing (e.g., ambient conditions), not irradiating the coating, or a combination thereof.

(1) Ambient Condition Curing Epoxies

In certain embodiments, a curing agent suitable for curing at ambient conditions comprises an amine moiety such as a polyamine adduct, which is an epoxy resin modified to comprise an amine moiety, a polyamide, a ketimine, an aliphatic amine, or a combination thereof. Examples of an aliphatic amine include ethylene diamine ("EDA"), diethylene triamine ("DETA"), triethylene tetraamine ("TETA"), or a combination thereof. Selection of a polyamine adduct generally produces a film with excellent solvent resistance, corrosion resistance, acid resistance, flexibility, impact resistance, or a combination thereof. Selection of a polyamide generally produces a film with superior adhesion, particularly to a moist or poorly prepared surface, good solvent resistance, excellent corrosion resistance, good acid resistance, superior flexibility retention, superior impact resistance retention, or a combination thereof. A ketimine is a reaction product of a primary amine and a ketone, and produces a coating and/or film with similar properties as a polyamine or amine adduct. However, the pot life is longer with a ketimine, and moisture (e.g., atmospheric humidity) activates this cure agent. Examples of an epoxide selected for curing at ambient conditions includes a low mass epoxide resins with an n value from 0 to 2.0, including all intermediate ranges and combinations thereof. In certain embodiments, an epoxy resin may be selected with an epoxy equivalent weight of 182 to 1750, including all intermediate ranges and combinations thereof. In specific aspects, the greater the n value of an epoxide resin, the longer the pot life in a two-pack coating, the greater the coating leveling property, the lower the film solvent resistance, the lower the film chemical resistance, the greater the film flexibility, or a combination thereof. In certain aspects, an ambient curing epoxide coating is a two-pack coating, wherein the epoxide resin is in one container and the curing agent in a second container. In typical aspects, the pot life upon admixing the coating components is two hours to two days. An ambient cure epoxide may be selected for an industrial coating (e.g., industrial maintenance coating), a marine coating, an aircraft primer, a pipeline coating, a HIPAC, or a combination thereof.

(2) Bake Curing Epoxies

In other embodiments, a curing agent suitable for curing by baking includes an amino resin (e.g., a urea or melamine-based amino resin), a phenolic resin, or a combination thereof. Since baking is generally needed to promote film formation, an epoxy coating comprising such a curing agent typically is a one-pack coating. In certain embodiments, an epoxy resin may be selected with an epoxy equivalent weight of 1750 to 3050, including all intermediate ranges and combinations thereof. An epoxy resin coating that comprises an amino resin cure agent typically is selected for a lower cure temperature. Such a coating may be selected as a can coating, a metal coating, an industrial coating (e.g., equipment, appliances), or a combination thereof. An epoxy coating comprises an phenolic resin cure agent typically possesses greater chemical resistance and/or solvent resistance, and is typically selected for a can coating, a pipeline coating, a wire coating, an industrial primer, or a combination thereof. Examples of an epoxide selected for curing by baking includes a higher mass epoxide resins with an n value from 9.0 to 12.0, including all intermediate ranges and combinations thereof. In certain embodiments, a heat-cured epoxy coating is a water-borne coating. Such a water-borne coating comprises a higher mass epoxide resin modified to comprise a terpolymer that comprises monomers of styrene, methacrylic, acrylate, or a combination thereof, and an amino resin, a phenolic resin, or a combination thereof. Such a water-borne coating is typically selected as a can coating.

(3) Electrodeposition Epoxies

Another example of a water-borne epoxide coating is an electrodeposition epoxy coating. In certain embodiments, an epoxy resin may be selected with an epoxy equivalent weight of 500 to 1500, including all intermediate ranges and combinations thereof. An anionic and/or cationic epoxy resin is electrically attracted to a surface for application. The surface removed from the coating bath, and the coating is baked cured into a film upon the surface. Such a water-borne coating may be selected for an automotive primer, described elsewhere herein.

(4) Powder Coating Epoxies

An epoxy coating may be a powder coating, wherein the various nonvolatile coating components are admixed. Examples of typical admixed components include an epoxy resin, a curing agent, and a pigment, an additive, or a combination thereof. In certain embodiments, an epoxy resin may be selected with an epoxy equivalent weight of 550 to 750, including all intermediate ranges and combinations thereof. The mixture is then melted, cooled, and powderized. The powder coating is typically applied by attraction to an electrostatic charge of a surface. The thermosetting coating is cured by baking. An epoxy powder coating may be selected as a pipe coating, an electrical devise coating, an industrial coating (e.g., appliance coating, automotive coating, furniture coating), or a combination thereof.

(5) Cycloaliphatic Epoxies

A cycloaliphatic epoxy binder possesses a ring structure, rather than the linear structure for the epoxy embodiments described above. Examples of a cycloaliphatic epoxide is ERL-4221 ("3,4-epoxycyclohexylmethyl 3,4-epoxycyclohexane carboxylate"), which has an epoxy equivalent weight of 131 to 143, bis(3,4-epoxycyclohexylmethyl) adipate, which has an epoxy equivalent weight of 190 to 210, 2-(3,4-epoxycyclohexyl-5,5-spiro-3,4-epoxy)cyclohexane-m-dioxane, which has an epoxy equivalent weight of 133-154, 1-vinyl-epoxy-3,4-epoxycyclohexane, which has an epoxy equivalent weight of 70 to 74, or a combination thereof. Usually, a cycloaliphatic epoxy coating is combined with another binder, such as a polyol, a polyol modified to comprise a carboxyl moiety, or a combination thereof. An acid may be used to initiate crosslinking, particularly with a polyol. A cycloaliphatic epoxy polyol coating may comprise a triflic acid salt (e.g., diethylammonium triflate) to produce a one-pack coating with a pot life of up to eight months. In certain embodiments, a cycloaliphatic epoxy coating is a UV radiation cured coating, wherein the coating comprises a compound that converts to a strong acid upon UV irradiation (e.g., an onium salt). In certain aspects, a UV radiation cured cycloaliphatic epoxy coating is a one-pack coating. A UV radiation cured cycloaliphatic epoxy coating generally possesses excellent flame resistance, water resistance, or a combination thereof, and may be selected as a can coating or an electrical equipment coating. A compound comprising a carboxyl moiety (e.g., a carboxyl modified polyol) readily crosslinks with a cycloaliphatic epoxy binder. However, such a cycloaliphatic epoxy coating comprising such an additional binder generally has a short pot life (e.g., less than eight hours). In certain aspects, a cycloaliphatic epoxy carboxylic acid binder coating is a two-pack coating. A cycloaliphatic epoxy carboxylic acid polyol coating generally possesses excellent adhesion, toughness, gloss, hardness, solvent resistance, or a combination thereof.

i. Polyhydroxyether Binders

A polyhydroxyether binder ("polyhydroxyether resin," "phenoxy binder," "phenoxy") chemically resembles a bisphenol A epoxy resin, though a polyhydroxyether binder lacks an epoxide moiety, and about 30 kDa in size. A polyhydroxyether coating is typically a thermoplastic coating. The polyhydroxyether binder comprises a hydroxyl moiety, and can be cross-linked with an additional binder such as an epoxide, a polyurethane comprising an isocyanate moiety, an amino resin, or a combination thereof. A thermosetting polyhydroxyether coating typically possesses excellent physical resistance properties, excellent chemical resistance, modest solvent resistance, or a combination thereof. In alternative embodiments, a polyhydroxyether binder temporary coating (e.g, a non-film forming coating) may be produced, for example, by selection of a polyhydroxyether binder that that comprises fewer or no crosslinkable moieties, selection of an addition binder that comprises fewer or no crosslinkable moieties, reducing the concentration of the a polyhydroxyether binder and/or additional binder, or a combination thereof.

j. Acrylic Resins

An acrylic resin ("acrylic polymer," "acrylic binder," "acrylic") is a binder comprising a polymer of an acrylate ester monomer, a methacrylate ester monomer, or combination thereof. An acrylic-coating generally possesses a superior property of water resistance and/or exterior use durability than a polyester-coating. Other properties that an acrylic-coating typically possesses include color stability, chemical resistance, resistance to a UV light, or a combination thereof. An acrylic resin may further comprise an additional monomer to confer a desirable property to the resin, coating and/or film. For example, a styrene, a vinyltoluene, or a combination thereof, generally improve alkali resistance. Examples of such properties include the acrylic resin's chemical reactivity (e.g., cross-linkability), acidity, alkalinity, hydrophobicity, hydrophilicity, glass transition temperature, or a combination thereof. However, a thermoplastic acrylic film generally possesses poor solvent (e.g., acetone, toluene) resistance. Like other thermoplastic films, a thermoplastic acrylic film is generally easy to repair by application of additional acrylic coating to an area of solvent damage. An acrylic-coating is often suitable for various surfaces (e.g., metal), and examples of such coatings include an aerosol lacquer, an automotive coating, an architectural coating, a clear coating, a coating for external environment, an industrial coating, or a combination thereof. An acrylic resin may be used to prepare a thermoplastic coating, a thermosetting coating, or a combination thereof. In certain aspects, an acrylic-coating is selected for use as a thermosetting coating, particularly in embodiments for use upon a metal surface. Acrylic resins generally are soluble in a solvent with a similar solubility parameter. Examples of solvents typically used to dissolve an acrylic resin include an aromatic hydrocarbon (e.g., toluene, a xylene); a ketone (e.g., methyl ethyl ketone), an ester, or a combination thereof.

The thermoplastic and/or thermosetting properties of an acrylic resin are related to the monomers that are comprised in the selected resin. Examples of an acrylate ester monomer include a butylacrylate, an ethylacrylate ("EA"), ethylhexylacrylate ("EHA"), or a combination thereof. Examples of a methacrylate ester monomer include a butylmethacrylate ("BMA"), an ethylmethacrylate, a methylmethacrylate ("MMA"), or a combination thereof. Standards for physical properties, chemical properties, and/or procedures for empirically determining the purity/properties of various acrylic monomers (e.g., acrylate esters, 2-ethylhexyl acrylate, n-butyl acrylate, ethyl acrylate, methacrylic acid, acrylic acid, methyl acrylate) are known to those of ordinary skill in the art (see, for example, "ASTM Book of Standards, Volume 06.04, Paint—Solvents; Aromatic Hydrocarbons," D3362-93, D3125-97, D4415-91, D3541-91, D3547-91, D3548-99, D3845-96, D4416-89, and D4709-02, 2002).

In alternative embodiments, an acrylic resin temporary coating (e.g, a non-film forming coating) may be produced, for example, by selection of an acrylic resin that that comprises fewer or no crosslinkable moieties, selection of an addition binder that comprises fewer or no crosslinkable moieties, reducing the concentration of the an acrylic resin and/or additional binder, using a bake cured an acrylic resin coating at temperatures less than is needed for curing (e.g., ambient conditions), selection of size range for a thermoplastic acrylic resin coating that is less suitable for film formation (e.g., 1 kDa to 75 kDa), selection of a thermoplastic acrylic resin with $T_g$ that is lower than the temperature ranges herein and/or 20° C. lower than the temperature range of use, or a combination thereof.

(1) Thermoplastic Acrylic Resins

A strait acrylic resin ("strait acrylic polymer," "strait acrylic binder") is a homopolymer or copolymer comprising an acrylate ester monomer and/or a methacrylate ester monomer. A strait acrylic resin may be used to formulate a thermoplastic coating, as cross-linking reactions are absent or limited without additional reactive moieties in the monomers. Generally, a thermoplastic film produced from an acrylic resin-coating will possess a lower elongation, an increased hardness, an increased tensile strength, greater UV resistance (e.g., chalk resistance), color retention, a greater $T_g$, or a combination thereof, with increasing methacrylate ester monomer content in the acrylic resin. However, the ester of a monomer may comprise various alcohol moieties, and an alcohol moiety of larger size generally reduces the $T_g$. Examples a $T_g$ value for a homopolymer strait acrylic resins with the include −100° C., poly(octadecyl methacrylate); −72° C., poly(tetradecyl methacrylate); −65° C., poly (lauryl methacrylate); −60° C., poly(heptyl acrylate); −60° C., poly(n-decyl methacrylate); −55° C., poly(n-butyl acrylate); −50° C., poly(2-ethoxyethyl acrylate); −50° C., poly (2-ethylbutyl acrylate); −50° C., poly(2-ethylhexyl acrylate); −45° C., poly(propyl acrylate); −43° C., poly(isobutyl acrylate); −38° C., poly(2-heptyl acrylate); −24° C., poly (ethyl acrylate); −20° C., poly(n-octyl methacrylate); −20°

C., poly(sec-butyl acrylate); −20° C., poly(ethylthioethyl methacrylate); −10° C., poly(2-ethylhexyl methacrylate); −5° C., poly(n-hexyl methacrylate); −3° C., poly(isopropyl acrylate); 6° C., poly(methyl acrylate); 11° C., poly(2-ethylbutyl methacrylate); 16° C., poly(cyclohexyl acrylate); 20° C., poly(n-butyl methacrylate); 35° C., poly(hexadecyl acrylate); 35° C., poly(n-propyl methacrylate); 43° C., poly(t-butyl acrylate); 53° C., poly(isobutyl methacrylate); 54° C., poly(benzyl methacrylate); 60° C., poly(sec-butyl methacrylate); 65° C., poly(ethyl methacrylate); 79° C., poly(3,3,5-trimethylcyclohexylmethacrylate); 81° C., poly(isopropyl methacrylate); 94° C., poly(isobornyl acrylate); 104° C., poly(cyclohexyl methacrylate); 105° C., poly(methyl methacrylate); 107° C., poly(t-butyl methacrylate); and 110° C., poly(phenyl methacrylate). Additionally, an estimated $T_g$ of a copolymer comprising one or more monomers of an acrylate and/or methyacrylate monomer can be made by using the following equation: $1/T_g = W_1/T_{g1} + W_2/T_{g2}$, wherein $W_1$ and $W_2$ are the are the molecular weight ratios of the first and second monomer, respectively; and wherein $T_{g1}$ and $T_{g2}$ are glass transition temperatures of the first and second monomer, respectively (Fox, T. G., 1956). For many embodiments (e.g., solvent-borne coatings), it is contemplated that a $T_g$ of 40° C. to 60° C., including all intermediate ranges and combinations thereof, will be suitable.

The thermoplastic properties of an acrylic resin are also related to the molecular mass of the selected resin. Increasing the polymer size of an acrylic resin promotes physical polymer entanglement during film formation. Typically, a thermoplastic film produced from an acrylic-coating will possess a lower flexibility, an increased exterior durability, an increased hardness, an increased solvent resistance, an increased tensile strength, a greater $T_g$, or a combination thereof, with increasing polymer size of the acrylic resin. However, increasing polymer size of an acrylic resin generally increases viscosity of a solution comprising a dissolved acrylic resin, which may make application to a surface more difficult, such as cobwebbing of coating during spray application and the changes of film properties generally will reach a plateau at 100 kDa. In most embodiments, it is contemplated that an acrylic resin will range in mass from 75 kDa to 100 kDa, including all intermediate ranges and combinations thereof.

Examples of such a thermoplastic acrylic-coating include a lacquer. In specific facets, the lacquer possesses a good, high, or spectacular gloss. In specific aspects, such a thermoplastic acrylic-coating further comprises a pigment. In specific aspects, a wetting agent is less preferred in a coating comprising an acrylic resin and a pigment, due to the ease of dispersion of a pigment with an acrylic resin. In certain aspects, a thermoplastic acrylic-coating may be selected to coat a metal surface, a plastic surface, or a combination thereof. However, in particular aspects, a thermoplastic acrylic coating is an automotive coating. Such an automotive coating may comprise an acrylic binder with a high temperature $T_g$ to produce a film of sufficient durability (e.g., hardness) for external use and contact with heated surfaces. In certain aspects, a thermoplastic acrylic coating comprises a binder with a $T_g$ to 90° C. to 110° C., including all intermediate ranges and combinations thereof. In additional aspects, an automotive coating comprises a plasticizer, a metallic pigment, or a combination thereof. In specific aspects, a binder for an automotive coating comprises a methylmethacrylate ester monomer. In specific facets, an automotive coating comprises poly(methyl methacrylate).

(2) Water-Borne Thermoplastic Acrylic Coatings

The thermoplastic acrylic coatings described above are solvent-borne coatings. In other embodiments, a thermoplastic acrylic resin may be a waterborne coating. A waterborne acrylic ("acrylic latex") typically is an emulsion, wherein the acrylic binder is dispersed in the liquid component. In general embodiments, an emulsifier (e.g., a surfactant) promotes dispersion. In certain embodiments, an acrylic latex coating comprises 0% to 20% coalescent per weight of binder. In most embodiments, it is contemplated that a water-borne acrylic resin will range in mass from 100 kDa to 1000 kDa, including all intermediate ranges and combinations thereof. In certain embodiments, a waterborne acrylic coating comprises an associative thickener ("rheology modifier"), which may enhance flow, brushability, splatter resistance, film build, or a combination thereof. A water-borne acrylic may be selected as an architectural coating. An associative thickener forms a network with acrylic resin latex particles by hydrophobic interactions. Hydroxyethyl cellulose ("HEC") changes the coating rheology by promoting flocculation, which tends to reduce gloss, flow, or a combination thereof. Selection of an acrylic resin with smaller size, greater hydrophobicity, or a combination thereof, and an associative thickener may produce higher gloss, better flow, lower roller splatter, or a combination thereof.

(i) Architectural Coatings

A flat interior coating typically comprises a vinyl acetate and a lesser amount of acrylate (e.g., butyl acrylate) monomers, which generally produces a film with suitable scrub resistance. A copolymer of acrylate and methacrylate may be selected for a semigloss or gloss coating. In certain embodiments, the acrylate resin has a $T_g$ to 20° C. to 50° C., including all intermediate ranges and combinations thereof. In some aspects, such a coating generally possesses good block resistance good print resistance, or a combination thereof. An acrylic resin that comprises a monomer that comprises a ureide moiety may be selected for enhanced film adhesion (e.g., to a coated surface), blistering resistance, or a combination thereof. An acrylic resin that comprises a styrene monomer may be selected for enhanced film water resistance.

An exterior latex coating typically produces a film with greater flexibility than an interior latex due to temperature changes and/or dimensional movement of a substrate (e.g., wood). In certain embodiments, the acrylic resin has a $T_g$ to 10° C. to 35° C., including all intermediate ranges and combinations thereof. The selection of a $T_g$ may be influences by the selection of the amount particulate material (e.g., pigment) in the coating to achieve a particular visual appearance. For example, a higher the pigment volume content ("PVC") that is typically selected to reduce gloss. However, to retain properties such as flexibility, a binder with a lower a $T_g$ may be selected for combination with the higher PVC. For example, flat exterior latex a coating generally possesses a pigment volume content of 40% to 60% and a $T_g$ of 10° C. to 15° C., including all intermediate ranges and combinations thereof, respectively. In another example, a semigloss or gloss exterior latex binder of a coating generally possesses a $T_g$ of 20° C. to 35° C., including all intermediate ranges and combinations thereof, respectively. In other embodiments, the exterior latex binder particle size is selected to be relatively small such as 90 nm to 110 nm, including all intermediate ranges and combinations thereof. In certain facets, a smaller latex particle size promotes adhesion of the coating and/or film, particularly to a surface that comprises a degraded (e.g., chalking) film. In certain other embodiments, a larger latex particle size may be selected to increase the coating and/or film's build (e.g., thickness). In certain aspects, a larger latex particle size ranges from, for example 325 nm to 375 nm, including all intermediate ranges and combinations thereof.

(ii) Industrial Coatings

A water-borne thermoplastic acrylic latex industrial coating typically comprises a binder with a $T_g$ of 30° C. to 70° C., including all intermediate ranges and combinations thereof. Such a coating typically is applied to a metal surface, and thus often further comprises a surfactant, an additive, or a combination thereof to improve an anti-corrosion property. In specific aspects, the industrial coating comprises an anti-corrosion pigments, anti-corrosion pigment enhancers, or a combination thereof. In contrast, a water-borne acrylic latex industrial maintenance coating typically is similar to an exterior flat architectural coating in selection of binders, though they preferably comprise anti-corrosion pigments, anti-corrosion pigment enhancers, and other anti-corrosion components for use on a metal surface.

(3) Thermosetting Acrylic Resins

Unless otherwise noted, the following thermosetting acrylic resins and/or coatings are preferably solvent-borne coatings. In certain embodiments an acrylic coating comprises a thermosetting acrylic resin. A thermosetting acrylic coating typically possesses superior hardness, superior toughness, superior temperature resistance, superior resistance to a solvent, superior resistance to a stain, superior resistance to a detergent, higher application of solids, relative to a thermoplastic acrylic coating. The average size of a thermosetting acrylic resin is typically less than a thermoplastic acrylic resin, which promotes a relatively lower viscosity and/or higher application of solids in a solution comprising a thermosetting acrylic resin. In certain embodiments, a thermosetting acrylic resin is from 10 kDa to 50 kDa, including all intermediate ranges and combinations thereof.

A thermosetting acrylic resin comprises a moiety capable of undergoing a cross-linking reaction. A monomer may comprise the moiety, and be incorporated into the polymer structure of an acrylic resin during resin synthesis (e.g., a styrene, a vinyltoluene), and/or the acrylic resin may be chemically modified after polymerization to comprise a chemical moiety. In additional embodiments, an acrylic resin may be selected to comprise chemical moieties, such as an amine, a carboxyl, an epoxy, a hydroxyl, an isocyanate, or a combination thereof, to confer a desirable property to the acrylic resin produced. Examples of such properties include the acrylic resin's chemical reactivity (e.g., cross-linkability), acidity, alkalinity, hydrophobicity, hydrophilicity, glass transition temperature, or a combination thereof. In general embodiments, an acrylic resin comprising a carboxyl moiety, a hydroxyl moiety, or a combination thereof, promotes a crosslinking reaction with another binder. In other embodiments, an acrylic resin may be chemically modified to comprise a methylol and/or methylol ether group, which is a resin capable of self-crosslinking.

(i) Acrylic-Epoxy Combinations

In certain embodiments, a thermosetting acrylic resin may be combined with an epoxide resin. In general embodiments, an acrylic resin comprising a carboxyl moiety may be selected for cross-linking with an epoxy resin. In specific aspects, an acrylic resin comprises 5% to 20% including all intermediate ranges and combinations thereof, of a monomer that comprises a carboxyl moiety, such as of an acrylic acid monomer, a methacrylic acid monomer, or a combination thereof. The carboxyl moiety may undergo a cross-linking reaction with an epoxide resin (e.g., a bisphenol A/epichlorohydrin epoxide resin) during film formation. In certain aspects, an epoxide resin cross-linked with an acrylic resin generally produces a film with good hardness, good alkali resistance, greater solvent resistance to a film, poorer UV resistance, or a combination thereof.

A thermosetting acrylic-epoxy coating may be selected for application to a metal surface. Examples of surfaces that an acrylic-epoxy coating is selected for use include an indoor surface, an indoor metal surface (e.g., an appliance), or a combination thereof. In certain aspects, an epoxide resin cross-linked with an acrylic resin generally produces a film with good hardness, good alkali resistance, greater solvent resistance to a film, poorer UV resistance, or a combination thereof. In some facets, an acrylic resin may be combined with an aliphatic epoxide resin to produce a film with relatively superior UV resistance than a bisphenol A/epichlorohydrin based epoxide resin. In another facet, an acrylic resin polymerized with an allyl glycidyl ether monomer, a glycidyl acrylate monomer, a glycidyl methacrylate monomer, or a combination thereof, may undergo a cross-linking reaction with an epoxide resin during film formation. In specific facets, a film produced from cross-linking an epoxide other than a bisphenol A/epichlorohydrin epoxide resin and an acrylic resin comprising an allyl glycidyl ether monomer, a glycidyl acrylate monomer, a glycidyl methacrylate monomer, or a combination thereof possesses a relatively superior UV resistance.

In certain embodiments, an acrylic epoxy coating comprises a catalyst to promote cross-linking during film formation. In specific aspects, the catalyst is a base such as a dodecyl trimethyl ammonium chloride, a tri(dimethylaminomethyl) phenol, a melamine-formaldehyde resin, or a combination thereof. In other embodiments, an acrylic epoxy coating is cured by baking at 150° C. to 190° C., including all intermediate ranges and combinations thereof. In particular aspects, film formation time of an acrylic epoxy coating is from 15 minutes to 30 minutes, including all intermediate ranges and combinations thereof. In certain embodiments, a thermosetting coating comprises an acrylic epoxide melamine-formaldehyde coating, wherein an acrylic resin, an epoxide resin and a melamine-formaldehyde resin undergo cross-linking during film formation.

(ii) Acrylic-Amino Combinations

In other embodiments, a thermosetting acrylic resin may be combined with an amino resin. In general embodiments, an acrylic resin comprising an acid (e.g., carboxyl) moiety, a hydroxyl moiety, or a combination thereof, may be selected for cross-linking with an amino resin. An acrylic amino coating, wherein the acrylic resin comprises an acid moiety, may be cured by baking at, for example 150° C. for 30 minutes. However, an acid moiety acrylic amino coating is typically undergoes a greater degree of reactions between amino resins, which reduces properties such as toughness. In specific aspects, an acrylic resin comprises a monomer that comprises a hydroxyl moiety such as a hydroxyethyl acrylate ("HEA"), a hydroxyethyl methacrylate ("HEMA"), or a combination thereof. An acrylic amino coating, wherein the acrylic resin comprises a hydroxyl moiety, typically comprises an acid catalyst to promote curing by baking at, for example 125° C. for 30 minutes. An acrylic amino coating, wherein the amino resin was prepared from urea, generally produces a film with lower gloss, less chemical resistance, or a combination thereof, than an amino resin prepared from another nitrogen compound. Selection of a melamine and/or benzoguanamine based amino coating generally produces a film with excellent weathering resistance, excellent solvent resistance, good hardness, good mar resistance, or a combination thereof, and such an acrylic amino coating may be selected for an automotive topcoat.

(iii) Acrylic-Urethane Combinations

In other embodiments, a thermosetting acrylic resin may be combined with an urethane resin. In general embodiments, an acrylic resin comprising an acid moiety, a hydroxyl moiety, or a combination thereof, may be selected for crosslinking with an urethane resin. In specific embodiments, an acrylic resin comprises a hydroxyl moiety, such as, for example, a moiety provided by a HEA monomer, a HEMA monomer, or a combination thereof. Selection of an aliphatic isocyanate urethane (e.g., hexamethylene diisocyanate based) generally produces a film with superior color, weathering, or a combination thereof relative to other urethanes. An acrylic urethane coating may comprise a catalyst, such as, for example, triethylene diamine, zinc naphthenate, dibutyl tin-di-laurate, or a combination thereof. An acrylic urethane coating cures at ambient conditions. However, an acrylic urethane coating typically is a two-pack coating to separate the reactive binders until application. An acrylic urethane coating generally produces a film with good weathering, good hardness, good toughness, good chemical resistance, or a combination thereof. An acrylic urethane coating may be selected an aircraft coating, an automotive coating, an industrial coating (e.g., an industrial maintenance coating), or a combination thereof.

(iv) Water-Borne Thermosetting Acrylics

In other embodiments, a thermosetting acrylic coating may be a waterborne coating (e.g., a latex coating). Typically, such a thermosetting acrylic coating comprises an acrylic resin with a hydroxyl moiety, an acid moiety, or a combination thereof. An acrylic resin may further comprise an additional monomer such as a styrene, a vinyltoluene, or a combination thereof. The acrylic resin typically is combined in a coating with an amino resin, an epoxy resin, or a combination thereof as previously described. A film produced from a water-borne thermosetting acrylic coating is similar in properties as a solvent-borne counterpart. Such a coating may be selected for surfaces such as masonry, wood, metal, or a combination thereof.

k. Polyvinyl Binders

A polyvinyl binder ("polyvinyl," "vinyl binder," "vinyl") is a binder comprising a polymer of a vinyl chloride monomer, a vinyl acetate monomer, or combination thereof. A solvent-borne polyvinyl coating may comprise a ketone, ester, chlorinated hydrocarbon, nitroparaffin, or a combination thereof, as a solvent. A solvent-borne polyvinyl coating may comprise a hydrocarbon (e.g., aromatic, aliphatic) as a diluent. A polyvinyl binder is generally insoluble in an alcohol, however, in embodiments wherein a solvent-borne polyvinyl coating that comprises an additional alcohol soluble binder, alcohol may comprise 0% to 20% of the liquid component. In embodiments wherein solvent-borne polyvinyl coating is cured by baking, a glycol ether and/or glycol ester may be used in the liquid component to enhance a rheological property. In other embodiments, the liquid component of a polyvinyl coating may comprise a plasticizer (e.g., a phthalate, a phosphate, a glycol ester), wherein the plasticizer if 1 to 25 parts per hundred parts polyvinyl binder, including all intermediate ranges and combinations thereof, for a non-plastisol or non-organosol coating. A polyvinyl-coating may be used to prepare a thermoplastic coating, a thermosetting coating, or a combination thereof. In specific aspects, a thermoplastic polyvinyl binder coating possesses a $T_g$ of 50° C. to 85° C., including all intermediate ranges and combinations thereof. However, in some aspects, a polyvinyl-coating/film possesses moderate resistance to heat, UV irradiation, or a combination thereof. In specific aspects, a polyvinyl-coating comprises a light stabilizer, a pigment, or a combination thereof. In particular facets, the light stabilizer, the pigment (e.g., titanium dioxide), or the combination thereof, improves the polyvinyl-coating and/or film's resistance to heat, UV irradiation, or a combination thereof.

In embodiments wherein a polyvinyl coating comprises a solvent-borne coating, it is contemplated that a polyvinyl resin will range in mass from 2 kDa to 45 kDa, including all intermediate ranges and combinations thereof. A typical solvent-borne polyvinyl coating comprises a polyvinyl resin, a liquid component wherein the liquid component comprises a solvent, and a plasticizer. A solvent-borne polyvinyl coating may additionally comprise a colorizing agent (e.g., a pigment), a light stabilizer, an additional binder, a cross-linker, or a combination thereof.

A polyvinyl binder typically possesses excellent adhesion for a plastic surface, an acrylic and/or acrylic coated surface, paper, or a combination thereof. A thermoplastic polyvinyl coating may be selected as a lacquer, a topcoat of a can coating (e.g., can interior surface), or a combination thereof. In some embodiments, an polyvinyl-coating may be selected to produce a film with such properties, for example, as excellent water resistance, excellent resistance to various solvents (e.g., an aliphatic hydrocarbon, an alcohol, an oil), excellent resistance to acid pH, excellent resistance to basic pH, inertness relative to food, or a combination thereof.

In many aspects, a polyvinyl resin is a copolymer that comprises a combination of a vinyl chloride monomer and vinyl acetate monomer. Often during resin synthesis (e.g., polymerization), a polyvinyl resin is prepared to further comprise monomers with specific chemical moieties to confer a property such as solubility in water, solubility in a solvent, compatibility with another coating component (e.g., a binder), or a combination thereof. In certain embodiments, a polyvinyl resin comprises a monomer comprising carboxyl moiety, a hydroxyl moiety (e.g., a hydroxyalkyl acrylate monomer), a monomer comprising an epoxy moiety, a monomer comprising a maleic acid, or a combination thereof. A carboxyl moiety may confer an increased adhesion property (e.g., excellent adhesion to metal). However, a polyvinyl resin comprising a carboxyl moiety is generally not compatible with a basic pigment. A thermosetting polyvinyl coating comprising a polyvinyl binder that comprises a carboxyl moiety and a polyvinyl binder that comprises an epoxy moiety generally possesses one or more excellent physical properties (e.g., flexibility), and may be selected as a coil coating. A hydroxyl moiety may confer cross-linkability, compatibility with another coating component, an increased adhesion property (e.g., good adhesion to aluminum), or a combination thereof. Additionally, after polymer synthesis, a polyvinyl resin can be chemically modified to comprise such a specific chemical moiety. In some embodiments, a polyvinyl resin is chemically modified to comprise a secondary hydroxyl moiety, an epoxy moiety, a carboxyl moiety, or a combination thereof. A polyvinyl resin comprising a secondary hydroxyl moiety may be combined with another binder such as an alkyd, an urethane, an amino-formaldehyde, or a combination thereof. A thermosetting polyvinyl amino-formaldehyde coating comprising a polyvinyl binder that comprises a hydroxyl moiety generally possesses good corrosion resistance, water resistance, solvent resistance, chemical resistance, and may be selected as a can coating, a coating for an interior wood surface, or a combination thereof. Standards for physical properties, chemical properties, and/or procedures for testing the purity/properties of various polyvinyl monomers (e.g., vinyl acetate) and polyvinyl resins (e.g., polymer components, polymer mass, shear viscosity for a higher mass resin, chlorine content) are described, for example, in "ASTM Book of Standards, Volume 06.04, Paint—Solvents; Aromatic Hydrocarbons," D2190-97, D2086-02, D2191-97, and D2193-97, 2002; "ASTM Book of Standards, Volume 06.03, Paint—Pigments, Drying Oils, Polymers, Resins, Naval Stores, Cellulosic Esters, and Ink Vehicles," D4368-89, D3680-89, and D1396-92, 2002; and in "ASTM Book of Standards, Volume 06.01, Paint—Tests for Chemical, Physical, and Optical Properties; Appearance," D2621-87, 2002.

In alternative embodiments, a polyvinyl resin temporary coating (e.g., a non-film forming coating) may be produced, for example, by selection of a polyvinyl resin that that comprises fewer or no crosslinkable moieties, selection of an addition binder that comprises fewer or no crosslinkable moieties, reducing the concentration of the a polyvinyl resin and/or additional binder, using a bake cured a polyvinyl resin coating at temperatures less than is needed for curing (e.g., ambient conditions), selection of size range for a plastisol or organisol polyvinyl resin coating that is less suitable for film formation (e.g., 1 kDa to 60 kDa), selection of a polyvinyl resin with $T_g$ that is lower than the temperature ranges herein and/or 20° C. lower than the temperature range of use, or a combination thereof.

(1) Plastisols and Organisols

A polyvinyl resin of 60 kDa to 110 kDa, including all intermediate ranges and combinations thereof, may be selected for use as an organosol or a plastisol. A plastisol is coating comprising a vinyl homopolymer binder and a liquid component, wherein the liquid component comprises a plasticizer comprising a minimum of 55 parts or more of plasticizer per hundred parts of homopolymer binder in the coating. In certain embodiments, a plastisol comprises, by weight, 0% to 10% including all intermediate ranges and combinations thereof, of a thinner (e.g., an aliphatic hydrocarbon). A plastisol coating typically comprises an additional vinyl binder. A plastisol may comprise a pigment, however, a low oil absorption pigment is preferred to avoid undesirable increase in coating viscosity given the liquid component used for a plastisol.

An organosol is similar to a plastisol, except the less than 55 parts of plasticizer per hundred parts of homopolymer binder is used in the coating. In typical embodiments, the liquid component of comprises a weak solvent that may act as a dispersant and a thinner (e.g., a hydrocarbon). In typical aspects, the reduced content of plasticizer produced a film with a superior hardness property relative to a plastisol. In additional embodiments, the nonvolatile component of an organisol is 50% to 55%, including all intermediate ranges and combinations thereof. An organosol coating typically comprises a second binder. In specific aspects, the second binder is a vinyl copolymer, an acrylic, or a combination thereof. In certain aspects, the second binder comprises a carboxyl moiety, a hydroxyl moiety, or a combination thereof. In further aspects, an organisol may comprise a third binder. In specific facets, the third binder comprises an amino resin, a phenolic resin prepared from formaldehyde, or a combination thereof. In additional facets, a second binder that comprises a hydroxyl moiety may undergo a thermosetting cross-linking reaction with a third binder. An organisol may comprise a pigment suitable for general polyvinyl coatings.

A plastisol or organisol typically is cured by baking. In general embodiments, baking is at a temperature of 175° C. to 180° C., including all intermediate ranges and combinations thereof. In general embodiments, a plastisol or organisol comprises a heat stabilizer. The heat stabilizer may protect a vinyl binder during baking. Examples of a suitable heat stabilizer include a combination of a metal salt of an organic acid and an epoxidized oil or a liquid epoxide binder. However, in an embodiment wherein the plastisol or organisol comprises a binder that comprises an carboxyl moiety, a metal salt is less preferred due to possible gellation of the coating, and may be substituted with a merapto tin and/or tin ester compound.

In embodiments wherein a plastisol or organisol comprise a binder with good adhesion properties for a surface such as a binder comprising carboxy moiety, the plastisol or organisol may be used as a single layer coating. For example, such an organisol may be selected to coat the end of a can. However, a plastisol or organisol typically is part of a multicoat system that comprises a primer to promote adhesion. In specific aspects, the primer comprises a vinyl resin comprising a carboxy moiety. In specific facets, the primer further comprises a thermosetting binder such as an amino-formaldehyde, phenolic, or a combination thereof, to enhance solvent resistance. In certain facets, it is preferred that a primer or other coat layer of a multicoat system possesses good solvent resistance to the plasticizers of the organosol and/or plastisol coat layer.

(2) Powder Coatings

A polyvinyl binder may be selected as a powder coating. Typically, coating components such as a polyvinyl binder and a plasticizer, colorizing agent, additive, or a combination thereof, admixed to prepare a powder coating. Such a powder coating is usually applied by a fluidized bed applicator, a spray applicator, or a combination thereof. In some aspects, the coating components are melted then ground into a powder. Such a powder coating is usually applied by an electrostatic spray applicator. The coating is cured by baking. A polyvinyl powder coating may be selected to coat a metal surface.

(3) Water-Borne Coatings

The previous discussions of polyvinyl coatings focused upon solvent-borne and powder coatings. A polyvinyl binder with a $T_g$ of 75° C. to 85° C., including all intermediate ranges and combinations thereof, may be selected for use in a dispersion waterborne coating. The liquid component may comprise a cosolvent such as a glycol ether, a plasticizer, or a combination thereof. Examples of a cosolvent include ethylene glycol monobutyl ether. The dispersion waterborne polyvinyl coating may be used as described for a solvent-borne polyvinyl coating. In another example, an organisol may be prepared with a plasticizer as a latex coating. Such a latex is suitable for selection as a primer coating. The latex coating is cured by baking.

1. Rubber Resins

In certain embodiments, a coating may comprise a rubber resin as a binder. A rubber may be either obtained from a biological source ("natural rubber"), synthesized from petroleum ("synthetic rubber"), or a combination thereof. Examples of synthetic rubber include polymers of styrene monomers, butadiene monomers, or a combination thereof. In alternative embodiments, a rubber temporary coating (e.g., a non-film forming coating) may be produced, for example, by selection of rubber resin that that comprises fewer or no crosslinkable moieties, selection of an addition binder that comprises fewer or no crosslinkable moieties, reducing the concentration of the a rubber resin and/or additional binder, or a combination thereof.

(1) Chlorinated Rubber Resins

In general embodiments, a rubber resin comprises a chlorinated rubber resin, wherein a rubber isolated from a biological source has been chemically modified by reaction with chlorine to produce a resin comprising 65% to 68% chlorine by weight, including all intermediate ranges and combinations thereof. A chlorinated rubber resins generally are in a molecular weight range of 3.5 kDa to 20 kDa, including all intermediate ranges and combinations thereof. A chlorinated rubber coating may comprise another binder, such as, for example, an acrylic resin, an alkyd resin, a bituminous resin, or a combination thereof. In specific aspects, a chlorinated rubber resin comprises 10% to 50%, by weight, including all intermediate ranges and combinations thereof, of the binder when in combination with an acrylic resin, an alkyd resin, or a combination thereof. In general embodiments, a chlorinated rubber coating is a solvent-borne coating. In certain aspects, a chlorinated rubber coating comprises a liquid component, such as, for example, a solvent, a diluent, a thinner, a plasticizer, or a combination thereof. A chlorinated rubber coating may be a thermoplastic coating. To reduce the $T_g$ of a film produced from a chlorinated rubber resin, the liquid component generally comprises a plasticizer. In certain aspects, a chlorinated rubber coating comprises 30% to 40%, by weight, including all intermediate ranges and combinations thereof, of plasticizer. In certain facets, a plasticizer is selected for water resistance (e.g., hydrolysis resistance) such as a bisphenoxyethylformal. In certain facets, a chlorinated rubber coating comprises light stabilizer, an epoxy resin, an epoxy plasticizer (e.g., epoxidized soybean oil), or combination thereof, to chemically stabilize a chlorinated resin, coating and/or film. In other embodiments, a chlorinated rubber coating comprises a pigment, an extender, or a combination thereof. In particular aspects, the pigment is a corrosion resistant pigment. A chlorinated rubber film are generally has good chemical resistance (e.g., acid resistance, alkali resistance), water resistance, or a combination thereof. Coatings comprising chlorinated rubber resins may be used, for example, on surfaces that contact gaseous, liquid and/or solid external environments. Examples of such uses include a coating for an architectural coating (e.g., a masonry coating), a traffic marker coating, a marine coating (e.g., a marine vehicle, a swimming pool), a metal primer, a metal topcoat, or a combination thereof.

(2) Synthetic Rubber Resins

Examples of synthetic rubber include polymers comprising a styrene monomer, a methylstyrene (e.g., α-methylstyrene) monomer, or a combination thereof. A polystyrene and/or polymethylstyrene coating may be a solvent-borne coating. Examples of a solvent include an aliphatic hydrocarbon, an aromatic hydrocarbon, a ketone, an ester, or a combination thereof. A polystyrene and/or polymethylstyrene coating may possess good water resistance, good chemical resistance, or a combination thereof. A polystyrene and/or polymethylstyrene coating may be selected as a primer, a lacquer, a masonry coating, or a combination thereof. A polystyrene homopolymer has a $T_g$ of 100° C., and in certain embodiments, a polystyrene coating is bake cured.

Standards for physical properties, chemical properties, and/or procedures for testing the purity/properties of a styrene monomer, a methylstyrene monomer, (e.g., α-methylstyrene), a resin comprising a styrene and/or methylstyrene monomer, are described, for example, in "ASTM Book of Standards, Volume 06.04, Paint—Solvents; Aromatic Hydrocarbons," D2827-00, D6367-99, D6144-97, D4590-00, D2119-96, D2121-00, and D2340-96, 2002.

Similar to the variability of $T_g$ previously described for a thermoplastic acrylic resin, a styrene copolymer with a lower a $T_g$ than polystyrene or other altered properties can be produced from polymerization with other monomers such as a butadiene monomer, an acrylic monomer, a maleate ester, an acrylonitrile, an allyl alcohol, a vinyltoluene, or a combination thereof. For example, a butadiene monomer decreases lightfastness, but confers self-crosslinkability to the resin. In another example, an acrylic resin increases the resin's solubility in an alcohol. In a further example, an allyl alcohol monomer confers crosslinkability in combination with a polyol. In certain embodiments, a styrene-butadiene copolymer resin may be selected. In certain aspects, a styrene-butadiene resin comprises a carboxyl moiety to improve an adhesion property, dispersibility in a liquid component, or a combination thereof. In particular facets, a styrene-butadiene coating comprises an emulsifier to increase dispersion in a liquid component, a light stabilizer, or a combination thereof. A styrene-butadiene coating may be a thermosetting coating, due to oxidative crosslinking of a butadiene double bond moiety. However, styrene-butadiene film may have poor chalking resistance, poor color stability, poor UV resistance, or a combination thereof. A styrene-butadiene coating may be selected as a corrosion resistant primer, a wood primer, or a combination thereof. A styrene-vinnyltoluene-acrylate copolymer coating may be selected for an exterior coating, a traffic marker paint, a metal coating (e.g., a metal lacquer), a masonry coating, or a combination thereof.

m. Bituminous Binders

A bituminous binder ("bituminous") is a binder comprising a hydrocarbon soluble in carbon disulfide, is black or dark colored, and is obtained from a bitumen deposit and/or as a product of petroleum processing. A bituminous binder typically is used in asphalt, tar, and other construction materials. However, in certain embodiments, a bituminous binder may be used in a coating of the present invention, particularly in embodiments wherein good resistance to a chemical such as a petroleum based solvent, an oil, water, or a combination thereof, is desired. Examples of a bituminous binder include a coal tar, a petroleum asphalt, a pitch, an asphaltite, or a combination thereof. In certain embodiments, a coal tar and/or pitch is combined with an epoxy resin to form a thermosetting coating. Such as coating may be selected as a pipeline coating. In other embodiments, an asphaltite and/or petroleum asphalt may be selected for use as an automotive coating (e.g., an underbody part coating). An asphaltite and/or petroleum asphalt coating may further comprise an additional binder such as an epoxy. In certain aspects, an asphaltite and/or petroleum asphalt coating is a solvent-borne coating. In specific aspects, an asphaltite and/or petroleum asphalt coating comprises a plasticizer. In further aspects, an asphaltite and/or petroleum asphalt coating comprises a wax to increase abrasion resistance.

In further embodiments, bituminous coating may be selected as a roof coating. Typically, a bituminous roof coating comprises an extender, a thixotrope, or a combination thereof. Examples of a thixotrope additive include asbestos, a silicon extender, a celluosic, a glass fiber, or a combination thereof. In some aspects, a bituminous roof coating comprises a solvent-borne coating or a water-borne coating. Examples of solvents that may be selected include a mineral spirit, an aliphatic hydrocarbon (e.g., a naphtha, a mineral spirit), an aromatic solvent (e.g., xylene, toluene) or a combination thereof. A bituminous roof coating may be selected as a primer, a topcoat, or a combination thereof. A bituminous roof topcoat typically further comprises a metallic pigment.

In certain aspects, a solvent-borne or water-borne bituminous coating is an emulsion comprising water and a bituminous binder. In specific facets, the emulsion further comprises a solvent, an extender (e.g., a silica), an emulsifier (e.g., a surfactant), or a combination thereof. The extender typically functions to stabilize the emulsion. In particular facets, the emulsion bituminous coating is a roof coating, a road coating, a sealer, a primer, a topcoat, or a combination thereof. In facets wherein an emulsion bituminous coating is selected as a sealer, an additional binder may be added to increase solvent resistance.

In alternative embodiments, a bituminous temporary coating (e.g, a non-film forming coating) may be produced, for example, by selection of an addition binder that comprises fewer or no crosslinkable moieties, reducing the concentration of the a bituminous resin and/or additional binder, or a combination thereof.

n. Polysulfide Binders

A polysulfide binder is a polymer produced from a reaction of sodium polysulfide, bis(2-chlorethyl)formal and 1,2,3-trichloropropane. Typically, a polysulfide binder is 1 kDa to 8 kDa, including all intermediate ranges and combinations thereof. A polysulfide binder comprises a thiol ("mercaptan") moiety capable of crosslinking with an additional binder. A polysulfide may undergo crosslinking by an oxidative reaction with an additional binder comprising a peroxide (e.g., dicumen hydroperoxide), a manganese dioxide, p-quinonedioxime, or a combination thereof. A polysulfide binder may be crosslinked with a glycidyl epoxide, though a tertiary amine is preferably part of the coating to promote this reaction. A polysulfide may undergo crosslinking with a binder comprising an isocyanate moiety, though it is preferred that the binder comprise a plurality of isocyanates. A polysulfide film typically possesses excellent UV resistance, good general weatherability properties, good chemical resistance, or a combination thereof.

In alternative embodiments, a polysulfide temporary coating (e.g, a non-film forming coating) may be produced, for example, by selection of an addition binder that comprises fewer or no crosslinkable moieties, reducing the concentration of the a bituminous resin and/or additional binder, or a combination thereof.

o. Silicone Binders

The previous described binders are molecules based on carbon, and are considered herein as "organic binders". A silicone binder ("silicone") is a binder molecule based on silicone. Examples of a silicone binder include a polydimethylsiloxane and a methyltriacetoxy silane, a methyltrimethoxysilane, a methyltricyclorhexylaminosilane, a fluorosilicone, a trifluoropropyl methyl polysiloxane, or a combination thereof. In general embodiments, a silicone binder comprises a crossreactive silicon moiety, examples of which are described below. A silicone coating may be selected for excellent resistance to irradiation (e.g., UV, infrared, gamma), excellent weatherability, excellent biodegradation resistance, flame resistance, excellent dielectric property, which is poor electrical conductivity with little detrimental effect on an electrostatic field, or a combination thereof. In specific aspects, a silicon coating is an industrial coating. In particular facets, a silicon coating is applied to an appliance part, a furnace part, a jet engine part, an incinerator part, or a missile part. In other embodiments, a silicon coating comprises an organic binder. In particular aspects, a silicon organic binder coating possesses superior heat resistance to an organic binder coating. In other aspects, the greater the silicon binder to organic binder ratio, the greater the crosslinking reactions, greater film hardness, reduced flexibility, or a combination thereof.

In general embodiments, a silicone coating is a thermosetting coating. Often, a silicon coating is a multi-pack coating due to a limited pot life one the coating components are admixed. The crosslinking reaction depends upon the binder's specific silicon moiety. A plurality of binders may be used, each comprising one or more crosslinking moieties. A binder comprising crosslinking SiOH and HOSi moieties generally comprises a cure agent such as a lead octoate, a zinc octoate, or a combination thereof. In general aspects, the thermosetting SiOH and HOSi silicon coating is bake cured (e.g., 250° C. for one hour). A binder comprising crosslinking SiOH and HSi moieties typically comprises a tin catalyst. A binder comprising crosslinking SiOH and ROSi moieties, wherein RO is an alkoxy moiety, also typically comprises a tin catalyst. A coating prepared using SiOH and ROSi silicon binder typically further comprises an iron oxide, a glass microballon, or a combination thereof to improve heat resistance. This type of silicon may be selected for rocket and jet engine parts. A binder comprising crosslinking SiOH and $CH_3COOSi$ moieties is moisture cured, and typically comprises a tin catalyst (e.g., an organotin compound). A binder comprising crosslinking SiOH and $R_2NOSi$ moieties, wherein $R_2NO$ is an oxime moiety, is also moisture cured, and typically comprises a tin catalyst. The moisture cured silicon coatings may be selected for one-pack silicon coatings, though film formation is generally slower than other types of silicon thermosetting coatings. A binder comprising crosslinking $SiCH=CH_2$ and $R_2NOSi$ moieties, wherein $R_2NO$ is an oxime moiety, typically comprises a platinum catalyst, and may be bake cured. A film produced by a $SiCH=CH_2$ and $R_2NOSi$ silicon coating possesses excellent toughness, flame resistance, or a combination thereof. Such a coating may be selected for a rocket part. However, coating components such as a rubber, a tin compound (e.g., an organotin), or a combination thereof, may inhibit platinum catalyzed film formation in this silicon coating.

In certain embodiments, a silicone coating is a solvent-borne coating. Examples of liquid components that may function as a silicon solvent include a chlorinated hydrocarbon (e.g., 1,1,1-trichloroethane), an aromatic hydrocarbon (e.g., a VMP naphtha, xylene), an aliphatic hydrocarbon, or a combination thereof. A silicone binder typically is insoluble or poorly soluble in an oxygenated compound such as an alcohol, a ketone, or a combination thereof, of relatively low molecular weight (e.g., ethanol, isopropanol, acetone). However, a fluorosilicone, which is a silicone binder that comprises a fluoride moiety, may be combined with a liquid component comprising a ketone such as methyl ethyl ketone, methyl isobutyl ketone, or a combination thereof. A fluorosilicone binder may be selected for producing a film with excellent solvent resistance. A silicon coating often comprises a pigment. In specific embodiments, a pigment comprises zinc oxide, titanium dioxide, zinc orthotitanate, or a combination thereof, which may improve a film's resistance to extreme temperature variations, such as those of outerspace. In specific embodiments, a silicon coating may comprise a silica extender (e.g., fumed silica), which often increases durability.

In certain embodiments, a silicon binder comprises a trifluoropropyl methyl polysiloxane binder. In certain aspects, a trifluoropropyl methyl polysiloxane binder may be selected for producing a film with excellent resistance to petroleum products (e.g., automotive fuel, aircraft fuel), but poor resistance to an acid or an alkali, particularly at baking conditions.

In alternative embodiments, a silicon temporary coating (e.g, a non-film forming coating) may be produced, for example, by selection of an addition binder that comprises fewer or no crosslinkable moieties, reducing the concentration of the a silicon resin and/or additional binder, using a bake-cured silicon coating at non-baking conditions, inclusion of a rubber, a tin compound (e.g., an organotin), or a combination thereof.

2. Liquid Components

A liquid component is a chemical composition that is in a liquid state while comprised in a coating and/or film. A liquid component is typically added to a coating composition, for example, to improve a rheological property for ease of application, alter the period of time that thermoplastic film formation occurs, alter an optical property (e.g., color, gloss) of a film, alter a physical property of a coating (e.g., reduce flammability) and/or film (e.g., increase flexibility), or a combination thereof.

As would be known to those of ordinary skill in the art, often a liquid component comprises a volatile liquid that is partly or fully removed (e.g., evaporated) from the coating during film formation. Examples of a volatile liquid include a volatile organic compound ("VOC"), water, or a combination thereof. In many embodiments, 0% to 100%, including all intermediate ranges and combinations thereof, of the liquid component is lost during film formation. Various environmental laws and regulations have encouraged the reduction of volatile organic compound use in coatings [see "Paint and Coating Testing Manual, Fourteenth Edition of the Gardner-Sward Handbook," (Koleske, J. V. Ed.), pp. 3-12, 1995]. As a consequence, a coating may comprise a solvent-borne coating, which typically comprises a VOC and was the coating usually selected prior to enactment of the environmental laws, a high solids coating, which is generally a solvent-borne coating formulated with a minimum amount of a VOC, a water-borne coating, which comprises water and typically even less VOC, or a powder coating, which comprises little or no VOC.

In many embodiments, a liquid component may comprise a liquid composition classified based upon function such as a solvent, a thinner, a diluent, a plasticizer, or a combination thereof. A solvent is a liquid component used to dissolve one or more coating components. A thinner is a liquid component used to reduce the viscosity of a coating, and often additionally confers one or more properties to the coating, such as, for example, dissolving a coating component (e.g., a binder), wetting a colorizing agent, acting as an antisettling agent, stabilizing a coating in storage, acting as an antifoaming agent, or a combination thereof. A diluent is a liquid component that does not dissolve a binder.

Liquid components can be classified, based on their chemical composition, as an organic compound, an inorganic compound, or a combination thereof. Preferred organic compounds include a hydrocarbon, an oxygenated compound, a chlorinated hydrocarbon, a nitrated hydrocarbon, a miscellaneous organic liquid component, or a combination thereof. A hydrocarbon consists of or consists essentially of one or more carbon and/or hydrogen atoms. Examples of a hydrocarbon include an aliphatic hydrocarbon, an aromatic hydrocarbon, a naphthene, a terpene, or a combination thereof. An oxygenated compound comprises of one or more carbon, hydrogen and/or oxygen atoms. Examples of an oxygenated compound include an alcohol, an ether, an ester, a glycol ester, a ketone, or a combination thereof. A chlorinated hydrocarbon comprises one or more carbon, hydrogen and/or chlorine atoms, but does not comprise an oxygen atom. A nitrated hydrocarbon comprises one or more carbon, hydrogen and/or nitrogen atoms, but does not comprise an oxygen atom. A miscellaneous organic liquid component is a liquid other than a chlorinated hydrocarbon and/or a nitrated hydrocarbon that comprises one or more carbon, hydrogen and/or other atoms. In certain aspects, a miscellaneous organic liquid component does not comprise an oxygen atom. Preferred inorganic compounds include ammonia, hydrogen cyanide, hydrogen fluoride, hydrogen cyanide, sulfur dioxide, or a combination thereof. However, an inorganic compound generally is used at temperatures less than room temperature, and at pressures greater than atmospheric pressure.

In certain embodiments, a liquid component may comprise an azeotrope. An azeotrope ("azeotropic mixture") is a solution of two or more liquid components at concentrations that produces a constant boiling point for the solution. An azeotrope BP ("A-BP") is the boiling point of an azeotrope. Often, the boiling point ("BP") of the majority component of an azeotrope is higher than the A-BP, and in some embodiments, such an azeotrope evaporates from a coating faster than a similar coating that does not comprise the azeotrope. However, in some aspects, a coating comprising an azeotrope with a superior evaporation property may possess a lower flash point temperature, a lower explosion limit, a reduced coating flow, greater surface defect formation, or a combination thereof, relative to a similar coating that does not comprise the azeotrope. Alternatively, an azeotrope may be selected for embodiments wherein a component's BP is increased. In specific aspects, a coating comprising such an azeotrope may have a relatively slower evaporation rate than a similar coating that does not comprise the azeotrope. It is contemplated that the greater the percentage of liquid component is an azeotrope, the greater the conference of an azeotrope's property to a coating. Thus, a specific range of 50% to 100%, 90% to 100%, or 95% to 100%, including all intermediate ranges and combinations thereof, is sequentially more preferred in embodiments wherein an azeotrope's property is desired as a property of a coating.

In some embodiments, a chemically non-reactive ("inert") liquid component may be selected. Typically, a liquid component is selected that is inert relative to a particular chemical reaction to prevent an undesirable chemical reaction with other coating components. An example of such an undesirable chemical reaction is a binder-liquid component reaction that is inhibitory to a desired binder-binder film-formation reaction. Examples of a liquid component that are generally inert in an acetal formation reaction include benzene, hexane, or a combination thereof. An example of a liquid component that is generally inert in a decarboxylation reaction includes quinoline. Examples of a liquid component that are generally inert in a dehydration reaction include benzene, toluene, xylene, or a combination thereof. An example of a liquid component that is generally inert in a dehydrohalogenation reaction includes quinoline. Examples of a liquid component that are generally inert in a diazonium compound coupling reaction include ethanol, glacial acetic acid, methanol, pyridine, or a combination thereof. Examples of a liquid component that are generally inert in a diazotization reaction include benzene, dimethylformamide, ethanol, glacial acetic acid, or a combination thereof. Examples of a liquid component that are generally inert in an esterification reaction include benzene, dibutyl ether, toluene, xylene, or a combination thereof. Examples of a liquid component that are generally inert in a Friedel-Crafts reaction include benzene, carbon disulfide, 1,2-dichloroethane, nitrobenzene, tetrachloroethane, tetrachloromethane, or a combination thereof. An example of a liquid component that is generally inert in a Grignard reaction includes diethyl ether. Examples of a liquid component that are generally inert in a halogenation reaction include dichlorobenzene, glacial acetic acid, nitrobenzene, tetrachloroethane, tetrachloromethane, trichlorobenzene, or a combination thereof. Examples of a liquid component that are generally inert in a hydrogenation reaction include an alcohol, dioxane, a hydrocarbon, glacial acetic acid, or a combination thereof. Examples of a liquid component that are generally inert in a ketene condensation reaction include acetone, benzene, diethyl ether, xylene, or a combination thereof. Examples of a liquid component that are generally inert in a nitration reaction include dichlorobenzene, glacial acetic acid, nitrobenzene, or a combination thereof. Examples of a liquid component that are generally inert in an oxidation reaction include glacial acetic acid, nitrobenzene, pyridine, or a combination thereof. Examples of a liquid component that are generally inert in a sulfonation reaction include dioxane, nitrobenzene, or a combination thereof.

A solvent-borne coating is a coating wherein 50% to 100%, the including all intermediate ranges and combinations thereof, of a coating's liquid component is not water. Generally, the liquid component of a solvent-borne coating comprises an organic compound, an inorganic compound, or a combination thereof. The liquid component of a solvent-borne coating may function as a solvent, a thinner, a diluent, a plasticizer, or a combination thereof. In certain embodiments, a solvent-borne coating may comprise water. In specific aspects, the water may function as a solvent, a thinner, a diluent, or a combination thereof. The water component of a solvent-borne coating may comprise 0% to 49.999%, the including all intermediate ranges and combinations thereof, of the liquid component. In certain embodiments, the water component of a water-borne coating may be fully or partly miscible in the non-aqueous liquid component. Examples of the percent of water that is miscible, by weight at 20° C., in various liquids typically used in solvent-borne coatings include 0.01% water in tetrachloroethylene; 0.02% water in ethylbenzene; 0.02% water in p-xylene; 0.02% water in tricholorethylene; 0.05% water in 1,1,1-tricholoroethane; 0.05% water in toluene; 0.1% water in hexane; 0.16% water in methylene chloride; 0.2% water in dibutyl ether; 0.2% water in tetrahydronaphthalene; 0.42% water in diisobutyl ketone; 0.5% water in cyclohexyl acetate; 0.5% water in nitropropane; 0.6% water in 2-nitropropane; 0.62% water in butyl acetate; 0.72% water in dipentene; 0.9% water in nitroethane; 1.2% water in diethyl ether; 1.3% water in methyl tert-butyl ether; 1.4% water in trimethylcyclohexanone; 1.65% water in isobutyl acetate; 1.7% water in butyl glycol acetate; 1.9% water in isopropyl acetate; 2.4% water in methyl isobutyl ketone; 3.3% water in ethyl acetate; 3.6% water in cyclohexanol; 4.0% water in trimethylcyclohexanol; 4.3% water in isophorone; 5.8% water in methylbenzyl alcohol; 6.5% water in ethyl glycol acetate; 7.2% water in hexanol; 7.5% water in propylene carbonate; 8.0% water in methyl acetate; 8.0% water in cyclohexanone; 12.0% water in methyl ethyl ketone; 16.2% water in isobutanol; 19.7% water in butanol; 25.0% water in butyl glycolate; or 44.1% water in 2-butanol.

Various examples of such liquid components are described herein, including properties often used to select a chemical composition for use as a liquid component for a particular coating composition. Additionally, standards for physical properties, chemical properties, and/or procedures for testing purity/properties, are described for various types of liquid components (e.g., hydrocarbons, cycloaliphatic hydrocarbons, aromatic hydrocarbons, alcohols, ketones, esters, glycol ethers, mineral spirits, miscellaneous solvents, plasticizers) in, for example, "ASTM Book of Standards, Volume 06.04, Paint—Solvents; Aromatic Hydrocarbons," D4790-99, D268-01, D3437-99, D1493-97, D235-02, D1836-02, D3735-02, D3054-98, D5309-02, D4734-98, D2359-02, D4492-98, D4077-00, D3760-02, D6526-00, D841-02, D843-97, D5211-01, D5471-97, D5871-98, D5713-00, D852-02, D1685-00, D4735-02, D3797-00, D3798-00, D5135-02, D5136-00, D5060-95, D3193-96, D3734-01, D1152-97, D770-95, D3622-95, D1007-00, D1719-95, D304-95, D319-95, D2635-01, D1969-01, D2306-00, D1612-95, D5008-01, D268-01, D1078-01, D329-02, D1363-94, D740-94, D2804-02, D1153-94, D3329-99, D2917-02, D3893-99, D4360-90, D2627-02, D2916-88, D2192-96, D4614-95, D3545-02, D3131-02, D3130-95, D1718-98, D4615-95, D3540-90, D1617-90, D2634-02, D5137-01, D3728-99, D4835-93, D4773-02, D3128-02, D331-95, D330-93, D4837-02, D4773-02, D4836-95, D5776-99, D5808-95, D5917-02, D6069-01, D6212-99, D6313-99, D6366-99, D6428-99, D6621-00, D6809-02, D5399-95, D6229-01, D6563-00, D6269-98, D3257-01, D847-96, D1613-02, D848-02, D1614-95, D4367-02, D4534-99, D2360-00, D1353-02, D1492-02, D849-02, D3961-98, D1364-02, D3160-96, D1476-02 and D1722-98, D853-97, D5194-96, D363-90, D1399-95, D1468-93, D3620-98, D3546-90, and D1721-97, 2002.

a. Solvents, Thinners, and Diluents

A coating may comprise a liquid component that may function as a solvent, a thinner, a diluent or a combination thereof. In one embodiment of a coating, a particular liquid component may function as a solvent, while in another coating composition comprising, for example, a different binder the same liquid component may function as a thinner and/or a diluent. Whether a liquid component functions primarily as a solvent, a thinner, or a diluent depends considerably upon the particular solvent and/or rheological property the liquid component confers to a specific coating composition. For example, the ability of the liquid component to function as a solvent, or lack thereof of such ability, relative to the other coating components generally differentiates a solvent from a diluent. A thinner is primarily included into a coating composition in combination with a solvent and/or diluent to alter a rheological property such as to reduce viscosity, enhance flow, enhance leveling, or a combination thereof. In addition to the ability of one of ordinary skill in the art to discern such differences of use for a specific liquid composition in a coating, examples of differing solubility properties for specific categories of liquid components, and empirical techniques for determining the solubility properties of a specific liquid component, relative to another coating component, are described herein.

A solute is a coating component dissolved by a solvent liquid component. A solute may be in solid, liquid or gas from prior to being dissolved. Solvency ("solvent power") is the ability of a solvent to dissolve a solute, maintain a solute in solution upon addition of a diluent, and reduce the viscosity of a solution. A solvent is typically used to produce a solvent-borne coating, wherein the coating possesses desirable a rheological property for application to a surface and/or creation of a film of a desirable thickness. Additionally, a solvent may contribute to an appearance property, a physical property, a chemical property, or a combination thereof, of a coating and/or film. In most embodiments, a solvent is a volatile component of a coating, wherein 50% to 100%, including all intermediate ranges and combinations thereof, of the solvent is lost (e.g., evaporates) during film formation. In certain aspects, the rate of solvent loss slows during application and/or film formation. Such a change in solvent loss rate may promote a desirable rheologically related property during application and/or initial film formation, such as ease of application, minimum sag, reduce excessive flow, or a combination thereof, while still promoting a desirable rheologically related property post-application, such as a desirable leveling property, a desirable adhesion property, or a combination thereof.

Depending upon the ability of a liquid component to dissolve, partly dissolve, or unsuccessfully dissolve a coating component, a coating may comprise, a real solution, a colloidal solution or a dispersion, respectively. Often the ability of a liquid component to dissolve a coating component is detrimentally affected by increasing particulate matter size and/or molecular mass of the coating component. For example, a real solution comprises a clear and/or homogenous liquid solution. In typical embodiments, a real solution is produced when a potential solute of 1.0 nm or less in diameter is combined with a solvent. A colloidal solution comprises a physically non-homogenous solution, which may be a clear to opalescent in appearance. Often, a colloidal solution is produced when a potential solute of between 1.0 nm to 100 nm ("0.1 µm") in diameter is combined with a solvent. A dispersion is a composition comprising two liquid and/or solid phases, which is typically turbid to milky in appearance. Generally, a dispersion is produced when a potential solute of greater than 0.1 µm in diameter is combined with a solvent. In many aspects, a coating composition may comprise a combination of a real solution, a colloidal solution and/or a dispersion, depending upon the various solubility's of coating components and liquid components. For example, a paint may comprise a real solution of a binder and a liquid component, and a dispersion of a pigment within the liquid component.

Depending upon other coating components, a liquid component may function as an active solvent or a latent solvent. An active solvent is capable of dissolving a solute. Additionally, an active solvent often reduces viscosity of a coating composition. In certain embodiments, an ester, a glycol ether, a ketone, or a combination thereof may be selected for use as an active solvent. A latent solvent, in pure form, does not demonstrate solute dissolving ability. However, the latent solvent may demonstrate the ability to dissolve a solute in a combination of an active solvent and the latent solvent; confer a synergistic improvement in the dissolving ability of an active solvent when combined with the active solvent, or a combination thereof. In certain embodiments, an alcohol may be selected for use as a latent solvent. In certain embodiments, a latent solvent is a thinner. A diluent, whether in pure form or in combination with an active solvent and/or a latent solvent, does not demonstrate solute dissolving ability, but may be combined with an active solvent and/or latent solvent to produce a liquid component with a suitable ability to dissolve a coating component. In certain embodiments, hydrocarbon may be selected for use as a diluent. In particular aspects, a hydrocarbon diluent comprises an aromatic hydrocarbon, an aliphatic hydrocarbon, or a combination thereof. In particular facets, an aromatic hydrocarbon diluent may be selected, due to a generally greater tolerance by a many solvents relative to an aliphatic hydrocarbon. In certain aspects, a diluent is used to alter a rheological property (e.g., reduce viscosity) of a coating composition, reduce cost of a coating composition, or a combination thereof.

The ability of a solvent to dissolve a potential solute is related to the intermolecular interactions between the solvent molecules, between the potential solute molecules, between the solvent and the potential solute, as well as the molecular size of the potential solute. Examples of intermolecular interactions include, for example, ionic ("Coulomb"), dipole-dipole ("directional"), ionic-dipole, induction ("permanent dipole/induced dipole"), dispersion ("nonpolar," "atomic dipole," "London-Van der Walls"), hydrogen bond, or a combination thereof. As is known to those of ordinary skill in the art, the sum of intramolecular interactions for a compound, relevant for the preparation of a solution, is the solubility parameter ("$\delta$"). The solubility parameter is a measure of the total energy needed to separate molecules of a liquid. Such a separation of molecules of a solvent occurs during the incorporation of the molecules of a solute during the dissolving process. The solubility parameter is the square root of the molar energy of vaporization of a liquid divided by the molar volume of a liquid, measured at 25° C. Additionally, the solubility parameter can also be expressed as the square root of the sum of the squares of the dispersion ("$\delta_d$"), polar ("$\delta_p$") and hydrogen bond ("$\delta_h$") solubility parameters.

Often, preparation of a coating composition may be aided by comparing the solubility parameter of a potential solvent and a potential solute (e.g., a binder) to ascertain the theoretical ability of a coating composition comprising a solution to be created. In many embodiments, coating components, wherein at least one coating component comprises a liquid, with a solubility parameter that is less than an absolute value of 6 are able to form a solution. The closer this value is to 0, the greater the general ability to form a solution. Additionally, the lower the individual absolute difference (e.g., six or less) between the dispersion solubility parameters of coating components, the polar solubility parameter of coating components, and/or the hydrogen bond solubility parameter of coating components, the generally greater ability to form a solution. The solubility parameter, dispersion solubility parameter, polar solubility parameter, and hydrogen bond solubility parameter, and methods for determining such values, and additional methods for determining the theoretical ability of coating components to form a solution have been described (see, for example, in "ASTM Book of Standards, Volume 06.03, Paint—Pigments, Drying Oils, Polymers, Resins, Naval Stores, Cellulosic Esters, and Ink Vehicles," D3132-84, 2002).

However, due to exceptions to the ability of certain liquid components and potential solute coating components to form solutions, empirically determining the ability of a solute to dissolve in a solvent may be desirable in certain embodiments. Standard techniques for determining the ability of a liquid component comprising one or more liquids to function as an active solvent, a latent solvent, a diluent, or a combination thereof, relative to one or more potential solutes are known to those of ordinary skill in the art. For example, the solvency of a liquid component comprising an active solvent (e.g., an oxygenated compound), a latent solvent, a diluent (e.g., a hydrocarbon), or a combination thereof, particularly for use in a lacquer coating, may be determined as described in "ASTM Book of Standards, Volume 06.04, Paint—Solvents; Aromatic Hydrocarbons," D1720-96, 2002). In an additional example, the solvency for a liquid component that primarily comprises a hydrocarbon, and comprises little or lacks an oxygenated compound, may be determined as described in "ASTM Book of Standards, Volume 06.04, Paint—Solvents; Aromatic Hydrocarbons," D1133-02, 2002). In a further example, the solvency of a solution comprising liquid component and an additional coating component (e.g., a binder) may be used to determined, as described in "ASTM Book of Standards, Volume 06.03, Paint—Pigments, Drying Oils, Polymers, Resins, Naval Stores, Cellulosic Esters, and Ink Vehicles," D1545-98, D1725-62, D5661-95, D5180-93, D6038-96, D5165-93, and D5166-97, 2002. In a supplemental example, the dilutability of a solution comprising liquid component (e.g., a solvent and diluent) and an additional coating component (e.g., a binder) may be used to determined, as described in "ASTM Book of Standards, Volume 06.03, Paint—Pigments, Drying Oils, Polymers, Resins, Naval Stores, Cellulosic Esters, and Ink Vehicles," D5062-96, 2002.

In certain embodiments, a liquid component may be selected on the basis of evaporation rate. The evaporation rate of a coating directly affects a physical aspect of film formation caused by loss of a liquid component, as well as the pot life of a coating, such as after a coating container is opened. Though the evaporation rate is known for various pure chemicals, one of ordinary skill in the art can empirically determine the evaporation rate of a liquid component and/or a coating, in "ASTM Book of Standards, Volume 06.01, Paint—Tests for Chemical, Physical, and Optical Properties; Appearance," D3539-87, 2002. Additionally, the boiling point range of a liquid component often is useful in estimating whether the liquid component will evaporate faster or slower relative to another liquid component. Examples of methods for measuring a boiling point for a liquid component (e.g., a hydrocarbon, a chlorinated hydrocarbon) are described in "ASTM Book of Standards, Volume 06.04, Paint—Solvents; Aromatic Hydrocarbons," D1078-01 and D850-02e1, 2002. The evaporation rate is also related to the flash point of a liquid component and/or coating. In certain embodiments, a liquid component may be selected on the basis of flash point and/or fire point, which is a measure of the danger of use of a flammable coating composition in, for example, storage, application in an indoor environment, etc. A flash point is the "lowest temperature at which the liquid gives off enough vapor to form an ignitable mixture with air to produce a flame when a source of ignition is brought close to the surface of the liquid under specified conditions of test at standard barometric pressure (760 mmHG, 101.3 kPa)," and a fire point is "the lowest temperature at which sustained burning of the sample takes place for at least 5 seconds" ["Paint and Coating Testing Manual, Fourteenth Edition of the Gardner-Sward Handbook" (Koleske, J. V. Ed.), pp. 140 and 142, 1995]. Examples of methods for measuring the flash point and/or fire point for a liquid component and/or a coating are described in and "ASTM Book of Standards, Volume 06.01, Paint—Tests for Chemical, Physical, and Optical Properties; Appearance," D1310-01, D3934-90, D3941-90, and D3278-96e1, 2002.

Though it is contemplated that most or all liquid component will be lost from a coating composition during film formation, a liquid component may still contribute to the visual properties of a coating and/or film. In embodiments wherein a liquid component is selected as a colorizing agent, the color and/or darkness of the liquid may be empirically measured (see, for example, "ASTM Book of Standards, Volume 06.04, Paint—Solvents; Aromatic Hydrocarbons," D1209-00, D1686-96, and D5386-93b, 2002); and "ASTM Book of Standards, Volume 06.01, Paint—Tests for Chemical, Physical, and Optical Properties; Appearance," D1544-98, 2002. In some embodiments, a liquid component and/or coating may be selected on the basis of odor (e.g., faint odor, pleasant odor, etc.). A coating or coating component can be evaluated for suitability in a particular application based on odor using, for example, techniques described in "ASTM Book of Standards, Volume 06.04, Paint—Solvents; Aromatic Hydrocarbons," D1296-01, 2002; and "ASTM Book of Standards, Volume 06.01, Paint—Tests for Chemical, Physical, and Optical Properties; Appearance," D6165-97, 2002.

(1) Hydrocarbons

A hydrocarbon is typically obtained as a petroleum product, a vegetable product, or a combination thereof. As a consequence of imperfect purification (e.g., distillation) from these sources, a hydrocarbon is often a mixture of chemical components. A hydrocarbon may be selected as an active solvent to dissolve an oil (e.g., a drying oil), an alkyd, an asphalt, a rosin, a petroleum product, or a combination thereof. A hydrocarbon is more suitable as a latent solvent or diluent in embodiments wherein an acrylic resin, an epoxide resin, a nitrocellulose resin, an urethane resin, or a combination thereof is to be dissolved. However, a hydrocarbon generally is immiscible in water.

(i) Aliphatic Hydrocarbons

In general embodiments, an aliphatic hydrocarbon may be selected as an active solvent for an alkyd, an oil, wax, a polyisobutene, a polyethylene, a poly(butyl acrylate), a poly(butyl methacrylate), a poly(vinyl ethers), or a combination thereof. In other embodiments, an aliphatic hydrocarbon may be selected as a diluent in combination with an additional liquid component. In alternative embodiments wherein an aliphatic hydrocarbon is selected as a non-solvent liquid component, a composition comprising a polar binder, a cellulose derivative, or a combination thereof, is usually insoluble. An aliphatic hydrocarbon is often selected as a liquid component in embodiments wherein a chemically inert liquid component is desired. Examples of an aliphatic hydrocarbon include, a petroleum ether, pentane (CAS No. 109-66-0), hexane (CAS No. 110-54-3), heptane (CAS No. 142-82-5), isododecane (CAS No. 13475-82-6), a kerosene, a mineral spirit, a VMP naphthas or a combination thereof. A hexane, a heptane, or a combination thereof, may be selected for a coating wherein rapid evaporation of such a liquid component is desired (e.g., a fast drying lacquer). An example of an azeotrope comprising an aliphatic hydrocarbon includes an azeotrope comprising hexane. Examples of an azeotrope comprising a majority of hexane (BP 65° C. to 70° C.) include those comprising 2.5% isobutanol (azeotrope BP 68.3° C.); 5.6% water (A-BP 61.6° C.); 21% ethanol (A-BP 58.7° C.); 22% isopropyl alcohol (A-BP 61.0° C.); 26.9% methanol (A-BP 50.0° C.); 37% methyl ethyl ketone (A-BP 64.2° C.); or 42% ethyl acetate (A-BP 65.0° C.).

As would be known to one of ordinary skill in the art, an aliphatic hydrocarbon can comprise a petroleum distillation product of heterogeneous chemical composition. Such an aliphatic hydrocarbon may be classified by a physical and/or chemical property (e.g., boiling point range, flash point, evaporation rate) (see, for example, "ASTM Book of Standards, Volume 06.04, Paint—Solvents; Aromatic Hydrocarbons," D235-02 and D3735, 2002). In certain embodiments, such a petroleum distillation product aliphatic hydrocarbon may be classified, for example, as a mineral spirit, a VMP naphthas or a kerosene (e.g., deodorized kerosene). A mineral spirit ("white spirit," "petroleum spirit") is a petroleum distillation fraction with a boiling point between 149° C. to 204° C., including all intermediate ranges and combinations thereof, and a flash point of 38° C. or greater. A mineral spirit may further be classified as a regular mineral spirit, which possesses the properties previously described for a mineral spirit; a high flash mineral spirit, which possesses a higher minimum flash point (e.g., 55° C. or greater); a low dry point mineral spirit ("Stoddard solvent"), which typically evaporates 50% faster than a regular mineral spirit; or an odorless mineral spirit, which generally possesses less odor than a regular mineral spirit, but may also possess relatively weaker solvency property. A mineral spirit may be selected for embodiments wherein a solvent and/or diluent is desired for an alkyd coating, a chlorinated rubber coating, an oil-coating, a vinyl chloride copolymer coating, or a combination thereof. A VMP naphtha possess a similar solvency property as a mineral spirit, but evaporates faster with a BP of 121° C. to 149° C., including all intermediate ranges and combinations thereof, and typically has a flash point of 4° C. or greater. A VMP naphtha may further be classified as a regular VMP naphtha, which possesses the properties previously described for a VMP naphtha; a high flash VMP naphtha, which possesses a higher minimum flash point (e.g., 34° C. or greater); or an odorless VMP naphtha, which generally possesses less odor than a regular mineral spirit. A VMP naphtha may be selected for a coating that is spray applied, an industrial coating, or a combination thereof. A petroleum ether is a petroleum distillation fraction with a boiling point between 35° C. to 80° C., including all intermediate ranges and combinations thereof, with a low flash point (e.g., −46° C.), and may be used in embodiments wherein rapid evaporation is desired.

(ii) Cycloaliphatic Hydrocarbons

In embodiments wherein a cycloaliphatic hydrocarbon is selected as a solvent, a composition comprising an oil, alkyd, bitumen, rubber, or a combination thereof, usually can be dissolved. In alternative embodiments wherein a cycloaliphatic hydrocarbon is selected as a non-solvent liquid component, a composition comprising a polar binder such as a urea-formaldehyde binder, a melamine-formaldehyde binder, a phenol-formaldehyde binder; a cellulose derivative, such as, a cellulose ester binder; or a combination thereof, is usually insoluble. A cycloaliphatic hydrocarbon is generally soluble in other organic solvents, but not soluble in water. Examples of a cycloaliphatic hydrocarbon include cyclohexane (CAS No. 110-82-7); methylcyclohexane (CAS No. 108-87-2); ethylcyclohexane (CAS No. 1678-91-7); tetrahydronaphthalene (CAS No. 119-64-2); decahydronaphthalene (CAS No. 91-17-8); or a combination thereof. Tetrahydronaphthalene is often selected for coatings wherein oxidation of a binder is preferable during film formation; a high gloss is preferable in a film, smooth surface is preferable in a film, or a combination thereof. An example of an azeotrope comprising a cycloaliphatic hydrocarbon includes an azeotrope comprising cyclohexane. Examples of an azeotrope comprising a majority of cyclohexane (BP 80.5° C. to 81.5° C.) include those comprising 8.5% water (A-BP 69.8° C.); 10% butanol (A-BP 79.8° C.); 14% isobutanol (A-BP 78.1° C.); 20% propanol (A-BP 74.3° C.); 37% methanol (A-BP 54.2° C.); or 40% methyl ethyl ketone (A-BP 72.0° C.).

(iii) Terpene Hydrocarbons

A terpene typically possesses a superior solvency property, stronger odor, or a combination thereof, relative to an aliphatic hydrocarbon. Examples of a terpene include wood terpentine oil (CAS No. 8008-64-2); pine oil (CAS No. 8000-41-7); α-pinene (CAS No. 80-56-8); β-pinene; dipentene (CAS No. 138-86-3); D-limonene (CAS No. 5989-27-5); or a combination thereof. Dipentene may be selected for embodiments wherein a superior solvency property, a slower evaporation rate, or a combination thereof, relative to a turpentine, is desired. Pine oil may be classified as an oxygenated compound, but is described under hydrocarbons due to convention by those of skill in the art. Pine oil generally comprises a terpene alcohol. Pine oil may be selected for embodiments wherein a greater range of solvency for solutes, a slow evaporation rate, or a combination thereof, is desired. An example of an azeotrope comprising a terpene includes an azeotrope comprising α-pinene. An example of an azeotrope comprising a majority of α-pinene (BP 154.0° C. to 156.0° C.) includes an azeotrope comprising 35.5% cyclohexanol (A-BP 149.9° C.).

As would be known to one of ordinary skill in the art, a terpene hydrocarbon ("terpene") can comprise a by-product from pines tree and/or citrus processing of heterogeneous chemical composition. Such a terpene hydrocarbon (e.g., a terpentine) may be classified by a physical and/or chemical property (see, for example, "ASTM Book of Standards, Volume 06.03, Paint—Pigments, Drying Oils, Polymers, Resins, Naval Stores, Cellulosic Esters, and Ink Vehicles," D804-02, D13-02, D233-02, D801-02, D802-02, and D6387-99, 2002. Examples of a terpentine include a gum turpentine, a steam-distilled wood turpentine, a sulfate wood turpentine, a destructively distilled wood turpentine, or a combination thereof. Both a gum turpentine and a sulfate wood turpentine generally comprise a combination of α-pinene and a lesser quantity of β-pinene. A steam-distilled wood terpentine generally comprises α-pinene and a lesser component of dipentene and one or more other terpenes. Destructively distilled wood turpentine generally comprises various aromatic hydrocarbons and a lesser quantity of one or more terpenes.

(iv) Aromatic Hydrocarbons

An aromatic hydrocarbon typically possesses a greater solvency property and/or odor relative to other hydrocarbon types. Examples of an aromatic hydrocarbon include benzene (CAS No. 71-43-2); toluene (CAS No. 108-88-3; "methylbenzene"); ethylbenzene (CAS No. 100-41-4); xylene (CAS No. 1330-20-7); cumene ("isopropylbenzene"; CAS No. 98-82-8); a type I high flash aromatic naphthas; a type II high flash aromatic naphthas; mesitylene (CAS No. 108-67-8); pseudocumene (CAS No. 95-63-6); cymol (CAS No. 99-87-6); styrene (CAS No. 100-42-5); or a combination thereof. Xylene typically comprises o-xylene (CAS No. 56004-61-6); m-xylene (CAS No. 108-38-3); p-xylene (CAS No. 41051-88-1); and trace ethylbenzene. Toluene may be selected for embodiments wherein rapid evaporation is desired. In specific aspects, toluene may be selected for a spray applied coating, an industrial coating, or a combination thereof. Xylene may be selected for embodiments wherein a moderate evaporation rate is desired. In specific aspects, xylene may be selected for an industrial coating. As would be known to one of ordinary skill in the art, an aromatic hydrocarbon may comprise a petroleum-processing product of heterogeneous chemical composition such as a high flash aromatic naphtha (e.g., type I, type II). A type I high flash aromatic naphtha and type II high flash aromatic naphtha possess a minimum flash point of 38° C. and 60° C., respectively. Standards for the characteristic chemical an/or physical property of an aromatic naphtha are known to those of ordinary skill in the art (see, for example, "ASTM Book of Standards, Volume 06.04, Paint—Solvents; Aromatic Hydrocarbons," D3734, 2002). A high flash naphtha typically has a slow evaporation rate. In specific embodiments, a high flash aromatic naphtha may be used in an industrial coating, a coating that is baked, or a combination thereof. An example of a high flash aromatic is Solvesso 100 (CAS No. 64742-95-6). Examples of an azeotrope comprising an aromatic hydrocarbon include an azeotrope comprising toluene or m-xylene. Examples of an azeotrope comprising a majority of toluene (BP 110° C. to 111° C.) include those comprising 27% butanol (A-BP 105.6° C.); or 44.5% isobutanol (A-BP 100.9° C.). Examples of an azeotrope comprising a majority of m-xylene (BP 137.0° C. to 142.0° C.) include those comprising 14% cyclohexanol (A-BP 143.0° C.); or 40% water (A-BP 94.5° C.).

(2) Oxygenated Compounds

An oxygenated compound ("oxygenated liquid compound") is typically chemically synthesized by standard chemical manufacturing techniques. As a consequence, an individual oxygenated compound is typically an extremely homogenous chemical composition, with singular, rather than a range of, chemical and physical properties. The oxygen moiety of an oxygenated compound generally enhances the strength and breadth of solvency for potential solutes relative to a hydrocarbon. Additionally, an oxygenated compound typically has some or complete miscibility with water. Examples of an oxygenated compound include an alcohol, an ester, a glycol ether, a ketone, or a combination thereof. As would be known to one of ordinary skill in the art, a liquid component often comprises a combination of an alcohol, an ester, a glycol ether, a ketone and/or an addition liquid to produce suitable chemical and/or physical properties for a coating and/or film.

(i) Alcohols

An alcohol comprises an alcohol moiety. However, a preferred "alcohol" comprises a single hydroxyl moiety. The alcohol moiety confers miscibility with water. Consequentially, increasing molecular size of an alcohol comprising a single alcohol moiety generally reduces miscibility with water. Alcohols typically possess a mild and/or pleasant odor. An alcohol is typically a poor primary solvent, though ethanol is an exception relative to a solute comprising a phenolic and/or polyvinyl resin. An alcohol may be selected as a latent solvent, co-solvent, a coupling solvent, a diluent, or combination thereof such as with solute comprising a nitrocellulose lacquer, melamine-formaldehyde, urea formaldehyde, alkyd, or combination thereof. Examples of an alcohol include methanol (CAS No. 67-56-1); ethanol (CAS No. 64-17-5); propanol (CAS No. 71-23-8); isopropanol (CAS No. 67-63-0); 1-butanol (CAS No. 71-36-3); isobutanol (CAS No. 78-83-1); 2-butanol (CAS No. 78-92-2); tert-butanol (CAS No. 75-65-0); amyl alcohol (CAS No. 71-41-0); isoamyl alcohol (123-51-3); hexanol (25917-35-5); methylisobutylcarbinol (CAS No. 108-11-2); 2-ethylbutanol (CAS No. 97-95-0); isooctyl alcohol (CAS No. 26952-21-6); 2-ethylhexanol (CAS No. 104-76-7); isodecanol (CAS No. 25339-17-7); cylcohexanol (CAS No. 108-93-0); methylcyclohexanol (CAS No. 583-59-5); trimethylcyclohexanol; benzyl alcohol (CAS No. 100-51-6); methylbenzyl alcohol (CAS No. 98-85-1); furfuryl alcohol (CAS No. 98-00-0); tetrahydrofurfuryl alcohol (CAS No. 97-99-4); diacetone alcohol (CAS No. 123-42-2); trimethylcyclohexanol (116-02-9); or a combination thereof. Furfuryl alcohol and tetrahydrofurfuryl alcohol may be selected as a primary solvent for a polyvinyl binder. Examples of an azeotrope comprising an alcohol include an azeotrope comprising butanol, ethanol, isobutanol, or methanol. Examples of an azeotrope comprising a majority of butanol (BP 117.7° C.) include those comprising 97% butanol and 3% hexane (A-BP 67° C.); 32% p-xylene (A-BP 115.7° C.); 32.8% butyl acetate (A-BP 117.6° C.); 44.5% water (A-BP 93° C.); or 50% isobutyl acetate (A-BP 114.5° C.). Examples of an azeotrope comprising a majority of ethanol (BP 78.3° C.) include those comprising 4.4% water (A-BP 78.2° C.); or 32% toluene (A-BP 76.7° C.). Examples of an azeotrope comprising a majority of isobutanol (BP 107.7° C.) include those comprising 2.5% hexane (A-BP 68.3° C.); 5% isobutyl acetate (A-BP 107.6° C.); 17% p-xylene (A-BP 107.5° C.); 33.2% water (A-BP 89.9° C.); or 48% butyl acetate (A-BP 80.1° C.). An example of an azeotrope comprising a majority of methanol (BP 64.6° C.) includes an azeotrope comprising 30% methyl ethyl ketone (A-BP 63.5° C.).

(ii) Ketones

A ketone comprises a ketone moiety. However, a preferred ketone comprises a single ketone moiety. A ketone generally possesses some miscibility with water, and a strong odor. In general embodiments, a ketone may be selected as a primary solvent, thinner, or combination thereof. Examples of a ketone include acetone (CAS No. 67-64-1); methyl ethyl ketone (CAS No. 78-93-3); methyl propyl ketone (CAS No. 107-87-9); methyl isopropyl ketone (CAS No. 563-80-4); methyl butyl ketone (CAS No. 591-78-6); methyl isobutyl ketone (CAS No. 108-10-1); methyl amyl ketone (CAS No. 110-43-0); methyl isoamyl ketone (CAS No. 110-12-3); diethyl ketone (CAS No. 96-22-0); ethyl amyl ketone (CAS No. 541-85-5); dipropyl ketone (CAS No. 110-43-0); diisopropyl ketone (CAS No. 565-80-0); cyclohexanone (CAS No. 108-94-1); methylcylcohexanone (CAS No. 1331-22-2); trimethylcyclohexanone (CAS No. 873-94-9); mesityl oxide (CAS No. 141-79-7); diisobutyl ketone (CAS No. 108-83-8); isophorone (CAS No. 78-59-1); or a combination thereof. Acetone may be selected for complete miscibility in water, fast evaporation, or a combination thereof. In certain embodiments, acetone may be used as a liquid component in an aerosol, a spay-applied coating, or a combination thereof. In specific aspects, acetone may be used as a thinner. In other aspects, acetone may be used in a coating wherein nitrocellulose, an acrylic, or a combination thereof, is dissolved. Methyl ethyl ketone, methyl isobutyl ketone, and isophorone may be selected in embodiments wherein a fast evaporation rate, moderate evaporation rate, or slow evaporation rate, respectively, is desired. In specific facets, isophorone may be selected for a baked coating, an industrial coating, or a combination thereof. Examples of an azeotrope comprising a ketone include an azeotrope comprising acetone, methyl ethyl ketone or methyl isobutyl ketone. Examples of an azeotrope comprising a majority of acetone (BP 56.2° C.) include those comprising 12% methanol (A-BP 55.7° C.); or 41% hexane (A-BP 49.8° C.). Examples of an azeotrope comprising a majority of methyl ethyl ketone (BP 79.6° C.) include those comprising 11% water (A-BP 73.5° C.); 32% isopropyl alcohol (A-BP 77.5° C.); or 34% ethanol (A-BP 74.8° C.). Examples of an azeotrope comprising a majority of methyl isobutyl ketone (BP 114° C. to 117° C.) include those comprising 24.3% water (A-BP 87.9° C.); or 30% butanol (A-BP 114.35° C.).

(iii) Esters

An ester may comprise an alkyl acetate, an alkyl propionate, a glycol ether acetate, or a combination thereof. An ester generally possesses a pleasant odor. In general embodiments, an ester possesses a solubility property that decreases with increasing molecular weight. A glycol ester acetate typically possesses a slow evaporation rate. In specific aspects, a glycol ester acetate may be selected as a retarder solvent, a coalescent, or a combination thereof. Examples of an ester include methyl formate (CAS No. 107-31-3); ethyl formate (CAS No. 109-94-4); butyl formate (CAS No. 592-84-7); isobutyl formate (CAS No. 542-55-2); methyl acetate (CAS No. 79-20-9); ethyl acetate (CAS No. 141-78-6); propyl acetate (CAS No. 109-60-4); isopropyl acetate (CAS No. 108-21-4); butyl acetate (CAS No. CAS-No.

123-86-4); isobutyl acetate (CAS No. 110-19-0); sec-butyl acetate (CAS No. 105-46-4); amyl acetate (CAS No. 628-63-7); isoamyl acetate (CAS No. 123-92-2); hexyl acetate (CAS No. 142-92-7); cyclohexyl acetate (CAS No. 622-45-7); benzyl acetate (CAS No. 140-11-4); methyl glycol acetate (CAS No. 110-49-6); ethyl glycol acetate (CAS No. 111-15-9); butyl glycol acetate (CAS No. 112-07-2); ethyl diglycol acetate (CAS No. 111-90-0); butyl diglycol acetate (CAS No. 124-17-4); 1-methoxypropyl acetate (CAS No. 108-65-6); ethoxypropyl acetate (CAS No. 54839-24-6); 3-methoxybutyl acetate (CAS No. 4435-53-4); ethyl 3-ethoxypropionate (CAS No. 763-69-9); isobutyl isobutyrate (CAS No. 97-85-8); ethyl lactate (CAS No. 97-64-3); butyl lactate (CAS No. 138-22-7); butyl glycolate (CAS No. 7397-62-8); dimethyl adipate (CAS No. 627-93-0); glutarate (CAS No. 119-40-0); succinate (CAS No. 106-65-0); ethylene carbonate (CAS No. 96-49-1); propylene carbonate (CAS No. 108-32-7); butyrolactone (CAS No. 96-48-0); or a combination thereof. Ethylene carbonate and propylene carbonate generally possess a high flash point, a slow evaporation rate, a weak odor, or a combination thereof. Ethylene carbonate is preferred for use in coatings at temperatures greater than 25° C. Examples of an azeotrope comprising an ester include an azeotrope comprising butyl acetate, ethyl acetate or methyl acetate. Examples of an azeotrope comprising a majority of butyl acetate (BP 124° C. to 128° C.) include those comprising 27% water (A-BP 90.7° C.) or 35.7% ethyl glycol (A-BP 125.8° C.). Examples of an azeotrope comprising a majority of ethyl acetate (BP 76° C. to 77° C.) include those comprising 5% cyclohexanol (A-BP 153.8° C.); 8.2% water (A-BP 70.4° C.); 22% methyl ethyl ketone (A-BP 76.7° C.); 23% isopropyl alcohol (A-BP 74.8° C.); or 31% ethanol (A-BP 71.8° C.). An example of an azeotrope comprising a majority of methyl acetate (BP 55.0° C.-57.0° C.) includes an azeotrope comprising 19% methanol (A-BP 54° C.).

(iv) Glycol Ethers

A glycol ether comprises an alcohol moiety and an ether moiety. The glycol ether generally possesses good solvency, high flash point, slow evaporation rate, mild odor, miscibility with water, or a combination thereof. In some embodiments, a glycol ether may be selected as a coupling solvent, a thinner, or a combination thereof. In particular aspects, a glycol ether may be selected as a liquid component of a lacquer. Examples of a glycol ether include methyl glycol (CAS No. 109-86-4); ethyl glycol (CAS No. 110-80-5); propyl glycol (CAS No. 2807-30-9); isopropyl glycol (CAS No. 109-59-1); butyl glycol (CAS No. 111-76-2); methyl diglycol (111-77-3); ethyl diglycol (CAS No. 111-90-0); butyl diglycol (CAS No. 112-34-5); ethyl triglycol (CAS No. 112-50-5); butyl triglycol (CAS No. 143-22-6); diethylene glycol dimethyl ether (CAS No. 111-96-6); methoxypropanol (CAS No. 107-98-2); isobutoxypropanol (CAS No. 23436-19-3); isobutyl glycol (CAS No. 4439-24-1); propylene glycol monoethyl ether (CAS No. 52125-53-8); 1-isopropoxy-2-propanol (CAS No. 3944-36-3); propylene glycol mono-n-propyl ether (CAS No. 30136-13-1); propylene glycol n-butyl ether (CAS No. 5131-66-8); methyl dipropylene glycol (CAS No. 34590-94-8); methoxybutanol (CAS No. 30677-36-2); or a combination thereof. An example of an azeotrope comprising a glycol ether includes an azeotrope comprising ethyl glycol. An example of an azeotrope comprising a majority of ethyl glycol (BP 134° C. to 137° C.) includes an azeotrope comprising 50% dibutyl ether (A-BP 127° C.).

(v) Ethers

Examples of an ether include diethyl ether (CAS No. 60-29-7); diisopropyl ether (CAS No. 108-20-3); dibutyl ether (CAS No. 142-96-1); di-sec-butyl ether (CAS No. 6863-58-7); methyl tert-butyl ether (CAS No. 1634-04-4); tetrahydrofuran (CAS No. 109-99-9); 1,4-dioxane (CAS No. 123-91-1); metadioxane (CAS No. 505-22-6); or a combination thereof. Tetrahydrofuran may be selected as a primary solvent for a polyvinyl binder. An example of an azeotrope comprising an ether includes an azeotrope comprising tetrahydrofuran. An example of an azeotrope comprising a majority of tetrahydrofuran (BP 66° C.) includes an azeotrope comprising 5.3% water (A-BP 64.0° C.).

(3) Chlorinated Hydrocarbons

A chlorinated hydrocarbon generally comprises a hydrocarbon, wherein the hydrocarbon comprises a chloride atom moiety. A chlorinated hydrocarbon generally possesses a very high degree of non-flammability, and consequently lacks a flash point. A chlorinated hydrocarbon may be selected for embodiments where high flash point is desired. In particular facets, a chlorinated hydrocarbon may be added to a liquid component to reduce the liquid component's flash point. In certain facets, it is less preferred that a chlorinated hydrocarbon be combined with a mineral spirit, methylene chloride, or a combination thereof, wherein reduction of the flash point is desired. In particular aspects, a chlorinated hydrocarbon (e.g., methylene chloride, trichloroethylene) may be selected as a solvent for removal of hydrophobic material from a surface (e.g., grease, an undesired coating and/or film). However, a chlorinated hydrocarbon may be less preferred due to an environmental regulation or law. Examples of a chlorinated hydrocarbon include methylene chloride (CAS No. 75-09-2; "dichloromethane"); trichloromethane (CAS No. 67-66-3); tetrachloromethane (CAS No. 56-23-5); ethyl chloride (CAS No. 75-00-3); isopropyl chloride (CAS No. 75-29-6); 1,2-dichloroethane (CAS No. 107-06-2); 1,1,1-trichloroethane (CAS No. 71-55-6; "methylchloroform"); trichloroethylene (CAS No. 79-01-6); 1,1,2,2-tetrachlorethane (CAS No. 79-55-6); 1,2-dichloroethylene (CAS No. 75-35-4); perchloroethylene (CAS No. 127-18-4); 1,2-dichloropropane (CAS No. 78-87-5); chlorobenzene (CAS No. 108-90-7); or a combination thereof. Methylene chloride may be selected for embodiments wherein a fast evaporation rate is desired. 1,1,1-trichloroethane may be selected for embodiments wherein a photochemically inert liquid component is desired. Additionally, methylene chloride may be selected as a coating remover. Examples of an azeotrope comprising a chlorinated hydrocarbon include an azeotrope comprising methylene chloride, trichloroethylene or 1,1,1-trichloroethane. Examples of an azeotrope comprising a majority of methylene chloride (BP 40.2° C.) include those comprising 1.5% water (A-BP 38.1° C.); 3.5% ethanol (A-BP 41.0° C.); or 8% methanol (A-BP 39.2° C.). Examples of an azeotrope comprising a majority of trichloroethylene (BP 86.7° C.) include those comprising 6.6% water (A-BP 72.9° C.); 27% ethanol (A-BP 70.9° C.); or 36% methanol (A-BP 60.2° C.). An example of an azeotrope comprising a majority of 1,1,1-trichloroethane (BP 74.0° C.) includes an azeotrope comprising 4.3% water (A-BP 65.0° C.).

(4) Nitrated Hydrocarbon

A nitrated hydrocarbon comprises a hydrocarbon, wherein the hydrocarbon comprises a nitrogen atom moiety. Examples of a nitrated hydrocarbon include a nitroparaffin, N-methyl-2-pyrrolidone ("NMP"), or a combination thereof. Examples of a nitroparaffin include nitroethane, nitromethane, nitropropane, 2-nitropropane ("2NP"), or a combination thereof. 2-nitropropane may be selected for embodiments as a substitute for butyl acetate relative to a solvent property, but wherein a greater evaporation rate is desired. N-methyl-2-pyrrolidone may be selected for embodiments wherein a strong solvent property, miscibility with water, high flash point, biodegradability, low toxicity, or a combination thereof is desired. In certain aspects, N-methyl-2-pyrrolidone may be used in a water-borne coating, a coating remover, or a combination thereof.

(5) Miscellaneous Organic Liquids

A miscellaneous organic liquid is a liquid comprising carbon that are useful as a liquid component for a coating, but are not readily classified as a hydrocarbon, an oxygenated compound, a chlorinated hydrocarbon, a nitrated hydrocarbon, or a combination thereof. Examples of a miscellaneous organic liquid include carbon dioxide; acetic acid, methylal (CAS No. 109-87-5); dimethylacetal (CAS No. 534-15-6); N,N-dimethylformamide (CAS No. 68-12-2); N,N-dimethylacetamide (CAS No. 127-19-5); dimethylsulfoxide (CAS No. 67-68-5); tetramethylene suflone (CAS No. 126-33-0); carbon disulfide (CAS No. 75-15-0); 2-nitropropane (CAS No. 79-46-9); N-methylpyrrolidone (CAS No. 872-50-4); hexamethylphosphoric triamide (CAS No. 680-31-9); 1,3-dimethyl-2-imidazolidinone (CAS No. 80-73-9); or a combination thereof. As would be known to one of ordinary skill in the art, carbon dioxide may function as a liquid component when prepared under pressure and temperature conditions to form a supercritical liquid. A supercritical liquid has properties between that of a liquid and a gas, and can be used in spray application of a coating wherein the appropriate pressure conditions can be maintained. Supercritical carbon dioxide may be formulated with a coating using the tradename technique Unicarb™ (Union Carbide Chemicals and Plastics Co., Inc.). Supercritical carbon dioxide may be selected as a substitute for a hydrocarbon diluent in embodiments wherein chemical inertness, non-flammability, rapid evaporation, or a combination thereof, is desirable. In certain aspects, 0% to 30%, including all intermediate ranges and combinations thereof, of a hydrocarbon liquid component may be replaced with supercritical carbon dioxide.

b. Plasticizers

In certain embodiments, a coating may comprise a plasticizer. A plasticizer may be selected for embodiments wherein the resin possesses an unsuitable brittleness and/or low flexibility property upon film formation. Properties a plasticizer typically confers to a coating and/or film include, for example, enhancing a flow property of a coating, lowering a film-forming temperature range, enhancing the adhesion property of a coating and/or film, enhancing the flexibility property of a film, lowering the $T_g$, improving film toughness, enhancing film heat resistance, enhancing film impact resistance, enhancing UV resistance, or a combination thereof. Since a function of a plasticizer typically is to alter a film's properties, most plasticizer's possess a high (e.g., baking temperature) boiling point, as such a compound is generally less volatile, with increasing boiling point temperature. In certain aspects, a plasticizer may function as a solvent, thinner, diluent, plasticizer, or combination thereof, for a coating composition and/or film at a temperature greater than ambient conditions.

A plasticizer is thought to interact with a binder by a polar interaction, but is chemically inert relative to the binder. A plasticizer typically will lower the $T_g$ of a binder below the temperature a coating comprising the binder will be applied to a surface. In many embodiments, a plasticizer have a vapor pressure less than 3 mm at 200° C., a mass of 200 Da to 800 Da, a specific gravity of 0.75 to 1.35, a viscosity of 50 cSt to 450 cSt, a flash point temperature greater than 120° C., or a combination thereof. Preferred plasticizers comprise an organic liquid (e.g., an ester). Standards for physical properties, chemical properties, and/or procedures for testing purity/properties, are described for plasticizers (e.g., undesired acidity, color, undesired copper corrosion, boiling point, ester content, odor, undesirable water contamination) in, for example, "ASTM Book of Standards, Volume 06.04, Paint—Solvents; Aromatic Hydrocarbons," D1613-02, D1209-00, D849-02, D1078-01, D1617-90, D1296-01, D608-90, and D1364-02, 2002; and "ASTM Book of Standards, Volume 06.01, Paint—Tests for Chemical, Physical, and Optical Properties; Appearance," D1544-98, 2002. Compatibility of a plasticizer with a binder and/or a solvent has been described (see, for example, Riley, H. E., "Plasticizers," *Paint Testing Manual*, American Society for Testing Materials, 1972). Additionally, techniques previously described for estimating solubility for liquid and an additional coating component may be applied for a plasticizer.

Various plasticizers comprise an ester of a monoalcohol and an acid (e.g., a dicarboxylic acid). In many embodiments, the monoalcohol comprises 4 to 13 carbons. In specific aspects, the monoalcohol comprises butanol, 2-ethylhexanol, isononanol, isooctyl, isodecyl, or a combination thereof. Examples of an acid include an azelaic acid, a phthalic acid, a sebacic acid, a trimellitic acid, an adipic acid, or a combination thereof. Examples of such plasticizers include di(2-ethylhexyl) azelate ("DOZ"); di(butyl) sebacate ("DBS"); di(2-ethylhexyl) phthalate ("DOP"); di(isononyl) phthalate ("DINP"); dibutyl phthalate ("DBP"); butyl benzyl phthalate ("BBP"); di(isooctyl) phthalate ("DIOP"); di(idodecyl) phthalate ("DIDP"); tris(2-ethylhexyl) trimellitate ("TOTM"); tris(isononyl) trimellitate ("TINTM"); di(2-ethylhexyl) adipate ("DOA"); di(isononyl) adipate ("DINA"); or a combination thereof.

A plasticizer may be classified by a moiety, such as, for example, as an adipate (e.g., DOA, DINA), an azelate (e.g., DOZ), a citrate, a chlorinated plasticizer, an epoxide, a phosphate, a sebacate (e.g., DBS), a phthalate (e.g., DOP, DINP, DIOP, DIDP), a polyester, or a trimellitate (e.g., TOTM, TINTM). An example of a citrate plasticizer includes acetyl tri-n-butyl citrate. Examples of an epoxide plasticizer include an epoxy modified soybean oil ("ESO"), 2-ethylhexyl epoxytallate ("2EH tallate"), or a combination thereof. Examples of a phosphate plasticizer include isodecyl diphenyl phosphate, tricresyl phosphate ("TPC"), isodecyl diphenyl phosphate, tri-2-ethylhexyl phosphate ("TOP"), or a combination thereof. Tricresyl phosphate may function as a plastizer, confer flame resistance, confer fungi resistance, or a combination thereof to a coating. Examples of a polyester plasticizer include an adipic acid polyester, an azelaic acid polyester, or a combination thereof. In certain aspects, a plasticizer is selected for water resistance (e.g., hydrolysis resistance, inertness toward water) such as a bisphenoxyethylformal.

c. Water-Borne Coatings

A water-borne coating ("water reducible coating") refers to a coating wherein components such as a pigment, a binder, an additive, or a combination thereof are dispersed in water. Often, an additional solvent, surfactant, emulsifier, wetting agent, dispersant, or a combination thereof promotes dispersion of a coating component. A latex coating refers to a water-borne coating wherein the binder is dispersed in water. Typically, a binder of a latex coating comprises a high molecular weight binder. Often a latex coating (e.g., a paint, a lacquer) is a thermoplastic coating. Film formation occurs by loss of the liquid component, typically through evaporation, and fusion of dispersed thermoplastic binder particles. Often, a latex coating further comprises a coalescing solvent (e.g., diethylene glycol monobutyl ether) that promotes fusion of the binder particles. In some embodiments, a film produced from a latex coating is more porous, possesses a lower moisture resistance property, is less compact (e.g., thicker), or a combination thereof, relative to a solvent-borne coating comprising similar non-volatile components. Specific procedures for determining the purity/properties of a latex coating, coating component (e.g., solids content, nonvolatile content, vehicles), and/or film have been described, for example, in "ASTM Book of Standards, Volume 06.01, Paint—Tests for Chemical, Physical, and Optical Properties; Appearance," D4747-02 and D4827-93, 2002; "ASTM Book of Standards, Volume 06.02, Paint—Products and Applications; Protective Coatings; Pipeline Coatings," D3793-00, 2002; and "ASTM Book of Standards, Volume 06.03, Paint—Pigments, Drying Oils, Polymers, Resins, Naval Stores, Cellulosic Esters, and Ink Vehicles," D5097-90 D4758-92, and D4143-89, 2002.

In certain embodiments, a water-borne coating is a coating wherein 50% to 100%, the including all intermediate ranges and combinations thereof, of a coating's liquid component is water. In general embodiments, the water component of a water-borne coating may function as a solvent, a thinner, a diluent, or a combination thereof. In certain embodiments, a water-borne coating may comprise an additional non-aqueous liquid component. In specific aspects, such an additional liquid component may function as a solvent, a thinner, a diluent, a plasticizer, or a combination thereof. An additional liquid component of a water-borne coating may comprise 0% to 49.999%, the including all intermediate ranges and combinations thereof, of the liquid component. Examples of additional liquid components in a water-borne coating include a glycol ether, an alcohol, or a combination thereof.

In certain embodiments, an additional liquid component of a water-borne coating may be fully or partly miscible in water. Examples of a liquid that is completely miscible in water, and visa versa, include methanol, ethanol, propanol, isopropyl alcohol, tert-butanol, ethylene glycol, methyl glycol, ethyl glycol, propyl glycol, butyl glycol, ethyl diglycol, methoxypropanol, methyldipropylene glycol, dioxane, tetrahydrofuran, acetone, diacetone alcohol, dimethylformamide or dimethyl sulfoxide. Examples of a liquid that is partly miscible in water, by weight at 20° C., include 0.02% ethylbenzene; 0.02% tetrachloroethylene; 0.02% p-xylene; 0.035% toluene; 0.04% diisobutyl ketone; 0.1% tricholorethylene; 0.19% trimethylcyclohexanol; 0.2% cyclohexyl acetate; 0.3% dibutyl ether; 0.3% trimethylcyclohexanone; 0.44% 1,1,1-tricholoroethane; 0.53% hexane; 0.58% hexanol; 0.67% isobutyl acetate; 0.83% butyl acetate; 1.2% isophorone; 1.4% nitropropane; 1.5% butyl glycol acetate; 1.7% 2-nitropropane; 2.0% methylene chloride; 2.0% methyl isobutyl ketone; 2.3% cyclohexanone; 2.9% isopropyl acetate; 2.9% methylbenzyl alcohol; 3.6% cyclohexanol; 4.5% nitroethane; 4.8% methyl tert-butyl ether; 6.1% ethyl acetate; 6.9% diethyl ether; 7.5% butanol; 7.5% butyl glycolate; 8.4% isobutanol; 12.5% 2-butanol; 21.4% propylene carbonate; 23.5% ethyl glycol acetate; 24% methyl acetate; or 26.0% methyl ethyl ketone. Examples of an azeotrope comprising a majority of water (BP 100° C.) include those comprising 16.1% isophorone (A-BP 99.5° C.); 20% 2-ethylhexanol (A-BP 99.1° C.); 20% cyclohexanol (A-BP 97.8° C.); 20.8% butyl glycol (A-BP 98.8° C.); or 28.8% ethyl glycol (A-BP 99.4° C.).

3. Colorants

A colorant ("colorizing agent") is a composition that confers a desirable optical property to a coating. Examples of desirable optical properties, depending upon the application of the present invention, include a reflection property, a light absorption property, a light scattering property, or a combination thereof. A colorant that increases the reflection of light may increase gloss. A colorant that increased light scattering may increase the opacity and/or confer a color to a coating and/or film. Light scattering of a broad spectrum of wavelengths can confer a white color to a coating and/or film. Scattering of a certain wavelength may confer a color associated with the wavelength to a coating and/or film. Light absorption also affects opacity and/or color. Light absorption over a broad spectrum confers a black color to a coating and/or film. Absorbance of a certain wavelength may eliminate the color associated with the wavelength from the appearance of a coating and/or film. Examples of colorants include pigments, dyes, extenders, or a combination thereof. Colorants (e.g., pigments, dyes) and procedures for determining the optical properties and physical properties (e.g., hiding power, transparency, light absorption, light scattering, tinting strength, color, particle size, particle dispersion, pigment content, color matching) of a colorant, coating component, coating and/or film are described in, for example, (in "Industrial Color Testing, Fundamentals and Techniques, Second, Completely Revised Edition," 1995; "Colorants for Non-Textile Applications," 2000). Various colorants are well known to those of ordinary skill in the art, and are often identified by their Colour Index ("CI") number (see, for example, "Colour Index International," 1971; and "Colour Index International," 1997). In some cases, a common name for a colorant encompasses several related colorants, which can be differentiated by CI number.

a. Pigments

A pigment is a composition that is insoluble in the other components of a coating, and further confers a desirable optical properties, confers a property affecting the application of the coating (e.g., a rheological property), confers a performance property to a coating, reduces the cost of the coating, or a combination thereof. In certain embodiment, a pigment confers a performance property to a coating such as a desirable corrosion resistance property, magnetic property, or a combination thereof. Examples of a pigment include an inorganic pigment, an organic pigment, or a combination thereof.

Pigments possess a variety of properties in addition to color that aid in the selection of a particular pigment for a specific application. Examples of such properties include a tinctorial property, an insolubility property, a corrosion resistance property, a durability property, a heat resistance property, an opacity property, a transparency property, or a combination thereof. A tinctorial property is the ability of a composition to produce a color, wherein a greater tinctorial strength indicating less of the composition is needed to achieve the color. A insolubility property is the ability of a composition to remain in a solid form upon contact with another coating component (e.g., a liquid component), even during a curing process involving chemical reactions (e.g., thermosetting, baking, irradiation). A corrosion resistance property is the ability of a composition to reduce the damage of a chemical (e.g., water, acid) that contacts metal.

Pigments (e.g., extenders, titanium pigments, inorganic pigments, surface modified pigments, bismuth vanadates, cadmium pigments, cerium pigment, complex inorganic color pigments, metallic pigments, benzimidazolone pigments, diketopyrrolopyrrole pigments, dioxazine violet pigments, disazocondensation pigments, isoindoline pigments, isoindolinone pigments, perylene pigments, phthalocyanine pigments, quinacridone pigments, quinophthalone pigments, thiazine pigments, oxazine pigments, zinc sulfide pigments, zinc oxide pigments, iron oxide pigments, chromium oxide pigments, cadmium pigments, cadmium sulfide, cadmium yellow, cadmium sulfoselenide, cadmium mercury sulfide, bismuth pigments, chromate pigments, chrome yellow, molybdate red, molybdate orange, chrome orange, chrome green, fast chrome green, ultramarine pigments, iron blue pigments, black pigments, carbon black, specialty pigments, magnetic pigments, cobalt-containing iron oxide pigments, chromium dioxide pigments, metallic iron pigments, barium ferrite pigments, anti-corrosive pigments, phosphate pigments, zinc phosphate, aluminum phosphate, chromium phosphate, metal phosphates, multiphase phosphate pigments, borosilicate pigments, borate pigments, chromate pigments, molybdate pigments, lead cyanamide pigments, zinc cyanamide pigments, iron-exchange pigments, metal oxide pigments, red lead pigment, red lead, calcium plumbate, zinc ferrite pigments, calcium ferrite pigments, zinc oxide pigments, powdered metal pigments, zinc dust, lead powder, flake pigments, nacreous pigments, interference pigments, natural pearl essence pigment, basic lead carbonate pigment, bismuth oxychloride pigment, metal oxide-mica pigments, metal effect pigments, transparent pigments, transparent iron oxide pigments, transparent iron blue pigment, transparent cobalt blue pigment, transparent cobalt green pigment, transparent iron oxide, transparent zinc oxide, luminescent pigments, inorganic phosphor pigments, sulfide pigments, selenide pigments, oxysulfide pigments, oxygen dominant phosphor pigments, halide phosphor pigments, azo pigments, monoazo yellow pigments, monoazo orange pigment, disazo pigments, β-naphthol pigments, naphthol AS pigments, salt-type azo pigments, benzimidazolone pigments, disazo condensation pigments, metal complex pigments, isoindolinone pigments, isoindoline pigments, polycyclic pigments, phthalocyanine pigments, quinacrindone pigments, perylene pigments, perinone pigments, diketopyrrolo pyrrole pigments, thioindigo pigments, anthrapyrimidine pigments, flavanthrone pigments, pyranthrone pigments, anthanthrone pigments, dioxanzine pigments, triarylcarbonium pigments, quinophthalone pigments) and their chemical properties, physical properties and/or optical properties (e.g., color, tinting strength, lightening power, scattering power, hiding power, transparency, light stability, weathering resistance, heat stability, chemical fastness, interactions with a binder), in coating component, coating and/or film, and techniques for determining such properties, are known to one of ordinary skill in the art (see, for example, Solomon, D. H. and Hawthorne, D. G., "Chemistry of Pigments and Fillers," 1983; "High Performance Pigments," 2002; "Industrial Inorganic Pigments," 2002; "Industrial Organic Pigments, Second, Completely Revised Edition," 1993).

As would be known to one of ordinary skill in the art, specific standards for physical properties, chemical properties, purity, and/or procedures for testing the purity/properties of various pigments (e.g., lead chromate, chromium oxide, phthalocyanine green, a phthalocyanine blue, molybdate orange, white zinc, zinc oxide, calcium carbonate, barium sulfate, aluminum silicate, diatomaceous silica, magnesium silicate, mica, calcium borosilicate, zinc hydroxy phosphite, aluminum powder, micaceous iron oxide, zinc phosphate, basic lead silicochromate, strontium chromate, ochre, lampblack, orange shellac, raw umber, burnt umber, raw sienna, burnt sienna, bone black, carbon black, red iron oxide, brown iron oxide, basic carbonate, white lead, white titanium dioxide, iron blue, ultramarine blue, chrome yellow, chrome orange, hydrated yellow iron oxide, zinc chromate yellow, red lead, para red toner, toluidine red toner, chrome oxide green, zinc dust, cuprous oxide, mercuric oxide, iron oxide, anhydrous aluminum silicate, black synthetic iron oxide, gold bronze powder, aluminum powder, strontium chromate pigment, basic lead silicochromate) for use in a coating are described, for example in "ASTM Book of Standards, Volume 06.03, Paint—Pigments, Drying Oils, Polymers, Resins, Naval Stores, Cellulosic Esters, and Ink Vehicles," D280-01, D2448-85, D126-87, D305-84, D3021-01, D3256-86, D2218-67, D3280-85, D50-90, D79-86, D1199-86, D602-81, D715-86, D603-66, D718-86, D604-81, D719-91, D605-82, D717-86, D607-82, D716-86, D4288-02, D4487-90, D4462-02, D4450-85, D962-81, D5532-94, D6280-98, D1648-86, D1649-01, D85-87, D209-81, D237-57, D763-01, D765-87, D210-81, D561-82, D3722-82, D3724-01, D34-91, D81-87, D1301-91, D1394-76, D261-75, D262-81, D1135-86, D211-67, D768-01, D444-88, D3872-86, D478-02, D1208-96, D83-84, D49-83, D3926-80, D475-67, D656-87, D970-86, D3721-83, D263-75, D520-00, D521-02, D283-84, D284-88, D3720-90, D3619-77, D769-01, D476-00, D267-82, D480-88, D1845-86, D1844-86, and D279-02, 2002; and in "ASTM Book of Standards, Volume 06.01, Paint—Tests for Chemical, Physical, and Optical Properties; Appearance," D5381-93 and D6131-97 2002.

(1) Corrosion Resistance Pigments

Addition of certain pigments may improve the corrosion resistance of a coating and/or film, or specifically, the protection of a metal surface coated with a coating and/or film from corrosion. Often, a primer comprises such pigments. Examples of corrosion resistance pigments include aluminum flake, aluminum triphosphate, aluminum zinc phosphate, ammonium chromate, barium borosilicate, barium chromate, barium metaborate, basic calcium zinc molybdate, basic carbonate white lead, basic lead silicate, basic lead silicochromate, basic lead silicosulfate, basic zinc molybdate, basic zinc molybdate-phosphate, basic zinc molybdenum phosphate, basic zinc phosphate hydrate, bronze flake, calcium barium phosphosilicate, calcium borosilicate, calcium chromate, calcium plumbate (CI Pigment Brown 10), calcium strontium phosphosilicate, calcium strontium zinc phosphosilicate, dibasic lead phosphite, lead chromosilicate, lead cyanamide, lead suboxide, lead sulfate, mica, micaceous iron oxide, red lead (CI Pigment Red 105), steel flake, strontium borosilicate, strontium chromate (CI Pigment Yellow 32), tribasic lead phophosilicate, zinc borate, zinc borosilicate, zinc chromate (CI Pigment Yellow 36), zinc dust (CI Pigment Metal 6), zinc hydroxy phosphite, zinc molybdate, zinc oxide, zinc phosphate (CI Pigment White 32), zinc potassium chromate, zinc silicophosphate hydrate, zinc tetraoxylchromate, or a combination thereof.

The selection of a corrosion resistant pigment may be made based on the mechanism of corrosion resistance it confers to a coating and/or film. Corrosion often occurs as a cathodic process wherein a metal surface acts as a cathode and passes electrons to an electron accepter moiety of a corrosive chemical, such as, for example, hydrogen, oxygen, or a combination thereof. Corrosion can also occur as an anodic process wherein ionized metal atoms then enter solution. Pigments such as, for example, mica, micaceous iron oxide, metallic flake pigments (e.g., aluminum, bronze, steel), or a combination thereof confer corrosion resistance to a coating and/or film by acting as a physical barrier between a metal surface and corrosive chemicals. However, a chemically reactive pigment such as a metal flake pigment be used in an environment at or near neutral pH (e.g., pH 6 to pH 8). Micaceous iron oxide can be selected for a primer, a topcoat, or a combination thereof, and can also function as a UV absorber. Aluminum flake may be selected for an industrial coating, an automotive coating, an architectural coating, a primer, or a combination thereof. Aluminum flake may additionally confer heat resistance, moisture resistance, UV resistance, or a combination thereof to a coating and/or film. Aluminum flake may also be stearate modified for use in a topcoat. However, aluminum flake may produce gas in a coating comprising more than 0.15% water. A metallic zinc pigment (e.g., zinc flake, zinc dust) acts by functioning as an anode instead of the metal surface (e.g., steel). However, the effectiveness of a coating's corrosion resistance fades as the zinc pigment is used up in protective reactions. A metallic zinc primer may be selected for a primer, particularly in combination with an epoxy topcoat, a urethane topcoat, or a combination thereof.

Red lead and/or basic lead silicochromate can confer an orange color, and may be selected for combination with an oil-based coating (e.g., a primer), as the pigment chemically reacts with an oil-based binder to produce a corrosion resistant lead soap in the coating and/or film. Red lead and/or basic lead is typically selected for a primer in an industrial steel coating.

A barium metaborate pigment acts by retarding an anodic process. A barium metaborate pigment is usual chemically modified by combination with silica to reduce solubility. A zinc borate combined with a zinc phosphate, a modified barium metaborate, or combination thereof demonstrates synergistic enhancement of corrosion resistance, as well as flame retardancy.

Zinc potassium chromate may confer a yellow color as well as an anticorrosive property. Zinc tetraoxylchromate can also confer a yellow color, and is typically selected for use in a two pack poly(vinyl butyryl) primer. Zinc oxide may be selected for an oleoresinous coating, a water-borne coating, a primer, or a combination thereof, and may be combined with a zinc chromate and/or calcium borosilicate, and additionally may improve thermosetting crosslinking density and/or act as a UV absorber. Strontium chromate may confer a yellow color, and may be selected for an aluminum surface, an aircraft primer, or a combination thereof. Strontium chromate may be combined with a zinc chromate in a water-borne coating, though it is preferred that total chromate content is less from 0.001% to 2%. Ammonium chromate, barium chromate and calcium chromate may be selected as a corrosion inhibitor, particularly as a flash rust inhibitor.

A zinc molybdate, zinc phosphate, zinc hydroxy phosphite, or a combination thereof may confer a white color. These zinc pigments function by reducing an anodic process, though zinc hydroxy phosphite may form corrosion resistant soap in an oleoresinous-coating. Basic zinc molybdate typically is selected for an alkyd-coating, an epoxide-coating, an epoxy ester-coating, a polyester-coating, a solvent-borne coating, or a combination thereof. Basic zinc molybdate-phosphate is similar to basic zinc molybdate, though it may provide superior corrosion resistance for a rusted steel surface. Basic calcium zinc molybdate may be selected for a water-borne coating, a two-pack polyurethane coating, a two-pack epoxy coating, or a combination thereof. A combination of basic calcium zinc molybdate and zinc phosphate may confer a superior adhesion property to a surface comprising iron, and may be selected for a water-borne coating or a solvent-borne coating. A zinc phosphate may be selected for an alkyd coating, a water-reducible coating, a coating cured by an acid and baking, or a combination thereof. A zinc phosphate is less preferred for a marine coating for salt water embodiments. A modified zinc phosphate, such as, for example, aluminum zinc phosphate, basic zinc phosphate hydrate, zinc silicophosphate hydrate, basic zinc molybdenum phosphate, or a combination thereof may confer improved corrosion resistance for a salt water embodiment. Zinc hydroxy phosphite may be selected for a solvent-borne coating.

An aluminum triphosphate typically confers a white color, acts by chelating iron ions, and is preferred for a surface that comprises iron. A grade I aluminum triphosphate is modified with zinc and silicate, and may be selected for an alkyd-coating, an epoxy coating, a solvent-borne coating, a primer, or a combination thereof. A grade II aluminum triphosphate is modified with zinc and silicate, and may be selected for a water-borne coating or a solvent-borne coating. A grade III aluminum triphosphate is modified with zinc, and may be selected for a water-borne coating or a solvent-borne coating.

A silicate pigment such as barium borosilicate, calcium borosilicate, strontium borosilicate, zinc borosilicate, a calcium barium phosphosilicate, a calcium strontium phosphosilicate, a calcium strontium zinc phosphosilicate, or a combination thereof, typically acts through inhibiting an anodic or cathodic process, as well as forming a corrosion resistant soap in an oleoresinous-coating. A grade I and/or III calcium borosilicate may be selected for a medium oil alkyd-coating, a long oil alkyd, an epoxy ester-coating, a solvent-borne coating, an architectural coating, an industrial coating, or a combination thereof, but is less preferred for a marine coating, an epoxide-coating, a water-borne coating, or a combination thereof. Calcium barium phosphosilicate grade I pigment may be selected for a solvent-borne epoxy-coating, to confer an antisettling property to a primer comprising zinc, or a combination thereof. Calcium barium phosphosilicate grade II pigment may be selected for a water-borne coating, an alkyd-coating, or a combination thereof. Calcium strontium phosphosilicate may be selected for a water-borne acrylic lacquer, a water-borne sealant, or a combination thereof. In aspects wherein a water-borne acrylic lacquer comprises calcium strontium phosphosilicate, it is preferred that a 1:1 ratio of zinc phosphate pigment is included. Calcium strontium zinc phosphosilicate may be selected for an alkyd-coating, an epoxide coating, a coating cured by a catalyst and baking, a water-borne coating, or a combination thereof.

(2) Camouflage Pigments

A camouflage pigment refers to a pigment typically selected to camouflage a surface (e.g., a military surface) from visual and, more preferred, infrared detection. Examples of a camouflage pigment include an anthraquinone black, a chromium oxide green, or a combination thereof. A chromium oxide green may be selected for embodiments wherein good chemical resistance, dull color, good heat stability, good infrared reflectance, good light fastness, good opacity, good solvent resistance, low tinctorial strength, or a combination thereof, is suitable. Anthraquinone black (CI Pigment Black 20) may be selected for good light fastness and moderate solvent resistance, and is often selected for camouflage coatings, due to its infrared absorption property.

(3) Color Property Pigments

A color property is the ability of a composition to confer a visual color and/or metallic appearance to a coating and/or a coated surface. Color pigments are often categorized by a common name recognized within the art, which often encompasses several specific color pigments, each identified by a CI number.

(i) Black Pigments

A black pigment is a pigment that confers a black color to a coating. Examples of black pigments, identified by common name with examples of specific pigments in parentheses, include aniline black; anthraquinone black; carbon black; copper carbonate; graphite; iron oxide; micaceous iron oxide; manganese dioxide; or a combination thereof.

Aniline black (e.g., CI Pigment Black 1); may be selected for a deep black color (e.g., strong light absorption, low light scattering) and/or fastness. Coatings comprising aniline black typically comprise relatively higher concentrations of binder, and thus often possesses a matt property.

Anthraquinone black (e.g., CI Pigment Black 20) may be selected for good light fastness and moderate solvent resistance.

Carbon black (e.g., CI Pigment Black 6, CI Pigment Black 7, CI Pigment Black 8) generally possesses properties such as chemical stability, good light fastness, good solvent resistance, heat stability, or a combination thereof. Carbon black is often categorized into separate grades, based on the intensity of black color ("jetness"). To reduce flocculation in preparing a coating comprising a carbon black pigment, such pigments may be incrementally added to a coating during preparation, chemically modified by surface oxidation, chemically modified by an organic compound (e.g., a carboxylic acid), or a combination thereof. Additionally, a carbon black pigment may absorb certain other coating components such as a metal soap drier. Typically, increasing the concentration of the susceptible component by, for example, two-fold will reduce this effect. A high jet channel black pigment is often selected for use in an automotive coating wherein a high jetness is desired. The other grades of carbon black pigments are often selected for architectural coatings.

Graphite (e.g., CI Pigment Black 10) may be selected for properties such as relative chemically inertness, low in color intensity, low in tinctorial strength, an anti-corrosive property, an increase in coating spreading rate, or a combination thereof.

Iron oxide (e.g., CI Pigment Black 11) may be selected for properties such as good chemical resistance, relative inertness, good solvent resistance, limited heat resistance, low tinctorial strength, or a combination thereof. Iron oxide possesses superior floating resistance than carbon black, particularly in combination with titanium dioxide.

Micaceous iron oxide may be selected for properties such as relative inertness, grayish appearance, shiny appearance, function as a UV absorber, function as an anti-corrosive pigment due to resistance to oxygen and moisture passage. However, over-dispersal of a micaceous iron oxide during coating preparation may damage the pigment.

(ii) Brown Pigments

A brown pigment is a pigment that confers a brown color to a coating. Examples of a brown pigment include azo condensation (CI Pigment Brown 23, CI Pigment Brown 41, CI Pigment Brown 42); benzimidazolone (CI Pigment Brown 25); iron oxide; metal complex brown; or a combination thereof. A synthetically produced iron oxide brown (CI Pigment Brown 6, CI Pigment Brown 7) may be selected for embodiments wherein a rich brown color, good light-fastness, or a combination thereof is suitable. A metal complex brown (CI Pigment Brown 33) may be selected for embodiments wherein high heat stability, good fastness, or a combination thereof is suitable. A metal complex brown may be used, for example, in a coil coating, a coating for a ceramic surface, or a combination thereof.

(iii) White Pigments

A white pigment is a pigment that confers a white color to a coating. Examples of a white pigment include antimony oxide; basic lead carbonate (CI Pigment White 25); lithopone; titanium dioxide; white lead; zinc oxide; zinc sulphide (CI Pigment White 7); or a combination thereof.

Antimony oxide (CI Pigment White 11) is chemically inert, and used in fire resistant coatings. In some embodiments, antimony oxide may be combined with titanium dioxide, particularly in a coating where chalking is undesirable and a white color in the coating is desired.

Titanium dioxide (CI Pigment White 6) is resistant to heat, many chemicals, and organic solvents, allowing use in many different applications where such properties are desirable. Titanium dioxide may be in the form of a crystal, such as an anatase crystal, a rutile crystal, or a combination thereof. Rutile is more opaque than anatase. Anatase has a greater ability to chalk and is whiter in color than rutile. In aspects wherein chalking is undesirable, a titanium dioxide crystal may be reacted with an inorganic oxide to enhance chalking resistance. Examples of such inorganic oxides include aluminum oxide, silicon oxide, zinc oxide, or a combination thereof.

White lead (CI Pigment White 1) is chemically reactive with acidic binders to form strong films with elastic properties, but also chemically reacts with sulphur to become black in color. It is less preferred in certain coatings due to the toxic nature of lead.

Zinc oxide (CI Pigment White 4) confers desirable properties such as resistance to mildew, as well as chemically reacting with oleoresin binders in film formation to enhance resistance to abrasion, to enhance resistance to moisture, to enhance hardness, and/or reduce chalking. However, these reactions may undesirably occur during storage. In some embodiments, it may be combined with titanium dioxide, particularly in a coating comprising an oleoresin binder when chalking is undesirable and a white color in the coating is desired.

Zinc sulfide (CI Pigment White 7) is chemically inert, and confers a strong chalking property. In certain embodiments, a zinc sulfide comprises a lithopone. A lithopone (CI Pigment White 5) comprises a mixture of ZnS and barium sulphate ($BaSO_4$), usually from 30% to 60% ZnS and 70% to 40% $BaSO_4$.

(iv) Pearlescent Pigments

A pearlescent pigment is a pigment that confers a pearl-like appearance to a coating. Examples of a white pigment include titanium dioxide and ferric oxide covered mica, bismuth oxychloride crystal, or a combination thereof.

(v) Violet Pigments

A violet pigment is a pigment that confers a violet color to a coating. However, a violet pigment is often used in combination with a red pigment or a blue pigment to produce a desirable color of an intermediate hue between red and blue. Additionally, a violet pigment is often combined with titanium dioxide to balance the slight yellow color of that white pigment. An example of a violet pigment includes dioxanine violet (CI Pigment Violet 23; CI Pigment Violet 37). A dioxazine violet may be selected for embodiments wherein high heat stability, good light fastness, good solvent fastness, or a combination thereof is suitable. CI Pigment Violet 23 ("carbazole violet") is relatively transparent and bluer than CI Pigment 37, and is typically used in a metallic coating. A dioxazine violet is susceptible to flocculation, loss in a powder coating, or a combination thereof, due to small particle size.

(vi) Blue Pigments

A blue pigment is a pigment that confers a blue color to a coating. Examples of a blue pigment include carbazol Blue; carbazole Blue; cobalt blue; copper phthalocyanine; dioxanine Blue; indanthrone; phthalocyanin blue; Prussian blue; ultramarine; or a combination thereof.

A cobalt blue (CI Pigment Blue 36) may be selected for embodiments wherein good chemical resistance, good lightfastness, good solvent fastness, or a combination thereof, is suitable. An indanthrone (CI Pigment Blue 60) may be selected for embodiments wherein a reddish-blue hue, good chemical resistance, good heat resistance, good solvent fastness, transparency, superior resistance to flocculation relative to a copper phthalocyanine, or a combination thereof, is suitable.

A copper phthalocyanine (CI Pigment Blue 15, CI Pigment Blue 15:1, CI Pigment Blue 15:2, CI Pigment Blue 15:3, CI Pigment Blue 15:4, CI Pigment Blue 15:6, CI Pigment Blue 16) may be selected for embodiments wherein good color strength, good tinctorial strength, good heat stability, good lightfastness, good solvent resistance, transparency, or a combination thereof, is suitable. CI Pigment Blue 15 is reddish in hue, but is chemically unstable upon contact with an aromatic hydrocarbon, and converts to a greenish blue compound. CI Pigment Blue 15:1 is form of CI Pigment Blue 15 chemically stabilized by chlorination, greener, and tinctorially weaker than CI Pigment Blue 15. CI Pigment Blue 15:2 is modified form of CI Pigment Blue 15 that is resistant to flocculation. CI Pigment Blue 15:3 is greenish-blue, while CI Pigment Blue 15:4 is modified form of CI Pigment Blue 15:3 that is resistant to flocculation. CI Pigment Blue 16 is relatively transparent. Examples of coatings wherein copper phthalocyanine are used include a metallic automotive coating. However, as described above, a copper phthalocyanine may be susceptible to flocculation due to small primary particle size, and various modified forms are known wherein flocculation is reduced. Examples of modifications used to reduce flocculation adding a sulfonic acid moiety; a sulfonic acid moiety and a long chain amine moiety; an aluminum benzoate; an acidic binder (e.g., a rosin); a chloromethyl moiety; or a combination thereof, to the phthalocyanine. A modified phthalocyanine may be selected for embodiments wherein superior color shade, dispersibility, gloss, or a combination thereof is suitable.

A Prussian blue (CI Pigment Blue 27) may be selected for embodiments wherein a strong color, good heat stability, good solvent fastness, or a combination thereof is suitable. However, a Prussian blue is chemically unstable in alkali conditions. An ultramarine (CI Pigment Blue 29) may be selected wherein a strong color, good heat stability, good light fastness, good solvent resistance, or a combination thereof is suitable. However, an ultramarine is chemically unstable in acidic conditions.

(vii) Green Pigments

A green pigment is a pigment that confers a green color to a coating. However, often a "green pigment" comprises a mixture of a yellow pigment and a blue pigment, with the properties of each component pigment generally retained. Examples of a green pigment include chrome green; chromium oxide green; halogenated copper phthalocyanine; hydrated chromium oxide; phthalocyanine green; or a combination thereof.

A chrome green ("Brunswick green," CI Pigment Green 15) comprises a combination of a Prussian blue and/or a copper phthalocyanine blue and a chrome yellow. A coating comprising a chrome green may be susceptible to floating and flooding defects. A chromium oxide green (CI Pigment Green 17) may be selected for embodiments wherein good chemical resistance, dull color, good heat stability, good infrared reflectance, good light fastness, good opacity, good solvent resistance, low tinctorial strength, or a combination thereof is suitable. A hydrated chromium oxide (CI Pigment Green 18) is similar to chromium oxide, and may be selected for embodiments wherein good light fastness, relatively brighter appearance, relatively greater transparency, relatively less heat stability, relatively less acid stability, or a combination thereof, is suitable. A phthalocyanine green (CI Pigment Green 7, CI Pigment Green 36) may be selected for embodiments wherein good chemical resistance, good heat stability, good light fastness, good solvent resistance, good tinctorial strength, color transparency, or a combination thereof is suitable. CI Pigment Green 7 may be selected for a bluish green color, while CI Pigment Green 36 may be selected for a yellower-greenish color. A phthalocyanine green is often selected for an automotive coating (e.g., a metallic coating), an industrial coating, an architectural coating, a powder coating, or a combination thereof.

(viii) Yellow Pigments

In certain embodiments, a coating may comprise a yellow pigment. A "yellow pigment" is a pigment that confers a yellow color to a coating. Examples of a yellow pigment include anthrapyrimidine; arylamide yellow; barium chromate; benzimidazolone yellow; bismuth vanadate (CI Pigment Yellow 184); cadmium sulfide yellow (CI Pigment Yellow 37); complex inorganic color pigment; diarylide yellow; disazo condensation; flavanthrone; isoindoline; isoindolinone; lead chromate; nickel azo yellow; organic metal complex; quinophthalone; yellow iron oxide; yellow oxide; zinc chromate; or a combination thereof.

An anthrapyrimidine pigment (CI Pigment Yellow 108) may be selected for embodiments wherein, moderate light fastness, moderate solvent resistance, a dull color, transparency, or a combination thereof is suitable.

An arylamide yellow ("Hansa® yellow," CI Pigment Yellow 1, CI Pigment Yellow 3, CI Pigment Yellow 65, CI Pigment Yellow 73, CI Pigment Yellow 74, CI Pigment Yellow 75, CI Pigment Yellow 97, CI Pigment Yellow 111) may be selected for embodiments wherein, poor heat stability, good light fastness, poor solvent resistance, moderate tinctorial strength, or a combination thereof is suitable. CI Pigment 1 and CI Pigment 74 are mid-yellow in hue. CI Pigment Yellow 3 is greenish in hue. CI Pigment Yellow 73 is mid-yellow in hue, and resistant to recrystallization during dispersion. CI Pigment 97 possesses superior solvent fastness than other arylamide yellow pigments, and has been used in a stoving enamel, an automotive coating, or a combination thereof. Other arylamide yellow pigments may be used in a water-borne coating, a coating comprising a white spirit liquid component, or a combination thereof.

A benzimidazolone yellow (CI Pigment Yellow 120, CI Pigment Yellow 151, CI Pigment Yellow 154, CI Pigment Yellow 175, CI Pigment Yellow 181, CI Pigment Yellow 194) may be selected for embodiments wherein, good chemical resistance, good heat stability, good light fastness, good solvent resistance, or a combination thereof is suitable. A benzimidazolone with larger particle size been used in an automotive coating, a powder coating, or a combination thereof.

A cadmium sulfide yellow (CI Pigment Yellow 37) may be selected for embodiments wherein good stability in basic pH, good heat stability, good light fastness, good opacity, good solvent fastness, or a combination thereof is suitable. However, a cadmium yellow comprises cadmium, which may limit suitability relative to an environmental law or regulation.

A complex inorganic color pigment ("mixed phase metal oxide," CI Pigment Yellow 53, CI Pigment Yellow 119, CI Pigment Yellow 164); may be selected for embodiments wherein, good chemical stability, good heat resistance, good light fastness, good opacity, good solvent fastness, or a combination thereof is suitable. However, a complex inorganic color pigment generally produces a pale color, and is often combined with an additional pigment (e.g., an organic pigment). A complex inorganic color pigment is often selected for an automotive coating, a coil coating, or a combination thereof. A bismuth vanadate is similar to a complex inorganic pigment, but possesses superior color of green-yellow hue, poorer light fastness, and greater use in a powder coating. A bismuth vanadate is often combined with a light stabilizer.

A diarylide yellow (CI Pigment Yellow 12, CI Pigment Yellow 13, CI Pigment Yellow 14, CI Pigment Yellow 17, CI Pigment Yellow 81, CI Pigment Yellow 83) may be selected for embodiments wherein, good chemical resistance, poor light fastness, good solvent resistance, good tinctorial strength, or a combination thereof is suitable. A diarylide yellow is not stable at a temperature of 200° C. or greater. CI Pigment Yellow 83 has superior light fastness than other diarylide yellow pigments, and has been used in an industrial coating, a powder coating, or a combination thereof.

A diazo condensation pigment (CI Pigment Yellow 93, CI Pigment Yellow 94, CI Pigment Yellow 95, CI Pigment Yellow 128, CI Pigment Yellow 166) may be selected for embodiments wherein, good chemical resistance, good heat stability, good solvent resistance, good tinctorial strength, or a combination thereof is suitable. A diazo condensation pigment typically is used in plastics, though CI Pigment Yellow 128 has been used in a coating such as an automotive coating.

A flavanthrone pigment (CI Pigment Yellow 24) may be selected for embodiments wherein, good heat stability, moderate light fastness, a reddish yellow hue superior to an anthrapyrimidine, transparency, or a combination thereof is suitable.

An isoindoline yellow pigment (CI Pigment Yellow 139, CI Pigment Yellow 185) may be selected for embodiments wherein, good chemical resistance, good heat stability, good light fastness, good solvent resistance, moderate tinctorial strength, or a combination thereof is suitable. An isoindolinone yellow pigment (CI Pigment Yellow 109, CI Pigment Yellow 110, CI Pigment Yellow 173) typically has been used in an automotive coating or an architectural coating. An isoindoline yellow pigment may be selected for embodiments wherein, good light fastness, good tinctorial strength, or a combination thereof is suitable. However, an isoindoline pigment is not stable in a basic pH. An isoindoline yellow pigment typically has been used in an industrial coating.

A lead chromate (CI Pigment Yellow 34) may be selected for embodiments wherein moderate heat stability, low oil absorption, good opacity, good solvent resistance, or a combination thereof is suitable. However, a lead chromate is susceptible to an acidic or a basic pH, and a lower light fastness so that the pigment darkens upon irradiation by light. The pH and lightfastness properties of commercially produced lead chromate are often improved by treatment of a lead chromate with silica, antimony, alumina, metal, or a combination thereof. Additionally, a lead chromate comprises lead and/or chromium, which may limit suitability relative to an environmental law or regulation. A lead chromate may comprise a lead sulfate, which is used to modify color. Examples of lead chromates include a lemon chrome, which comprises from 20% to 40% lead sulfate and is greenish yellow in color; a middle chrome, which comprises little lead sulfate and is reddish yellow in color; orange chrome, which comprises no detectable lead sulfate; and primrose chrome, which comprises from 45% to 55% lead chrome and is greenish yellow in color.

An organic metal complex (CI Pigment Yellow 129, CI Pigment Yellow 153) may be selected for embodiments wherein good solvent resistance is suitable. An organic metal complex typically is transparent and dull in color.

A quinophthalone pigment (CI Pigment Yellow 138) may be selected for embodiments wherein, good heat stability, good light fastness, good solvent resistance, a reddish yellow hue, or a combination thereof is suitable. A quinophthalone can be either highly opaque or transparent. A quinophthalone pigment has been used as a substitute for chrome as a pigment.

A yellow iron oxide (CI Pigment Yellow 42, CI Pigment Yellow 43) may be selected for embodiments wherein good covering power, good disperability, good resistance to chemicals, good light fastness, good solvent resistance, a yellow with greenish hue is desired, or a combination thereof is suitable. A yellow iron oxide can function as a U.V. absorber. However, a yellow iron oxide is generally of duller color relative to other pigments, and is susceptible to temperatures of 105° C. or greater. Additionally, a yellow iron oxide may comprise a α-crystal, a β-crystal, a γ-crystal, or a combination thereof. Overdispersion may damage the needle-shape crystal structure, which can reduce the color intensity. Additionally, a transparent yellow iron oxide can be prepared by selecting particles with minimum size, and such a pigment is used, for example, in an automotive coating or a wood coating.

(ix) Orange Pigments

In certain embodiments, a coating may comprise an orange pigment. An "orange pigment" is a pigment that confers an orange color to a coating. Examples of an orange pigment include perinone orange; pyrazolone orange; or a combination thereof.

A perinone orange pigment (CI Pigment Orange 43) may be selected for embodiments wherein very good resistance to heat, good light fastness, good solvent resistance, high tinctorial strength, or a combination thereof is suitable.

A pyrazolone orange pigment (CI Pigment Orange 13, CI Pigment Orange 34) is similar to a diarylide yellow pigment, and may be selected for embodiments wherein moderate resistance to heat, poor light fastness, moderate solvent resistance, high tinctorial strength, or a combination thereof is suitable. However, CI Pigment Orange 34 possesses greater lightfastness relative to CI Pigment Orange 13, and has been used in an industrial coating and/or a replacement for chrome.

(x) Red Pigments

In certain embodiments, a coating may comprise a red pigment. A "red pigment" is a pigment that confers a red color to a coating. Examples of an red pigment include anthraquinone; benzimidazolone; BON arylamide; cadmium red; cadmium selenide; chrome red; dibromanthrone; diketopyrrolo-pyrrole pigment (CI Pigment Red 254, CI Pigment Red 255, CI Pigment Red 264, CI Pigment Red 270, CI Pigment Red 272); disazo condensation pigment (CI Pigment Red 144, CI Pigment Red 166, CI Pigment Red 214, CI Pigment Red 220, CI Pigment Red 221, CI Pigment Red 242); lead molybdate; perylene; pyranthrone; quinacridone; quinophthalone; red iron oxide; red lead; toluidine red; tonor pigment (CI Pigment Red 48, CI Pigment Red 57, CI Pigment Red 60, CI Pigment Red 68); β-naphthol red; or a combination thereof.

A lead molybdate red pigment (CI Pigment Red 104) may be selected for embodiments wherein good resistance to heat, moderate resistance to basic pH, good opacity, excellent solvent resistance, or a combination thereof is suitable. A molybdate red is bright in color, and is often combined with an organic pigment to extend a color range. However, a molybdate is easy to disperse, and overdispersion may damage this pigment. Additionally, a molybdate red comprising lead and/or chromium may have limited suitability relative to an environmental law or regulation.

A cadmium red pigment (CI Pigment Red 108) may be selected for embodiments wherein excellent resistance to heat, good lightfastness, poor resistance to acidic pH, good opacity, excellent solvent resistance, or a combination thereof is suitable. However, a cadmium red comprises cadmium, and may have limited suitability relative to an environmental law or regulation.

A red iron oxide pigment (CI Pigment Red 101, CI Pigment Red 102) may be selected for embodiments wherein excellent resistance to heat, good lightfastness, poor resistance to acidic pH, good opacity, excellent solvent resistance, or a combination thereof is suitable. However, a cadmium red comprises cadmium, and may have limited suitability relative to an environmental law or regulation.

β-naphthol red (CI Pigment Red 3) may be selected for embodiments wherein modest heat resistance, good lightfastness, modest solvent resistance, or a combination thereof is suitable.

BON arylamide (CI Pigment Red 2, CI Pigment Red 5, CI Pigment Red 12, CI Pigment Red 23, CI Pigment Red 112, CI Pigment Red 146, CI Pigment Red 170) comprises various pigments that generally have good lightfastness, good solvent resistance, or a combination thereof.

Tonor pigment (CI Pigment Red 48, CI Pigment Red 57, CI Pigment Red 60, CI Pigment Red 68) comprises various pigments that generally have good solvent resistance, but often have poor acid resistance, poor alkali resistance, or a combination thereof.

Benzimidazolone (CI Pigment Red 171, CI Pigment Red 175, CI Pigment Red 176, CI Pigment Red 185, CI Pigment Red 208) comprises various pigments that generally have good heat stability, excellent solvent resistance, or a combination thereof.

Disazo condensation pigment (CI Pigment Red 144, CI Pigment Red 166, CI Pigment Red 214, CI Pigment Red 220, CI Pigment Red 221, CI Pigment Red 242) comprises various pigments that generally have excellent heat stability, good solvent resistance, or a combination thereof.

Quinacridone (CI Pigment Red 122, CI Pigment Red 192, CI Pigment Red 202, CI Pigment Red 207, CI Pigment Red 209) comprises a various pigments that generally have bright color, excellent heat stability, excellent solvent resistance, excellent chemical resistance, good lightfastness, or a combination thereof.

Perylene (CI Pigment Red 123, CI Pigment Red 149, CI Pigment Red 178, CI Pigment Red 179, CI Pigment Red 190, CI Pigment Red 224) comprises a various pigments that generally have excellent heat stability, excellent solvent resistance, excellent lightfastness, or a combination thereof.

Anthraquinone (CI Pigment Red 177) has a bright color, good heat stability, good solvent resistance, good lightfastness, or a combination thereof.

Dibromanthrone (CI Pigment Red 168) has a bright color, moderate heat stability, good solvent resistance, excellent lightfastness, or a combination thereof.

Pyranthrone (CI Pigment Red 216, CI Pigment Red 226) has a dull color, moderate heat stability, good solvent resistance, poor lightfastness in combination with titanium dioxide, or a combination thereof.

Diketopyrrolo-pyrrole pigment (CI Pigment Red 254, CI Pigment Red 255, CI Pigment Red 264, CI Pigment Red 270, CI Pigment Red 272) comprises a various pigments that generally have a bright color, good opacity, excellent heat stability, excellent solvent resistance, or a combination thereof.

(xi) Metallic Pigments

In certain embodiments, a coating may comprise a metallic pigment. A "metallic pigment" is a pigment that confers a metallic appearance to a coating, and as previously described, is often a corrosion resistance pigment. A metallic pigment may be selected for a topcoat, particularly to confer a metallic appearance, a primer, particularly to confer a corrosion resistance property, an automotive coating, an industrial coating, or a combination thereof. Metallic flake pigments are preferred for embodiments wherein UV and/or infrared resistance is to be conferred to a coating. Additionally, as some enzymes comprise a metal atom in the active site, inclusion of a metallic pigment and/or other composition comprising a metal during coating preparation, or addition later (e.g., a multipack coating) may stimulate a desired enzyme activity. Examples of a metallic pigment include aluminum flake (CI Pigment Metal 1); aluminum non-leafing, gold bronze flake, zinc dust, stainless steel flake, nickel (e.g., flake, powder), or a combination thereof.

(4) Extender Pigments

An extender pigment ("inert pigment," "extender," "inert," "filler") is a substance that is insoluble in the other components of a coating, and further confers a desirable optical property (e.g., opacity, gloss), a rheological property, physical property, an antisettling property, or a combination thereof, to the coating and/or film. An extender pigment is often white or near white in color, and typically are used to provide a cheap partial substitute for a more expensive white pigment (e.g., titanium dioxide). Often an extender has a refractive index below 1.7. In some aspects, an extenders refractive index is 1.30 to 1.70, including all intermediate ranges and combinations thereof. Examples of an inorganic extender include a barium sulphate (CI Pigment White 21, CI Pigment White 22); 1); a calcium carbonate (CI Pigment White 18); a calcium sulphate; a silicate (CI Pigment White 19, CI Pigment White 26); a silica (CI Pigment White 27); or a combination thereof.

Calcium carbonate ("calcite," "whiting," "limestone," CI Pigment White 18) is generally chemically inert with the exception of reactions with an acid. Calcium carbonate may be used in a water-borne coating or a solvent-borne coating. Properties specifically associated with calcium carbonate include conferring settling resistance, sag resistance, or a combination thereof. Precipitated calcium carbonate obtained from processing of limestone, and may have superior opacity.

Kaolin ("china clay") is typically selected for a latex coating, an alkyd coating, an architectural coating, or a combination thereof. In addition to the typical properties of an extender (e.g., opacity), kaolin can confer scrub resistance to a coating.

Talc is a hydrated magnesium aluminum silicate, and is soluble in water. Talc may be selected for an architectural coating (e.g., interior, exterior), a primer, a traffic marker coating, an industrial coating, or a combination thereof. Talc comprising a platy particle shape can confer chemical resistance, water resistance, improved flow property, or a combination thereof.

Silica is silicon dioxide, and may be classified as crystalline silica, diatomaceous silica or synthetic silica. Crystalline silica is produced from crushed and ground quartz, and may be selected for an architectural coating, an industrial coating, a primer, a latex coating, a powder coating, or a combination thereof. Crystalline silica may confer burnish resistance to a coating and/or film. Diatomaceous silica ("diatomaceous earth," "diatomite") is the mineral fossil of diatoms which were single celled aquatic plants. Diatomaceous silica may be selected for an architectural coating, a latex coating, or a combination thereof. Diatomaceous silica may also function as a flattening agent. Synthetic silica is produced from chemical reactions, and includes, for example, precipitated silica, fumed silica, or a combination thereof. Precipitated silica may be selected for an industrial coating, a solvent-borne coating, or a combination thereof. Precipitated silica may also function as a flattening agent. Fumed silica may be selected for an industrial coating. Fumed silica may also function as a flattening agent, a rheology modifier, or a combination thereof.

Mica is a hydrous silica aluminum potassium silicate, and typically comprises plate shaped particles. Mica may be selected for an architectural coating, an exterior coating, a traffic marker coating, a primer, or a combination thereof. Mica may also confer durability, moisture resistance, corrosion resistance, heat resistance, chemical resistance, cracking resistance, sagging resistance, or a combination thereof, to a coating and/or film.

Barium sulfate may be classified as baryte or a blanc fixe. Baryte may be selected for an automotive coating, an industrial coating, a primer, an undercoat, or a combination thereof. Blanc fixe has good opacity for an extender, and may be selected for an automotive coating, an industrial coating, or a combination thereof.

Wollastonite is a calcium metasilicate, and may be selected for a latex coating. Wollasonite may also function as an alkali pH buffer. Surface modified wollasonite may be selected for an industrial coating.

Nepheline syenite is an anhydrous sodium potassium aluminum silicate, and may be selected for an architectural coating, a latex coating, an interior coating, an exterior coating, or a combination thereof. Nepheline syenite may function may confer cracking resistance, scrub resistance, or a combination thereof.

Sodium aluminosilicate may be selected for a latex coating, an architectural coating, or a combination thereof. Sodium aluminosilicate may also function as a flattening agent.

Alumina trihydrate may be selected for an architectural coating, a thermoplastic coating, a thermosetting coating, or a combination thereof. Alumina trihydrate may confer flame retardancy to a film.

b. Dyes

A dye is a composition that is soluble in the other components of a coating, and further confers a desirable color property to the coating. It is contemplated that many of the compounds that give a microorganism derived particulate material of the present invention color such as photosynthetic pigment and/or carotenoid pigment, will be partly or fully soluble in many non-aqueous liquids described herein. It is further contemplated that a microorganism derived particulate material of the present invention is added to a coating comprising such a liquid component, the material may act as a dye, as well as a pigment and/or extender, due to the dissolving of colored compounds into the liquid component.

4. Coating Additives

A coating additive is any material which is added to a coating to confer a desirable property other than that described for a binder, a liquid component, a colorizing agent, or a combination thereof. It is contemplated that, in addition to the examples of additives described herein, any additive known to one of ordinary skill in the art, in light of the present disclosures, may be included in a composition of the present invention.

Examples of coating additives include a microorganism based particulate material of the present invention, as well as an antifloating agent, an antiflooding agent, an antifoaming agent, an antisettling agent, an antiskinning agent, a catalyst, a corrosion inhibitor, a film-formation promoter, a leveling agent, a matting agent, a neutralizing agent, a preservative, a thickening agent, a wetting agent, or a combination thereof. The content for an individual coating additive in a coating generally is 0.001% to 20.0%, including all intermediate ranges and combinations thereof. However, in most embodiments, it is contemplated the concentration of a single additive in a coating will comprise between 0.001% and 10.0%, including all intermediate ranges and combinations thereof.

a. Preservatives

A coating may comprise a preservative to reduce or prevent the deterioration of a coating and/or film by a microorganism. As would be known to one of ordinary skill in the art, a microorganism is generally considered a contaminant capable damaging a film and/or coating the point of suitable usefulness in a given embodiment. A surprising and unexpected aspect of the present invention is the discovery of the suitability of a microorganism based particulate material of the present invention for use as a purposefully added coating component. However, it is preferred that a coating comprising a microorganism based particulate material of the present invention also comprises a preservative. It is contemplated that continued growth of a microorganism from the microorganism base particulate material of the present invention would be detrimental to a coating and/or film, and a preservative may reduce or prevent such growth. It is further contemplated that a contaminating microorganism could use the microorganism based particulate material of the present invention as a readily available source of nutrients for growth, and a preservative may reduce or prevent such growth. It is also contemplated that the amount of preservative added to a coating comprising a microorganism based particulate material of the present invention may be increased relative to a preservative content of a similar coating lacking such an added microorganism based particulate material. In certain aspects, it is contemplated that the amount of preservative may be increased 1.1 to 10-fold or more, including all intermediate ranges and combinations thereof, the amount of an example of a preservative content described herein or as would be known to one of ordinary skill in the art in light of the present disclosures.

Examples of preservatives include a biocide, which kills an organism, a biostatic, which reduces or prevents the growth of an organism, or a combination thereof. Examples of a biocide include, for example, a bactericide, a fungicide, an algaecide, or a combination thereof. Examples of bacteria commonly found to contaminate a coating and/or film include *Pseudomonas* spp., *Aerobacter* spp., *Enterobacter* spp., *Flavobacterium* spp. (e.g., *Flavobacterium marinum*),

*Bacillus* spp., or a combination thereof. Examples of fungi commonly found to contaminate a coating and/or film include *Aureobasidium pullulans, Alternaria dianthicola, Phoma pigmentivora,* or a combination thereof. Examples of algae commonly found to contaminate a coating and/or film include *Oscillotoria* sp., *Scytonema* sp., *Protoccoccus* sp., or a combination thereof. Techniques are known to those of ordinary skill in the art for determining microbial contamination of a coating and/or coating component (see, for example, "ASTM Book of Standards, Volume 06.01, Paint—Tests for Chemical, Physical, and Optical Properties; Appearance," D5588-97, 2002).

In addition to the disclosures herein, a preservative and use of a preservative in a coating is known to those of skill in the art, and all such materials and techniques for using a preservative in a coating may be applied in the practice of the present invention (see, for example, Flick, E. W. "Handbook of Paint Raw Materials, Second Edition," 263-285 and 879-998, 1989; in "Paint and Coating Testing Manual, Fourteenth Edition of the Gardner-Sward Handbook," (Koleske, J. V. Ed.), pp 261-267 and 654-661, 1995; in "Paint and Surface Coatings, Theory and Practice, Second Edition," (Lambourne, R. and Strivens, T. A., Eds.), pp. 193-194, 371-382 and 543-547, 1999; Wicks, Jr., Z. W., Jones, F. N., Pappas, S. P. "Organic Coatings, Science and Technology, Volume 1: Film Formation, Components, and Appearance," pp. 318-320, 1992; Wicks, Jr., Z. W., Jones, F. N., Pappas, S. P. "Organic Coatings, Science and Technology, Volume 2: Applications, Properties and Performance," pp. 145, 309, 319-323 and 340-341, 1992; and in "Paints, Coatings and Solvents, Second, Completely Revised Edition," (Stoye, D. and Freitag, W., Eds.) pp 6, 127 and 165, 1998.

A coating, film, surface, or a combination thereof may be detrimentally affected by the presence of a living microorganism. For example, a living microorganism can alter viscosity due to damage to a cellulosic viscosifier; alter a rheological property by increasing the gelling of a coating; produce an undesirable color alteration ("discoloration") by production of a colorizing agent; produce undesirable gas and increase foam; produce an undesirable odor; lower pH; damage a preservative; produce slime; reduce adhesion by a film; increase corrosion of a metal surface by moisture production by an organism; increase corrosion of a metal surface by film damage; damage a wooden surface by colonization (e.g., fungal colonization); or a combination thereof. These changes can lead to the coating and/or film becoming unsuitable for use. The undesirable growth of a microorganism is generally more prevalent in a water-borne coating, as the solvent component of a solvent borne-coating usually acts as a preservative. However, a film is generally susceptible to such damage by growth of a microorganism after loss of a solvent (e.g., evaporation) during film formation. Additionally, various bacteria (e.g., *Bacillus* spp.) and fungi produce spores, which are cells that are relatively durable to unfavorable conditions (e.g., cold, heat, dehydration, a biocide), and may persist in a coating and/or film for months or years prior to germinating into a damaging colony of cells.

In certain embodiments, a preservative may comprise an in-can preservative, an in-film preservative, or a combination thereof. An in-can preservative is a composition that reduces or prevents the growth of a microorganism prior to film formation. Addition of an in-can preservative during a water-borne coating production typically occurs with the introduction of water to a coating composition. Typically, an in-can preservative is added to a coating composition for function during coating preparation, storage, or a combination thereof. An in-film preservative is a composition that reduces or prevents the growth of a microorganism after film formation. In many embodiments, an in-film preservative is the same chemical as an in-can preservative, but added to a coating composition at a higher (e.g., two-fold) concentration for continuing activity after film formation.

Examples of preservatives that have been used in coatings include a metal compound (e.g., an organo-metal compound) biocide, an organic biocide, or a combination thereof. Examples of a metal compound biocide include barium metaborate, which is a fungicide and bactericide; copper(II) 8-quinolinolate, which is a fungicide; phenylmercuric acetate, tributyltin oxide, which is less preferred for use against Gram-negative bacteria; tributyltin benzoate, which is a fungicide and bactericide; tributyltin salicylate, which is a fungicide; zinc 2-pyridinethiol-N-oxide, which is a fungicide; zinc oxide, which is a fungistatic/fungicide and algaecide; a combination of zinc-dimethyldithiocarbamate and zinc 2-mercaptobenzothiazole, which acts as a fungicide; zinc 2-pyridinethiol-N-oxide, which is a fungicide; a metal soap; or a combination thereof. Examples of metals comprised in a metal soap biocide include copper, mercury, tin, zinc, or a combination thereof. Examples of an organic acid comprised in a metal soap biocide include a butyl oxide, a laurate, a naphthenate, an octoate, a phenyl acetate, a phenyl oleate, or a combination thereof.

An example of an organic biocide that acts as an algaecide includes 2-methylthio-4-tert-butylamino-6-cyclopropylamino-s-triazine. Examples of an organic biocide that acts as a bactericide include a combination of 4,4-dimethyloxazolidine and 3,4,4-trimethyloxazolidine; 5-hydroxymethyl-1-aza-3,7-dioxabicylco(3.3.0.)octane; 2(hydroxymethyl)-aminoethanol; 2-(hydroxymethyl)-amino-2-methyl-1-propanol; hexyhydro-1,3,5-tri-ethyl-5-triazine; 1-(3-chloroallyl)-3,5,7-triaza-1-azonia-adamantane chloride; 1-methyl-3,5,7-triaza-1-azonia-adamantane chloride; p-chloro-m-cresol; an alkylamine hydrochloride; 6-acetoxy-2,4-dimethyl-1,3-dioxane; 5-chloro-2-methyl-4-isothiazolin-3-one; 2-methyl-4-isothiazolin-3-one; 1,3-bis(hydroxymethyl)-5,5-dimethylhydantoin; hydroxymethyl-5,5-dimethylhydantoin; or a combination thereof. Examples of an organic biocide that acts as a fungicide include a parabens; 2-(4-thiazolyl)benzimidazole; N-trichloromethyl-thio-4-cyclohexene-1,2-dicarboximide; 2-n-octyl-4-isothiazoline-3-one; 2,4,5,6-tetrachloro-isophthalonitrile; 3-iodo-2-propynyl butyl carbamate; N-(trichloromethyl-thio) phthalimide; tetrachloroisophthalonitrile; potassium N-hydroxy-methyl-N-methyl-dithiocarbamate; sodium 2-pyridinethiol-1-oxide; or a combination thereof. Examples of a parbens include butyl parahydroxybenzoate; ethyl parahydroxybenzoate; methyl parahydroxybenzoate; propyl parahydroxybenzoate; or a combination thereof. Examples of an organic biocide that acts as an bactericide and fungicide include 2-mercaptobenzo-thiazole; a combination of 5-chloro-2-methyl-3(2H)-isothiazoline and 2-methyl-3(2H)-isothiazolone; a combination of 4-(2-nitrobutyl)-morpholine and 4,4'-(2-ethylnitrotrimethylene dimorpholine; tetrahydro-3,5-di-methyl-2H-1,3,5-thiadiazine-2-thione; potassium dimethyldithiocarbamate; or a combination thereof. An example of an organic biocide that acts as an algaecide and fungicide includes diiodomethyl-p-tolysulfone. Examples of an organic biocide that acts as an algaecide, bactericide and fungicide include glutaraldehyde; methylenebis(thiocyanate); 1,2-dibromo-2,4-dicyanobutane; 1,2-benzisothiazoline-3-one; 2-(thiocyanomethyl-thio)benzothiazole; or a combination thereof. An example of an organic biocide that acts as an algaecide, bactericide, fungicide and molluskicide includes 2-(thiocyanomethyl-thio)benzothiozole and methylene bis(thiocyanate).

In certain embodiments an environmental law or regulation may encourage the selection of an organic biocide such as a benzisothiazolinone derivative. An example of a benzisothiazolinone derivative is Busan™ 1264 (Buckman Laboratories, Inc.), Proxel™ GXL (Avecia Inc.), or Preventol® VP OC 3068 (Bayer Corporation), which comprises 1,2-benzisothiazolinone (CAS No. 2634-33-5). In the case of Busan™ 1264, the primary use is a bactericide and/or fungicide at 0.03% to 0.5% in a water-borne coating.

Often, a preservative is a proprietary commercial formulation and/or a compound sold under a tradename. Examples include organic biocides under the tradename Nuosept® (International Specialty Products), which are typically used in a water-borne coating. Specific examples of a Nuosept® biocide includes Nuosept® 95, which comprises a mixture of bicyclic oxazolidines, and is typically added to 0.2% to 0.3% concentration to a coating composition; Nuosept® 145, which comprises an amine reaction product, and is typically added to 0.2% to 0.3% concentration to a coating composition; Nuosept® 166, which comprises 4,4-dimethyloxazolidine, and is typically added to 0.2% to 0.3% concentration to a basic pH water-borne coating composition; or a combination thereof. A further example is Nuocide® (International Specialty Products) biocides, which are typically used fungicides and/or algaecides. Examples of a Nuocide® biocide is Nuocide® 960, which comprises 96% tetrachlorisophthalonitrile (CAS No. 1897-45-6), and is typically used at 0.5% to 1.2% in a water-borne or solvent-borne coating as a fungicide; Nuocide® 2010, which comprises chlorothalonil and IPBC at 30%, and is typically used at 0.5% to 2.5% in a coating as a fungicide and algaecide; Nuocide® 1051 and Nuocide® 1071, each which comprises 96% N-cyclopropyl-N-(1-dimethylethyl)-6-(methylthio)-1,3,5-triazine-2,4-diamine, and is typically used as an algaecide in antifouling coatings at 1.0% to 6.0% or water-based coatings at 0.05% to 0.2%, respectively; and Nuocide® 2002, which comprises chlorothalonil and a triazine compound at 30%, and is typically used at 0.5% to 2.5% in a coating and/or a film as a fungicide and algaecide.

An additional example of a tradename biocide for coatings includes Vancide® (R. T. Vanderbilt Company, Inc.). Examples of a Vancide® biocide include Vancide® TH, which comprises hexahydro-1,3,5-triethyl-s-triazine, and is generally used in a water-borne coating; Vancide® 89, which comprises N-trichloromethylthio-4-cyclohexene-1,2-dicarboximide and related compounds such as captan, and is used as a fungicide in a coating composition; or a combination thereof. A bactericide and/or fungicide for coatings, particularly a water-borne coating, is a Dowicil™ (Dow Chemical Company). Examples of a Dowicil™ biocide include Dowicil™ QK-20, which comprises 2,2-dibromo-3-nitrilopropionamide (CAS No. 10222-01-2), and is used as a bactericide at 100 ppm to 2000 ppm in a coating; Dowicil™ 75, which comprises 1-(3-chloroallyl)-3,5,7-triaza-1-azoniaadamantane chloride (CAS No. 51229-78-8), and is used as a bactericide at 500 ppm to 1500 ppm in a coating; Dowicil™ 96, which comprises 7-ethyl bicyclooxazolidine (CAS No. 7747-35-5), and is used as a bactericide at 1000 ppm to 2500 ppm in a coating; Bioban™ CS-1135, which comprises 4,4-dimethyloxazolidine (CAS No. 51200-87-4), and is used as a bactericide at 100 ppm to 500 ppm in a coating; or a combination thereof. An additional example of a tradename biocide for coatings includes Kathon® (Rohm and Haas Company). An example of a Kathon® biocide includes Kathon® LX, which typically comprises 5-chloro-2-methyl-4-isothiazolin-3-one (CAS no 26172-55-4) and 2-methyl-4-isothiazolin-3-one (CAS no 2682-20-4) at 1.5%, and is added from 0.05% to 0.15% in a coating. Examples of tradename fungicides and algaecides include those described for Fungitrol® (International Specialty Products), which are often formulated for solvent-borne and water-borne coatings, and in-can and film preservation. An example is Fungitrol® 158, which comprises 15% tributyltin benzoate (15%) and 21.2% alkylamine hydrochlorides, and is typically used at 0.35% to 0.75% in a water-borne coating for in-can and film preservation. An additional example is Fungitrol® 11, which comprises N-(trichloromethylthio) phthalimide, and is typically used at 0.5% to 1.0% as a fungicide for solvent-borne coating. A further example is Fungitrol® 400, which comprises 98% 3-iodo-2-propynl N-butyl carbamate ("IPBC") (Cas No. 55406-53-6), and is typically used at 0.15% to 0.45% as a fungicide for a water-borne or a solvent-borne coating.

As would be known to one of ordinary skill in the art, determination of whether damage to a coating and/or film is due to microorganisms (e.g., film algal defacement, film fungal defacement), as well as the efficacy of addition of a preservative to a coating and/or film composition in reducing microbial damage to a coating and/or film, may be empirically determined by techniques such as those that are described in "ASTM Book of Standards, Volume 06.01, Paint—Tests for Chemical, Physical, and Optical Properties; Appearance," D3274-95, D4610-98, D2574-00, D3273-00, D3456-86, D5589-97, and D5590-00, 2002; and in "Paint and Coating Testing Manual, Fourteenth Edition of the Gardner-Sward Handbook," (Koleske, J. V. Ed.), pp. 654-661, 1995. Examples of microorganisms typically selected in such procedures as positive controls of a coating and/or film damaging microorganism include, for example, *Aspergillus oryzae* (ATCC 10196), *Aspergillus flavus* (ATCC 9643), *Aspergillus niger* (ATCC 9642), *Pseudomonas aeruginosa* (ATCC 10145), *Aureobasidium pullulans* (ATCC 9348), *Penicillium citrinum* (ATCC 9849), *Penicillium funiculosum* (ATCC 9644), or a combination thereof.

b. Wetting Additives and Dispersants

It is contemplated that one or more types of particulate matter may be incorporated into a coating composition of the present invention. As is known to those of ordinary skill in the art, physical force and/or chemical additives are used to promote a desirable level of dispersion of particulate matter in a coating composition, for purposes such as coating homogeneity and ease of application. Depending upon whether such an additive is admixed earlier or latter in a coating composition, such an additive is known as a wetting agent or a dispersant, respectively, though it is common that an additive has dual classification. A wetting agent and/or a dispersant often can be used to reduce the particulate matter grinding time during coating preparation, improve wetting of particulate matter, improve dispersion of particulate matter, improve gloss, improve leveling, reduce flooding, reduce floating, reduce viscosity, reduce thixotropy, or a combination thereof.

(1) Wetting Additives

As is known to those of ordinary skill in the art, preparation of a coating comprising particulate material often comprises a step wherein the particulate material is dispersed in an additional coating component. An example of this type of dispersion step is the dispersion of a pigment into a combination of a liquid component and a binder to form a material known as a millbase. A wetting additive ("wetting agent") is a composition added to promote dispersion of particulate material during coating preparation.

In certain embodiments, a wetting agent is a molecule that comprises a polar region and a nonpolar region. An example is an ethylene oxide molecule comprising a hydrophobic moiety. Such a wetting agent is thought to act by reducing interfacial tension between a liquid component and particulate matter. In specific aspects, a wetting agent comprises a surfactant. Examples of such a wetting agent include pine oil, which is typically added at 1% to 5% of the total coating liquid component, including all intermediate ranges and combinations thereof. Other examples of wetting agents include a metal soap, such as, for example, calcium octoate, zinc octoate, aluminum stearate, zinc stearate, or a combination thereof. An additional example of a wetting agent is bis(2-ethylhexyl)sulfosuccinate ("Aerosol OT") (Cas No. 577-11-7); (octylphenoxy)polyethoxyethanol octylphenyl-polyethylene glycol ("Igepal-630") (Cas no. 9036-19-5); nonyl phenoxy poly(ethylene oxy) ethanol ("Tergitol NP-14") (Cas No. 9016-45-9); ethylene glycol octyl phenyl ether ("Triton X-100") (CAS No. 9002-93-1); or a combination thereof.

Often a wetting agent and/or dispersant is a proprietary formulation and/or commonly available under a trade name. Examples include an Anti-Terra® or Disperbyk® (BYK-Chemie GmbH) and EnviroGem® or Surfynol® (Air Products and Chemicals, Inc.) wetting agents and/or dispersants. An example is Anti-Terra®-U, which comprises a 50% solution of an unsaturated polyamine amide salt and a lower molecular weight acid, dissolved in xylene and isobutanol, and preferred for used in a solvent-borne coating. Anti-Terra®-U is typically added from 1% to 2% to an inorganic pigment, 1% to 5% to an organic pigment, and at 0.5% to 1.0% to titanium dioxide, and 30% to 50% to a bentonite. An example of a Disperbyk® is Disperbyk®, which comprises a polycarboxylic acid polymer alkylolammonium salt and water, and is added to 0.3% to 1.5% to the solvent-borne or water-borne coating composition. A further example is Disperbyk®-101, which comprises a 52% solution of a long chain polyamine amide salt and a polar acidic ester, dissolved in a mineral spirit and butylglycol, and preferred for used in a solvent-borne coating. The ranges for addition to particulate material for Disperbyk®-101 is similar to Anti-Terra®-U. An additional example is Disperbyk®-108, which comprises over 97% of a hydroxyfunctional carboxylic acid ester that includes moieties with pigment affinity, and is typically added from 3% to 5% to an inorganic pigment, 5% to 8% to an organic pigment. However, Disperbyk®-108 is typically added at 0.8% to 1.5% to titanium dioxide, or 8% to 10% to a carbon black, and is preferred for coatings lacking a non-aqueous solvent. A supplemental example is EnviroGem® AD01, which comprises a non-ionic wetting agent with a defoaming property, and is added to 0.1% to 2% to a water-borne coating composition. An additional example is Surfynol® TG (Air Products and Chemicals, Inc.), which comprises a non-ionic wetting agent, and is added to 0.5% to 5% to a water-borne coating composition. A further example is Surfynol® 104 (Air Products and Chemicals, Inc.), which comprises a non-ionic wetting agent, dispersant, and defoamer, and is added to 0.05% to 3% to a water-borne coating composition.

(2) Dispersants

As is known to those of ordinary skill in the art, maintenance of the dispersal of particulate matter comprised within a coating composition is often promoted by the addition of a dispersant. A dispersant ("dispersing additive," "deflocculant," "antisettling agent") is a composition that is added to promote continuing dispersal of particulate matter. In specific aspects, a dispersant is added to a coating composition to reduce or prevent flocculation. Flocculation is the process wherein a plurality of primary particles that have been previously dispersed form an agglomerate. In other aspects, a dispersant is added to a coating composition to prevent sedimentation of particulate matter. Standard procedures to determining the degree of settling by particulate matter in a coating (e.g., paint) are described, for example, in "ASTM Book of Standards, Volume 06.02, Paint—Products and Applications; Protective Coatings; Pipeline Coatings," D869-85, 2002.

Often a dispersant is a compound comprising phosphate, such as, for example, tetra-potassium pyrophosphate or "TKPP" (CAS No. 7320-34-5). Examples of a tradename/proprietary phosphate compounds are those known as a Strodex™ (Dexter Chemical L.L.C.), including Strodex™ PK-90, Strodex™ PK-0VOC, and/or Strodex™ MOK-70, which comprise a phosphate ester surfactant.

In some aspects, a dispersant may be a particulate material. Examples include Winnofil® SPT Premium, Winnofil® S, Winnofil® SPM, and Winnofil® SPT (Solvay Advanced Functional Minerals), which comprise 97.4% calcium carbonate (CAS No. 471-34-1) coated with 2.6% fatty acid (CAS No. 64755-01-7) and generally used at 2% to 3%.

Various preparations of modified montmorillonite clay are known in the art as a dispersant. Examples include those under the name Bentone® (Elementis Specialties, Inc). Bentone® 34 (Elementis Specialties, Inc), which comprises tetraallkyl ammonium bentonite, and is prepared with 33% or more polar solvent prior to addition to a coating composition. M-P-A® 14 (Elementis Specialties, Inc.), which comprises a montmorillonite clay modified by and organic chemical, and is prepared with 33% or more polar solvent prior to addition to a solvent-borne coating composition. Bentone® SD-1 (Elementis Specialties, Inc.), which comprises a montmorillonite clay modified by and organic chemical, and typically added from 0.2% to 2% by weight to a solvent-borne coating composition, particularly those comprising an aliphatic liquid component.

A further example of a dispersant is a castor wax formulation under the trade names Crayvallac® SF, Crayvallac® MT, and Crayvallac® AntiSettle CVP (Cray Valley Limited), each of which are typically added from 0.2% to 1.5% as a dispersant, thixotropy additive, anti-sagging agent, or a combination thereof. Crayvallac® AntiSettle CVP comprises caster wax ("hydrogenated caster oil"), and is suitable for a solvent free epoxy-coating and a mineral spirit liquid component. Crayvallac® SF and Crayvallac® MT each comprise amide modified caster wax, and may be used in an epoxy-coating, an acrylic-coating, a chlorinated rubber-coating, or a combination thereof. Crayvallac® SF and Crayvallac® MT are preferred for use with a liquid component comprising an aromatic hydrocarbon, an alcohol, a glycol ether, or a combination thereof with Crayvallac® MT being also preferred for use with a mineral spirit.

c. Buffers

In certain embodiments, it is preferred to maintain a coating's pH within a certain range. A coating may be acidic, which is a pH between 0 and 7, including all intermediate ranges and combinations thereof, or basic, which is a pH between 7 and 14, including all intermediate ranges and combinations thereof. A neutral pH is pH 7.0, and it is contemplated that a coating may have a neutral pH, or a pH that is near neutral, which is a pH between 6.5 and 7.5, including all intermediate ranges and combinations thereof. A buffer may be added to maintain a coating's pH as acidic, basic, neutral, or near neutral. In certain aspects, a basic pH is preferred to optimize the function of a preferred enzyme, such as, for example, OPH. Examples of buffers include a bicarbonate (e.g., an ammonium bicarbonate), a monobasic phosphate buffer, a dibasic phosphate buffer, Trizma base, a zwitterionic buffer, triethanolamine, or a combination thereof. In particular facets, a buffer such as a bicarbonate, may provide a ligand or co-substrate (e.g., water) on activator (e.g., carbon dioxide) to an enzyme to promote an enzymatic reaction.

d. Rheology Modifiers

A rheology modifier ("rheology control agent," "rheology additive," "thickener and rheology modifier," "TRM," "rheological and viscosity control agent," "viscosifier," "viscosity control agent," "thickener") is a composition that alters (e.g., increases, decreases, maintains) a rheological property of a coating. A thickener ("thickening agent") increases and/or maintains viscosity. A rheological property is a property of flow and/or deformation. Examples of a rheological property include viscosity, brushability, leveling, sagging, or a combination thereof. Viscosity is a measure of a fluid's resistance to flow (e.g., a shear force). Brushability is the ease a coating can be applied using an applicator (e.g., a brush). Leveling is the ability of a coating to flow into and fill uneven areas of coating thickness (e.g., brush marks) after application to a surface and before sufficient film formation to end such flow. Sagging is the gravitationally induced downward flow of a coating after application to a surface and before sufficient film formation to end such flow. It is specifically contemplated that a microorganism based particulate material of the present invention may be added to a coating as a rheology modifier.

A rheology modifier that alters viscosity (e.g., increases, decreases, maintains) is known as a "viscosifier." During application, a coating is usually subjected to a shear force $10^3$ $s^{-1}$ to $10^4$ $s^{-1}$ by techniques such as brush application, and a shear force up to or greater than $10^6$ $s^{-1}$ by techniques including, for example, blade application, high-speed roller application, spray application, or a combination thereof. As would be known to one of ordinary skill in the art, a coating typically is formulated to possess a viscosity upon the shear force of application that promotes the ease of application. An example of a coating viscosity during application is between 0.5 P ("50 mPa s") to 2.5 P ("250 mPa s"), including all intermediate ranges and combinations thereof. In certain aspects, a coating may possess a viscosity greater or lower than this range, however, it is contemplated such a viscosity may make the coating more difficult to apply using the above application techniques. Post-preparation and/or post-application, a coating is usually subjected to a shear force of 10 $s^{-1}$ to $10^{-3}$ $s^{-1}$ produced, for example, by forces such as gravity, capillary pressure, or a combination thereof. In embodiments wherein a coating's viscosity is too high at these levels of shear force, leveling during and/or after application may be undesirably low. In embodiments wherein a viscosity is to low at these levels of shear force, a coating may suffer in-can settling, sagging during or after application, or a combination thereof. A preferred viscosity of a coating post-preparation and/or application is between 100 P ("10 Pa s") to 1000 P ("100 Pa s"), the including all intermediate ranges and combinations thereof. Of course, the viscosity of a coating will change post-application in embodiments wherein film formation occurs; however, the post-application viscosity refers to the viscosity prior to completion of film formation, and may be determined immediately post-application (e.g., within seconds, within minutes) as appropriate to the coating, as would be known to one of ordinary skill in the art. In certain aspects, a coating may possess a viscosity greater or lower than this range, however, it is contemplated such a viscosity may make the coating more prone to sagging and/or settling defects.

A rheology modifier is typically added to alter and/or maintain a rheology property within a desired range post-formulation, during application, post-application, or a combination thereof. In specific embodiments, a rheology modifier alters viscosity at or above $10^3$ $s^{-1}$ and/or at or below 10 $s^{-1}$. Viscosity, including non-Newtonian (e.g., shear-thinning) viscosity for coatings and/or coating components (e.g., binders, binder solutions, vehicles) upon formulation with or without a viscosity modifier can be empirically determined, particularly for shear rates comparable to application techniques (e.g., blade, brush, roller, spray) by standard techniques such as in "ASTM Book of Standards, Volume 06.01, Paint—Tests for Chemical, Physical, and Optical Properties; Appearance," D562-01, D2196-99, D4287-00, D4212-99, D1200-94, D5125-97, and D5478-98, 2002; "ASTM Book of Standards, Volume 06.02, Paint—Products and Applications; Protective Coatings; Pipeline Coatings," D4958-97, 2002; and "ASTM Book of Standards, Volume 06.03, Paint—Pigments, Drying Oils, Polymers, Resins, Naval Stores, Cellulosic Esters, and Ink Vehicles," D1545-98, D1725-62, D6606-00 and D6267-98, 2002. Additionally, other rheological properties can be determined to aid formulation of a coating of the present invention using techniques known to those of ordinary skill in the art. For example, brush drag, which is the resistance during coating (e.g., a latex) application using a brush, can be determined by standard techniques, such as, for example, in "ASTM Book of Standards, Volume 06.02, Paint—Products and Applications; Protective Coatings; Pipeline Coatings," D4040-99, 2002. In an additional example, leveling and sagging can be empirically determined for a coating by standard techniques such as in "ASTM Book of Standards, Volume 06.02, Paint—Products and Applications; Protective Coatings; Pipeline Coatings," D4062-99 and D4400-99, 2002.

As would be known to one of ordinary skill in the art, the addition of a coating component to a coating composition typically alters a rheological property, and many coating components have multiple classifications to include function as a rheology modifier. Examples of coating components more commonly added for function as a rheology modifier includes an inorganic rheology modifier, an organometallic rheology modifier, an organic rheology modifier, or a combination thereof. An example of an inorganic rheology modifier includes a silicate such as a montmorillonite silicate. An example of a montomorillonite silicate includes aluminum silicate, a bentonite, magnesium silicate, or a combination thereof. A silicate rheology modifier typically confers a superior washfastness property, a superior abrasion resistance property, or a combination thereof, to a coating relative to an organic rheology modifier. An example of an organic rheology modifier includes a cellulose ether, a hydrogenated oil, a polyacrylate, a polyvinylpyrrolidone, a urethane, or a combination thereof. Organic rheology modifiers of a polymeric nature (e.g., a cellulose ether, a urethane, a polyacrylate, etc.) are sometimes used as an associative thickener, and are preferred for a latex coating. An organic rheology modifier typically confers a greater water retention capacity property ("open time") to a coating relative to a silicate rheology modifier. A common example of a cellulose ether is a methyl cellulose, a hydroxyethyl cellulose, or a combination thereof. An example of a hydroxyethyl cellulose includes Natrosol® (Hercules Incorporated); Cellosize™ (Dow Chemical Company); or a combination thereof. An example of hydrogenated oil includes hydrogenated castor oil. An example of a urethane rheology modifier ("associative thickener") includes a hydrophobically modified ethylene oxide urethane ("HEUR"), which comprises a polyethylene glycol block covalently linked by urethane, and has both a hydrophilic and hydrophobic regions capable of use in an aqueous environment. An example of a HEUR includes a block of polyethylene oxide linked by an urethane and modified with a nonyl phenol hydrophobe (Rohm and Haas Company). Often a urethane rheology modifier confers a superior leveling property over another type of organic rheology modifier. An example of an organometallic rheology modifier includes a titanium chelate, a zirconium chelate, or a combination thereof.

In addition to the disclosures herein, a rheology modifier and use of a rheology modifier in a coating is known to those of skill in the art, and such compositions and techniques may be included in the practice of the present invention (see, for example, Flick, E. W. "Handbook of Paint Raw Materials, Second Edition," 808-843 and 879-998, 1989; in "Paint and Coating Testing Manual, Fourteenth Edition of the Gardner-Sward Handbook," (Koleske, J. V. Ed.), pp 268-285 and 348-349, 1995; in "Paint and Surface Coatings, Theory and Practice, Second Edition," (Lambourne, R. and Strivens, T. A., Eds.), pp. 73, 218, 227, 352, 558-559 and 718, 1999; Wicks, Jr., Z. W., Jones, F. N., Pappas, S. P. "Organic Coatings, Science and Technology, Volume 2: Applications, Properties and Performance," pp. 42, 215, 293, 315, 320 and 323-328, 1992; and in "Paints, Coatings and Solvents, Second, Completely Revised Edition," (Stoye, D. and Freitag, W., Eds.) pp 6, 128 and 166-167, 1998.

e. Defoamers

A coating sometimes comprises a gas capable of forming a bubble ("foam") that can undesirably alter a physical and/or aesthetic property. Undesirable gas incorporation into a coating composition is often a side affect of coating preparation processes, and a particular bane of latex coatings. Often, a wetting agent and/or a dispersant used in a coating may promote creation or retention of foam. Additionally, microorganisms can produce gas, and in certain embodiments, a coating comprising a microorganism based particulate material of the present invention may also comprise a defoamer. A defoamer ("antifoaming agent," "antifoaming additive") is a composition that releases gas (e.g., air) and/or reduces foaming in a coating during production, application, film formation, or a combination thereof. A defoamer often acts by lowering the surface tension around a bubble, allowing merging of a bubble with a second bubble, which produces a larger and less stable bubble that collapses.

Examples of a defoamer include an oil (e.g., a mineral oil, a silicon oil), a fatty acid ester, dibutyl phosphate, a metallic soap, a siloxane, a wax, an alcohol comprising between six to ten carbons, or a combination thereof. An example of an oil defoamer is pine oil. In some aspects, an antifoaming agent is combined with an emulsifier, a hydrophobic silica, or a combination thereof. Examples of a tradename defoamer is a TEGO® Foamex 8050 (Goldschmidt Chemical Corp.), which comprises a polyether siloxane copolymer and fumed silica, and typically is used at 0.1% to 0.5% during coating preparation; and BYK®-31 (BYK-Chemie), which comprises a paraffin mineral oil and hydrophobic compounds, and typically is used at 0.1% to 0.5% in a coating.

f. Catalysts

A catalyst is an additive that promotes film formation by catalyzing a cross-linking reaction in a thermosetting coating. Examples of a catalyst include a drier, an acid or a base, and the selection of the type of catalyst is specific to the chemistry of the film formation reaction.

(1) Driers

A drier ("siccative") catalyzes is an oxidative film formation reaction, such as those that occur in an oil-based coating. In addition to the disclosures herein, an drier and use of an drier in a coating is known to those of skill in the art, and such materials and techniques for using an drier in a coating may be applied in the practice of the present invention (see, for example, Flick, E. W. "Handbook of Paint Raw Materials, Second Edition," pp. 73-93 and 879-998, 1989; in "Paint and Coating Testing Manual, Fourteenth Edition of the Gardner-Sward Handbook," (Koleske, J. V. Ed.), pp 30-35, 1995; in "Paint and Surface Coatings, Theory and Practice, Second Edition," (Lambourne, R. and Strivens, T. A., Eds.), pp. 190-192, 1999; Wicks, Jr., Z. W., Jones, F. N., Pappas, S. P. "Organic Coatings, Science and Technology, Volume 1: Film Formation, Components, and Appearance," pp. 138, 317-318, 1992; Wicks, Jr., Z. W., Jones, F. N., Pappas, S. P. "Organic Coatings, Science and Technology, Volume 2: Applications, Properties and Performance" pp. 138, 197-198, 330, 344, 1992; and in "Paints, Coatings and Solvents, Second, Completely Revised Edition," (Stoye, D. and Freitag, W., Eds.) pp. 11, 48, 165, 1998.

A drier may comprise a metal drier, an alternative drier, a feeder drier, or a combination thereof. Usually a drier comprising a metal ("a metal drier") catalyzes the oxidative reaction. Examples of a metal typically used in a drier includes aluminum, barium, bismuth, calcium, cerium, cobalt, iron, lanthanum, lead, manganese, neodymium, potassium, vanadium, zinc, zirconium, or a combination thereof. Examples of types of metal driers include an inorganic metal salt, a metal-organic acid salt ("soap"), or a combination thereof. A "salt" is the composition formed between the anion of an acid and the cation of a base. Typically, the acid and base of a salt interact by an ionic bond. Examples of organic acids used in such a soap include a monocarboxylic acid of 7 to 22 carbon atoms. Examples of such a monocarboxylic acid include a linoleate, a naphthenate, a neodecanoate, an octoate, a rosin, a synthetic acid, a tallate, or a combination thereof. Examples of a drier comprising a synthetic acid include those under the tradenames Troymax™ (Troy Corporation). Though most driers are water insoluble, water dispersible driers can be prepared by combining a surfactant with a naphthenate drier and/or a synthetic acid drier. However, water dispersible driers are typically obtained under a tradename such as, for example, Troykyd® Calcium WD, Troykyd® Cobalt WD, Troykyd® Manganese WD Troykyd® Zirconium WD (Troy Corporation). Additionally, a potassium soap, lithium soap, or a combination thereof, has limited aqueous solubility.

A primary drier ("surface drier," "active drier," "top drier") acts at the coating-external environment interface. A secondary drier ("auxiliary drier," "through drier") acts throughout the coating. Examples of primary driers include metal driers comprising cobalt, manganese, vanadium, or a combination thereof. Examples of secondary driers include metal driers comprising aluminum, barium, calcium, cerium, iron, lanthanum, lead, manganese, neodymium, zinc, zirconium, or a combination thereof. A rare earth drier comprises lanthanum, neodymium, cerium, or a combination thereof.

In many embodiments, it is contemplated that a coating will comprise from 0.01% to 0.1%, including all intermediate ranges and combinations thereof, of an individual metal of a primary drier, by weight of the non-volatile components of a coating composition. In many embodiments, it is contemplated that a coating will comprise from 0.1% to 1.0%, including all intermediate ranges and combinations thereof, of an individual metal of a secondary drier, by weight of the non-volatile components of a coating composition. Standard physical and/or chemical properties for various driers comprising a metal (e.g., calcium, cerium, cobalt, iron, lead, manganese, nickel, rare earth, zinc, zirconium), and procedures for determining various metals' content for a driers are described in, for example, "ASTM Book of Standards, Volume 06.04, Paint—Solvents; Aromatic Hydrocarbons," D600-90, 2002; and "Volume 06.01, Paint—Tests for Chemical, Physical, and Optical Properties; Appearance," D2373-85, D2374-85, D2375-85, D2613-01, D3804-02, D3969-01, D3970-80, D3988-85, and D3989-01, 2002; and ASTM Book of Standards, Volume 06.01, Paint—Tests for Chemical, Physical, and Optical Properties; Appearance," D564-87, 2002.

It is particularly preferred that in embodiments wherein a secondary drier is used, it is combined with a primary drier, as the activity of most secondary driers are often very limited when acting without the presence of a primary drier. Skinning is film-formation disproportionately at the coating-external environment interface. Skinning often results in undesirable wrinkle formation ("wrinkling") in the film. A primary drier undesirably promotes skinning when acting without the presence of a secondary drier. In certain aspects, zinc may be selected for reducing wrinkling in thick films. In other aspects, calcium and/or zirconium may be selected instead of lead, which may be limited due to an environmental law or regulation. In some facets, an iron drier, rare earth drier, or combination thereof, may be selected for use during film formation by baking. However, an iron drier may darken a coating. In further aspects, an aluminum drier may be selected for an alkyd-coating.

An alternative drier is a type of drier developed for use in a high solid and/or water-borne coating, due to the inefficiency of a metal-soap drier in these types of coatings. Often, an alternative drier is combined with a metal-soap drier. An example of a metal soap drier include a 1,10-phenanthronine, 2,2'-dipyridyl. A feeder drier is a type of drier designed to prolong the pot life of a coating in embodiments wherein a metal soap drier is absorbed by a coating component such as a carbon black pigment, an organic red pigment, or a combination thereof. A feeder drier dissolves over time into the coating, thereby providing a continual supply of drier. An example a feeder drier include a tradename composition such as Troykyd® Perma Dry (Troy Corporation).

(2) Acids

An acid catalyzes amino resin cross-linking between a plurality of amino resins and/or an amino resin and an addition resin, though an acid is more effective in promoting cross-linking between the additional resin and an amino resin. A coating may comprise a strong acid, a weak acid, or a combination thereof. Examples of an acid include a strong acid or a weak acid. The rate of curing is typically accelerated by selection of a strong acid over a weak acid. Examples of a strong acid include, p-toluenesulfonic acid ("PTSA"), dodecylbenzenesulfonic acid ("DDBSA"), or a combination thereof. Examples of a weak acid include phenyl acid phosphate ("PAP"), butyl acid phosphate ("BAP"), or a combination thereof.

(3) Bases

A base catalyzes cross-linking between an acrylic resin and an epoxy resin in film formation. In specific aspects, the base comprises, for example, a dodecyl trimethyl ammonium chloride, a tri(dimethylaminomethyl) phenol, a melamine-formaldehyde resin, or a combination thereof.

(4) Urethane Catalysts

In specific aspects, a urethane coating comprises a catalyst to accelerate the reaction between an isocyanate moiety and a reactive hydrogen moiety. Examples of such a urethane catalyst include a tin compound, a zinc compound, a tertiary amine, or a combination thereof. Examples of a zinc compound include zinc octoate, zinc naphthenate, or a combination thereof. Examples of a tin compound include dibutyltin dilaurate, stannous octoate, or a combination thereof. An example of a tertiary amine includes a triethylene diamine.

g. Antiskinning Agent

An antiskinning agent is a composition, other than a drier, that reduces film-formation at the coating-external environment interface, reduce shrinkage ("wrinkling"), or a combination thereof. Such antiskinning agents are often used to protect coatings from undesired film-formation after a container of coating has been opened, during normal film-formation, or a combination thereof. Examples of antiskinning agents, with commonly used coating concentrations in parentheses, include butyraloxime (0.2%), cyclohexanone oxime, dipentene, exkin 1, exkin 2, exkin 3, guaiacol (0.001% to 0.1%), methyl ethyl ketoxime (0.2%), pine oil (1% to 2%), or a combination thereof. Generally, an antiskinning agent acts by reducing the rate of film-formation and/or promotes even film-formation throughout a coating by slowing an oxidative reaction that occurs as part of film formation. Examples of antioxidant antiskinning agents include a phenolic antioxidant, an oxime, or a combination thereof. Example of a phenolic antioxidant includes guaiacol, 4-tert-butylphenol, or a combination thereof. Oximes tend to evaporate such as during film formation, are colorless, do not affect a coating's color property, and generally do not significantly alter the time of film-formation. Examples of an oxime include, butyraldoxime, methyl ethyl ketoxime, cyclohexanone oxime, or a combination thereof. In certain facets, an oxime is used to slow skinning promoted by a copper drier.

h. Light Stabilizers

A coating, a film and/or a surface may be undesirably altered by contact with an environmental agent such as, for example, oxygen, pollution, water (e.g., moisture), and/or irradiation with light (e.g., UV light). To reduce such damaging alterations to a coating and/or film, it is contemplated that a coating composition may comprise a light stabilizer. A light stabilizer ("stabilizer") is a composition that reduces or prevents damage to a coating, film and/or surface by an environmental agent. Such agents may alter the color, cause a separation between two layers of film ("delamination"), promote chalking, promote crack formation, reduce gloss, or a combination thereof. This is a particular problem for a film in an exterior environment, such as, for example, an automotive film. Additionally, wood surfaces are susceptible to damage by environmental agents, particularly UV light.

Typically, a light stabilizer may comprise a UV absorber, a radical scavenger, or a combination thereof. A UV absorber is a composition that absorbs UV light. Examples of UV absorbers include a hydroxybenzophenone, a hydroxyphenylbenzotriazole, a hydrozyphenyl-S-triazine, an oxalic anilide, yellow iron oxide, or a combination thereof. A hydroxyphenylbenzotriazole generally demonstrates the broadest range of UV wavelength absorption, and converts the absorbed UV light into heat. Additionally, a hydroxyphenylbenzotriazole and/or a hydrozyphenyl-S-triazine usually have the longest effective use in a film due to a higher resistance to photochemical reactions, relative to a hydroxybenzophenone or an oxalic anilide.

A radical scavenger light stabilizer (e.g., a sterically hindered amine) is a composition that chemically reacts with a radical ("free radical"). Examples of a sterically hindered amine ("hindered amine light stabilizer," "HALS") include the ester derivatives of decanedioic acid, such as HALS I ["bis(1,2,2,6,6,-pentamethyl-4-poperidinyl) ester"], which is used in non-acid catalyzed coatings; HALS II ["bis(2,2, 6,6,-tetramethyl-1-isooctyloxy-4-piperidinyl) ester"], which is typically used in an acid catalyzed coating.

For embodiments wherein a coating, film, and/or surface is primarily located in-doors, a range of 1% to 3%, including all intermediate ranges and combinations thereof, of a light stabilizer relative to binder content is contemplated. A range of 1% to 5%, including all intermediate ranges and combinations thereof, of a light stabilizer relative to binder content is contemplated for exterior uses. Additionally, a combination of a UV absorber and a radical scavenger light stabilizer are contemplated in some embodiments, as the heat released by a UV absorber may promote radical formation. Light stabilizers are often commercially produced, and examples of UV absorber and/or a radical scavenger light stabilizer sold under a tradename include Tinuvin® (Ciba Specialty Chemicals) or Sanduvor® [Clariant LSM (America) Inc.].

i. Corrosion Inhibitors

A coating comprising a liquid component that comprises water, particularly a water-borne coating, may promote corrosion in a container comprising iron, particularly at the lining, seams, handle, etc. A corrosion inhibitor reduces corrosion by water or another chemical. Examples of a corrosion inhibitor includes a chromate, a phosphate, a molybdate, a wollastonite, a calcium ion-exchanged silica gel, a zinc compound, a borosilicate, a phosphosilicate, a hydrotalcite, or a combination thereof.

In certain embodiments, a corrosion inhibitor is an in-can corrosion inhibitor, a flash corrosion inhibitor, or a combination thereof. An in-can corrosion inhibitor ("can-corrosion inhibitor") is a composition that that reduces or prevents such corrosion. Examples of an in-can corrosion inhibitor are sodium nitrate, sodium benzoate, or a combination thereof. These compounds are typically used at a concentration of 1% each in a coating composition. In-can corrosion inhibitor are often commercially produced, and an example includes SER-AD® FA179 (Condea Servo LLC.), typically used at 0.3% in a coating composition. A flash corrosion inhibitor ("flash rust inhibitor") is a composition that reduces or prevents corrosion produced by application of a coating comprising water to a metal surface (e.g., an iron surface). Often, in-can corrosion inhibitors at increased concentrations are added to a coating composition to act as a flash corrosion inhibitor. An example of a flash corrosion inhibitor includes sodium nitrite, ammonium benzoate, 2-amino-2-methyl-propan-1-ol ("AMP"), SER-AD® FA179 (Condea Servo LLC.), or a combination thereof. Standard procedures to determining the effectiveness of corrosion inhibition by a coating comprising a flash rust inhibitor are described, for example, in "ASTM Book of Standards, Volume 06.02, Paint—Products and Applications; Protective Coatings; Pipeline Coatings," D5367-00, 2002.

j. Dehydrators

In some embodiments, preventing moisture from contacting coating component such as a binder, solvent, pigment, or a combination thereof, may be desired. For example, certain urethane coatings undergo film-formation in the presence of moisture, as well as produce a film with increased yellowing, increased hazing and/or decreased gloss. A dehydrator may be added during coating production and/or storage to minimalize contact with moisture. Examples of a dehydrator include Additive TI (Bayer Corporation), Additive OF (Bayer Corporation), or a combination thereof. Additive TI comprises a compound with one reactive isocyanate moiety, and it is capable of reacting with compounds with a chemically reactive hydrogen such as water, an alcohol, a phenol, or an amide. However, in a preferred reaction with water, the reaction products are carbon dioxide and toluenesulfonamide. The toluenesulfonamide is generally inert relative to a urethane binder, and soluble in many non-aqueous liquid components. In certain embodiments, a urethane coating may comprise 0.5% to 4% Additive TI. Additive OF is a dehydrator generally used in a urethane coating. In certain embodiments, a urethane coating may comprise 1% to 3% Additive OF.

k. Electrical Additives

In some embodiments, it is desirable to include an additive to alter an electrical property of a coating (e.g., electrical conductivity, electrical resistance). Examples of an additive to alter an electrical property of a coating and/or coating component include an anti-static additive, an electrical resistance additive, or a combination thereof. An anti-static additive may be included in a coating composition comprising a flammable component to reduce the chance of an electrostatic spark occurring and igniting the coating. An anti-static additive is a composition that increases the electrical conductivity of a coating. An example of a flammable component is a hydrocarbon solvent. Examples of an anti-static additive include Stadis® 425 (Octel-Starreon LLC USA), Stadis® 450 (Octel-Starreon LLC USA), or a combination thereof. An electrical resistance additive is a composition that reduces the resistance to electricity by a coating. An electrical resistance additive may be included in a coating to improve the ability of a coating to be applied to a surface using an electrostatic spray applicator. For example, an oxygenated compound (e.g., a glycol ether) often possesses a high electrical conductivity, which can make use of an electrostatic spray applicator to apply a coating comprising an oxygenated compound relatively more difficult than a similar coating lacking an oxygenated compound. Examples of an electrical resistance additive include Ramsprep, Byk-ES 80 (BYK-Chemie GmbH), or a combination thereof. Byk-ES 80 comprises, for example, an unsaturated acidic carboxylic acid ester alkylolammonium salt, and typically is added between 0.2% and 2% to a coating composition. Additionally, techniques for determining an electrical property (e.g., electrical resistance) of a coating comprising an electrical additive are known to those of ordinary skill in the art (see, for example, "ASTM Book of Standards, Volume 06.01, Paint—Tests for Chemical, Physical, and Optical Properties; Appearance," D5682-95, 2002).

l. Anti-Insect Additives

Certain coatings may serve a protective role for a surface or surrounding environment against insects, and thus may comprise an anti-insect agent. An example of a surface where a coating comprising an anti-insect agent may be desirable is a wooden surface. Examples of an area where coating comprising an anti-insect agent may be desirable would be a storage facility, such as a cargo hold of a ship or railcar. An anti-insect agent is a composition that, upon contact, is detrimental to the well-being (e.g., life, reproduction) of an invertebrate pest (e.g., an insect, an arachnid, etc). Examples of anti-insect additives that have been used in coatings include copper naphthenate, tributyl tin oxide, zinc oxide, 6-chloro epoxy hydroxy naphthalene, 1-dichloro 2,2'bis-(p-chlorophenyl)ethane, or a combination thereof.

5. Coating Preparation

As would be known to one of ordinary skill in the art, a coating may comprise insoluble particulate material. Particulate material may comprise a primary particle, an agglomerate, an aggregate, or a combination thereof. A primary particle is a single particle not in contact with a second particle. An agglomerate is two or more particles in contact with each other, and generally can be separated by a dispersion technique, a wetting agent, a dispersant, or a combination thereof. An aggregate is two or more particles in contact with each other, which are generally difficult to separate by a dispersion technique, a wetting agent, a dispersant, or a combination thereof.

Usually, a pigment, an extender, certain types of rheology modifiers, certain types of dispersants, or a combination thereof are the major sources of particulate material in a coating. In the present invention, microorganism derived particulate material will also be a source of particulate material in a coating. In certain embodiments, a micoorganism-based particulate matter of the present invention may be used in combination with and/or as a substitute for a pigment, an extender, a rheology modifier, a dispersant, or a combination thereof. In specific facets, a micoorganism-based particulate matter of the present invention may substitute for 0.001% to 100%, including all intermediate ranges and combinations thereof, of a pigment, an extender, a rheology modifier, a dispersant, or a combination thereof. It is contemplated that any technique used in the preparation of a coating that comprises a pigment, extender or any other form of particulate material described herein or would be known to one of ordinary skill in the art may be applied in the preparation of a coating comprising the microorganism derived particulate material of the present invention. Incorporation of particulate materials (e.g., pigments), assays for determining a rheological property and/or a related property (e.g., viscosity, flow, molecular weight, component concentration, particle size, particle shape, particle surface area, particle spread, dispersion, flocculation, solubility, oil absorption values, CPVC, hiding power, corrosion resistance, wet abrasion resistance, stain resistance, optical properties, porosity, surface tension, volatility, settling, leveling, sagging, slumping, draining, floating, flooding, cratering, foaming, splattering,) of a coating component and/or a coating (e.g., pigment, binder, vehicle, surfactant, dispersant, paint) and procedures for determining such properties, as well as procedures for large scale (e.g., industrial) coating preparation (e.g., wetting, pigment dispersion into a vehicle, milling, letdown) are described in, for example, in Patton, T. C. "Paint Flow and Pigment Dispersion, A Rheological Approach to Coating and Ink Technology," 1979.

In many embodiments, dispersion of the particulate material is promoted by application of physical force (e.g., impact, shear) to the composition. Techniques such as grinding and/or milling are typically used to apply physical force for dispersion of particulate matter. Though it is contemplated that such application of physical force may be used in the dispersal of the microorganism based particulate material of the present invention, such force may damage the structural integrity of the cell wall and/or cell membrane that confers size and shape to the material. The average particle size and shape will be altered by the degree of damage to the cell wall and/or cell membrane, which may alter a physical property, a chemical property, an optical property, or a combination thereof, of a microorganism based particulate material of the present invention. Examples of a physical property that may be altered by cell fragmentation include a rheological property, such as the contribution to viscosity, flow, etc., the tendency to form a primary particle, an agglomerate, an aggregate, etc. An example of a chemical property that may be altered includes allowing greater contact between amine and hydroxyl moieties of internally located biomolecules (e.g., a proteinaceous molecule) with a coating component, which may undergo a chemical reaction (e.g., crosslinking) with a binder. An example of an optical property that may be altered includes an alteration in the gloss characteristic of a coating and/or film by a reduction in particle size due to cell fragmentation.

A preferred embodiment of the microorganism based particulate material is the material in the form of a "whole cell material," which refers to particulate material resembling an intact living cell upon microscopic examination, in contrast to cell fragments of varying shape and size. It is contemplated that such whole cell particulate material of the present invention will encapsulate an expressed biomolecule (e.g., an enzyme) located in and/or internal to a cell wall and/or cell membrane. In certain aspects, the encapsulation of a biomolecule by a whole cell particle may provide greater protection of the biomolecule from a coating component (e.g., a solvent, a binder, an additive), a coating related chemical reaction (e.g., thermosetting film formation), a potentially damaging agent a coating and/or film may contact (e.g., a chemical, a solvent, a detergent, etc.), or a combination thereof, relative to a biomolecule located on the external surface of a cell or otherwise not comprised within and/or encapsulated by a cell wall and/or cell membrane. As would be known to those of ordinary skill in the art, any preparation of a microorganism will comprise a certain percentage of cell fragments, which comprise pieces of a cell wall, cell membrane, and other cell components (e.g., an expressed biomolecule). The whole cell microorganism based particulate material of the present invention will comprise 50% to 100%, including all intermediate ranges and combinations thereof of whole cell material. The percentage of whole cell material and cell fragments may be determined by any applicable technique known to one of ordinary skill in the art such as microscopic examination, centrifugation, etc, as well as any technique described herein for determining the properties of a pigment, extender, or other particulate material either alone or comprises in a coating. It is contemplated that in some aspects, cell fragments may be used as microorganism based particulate material. The cell fragment microorganism based particulate material of the present invention will comprise 50% to 100%, including all intermediate ranges and combinations thereof of cell fragment material.

For example, during typical preparation of a water-borne and/or solvent-borne coating comprising particulate material such as a pigment and/or extender, the particulate material is dispersed into a paste known as a "grind" or "millbase." A combination of a binder and a liquid component know as a "vehicle" is used to disperse the particulate material into the grind. Often, a wetting additive is included to promoted dispersion of the particulate material. Additional vehicle and/or additives are admixed with the grind in a stage referred to as the "letdown" to produce a coating of a desired composition and/or properties. These techniques and others for coating preparation are well known to those of ordinary skill in the art [see, for example, in "ASTM Book of Standards, Volume 06.01, Paint—Tests for Chemical, Physical, and Optical Properties; Appearance," D6619-00, 2002; in "Paint and Surface Coatings, Theory and Practice, Second Edition," (Lambourne, R. and Strivens, T. A., Eds.), pp. 286-329, 1999; and in "Paints, Coatings and Solvents, Second, Completely Revised Edition," (Stoye, D. and Freitag, W., Eds.) pp. 178-193, 1998.] It is specifically contemplated that these techniques may be used in preparing a coating comprising the microorganism based particulate matter of the present invention, wherein the particulate matter of the present invention is treated as a pigment, extender, or other such particulate material dispersed into a coating.

In another example, the effectiveness of the conversion of agglomerates and/or an aggregates into primary particles in the grind (e.g., pigments, pigment-vehicle combinations, pastes), and latter stages (e.g., lacquer, paint) are typically measured to insure quality, using techniques such as, for example, those described in "ASTM Book of Standards, Volume 06.01, Paint—Tests for Chemical, Physical, and Optical Properties; Appearance," D1210-96, 2002; "ASTM Book of Standards, Volume 06.02, Paint—Products and Applications; Protective Coatings; Pipeline Coatings," D2338-02, D1316-93, and D2067-97, 2002; and in "ASTM Book of Standards, Volume 06.03, Paint—Pigments, Drying Oils, Polymers, Resins, Naval Stores, Cellulosic Esters, and Ink Vehicles," D185-84, 2002. It is specifically contemplated that these techniques for the preparation of coatings comprising a pigment, exender, or other particulate material may be used in the practice of the present invention in the preparation of a coating comprising a microorganism based particulate material of the present invention.

In a further example, a microorganism based particulate material of the present invention may be adapted for use in standard coating formulation techniques to optimize a coating composition for desired properties. As is known to those of ordinary skill in the art, the pigment volume concentration is the volume of pigment in the total volume solids of a dry film. The volume solids is the fractional volume of binder and pigment in the total volume of a coating. It is contemplated that in calculating the PVC, the content of a microorganism based particulate material of the present invention would be included in this or related calculations as a pigment or extender. A related calculation to the PVC that is specifically contemplated is the critical pigment volume concentration ("CPVC") is the formulation of pigment and binder wherein the coating comprises the minimum amount of binder to fill the voids between the pigment particles. A pigment to binder concentration that exceeds the CVPC threshold produces a coating with empty spaces wherein gas (e.g., air, evaporated liquid component), may be trapped. Various properties rapidly change above the CPVC. For example, corrosion resistance, scrub resistance, stain resistance, opacity, moisture resistance, rigidity, gloss, or a combination thereof, are more rapidly reduced above the CPVC, while reflectance is often increased. However, in certain embodiments, coating may be formulated above the CPVC and still produce a film suitable for given use upon a surface. Standard procedures for determining CPVC are known to those of ordinary skill in the art [see, for example, in "ASTM Book of Standards, Volume 06.01, Paint—Tests for Chemical, Physical, and Optical Properties; Appearance," D1483-95, D281-95, and D6336-98, 2002; and in "Paint and Coating Testing Manual, Fourteenth Edition of the Gardner-Sward Handbook," (Koleske, J. V. Ed.), pp. 252-258, 1995].

The physical and/or optical properties of a coating are affected by the size of particulate material comprised within the coating. For example, inclusion of a physically hard particulate material, such as a silica extender, may increase the abrasion resistance of a film. In another example, gloss is reduced when particulate material of a larger average particle size increases the roughness of the surface of a coating and/or film. Standard procedures for determining particle properties (e.g., size, shape) are known to those of ordinary skill in the art (see, for example, "ASTM Book of Standards, Volume 06.03, Paint—Pigments, Drying Oils, Polymers, Resins, Naval Stores, Cellulosic Esters, and Ink Vehicles," D1366-86 and D3360-96, 2002; and in "Paint and Coating Testing Manual, Fourteenth Edition of the Gardner-Sward Handbook," (Koleske, J. V. Ed.), pp. 305-332, 1995).

It is also contemplated that a biomolecule composition, particularly one prepared as a particulate or powder material, may be incorporated into a powder coating. Specific procedures for determining the properties (e.g., particle size, surface coverage, optical properties) of a powder coating and/or film have been described, for example, in "ASTM Book of Standards, Volume 06.02, Paint—Products and Applications; Protective Coatings; Pipeline Coatings," D3451-01, D2967-02a, D4242-02, D5382-02 and D5861-95, 2002.

In some embodiments, the dispersion of particulate material ("fineness of grind") in a coating is, in Hegman units ("Hu"), 0.0 Hu to 8.0 Hu, including all intermediate ranges and combinations thereof. The dispersion of particulate material content of a coating can be empirically determined, for example, as described in "ASTM Book of Standards, Volume 06.01, Paint—Tests for Chemical, Physical, and Optical Properties; Appearance," D1210-96, 2002. The size of particulate matter in a coating can affect gloss, with smaller particle size generally more conducive for a higher gloss property of a coating and/or film. It is contemplated that a whole cell particulate material of the present invention will possess similar size and shape as the organism from which it was derived. For example, *E. coli* is about 2 μm in length and 0.8 μm in diameter, maize cells vary more in size, but a size of about 65 μm in diameter may be found in some cell types, and *Saccaromyces cerivsia* is about 10 μm in diameter. Of course, processing and purifying techniques may reduce the particle size by fragmentation of the cell wall and membrane, and it is contemplated that a biomolecule composition of the present invention may be prepared to an average particle size for a specific purpose (e.g., gloss). In certain facets, a visibly coarse and/or low gloss coating (e.g., a low gloss finish, a flat latex paint) has a dispersion of particulate material of 2.0 Hu to 4.0 Hu. A particle size of 100 μm to 50 μm is associated with a dispersion of 0.0 Hu to 4.0 Hu. In some aspects, a semi-gloss or gloss coating has a dispersion of particulate material of 5.0 Hu to 7.5 Hu. A particle size of 50 μm to 40 μm, 40 μm to 26 μm, 26 μm to 13 μm, and 13 μm to 6 μm is associated with a dispersion of 4.0 Hu to 5.0 Hu, 5.0 Hu to 6.0 Hu, 6.0 Hu to 7.0 Hu, and 7.0 Hu to 7.5 Hu, respectively. In other aspects, a high gloss coating has a dispersion of particulate material of 7.5 Hu to 8.0 Hu. A particle size of 6 μm to 3 μm and 3 μm to 0.1 μm is associated with a dispersion of 7.5 Hu to 7.75 Hu and 7.75 Hu to 8.0 Hu, respectively. In embodiments wherein a coating comprises a combination of particulate materials, wherein the different particulate materials such as a combination of a microorganism derived particulate material of the present invention and one or more of different pigments, with each type of particulate material possessing a different average particle size, it is contemplated that the gloss will be affected most by the particle size of the largest type of particulate material added. However, gloss can also be empirically determined for a coating and/or film, as described herein or as would be known to one of ordinary skill in the art in light of the present disclosures.

6. Empirically Determining the Properties of Biomolecule, Coatings and/or Film

A coating with a desired set of properties for a particular use may be prepared by varying the ranges and/or combinations of coating components, and such coating selection and preparation is within the ability of one of ordinary skill in the art in light of the present disclosures. For example, as would be known to those of ordinary skill in the art, a variety of assays are available to measure various properties of a coating, coating application, and/or a film to determine the degree of suitability of a coating composition for use in a particular application.

It is contemplated that in general embodiments, a coating comprising a microorganism derived particulate material of the present invention may be subjected to one or more of such assays. Additionally, a microorganism derived particulate material may further comprise a desired biomolecule (e.g., a colorant, an enzyme), whether endogenously or recombinantly produced, that may confer a desired property to a coating and/or film of the present invention. As used herein, "bioactivity" refers to desired property such as color, enzymatic activity, etc, conferred to a coating by a biomolecule of a microorganism derived particulate material of the present invention. As used herein, "bioactivity resistance" refers to the ability of a biomolecule to confer a desired property during and/or after contact with a stress condition normally assayed for in a standard coating and/or film assay procedure. Examples of such a stress condition includes, for example, a temperature (e.g., a baking condition), contact with a coating component (e.g., an organic liquid component), contact with a chemical reaction (e.g., thermosetting film formation), contact with coating and/or film damaging agent (e.g., weathering, detergents, solvents), etc. In specific facets, wherein a microorganism derived particulate material of the present invention that comprises a desired biomolecule, a biomolecule may possess a greater bioactivity resistance such as determined with standard assay procedure, than a purified or partly purified-like biomolecule.

It is contemplated that such bioactivity resistance may be determined using a standard procedure for a coating and/or film described herein or as would be known to one of ordinary skill in the art in light of the present disclosures. In one example, it is contemplated that a microorganism derived particulate material may comprise a desired colorant such as a chlorophyll, a carotenoid, etc, which may undergo a desired or undesired change in its optical characteristics (e.g., color, opacity) upon baking at a particular temperature. Various procedures for measuring the visual properties of a coating and/or film are described herein or would be known to those of ordinary skill in the art in light of the present disclosures may be used to determine the properties and/or tolerances of any such colorant.

In an additional example, any assay described herein or would be known to one of ordinary skill in the art in light of the present disclosures may be used to determine the bioactivity resistance wherein an enzyme retains detectable enzymatic activity upon contact with a condition typically encounter in a standard assay. Additionally, in certain aspects, it is contemplated that a coating and/or film comprising an enzyme may lose part of all of a detectable, desirable bioactivity during the period of time of contact with standard assay condition, but regain part or all of the enzymatic bioactivity after return to non-assay conditions. An example of this process is the thermal denaturation of an enzyme at an elevated temperature range into a configuration with lowered or absent bioactivity, followed by refolding of an enzyme, upon return to a preferred temperature range for the enzyme, into a configuration possessing part or all of the enzymatic bioactivity detectable prior to contact with the elevated temperature. In another example, an enzyme may demonstrate such an increase in bioactivity upon removal of a solvent, chemical, etc.

In some embodiments, an enzyme identified as having a desirable enzymatic property for one or more target substrates may be selected for incorporation into a composition of the present invention. The determination of an enzymatic property may be conducted using any technique described herein or known to those of ordinary skill in the art, in light of the present disclosures. For example, the determination of the rate of cleavage of a substrate, with or without a competitive or non-competitive enzyme inhibitor, can be utilized in determining the enzymatic properties of an enzyme, such as $V_{max}$, $K_m$, $K_{cat}/K_m$ and the like, using analytical techniques such as Lineweaver-Burke analysis, Bronsted plots, etc (Dumas, D. P. et al., 1989a; Dumas, D. P. et al., 1989b; Dumas, D. P. et al., 1990; Caldwell, S. R. and Raushel, F. M., 1991c; Donarski, W. J. et al., 1989; Raveh, L. et al., 1992; Shim, H. et al., 1998; Watkins, L. M. et al., 1997a; diSioudi, B. et al., 1999; Hill, C. M., 2000; Hartleib, J. and Ruterjans, H., 2001b; Lineweaver, H. and Burke, D., 1934; Segel, I. H., 1975). It is contemplated that any such analysis may be used to identify an enzyme with a specifically desirable enzymatic property for one or more substrates.

In a specific example, phosphoric triester hydrolases have demonstrated the ability to degrade a wide variety of OP compounds. Methods for measuring the ability of an enzyme to degrade an OP compound are known to those of ordinary skill in the art. It is contemplated that any such technique may be utilized to determine enzymatic activity of a composition of the present invention for a particular OP compound.

Techniques for measuring the kinetics of enzymatic detoxification for various OP-compounds comprising a P—S bond at the phosphorous center (e.g., an OP-phosphonothiolate) such as VX ["EA 1701," "TX60," "O-ethyl-S-(diisopropylaminoethyl) methylphosphonothioate"]; Russian VX ["R-VX," "O-isobutyl-S-(diisopropylaminoethyl) methylphosphonothioate"], tetriso["O,O-diisopropyl S-(2-diisopropylaminoethyl) phosphorothiolate"], echothiophate ("phospholine," "O,O-diethyl-phosphorothiocholine"), malathion ["phosphothion," "S-(1,2-dicarbethoxyethyl)-O,O-dimethyl dithiophosphate"], dimethoate ["Cygon®," "Dimetate®," "O,O-dimethyl-S—(N-methylcarbomoylmethyl)phosphorodithioate"], EA 5533 ["OSDMP," "O,S-diethyl methylphosphonothioate"], IBP ("Kitazin P," "O,O-diisopropyl-S-benzylphosphothioate"), acephate ("O,S-dimethyl acetyl phosphoroamidothioate"), azinophos-ethyl ["S-(3,4-dihydro-4-oxobenzo(d)-1,2,3-triazin-3-yl methyl-O,O-diethyl) phosphorothioate"], demeton S ["VX analogue," "O,O-diethyl-S-2-ethylthiolethyl phosphorothioate"], malathion ["Phosphothion," "S-(1,2-dicarbethoxyethyl)-O,O-dimethyl dithiophosphate"], and phosalone ["O,O-diethyl-S-(6-chloro-2-oxobenzoxazolin-3-yl-methyl) phosphorodithioate"], have been described (see, for example, diSioudi, B. D. et al., 1999; Hoskin, F. C. G. et al., 1995; Watkins, L. M. et al., 1997a; Kolakowski, J. E. et al., 1997; Gopal, S. et al., 2000; and Rastogi, V. K. et al., 1997).

Techniques for measuring the kinetics of enzymatic detoxification for various OP-compounds comprising a P—F bond at the phosphorous center (e.g., an OP-phosphonofluoridate) such as soman ("1,2,2-trimethylpropyl-methylphosphonofluoridate"), sarin ("isopropylmethylphosphonofluoridate"), DFP ("O,O-diisopropyl phosphorofluoridate"), alpha ("1-ethylpropylmethyl-phosphonofluoridate"), and mipafox ("N,N'-diisopropyl-phosphorofluorodiamidate") have been described (see, for example Dumas, D. P. et al., 1990; Li, W.-S. et al., 2001; diSioudi, B. D. et al., 1999; Hoskin, F. C. G. et al., 1995; Gopal, S. et al., 2000; and DeFrank, J. and Cheng, T., 1991).

A technique for measuring the kinetics of enzymatic detoxification for an OP-compound comprising a P—CN bond at the phosphorous center (e.g., an OP-phosphonocyanate) such as tabun ("ethyl N,N-demethylamidophosphorocyanidate") has been described (see, for example, Raveh, L. et al., 1992).

Techniques for measuring the kinetics of enzymatic detoxification for various OP-compounds comprising a P—O bond at the phosphorous center (e.g., an OP-triester) such as paraoxon ("diethyl p-nitrophenylphosphate"), the soman analogue O-pinacolyl p-nitrophenyl methylphosphonate, the sarin analogue O-isopropyl p-nitrophenyl methylphosphonate, NPPMP ("p-nitrophenyl-o-pinacolyl methylphosphonate"), coumaphos ["O,O-diethyl O-(3-chloro-4-methyl-2-oxo-2H-1benzyran-7-yl)phosphorothioate], cyanophos ["O,O-dimethyl p-cyanophenyl phosphorothioate"], diazinon ("O,O-diethyl O-2-iso-propyl-4-methyl-6-pyrimidyl phosphorothiate"), dursban ("O,O-diethyl O-3,5,6-trichloro-2-pyridyl phosphorothioate"), fensulfothion {"O,O-diethyl [p-(methylsulfinyl)phenyl]phosphorothioate"}, parathion ("O,O-diethyl O-p-nitrophenyl phosphorothioate"), methyl parathion ("O,O-dimethyl p-nitrophenyl phosphorothioate"), ethyl parathion ["O,O-diethyl-O-(4-nitrophenyl)phosphorothioate"], EPN ("O-ethyl 0-(4-nitrophenyl) phenylphosphonothioate"), DEPP ("diethylphenylphosphate"), NPEPP ("p-nitrophenylethylphenylphosphinate") have been described (see, for example, Dumas, D. P. et al., 1990; Li, W.-S. et al., 2001; diSioudi, B. D. et al., 1999; Watkins, L. M. et al., 1997a; Gopal, S. et al., 2000; Mulbry, W. and Karns, J., 1989; Hong, S.-B. and Raushel, F. M., 1996; and Dumas, D. P. et al., 1989b).

In one example, the cleavage rate of a phosphonothiolate OP substrate comprising a P—S bond can be measured using a method known as the Ellman reaction. All such substrates produce a P—S bond cleavage product comprising a free thiol group, which can chemically react with the Ellman's reagent, 5,5'-dithio-bis-2-nitrobenzoic acid ("DTNB"). This reaction produces 5'-thiol-2-nitrobenzoate anions with a maximum absorbency at 412 nm. P—S cleavage can be determined by the appearance of the free thiol group, measured using a spectrophotometer (Rastogi, V. H. et al., 1997; Gopal, S. et al., 2000; diSioudi, B. et al., 1999; Watkins, L. M. et al., 1997a; Hoskin, F. C. G. et al., 1995; Chae, M. Y. et al., 1994; Ellman, G. L. et al., 1961).

In an additional example, the cleavage of an OP substrate can be measured by detecting the production of a cleavage product that comprises a released ion. In a further example, the cleavage of a phosphonofluoridate can be measured by the release of cleavage product comprising a fluoride ion ($F^-$) using a fluoride ion specific electrode and a pH/mV meter (Hartleib, J. and Ruterjans, H., 2001a; Gopal, S. et al., 2000; diSioudi, B. et al., 1999; Watkins, L. M. et al., 1997a; DeFrank, J. and Cheng, T., 1991; Dumas, D. P. et al., 1990; Dumas, D. P. et al., 1989a). In another example, the cleavage of a phosphonocyanate can be measured by the release of a cleavage product comprising a cyanide ion ($CN^-$) using a cyanide selective electrode with a pH meter (Raveh, L. et al., 1992).

In another example, cleavage of an OP substrate can be measured, for example, by $^{31}P$ NMR spectroscopy. For example, the disappearance of VX and the formation of the cleavage product ethyl methylphosphonic acid ("EMPA"), has been measured using this technique (Kolakowski, J. E. et al., 1997; Lai, K. et al., 1995). In another example, the disappearance of tabun and the appearance of the N,N-dimethylamindophosphoric acid cleavage product has been measured by $^{31}P$ NMR spectroscopy (Raveh, L. et al., 1992). In a further example, the disappearance of DFP and appearance of a $F^-$ cleavage product has been determined using $^{19}F^-$ and $^{31}P$ NMR spectroscopy (Dumas, D. P. et al., 1989a).

The cleavage of many OP compounds' such as paraoxon, coumaphos, cyanophos, diazinon, dursban, fensulfothion, parathion, methyl parathion, DEPP, and various phosphodiesters, can be determined by measuring the production of a cleavage product spectrophotometrically at visible or UV wavelengths (Dumas, D. P. et al., 1989b). For example, the cleavage of DEPP can be measured at 280 nm, using a spectrophotometer to detect a phenol cleavage product (Watkins, L. M. et al., 1997a; Hong, S.-B. and Raushel, F. M., 1996). In a further example, various phosphodiesters (e.g., ethyl-4-nitrophenyl phosphate) have been made to evaluate OPH cleavage rates, and their cleavage measured at 280 nm by the production of a substituted phenol cleavage product (Shim, H. et al., 1998). In a further example, paraoxon is often used as to measure OPH activity, because it is both rapidly hydrolyzed by the enzyme and produces a visible cleavage product. To determine kinetic properties, the production of paraoxon's cleavage product, p-nitrophenol, is measured with a spectrophotometer at 400 nm or 420 nm (Dumas, D. P. et al., 1990; Kuo, J. M. and Raushel, F. M., 1994; Watkins, L. M. et al., 1997a; Gopal, S. et al., 2000). In an additional example, NPPMP cleavage can also be measured by the release of p-nitrophenol as a cleavage product (diSioudi, B. et al., 1999). In a further example, chiral and non-chiral phosphotriesters have been created to produce p-nitrophenol as a cleavage product, and thus adapt the method used in measuring paraoxon cleavage in determining the general binding and/or cleavage preference of an enzyme for a phosphoryl group $S_p$ enantiomer, $R_p$ enantiomer or non-chiral substrate (Chen-Goodspeed, M. et al., 2001a; Chen-Goodspeed, M. et al., 2001b; Wu, F. et al., 2000a; Steubaut, W. et al., 1975). In an example, chiral sarin and soman analogues have been created wherein the fluoride comprising moiety of the P—F bond has been replaced by p-nitrophenol, allowing detection of the CWA analogs' cleavage rates using the adapted method for paraoxon cleavage measurement (Li, W.-S. et al., 2001).

Other techniques are known to those of skill in the art for measuring OP detoxification activity, such as, for example, determining the loss of acetylcholinesterase inhibitory potency of an OP compound due to contact with an enzyme (Hoskin, F. C. G., 1990; Luo, C. et al., 1999; Ashani, Y. et al., 1998).

General procedures for empirically determining the purity/properties of various coating components and/or coating compositions are known to those of ordinary skill in the art, and may be applied in the practice of the present invention. Such procedures include measurement of density, volume solids and/or specific gravity, of a coating component and/or coating composition, for purposes such as verification of component identity, aid in coating formulation, maintaining coating batch to batch consistency, etc. Examples of standard techniques for determining density of various solvents, liquids (e.g., a liquid coating), pigments, coatings (e.g., a powder coating) include those described in "ASTM Book of Standards, Volume 06.04, Paint—Solvents; Aromatic Hydrocarbons," D2935-96, D1555M-00, D1555-95, and D3505-96, 2002; "ASTM Book of Standards, Volume 06.01, Paint—Tests for Chemical, Physical, and Optical Properties; Appearance," D1475-98 and D215-91, 2002; "ASTM Book of Standards, Volume 06.03, Paint—Pigments, Drying Oils, Polymers, Resins, Naval Stores, Cellulosic Esters, and Ink Vehicles," D153-84 and D153-84, 2002; "ASTM Book of Standards, Volume 06.02, Paint—Products and Applications; Protective Coatings; Pipeline Coatings," D5965-02, 2002; and "Paint and Coating Testing Manual, Fourteenth Edition of the Gardner-Sward Handbook," (Koleske, J. V. Ed.), pp. 289-304, 1995.

Standard surface specification and/or procedures for preparing a surface (e.g., glass, wood, steel) for empirically measuring a physical and/or visual property of a coating (e.g., a paint, a varnish, a lacquer) and/or film are known to those of ordinary skill in the art (see, for example, "ASTM Book of Standards, Volume 06.01, Paint—Tests for Chemical, Physical, and Optical Properties; Appearance," D3891-96, D609-00, and D2201-99, 2002; and "ASTM Book of Standards, Volume 06.02, Paint—Products and Applications; Protective Coatings; Pipeline Coatings," D358-98, D4227-99, and D4228-99, 2002). Specific procedures for preparing a metal surface and an evaluating a coating (e.g., a primer, a paint) applied to a metal surface are known to those of ordinary skill in the art (see, for example, "ASTM Book of Standards, Volume 06.02, Paint—Products and Applications; Protective Coatings; Pipeline Coatings," D3276-00, D5161-96, D4417-93, D3322-82, D2092-95, D5065-01, D5723-95, D6386-99, and D6492-99, 2002). Specific procedures for evaluating a coating applied to a plastic surface are known to those of ordinary skill in the art (see, for example, "ASTM Book of Standards, Volume 06.02, Paint—Products and Applications; Protective Coatings; Pipeline Coatings," D3002-02, 2002).

Standard procedures for determining the stability of a coating (e.g., a water-borne coating, a UV irradiation cured coating) in a container prior and/or after opening the container are known to those of ordinary skill in the art (see, for example, "ASTM Book of Standards, Volume 06.02, Paint—Products and Applications; Protective Coatings; Pipeline Coatings," D2243-95 and D4144-94, 2002).

Standard procedures for evaluating an applicator (e.g., a brush, a roller, a fabric, a spray applicator, an electrocoat bath) and/or a coating being applied by an applicator are known to those of ordinary skill in the art (see, for example, "ASTM Book of Standards, Volume 06.02, Paint—Products and Applications; Protective Coatings; Pipeline Coatings," D6737-01, D5913-96, D5959-96, D5301-92, D5068-02, D5069-92, D4707-97, D5286-01, D6337-98, D4285-83, and D5327-97, 2002; and "ASTM Book of Standards, Volume 06.01, Paint—Tests for Chemical, Physical, and Optical Properties; Appearance," D1978-91, D5794-95, D4370-01, D4399-90, and D4584-86, 2002.

Standard procedures for preparing a coating (e.g., a paint, a varnish, a lacquer) and/or film layer upon a surface for empirically measuring a physical and/or visual property are known to those of ordinary skill in the art (see, for example, "ASTM Book of Standards, Volume 06.01, Paint—Tests for Chemical, Physical, and Optical Properties; Appearance," D3924-80, D823-95, and D4708-99, 2002; "ASTM Book of Standards, Volume 06.02, Paint—Products and Applications; Protective Coatings; Pipeline Coatings," D6206-97, D1734-93, and D4400-99, 2002; and "Paint and Coating Testing Manual, Fourteenth Edition of the Gardner-Sward Handbook," (Koleske, J. V. Ed.), pp. 415-423, 1995.

Standard procedures for empirically determining the degree and duration of film formation of various coating compositions are known to those of ordinary skill in the art, and may be applied in the practice of the present invention. Example of a standard technique for determining the degree/duration of film formation by loss of a volatile coating component and/or a cross-linking reaction for a coating (e.g., an oil-coating, a UV cured coating, an thermosetting powder coating) include those described in "ASTM Book of Standards, Volume 06.01, Paint—Tests for Chemical, Physical, and Optical Properties; Appearance," D3539-87, D1640-95 and D5895-01e1, 2002; "ASTM Book of Standards, Volume 06.02, Paint—Products and Applications; Protective Coatings; Pipeline Coatings," D4217-02, D3732-82, D2091-96, D711-89, D4752-98, and D5909-96a, 2002; "ASTM Book of Standards, Volume 06.03, Paint—Pigments, Drying Oils, Polymers, Resins, Naval Stores, Cellulosic Esters, and Ink Vehicles," D2575-70 and D2354-98, 2002; and "Paint and Coating Testing Manual, Fourteenth Edition of the Gardner-Sward Handbook," (Koleske, J. V. Ed.), pp. 407-414, 1995. Additionally, the temperature generated by a film formation reaction by a coating (e.g., a wood coating) may also be determined by one of ordinary skill in the art (see, for example, "ASTM Book of Standards, Volume 06.02, Paint—Products and Applications; Protective Coatings; Pipeline Coatings," D3259-95, 2002). Further, standard techniques for evaluating baking conditions on an organic coating and/or film are known to those of ordinary skill in the art, (see, for example, "ASTM Book of Standards, Volume 06.01, Paint—Tests for Chemical, Physical, and Optical Properties; Appearance," D2454-95, 2002).

In embodiments wherein film formation at room temperature is preferred in a coating, a standard procedure that would be known to one of ordinary skill in that art may be used for measuring film formation rate and/or stages (see for example, "ASTM Book of Standards, Volume 06.01, Paint—Tests for Chemical, Physical, and Optical Properties; Appearance," D1640-95, 2002. In certain aspects wherein the ability of an oil to undergo film formation is to be determined, a standard procedure described in "ASTM Book of Standards, Volume 06.03, Paint—Pigments, Drying Oils, Polymers, Resins, Naval Stores, Cellulosic Esters, and Ink Vehicles," D1955-85, 2002, may be used. In embodiments wherein the hardness of a film produced by a coating composition is measured (e.g., an organic coating), a standard procedure such as, for example, "ASTM Book of Standards, Volume 06.01, Paint—Tests for Chemical, Physical, and Optical Properties; Appearance," D3363-00, D4366-95, and D1474-98, 2002.

Examples of a standard technique for determining the coating and/or film thickness after application to various surface types are described in "ASTM Book of Standards, Volume 06.01, Paint—Tests for Chemical, Physical, and Optical Properties; Appearance," D1212-91, D4414-95, D1005-95, D1400-00, D1186-01, and D6132-97, 2002; "ASTM Book of Standards, Volume 06.02, Paint—Products and Applications; Protective Coatings; Pipeline Coatings," D5235-97, D4138-94, D2200-95, and D5796-99, 2002; and "Paint and Coating Testing Manual, Fourteenth Edition of the Gardner-Sward Handbook," (Koleske, J. V. Ed.), pp. 424-438, 1995.

Examples of a standard technique for determining the adhesion of a coating and/or film to various surface types are described in "ASTM Book of Standards, Volume 06.01, Paint—Tests for Chemical, Physical, and Optical Properties; Appearance," D3359-02, D5179-98, and D2197-98, 2002; "ASTM Book of Standards, Volume 06.02, Paint—Products and Applications; Protective Coatings; Pipeline Coatings," D4541-02 D3730-98, D4145-83, D4146-96, and D6677-01, 2002; and "Paint and Coating Testing Manual, Fourteenth Edition of the Gardner-Sward Handbook," (Koleske, J. V. Ed.), pp. 513-524, 1995. Additionally, standard procedures for determining the ability of one or more layers of a multicoat system to function (e.g., adhere, weather) together are described in, for example, "ASTM Book of Standards, Volume 06.02, Paint—Products and Applications; Protective Coatings; Pipeline Coatings," D5064-01, 2002.

Various standard techniques for determining the physical properties (e.g., flexibility, tensile strength, toughness, impact resistance, hardness, mar resistance, blocking resistance) relevant to the durability of a film and/or the degree of film formation are known to those of ordinary skill in the art. Such procedures may be used to empirically characterize a film, and determine whether a coating composition produces a film suitable for a given application. Flexibility is the film's ability to undergo stress from bending and/or flexing without discernable damage (e.g., cracking). Examples of a standard technique for determining the flexibility of a film under mechanical or temperature stress are described in "ASTM Book of Standards, Volume 06.01, Paint—Tests for Chemical, Physical, and Optical Properties; Appearance," D522-93a and D4145-83, 2002; "ASTM Book of Standards, Volume 06.02, Paint—Products and Applications; Protective Coatings; Pipeline Coatings," D4145-83, D4146-96, and D1211-97, 2002; and "Paint and Coating Testing Manual, Fourteenth Edition of the Gardner-Sward Handbook," (Koleske, J. V. Ed.), pp. 547-554, 1995. Related to flexibility is the tensile strength of a film, which is the ability of a film to undergo tensile deformation without developing discernable damage (e.g., cracking, tearing). Examples of a standard technique for determining the tensile strength of a film are described in "ASTM Book of Standards, Volume 06.01, Paint—Tests for Chemical, Physical, and Optical Properties; Appearance," D2370-98 and D522-93a, 2002; and "Paint and Coating Testing Manual, Fourteenth Edition of the Gardner-Sward Handbook," (Koleske, J. V. Ed.), pp. 534-545, 1995. Toughness is the film's ability to undergo strain imposed in a short period of time (e.g., one second or less) without discernable damage (e.g., breaking, tearing). Examples of a standard technique for determining the toughness of a film (e.g., a film for a pipeline) are described in "ASTM Book of Standards, Volume 06.01, Paint—Tests for Chemical, Physical, and Optical Properties; Appearance," D2794-93, 2002; "ASTM Book of Standards, Volume 06.02, Paint—Products and Applications; Protective Coatings; Pipeline Coatings," G14-88, 2002; and "Paint and Coating Testing Manual, Fourteenth Edition of the Gardner-Sward Handbook," (Koleske, J. V. Ed.), pp. 547-554, 1995. Impact resistance is the ability of a film to undergo impact with an indenter without developing discernable damage at the dimple site (e.g., cracking). Examples of a standard technique for determining the impact resistance of a film (e.g., a film for a pipeline) are described in "ASTM Book of Standards, Volume 06.01, Paint—Tests for Chemical, Physical, and Optical Properties; Appearance," D2794-93, 2002; "ASTM Book of Standards, Volume 06.02, Paint—Products and Applications; Protective Coatings; Pipeline Coatings," G13-89 and G14-88, 2002; and "Paint and Coating Testing Manual, Fourteenth Edition of the Gardner-Sward Handbook," (Koleske, J. V. Ed.), pp. 553-554, 1995. Hardness is the film's ability to undergo an applied static force without developing discernable damage (e.g., a scratch, an indentation). Examples of a standard technique for determining the hardness of a film are described in "ASTM Book of Standards, Volume 06.01, Paint—Tests for Chemical, Physical, and Optical Properties; Appearance" D1640-95, D1474-98, D2134-93, D4366-95, and D3363-00, 2002; and "Paint and Coating Testing Manual, Fourteenth Edition of the Gardner-Sward Handbook," (Koleske, J. V. Ed.), pp. 555-584, 1995. Mar resistance ("mar abrasion resistance") is the film's ability to undergo an applied dynamic force without developing a change in the film surface appearance (e.g., gloss) due to a permanent deformation (e.g., an indentation). Examples of a standard technique for determining the mar resistance of a film are described in "ASTM Book of Standards, Volume 06.01, Paint—Tests for Chemical, Physical, and Optical Properties; Appearance," D5178-98 and D6037-96, 2002; and "Paint and Coating Testing Manual, Fourteenth Edition of the Gardner-Sward Handbook," (Koleske, J. V. Ed.), pp. 525-533 and 579-584, 1995. Abrasion resistance ("wear abrasion resistance") is the film's ability to undergo an applied dynamic force (e.g., washing) without removal of film material. Examples of a standard technique for determining the abrasion resistance (e.g., burnish resistance) of a film are described in "ASTM Book of Standards, Volume 06.01, Paint—Tests for Chemical, Physical, and Optical Properties; Appearance," D968-93 and D4060-01, 2002; "ASTM Book of Standards, Volume 06.02, Paint—Products and Applications; Protective Coatings; Pipeline Coatings," D3170-01, D4213-96, D5181-91, D4828-94, D2486-00, D3450-00, D6736-01, and D6279-99e1, 2002; and "Paint and Coating Testing Manual, Fourteenth Edition of the Gardner-Sward Handbook," (Koleske, J. V. Ed.), pp. 525-533, 1995. Blocking resistance ("block resistance") is the ability of a film to resist adhering to a second film, particularly when the two films are pressed together (e.g., a coated door and coated doorframe). Examples of a standard technique for determining the blocking resistance of a film are described in "ASTM Book of Standards, Volume 06.02, Paint—Products and Applications; Protective Coatings; Pipeline Coatings," D2793-99 and D3003-01, 2002. Abrasion resistance ("wear abrasion resistance") is the film's ability to undergo an applied dynamic force (e.g., washing) without removal of film material. Slip resistance is a coating's (e.g., a floor coating) slipperiness, and can be evaluated as described in "Paint and Coating Testing Manual, Fourteenth Edition of the Gardner-Sward Handbook," (Koleske, J. V. Ed.), pp. 600-606, 1995.

Weathering resistance is film's ability to endure and/or protect a surface from an external environmental condition. Examples of environmental conditions that may damage a film and/or surface include contact with varying conditions of temperature, moisture, sunlight (e.g., UV resistance), pollution, biological organisms, or a combination thereof. Examples of a standard technique for determining the weathering resistance of a film (e.g., an automotive film, an external architectural film, a varnish, a wood coating, a steel coating) by evaluating the degree of damage (e.g., fungal growth, color alteration, dirt accumulation, gloss loss, chalking, cracking, blistering, flaking, erosion, surface rust), are described in "ASTM Book of Standards, Volume 06.01, Paint—Tests for Chemical, Physical, and Optical Properties; Appearance," D4141-01, D1729-96, D660-93, D661-93, D662-93, D772-86, D4214-98, D3274-95, D714-02, D1654-92, D2244-02, D523-89, D1006-01, D1014-95, and D1186-01, 2002; "ASTM Book of Standards, Volume 06.02, Paint—Products and Applications; Protective Coatings;

Pipeline Coatings," D3719-00, D610-01, D1641-97, D2830-96, and D6763-02, 2002; and "Paint and Coating Testing Manual, Fourteenth Edition of the Gardner-Sward Handbook," (Koleske, J. V. Ed.), pp. 619-642, 1995. Additionally, standard techniques are known to those of ordinary skill in the art for determining the resistance of a film to artificial weathering conditions. These procedures are used to contact a film with a simulated weathering condition (e.g., heat, moisture, light, UV irradiation) at an accelerated timetable are described in "ASTM Book of Standards, Volume 06.01, Paint—Tests for Chemical, Physical, and Optical Properties; Appearance," D822-01, D4587-01, D5031-01, D6631-01, D6695-01, D5894-96, and D4141-01, 2002; "ASTM Book of Standards, Volume 06.02, Paint—Products and Applications; Protective Coatings; Pipeline Coatings," D5722-95, D3361-01 and D3424-01, 2002; and "Paint and Coating Testing Manual, Fourteenth Edition of the Gardner-Sward Handbook" (Koleske, J. V. Ed.), pp. 643-653, 1995.

Standard techniques for determining a film's resistance to damage by various chemicals are known to those of ordinary skill in the art. Examples of chemicals that can be used in such procedures include an acid (e.g., 3% acetic acid), a base, an alcohol (e.g., 50% ethyl alcohol, hydrochloric acid, sulfuric acid), a detergent (e.g., a sodium phosphate solution), gasoline, a glycol based antifreeze, an oil (e.g., a vegetable oil, a lubricating petroleum oil, a grease), a solvent, water (e.g., a salt solution, a salt vapor), a polish abrasive, another coating (e.g., graffiti), or a combination thereof. Standard techniques for determining the chemical resistance of a film (e.g., an architectural film, an automotive film, a paint, a lacquer, a varnish, a traffic-coating, a metal surface-film) by evaluating possible damage (e.g., adhesion loss, alteration of gloss, blistering, discoloration, loss of hardness, staining, swelling, wrinkling) are described in, for example, "ASTM Book of Standards, Volume 06.02, Paint—Products and Applications; Protective Coatings; Pipeline Coatings," D1308-02, D2571-95, D2792-69, D4752-98, D3260-01, D6137-97, D6686-01, D6688-01, and D6578-00, 2002; "ASTM Book of Standards, Volume 06.01, Paint—Tests for Chemical, Physical, and Optical Properties; Appearance," D2370-98, D2248-01a, and D870-02, 2002; "ASTM Book of Standards, Volume 06.03, Paint—Pigments, Drying Oils, Polymers, Resins, Naval Stores, Cellulosic Esters, and Ink Vehicles," D1647-89, 2002; and "Paint and Coating Testing Manual, Fourteenth Edition of the Gardner-Sward Handbook," (Koleske, J. V. Ed.), pp. 662-666, 1995. Additionally, examples of a standard technique for determining the solvent resistance of a film are described in "ASTM Book of Standards, Volume 06.02, Paint—Products and Applications; Protective Coatings; Pipeline Coatings," D4752-98 and D5402-93, 2002.

Standard techniques for determining a film's and/or surface's (e.g., metal, wood) resistance to water permeability and/or damage (e.g., corrosion, blistering, adhesion reduction, hardness alteration, color alteration, gloss alteration) by contact with water and/or moisture are described in, for example, "ASTM Book of Standards, Volume 06.01, Paint—Tests for Chemical, Physical, and Optical Properties; Appearance," D870-02, D1653-93, D1735-02, D2247-02, and D4585-99, 2002; and "ASTM Book of Standards, Volume 06.02, Paint—Products and Applications; Protective Coatings; Pipeline Coatings," D2065-96, D2921-98, D3459-98, and D6665-01, 2002.

Standard techniques for determining a film's resistance to damage by a temperature greater than ambient condition are known to those of ordinary skill in the art. Thermal resistance is the film's ability to undergo stress from a temperature at or below 200° C. without discernable damage, while heat resistance is the film's ability to undergo stress from a temperature above 200° C. (e.g., fire resistance, fire retardancy, flame resistance) without discernable damage. Standard techniques for determining the thermal and/or heat resistance of a film (e.g., a metal-film, a wood-lacquer) by evaluating possible damage (e.g., adhesion loss, alteration of gloss, blistering, chalking, discoloration) are described in, for example, "ASTM Book of Standards, Volume 06.01, Paint—Tests for Chemical, Physical, and Optical Properties; Appearance," D2370-98, D2485-91, D1360-98, D4206-96, and D3806-98, 2002; and "ASTM Book of Standards, Volume 06.02, Paint—Products and Applications; Protective Coatings; Pipeline Coatings," D1211-97 and D6491-99, 2002.

In some embodiments, it may be desirable to measure the component composition of a coating and/or film such as to verify the presence, absence and/or amount of one or more coating components in a particular formulation. Standard procedures for sampling a coating and/or film, and analyzing the material composition (e.g., a pigment, a binder, liquid component, toxic material), have been described in, for example, "ASTM Book of Standards, Volume 06.01, Paint—Tests for Chemical, Physical, and Optical Properties; Appearance," D2371-85, D5380-93, D2372-85, D2698-90, D3723-84, D4451-02, D4563-02, D5145-90, D3925-02, D2348-02, D2245-90, D3624-85a, D3717-85a, D2349-90, D2350-90, D2351-90, D2352-85, D3271-87, D3272-76, D4017-02, D3792-99, D4457-02, D6133-00, D6191-97, D4764-01, D3718-85a, D3335-85a, D6580-00, E848-94, D4834-88, D4358-84, D2621-87, D3618-85a, D6438-99, D4359-90, D3168-85, and D4948-89, 2002; "ASTM Book of Standards, Volume 06.02, Paint—Products and Applications; Protective Coatings; Pipeline Coatings," D5702-02, 2002; and "ASTM Book of Standards, Volume 06.03, Paint—Pigments, Drying Oils, Polymers, Resins, Naval Stores, Cellulosic Esters, and Ink Vehicles," D1469-00, 2002.

The nonvolatile content of a coating component and/or coating ("total solids content") can provide an estimate, for example, of the volume of film that will be produced by a coating or coating component (e.g., a paint, a clear coating, an electrocoat bath applied coating, a binder solution, an emulsion, a varnish, an oil, a drier, a solvent) and/or the surface area a coating can cover relative to a film's thickness. The nonvolatile content of coating and/or coating component can be determined by any technique known in the art (see, for example, "ASTM Book of Standards, Volume 06.01, Paint—Tests for Chemical, Physical, and Optical Properties; Appearance," D6093-97, D2697-86, D1259-85, D1644-01, D2832-92, and D4209-82 D5145-90, 2002; "ASTM Book of Standards, Volume 06.02, Paint—Products and Applications; Protective Coatings; Pipeline Coatings," D4713-92, D5095-91, 2002; and "ASTM Book of Standards, Volume 06.03, Paint—Pigments, Drying Oils, Polymers, Resins, Naval Stores, Cellulosic Esters, and Ink Vehicles," D4139-82, 2002. Additionally, the volatile component of a coating can provide an estimate, for example, of VOC release and/or thermoplastic film formation time. The nonvolatile content of coating and/or coating component (e.g., a paint, a clear coating, an automotive coating, an emulsion, a binder solution, a varnish, an oil, a drier, a solvent) can be determined by any technique known in the art (see, for example, "ASTM Book of Standards, Volume 06.01, Paint—Tests for Chemical, Physical, and Optical Properties; Appearance," D2369-01e1, D2832-92, D3960-02, D4140-82, D4209-82, D5087-02 and D6266-00a, 2002;

and "ASTM Book of Standards, Volume 06.02, Paint—Products and Applications; Protective Coatings; Pipeline Coatings," D5403-93, 2002.

Standard procedures for determining the visual appearance of a coating component, coating and or film (e.g., reflectance, retroreflectance, fluorescence, photoluminescent light transmission, color, tinting strength, whiteness, measurement instruments, computerized data analysis) have been described, for example, in "ASTM Book of Standards, Volume 06.01, Paint—Tests for Chemical, Physical, and Optical Properties; Appearance," E284-02b, E312-02, E805-01a, E179-96, E991-98, E1247-92, E308-01, E313-00, E808-01, E1336-96, E1341-96, E1347-97, E1360-90, D332-87, D387-00, E1455-97, E1477-98a, E1478-97 E1164-02, E1331-96, E1345-98, E1348-02, E1349-90, D5531-94, D3964-80, E1651-94, E1682-96, E1708-95, E1767-95, E1808-96, E1809-01, E2022-01, E2072-00, E2073-02, E2152-01, E2153-01, D1544-98, E259-98, D3022-84, D1535-01, E2175-01, E2214-02, and E2222-02, 2002; "ASTM Book of Standards, Volume 06.02, Paint—Products and Applications; Protective Coatings; Pipeline Coatings," D4838-88 and D5326-94a, 2002; and "ASTM Book of Standards, Volume 06.03, Paint—Pigments, Drying Oils, Polymers, Resins, Naval Stores, Cellulosic Esters, and Ink Vehicles," D2090-98, D2090-98 and D6166-97, 2002. Specific techniques for matching two or more colored coatings and/coating components to minimalize differences (e.g., metamerism) have been described, for example, in "ASTM Book of Standards, Volume 06.01, Paint—Tests for Chemical, Physical, and Optical Properties; Appearance," D4086-92a, E1541-98 D2244-02 2002. Specific techniques for determining differences in the color of a coatings and/coating components, particularly to insure color consistency of a coating composition, "ASTM Book of Standards, Volume 06.01, Paint—Tests for Chemical, Physical, and Optical Properties; Appearance," D1729-96, D2616-96, E1499-97, and D3134-97, 2002.

Gloss is the film's "angular selectivity of reflectance, involving surface-reflected light, responsible for the degree to which reflected highlights or images of objects may be seen as superimposed on a surface" ("ASTM Book of Standards, Volume 06.01, Paint—Tests for Chemical, Physical, and Optical Properties; Appearance," E284-02b, 2002). An example of a high gloss coating would be a paint film with a glass-like surface appearance, as opposed to a low-gloss ("flat") paint. Standard techniques for determining the gloss (e.g., specular gloss, sheen, haze, image clarity, waviness, directionality) of a coating and/or film are described, for example, in "ASTM Book of Standards, Volume 06.01, Paint—Tests for Chemical, Physical, and Optical Properties; Appearance," E284-02b, D523-89, D4449-90, E167-96, E430-97, D4039-93, D5767-95, and D2244-02, 2002; "ASTM Book of Standards, Volume 06.02, Paint—Products and Applications; Protective Coatings; Pipeline Coatings," D3928-00a, 2002; and "Paint and Coating Testing Manual, Fourteenth Edition of the Gardner-Sward Handbook," (Koleske, J. V. Ed.), pp. 470-480, 1995.

7. Preferred Use of the Invention

In certain embodiments, the compositions and methods of the present invention have use in three primary markets that will benefit from a susceptible surface covered with a self-decontaminating coating: domestic military, friendly foreign military/civilian, and domestic civilian. It is contemplated that for military use, a self-decontaminating coating has utility on a surface of a vehicle, a trailer, a barrack, a decontamination shelter, a piece of equipment (e.g., a piece of electronic equipment) or a combination thereof.

It is further contemplated that a biomolecular composition of the present invention may have dual military and/or civilian use in a method for facilitating the disposal of a chemical waste, including but not limited to, a CWA, a pesticide or a combination thereof. A particular dual use embodiment of the present invention includes coating a surface that may be in a facility where there would be an unexceptable delay to the use of a piece of equipment, a space (e.g., a room, a command center, a computer center), a vehicle (e.g., a public transportation vehicle, an emergency vehicle) or a combination thereof if the facility was subjected to or suspected of exposure to, a dangerous chemical (e.g., a nerve agent). In some aspects, the piece of equipment, the space, and/or the vehicle may be used by a military personnel, an emergency personnel or a combination thereof. In specific facets, the piece of equipment, the space, and/or the vehicle is a critical piece of equipment, space and/or vehicle. It is contemplated that such a facility may be contacted with a chemical from a chemical weapon attack (e.g., a CWA gas attack), an accidental release of a chemical, or a combination thereof. Examples of such facilities include a control room at a military base, an airport, a nuclear power plant, a hospital, or a combination thereof. It is an aspect of the disclosure that a facility (i.e., a space, a vehicle, a piece of equipment) that may be subject to exposure to a chemical (e.g., a nerve agent) may be coated with the disclosed compositions and would then be detoxified and safe after contact with the chemical.

Civilian applications contemplated include a coating of a surface in contact with air, such as for example, a ventilation intake or an air filter, as well as a surface (e.g., an interior surface, an exterior surface) comprised in a hospital clean room, a community safe room, a control room for a nuclear plant, a control room for a chemical plant, a control room for a power plant, a control room for a water plant, a government building, an industrial building, a facility for public transportation (e.g., a train, a subway, a plane, an airport), and a surface of an equipment by a first responder, or any combination of the forgoing.

It is contemplated that for each formulation of a coating and a biomolecular composition of the present invention, enzymatic decontamination parameters based on chemical (e.g., CWA simulant) degradation assessment will be established in a range of exterior weathering conditions. If a specific formulation of enzyme composition in a coating remains active after exposure to exterior weathering conditions, there is a significant utility for using the bioactive painted surfaces in exterior and field application. For example, it is contemplated that a biomolecular composition of the present invention incorporated in standard formulations of water-based or latex-based paint will result in minimal to no changes in the durability of the paint based on standard exterior weathering conditions. In a general aspect of the present invention, a weathering study may indicate a need to reformulate a composition to improve a particular property (e.g., enhance biomolecular composition stability). In this aspect, it is contemplated that standard methods, known to those of skill in the art (e.g., encapsulation), may be used to increase stability and re-test the resulting formulation. Application of such methods can be used to modify various formulations to produce a composition with one or more properties optimized to a particular application, as described herein and as would be know to one of ordinary skill in the art in light of the present disclosures.

8. Combinations of Decontamination Compositions and Methods

In certain embodiments, a composition or method of the present invention may be combined with another composition method for decontamination (e.g., detoxification, degradation) of a chemical. In preferred aspects, the additional composition or method comprises one for decontamination of a pesticide or chemical warfare agent. Such additional compositions and methods are known in the art (Yang, Y. C. et al., 1992), and may be applied prior, during and/or after application of a composition and/or method of the present invention. In particularly preferred embodiments, such a combination of a composition and/or method disclosed herein with a traditional composition and/or method produces greater decontamination than that achieved without such a combination.

Additional compositions that are contemplated include, but are not limited to, a caustic agent; a decontaminating foam (e.g., Sandia, Decon Green); an application of intensive heat and carbon dioxide for a sustained period; an incorporation of a material into a coating that, when exposed to sustained high levels of UV light, degrades a chemical; a chemical agent resistant coating; or a combination thereof. Examples of a caustic agent include, a bleaching agent, DS2, or a combination thereof.

As used herein, a "caustic agent" is a composition capable of destroying usually via a chemical reaction, a material, unfortunately including animal tissue such as skin. Thus, application of a caustic agent is often accompanied by the wearing of protective gear for those not contaminated or suspected of being contaminated, as would be understood by those of ordinary skill in the art. Certain caustic agents, such as for example, a bleaching agent or decontamination solution 2 ("DS2"), have specifically been formulated and/or used to decontaminate chemical warfare agents. Both G agents and VX can be decontaminated with these caustic agents. As used herein, a "bleaching agent" refers to a reactive chemical compound capable breaking a double bond in another chemical compound, which is often a useful property for degrading a toxic or otherwise undesirable chemical. Examples of a bleaching agent include a bleach powder, a bleach solution, or a combination thereof. A bleach powder may comprise, but is not limited to, Ca(OCl)Cl and Ca(OCl)$_2$ ("high test hypochlorite," "HTH"); Ca(OCl)$_2$ and CaO ("super tropical bleach," "STB"); Ca(OCl)$_2$ and MgO ("Dutch powder"); or a combination thereof. A bleach solution may comprise, but is not limited to, NaOCl ("bleach"), usually 2% to 6% wt in water; a HTH slurry, usually 7% HTH wt in water; a STB slurry, usually 7% to 70% wt in water; activated solution of hypochlorite ("ASH"), usually 0.5% Ca(OCl)$_2$ and 0.5% sodium dihydrogen phosphate buffer and 0.05% detergent in water; self-limited activated solution of hypochlorite ("SLASH"), usually 0.5% Ca(OCl)$_2$ and 1.0% sodium citrate and 0.2% citrate acid and 0.05% detergent in water; or a combination thereof. Bleach, Dutch powder, ASH and SLASH are generally applied to skin and equipment for decontamination, while HTH and STB are generally applied to equipment and terrain for decontamination. VX is preferably decontaminated at an acid pH, wherein it is more soluble (Yang, Y. C. et al., 1992).

DS2 was developed to function at various temperatures (i.e., −25° C. to 52° C.), particularly those below the freezing point of most aqueous compositions. It usually comprises 70% diethylenetriamine (H$_2$NCH$_2$CH$_2$NHCH$_2$CH$_2$NH$_2$), 28% ethylene glycol monomethyl ether (CH$_3$OCH$_2$CH$_2$OH), and 2% sodium hydroxide (NaOH). DS2 is noncorrosive to many metals, but is damaging to many paints, leathers, rubber materials, plastics and skin. Contact with a paint is generally limited to 30 minutes or less. An aqueous rinse is generally used to remove DS2, and exposure to air and/or water degrades DS2 (Yang, Y. C. et al., 1992).

Various other decontamination compositions and methods are known to those of skill in the art. Examples of a decontaminating foam include Sandia, Decon Green, or a combination thereof. Examples of an incorporation of a material include incorporation of TiO$_2$ and porphyrins into acetonitrile coatings that, when exposed to a sustained high level of UV light in an oxygen environment (e.g., air), degrade a chemical agent (e.g., mustard). Addition of water to the acetonitrile coating comprising TiO$_2$ and porphyrins will aid the degradation of VX to non-toxic compounds (Buchanan, J. H. et al., 1989; Fox, M. A., 1983). Additionally, CARCs have been developed to withstand repeated decontamination efforts.

Decontamination compositions are often prepared and packaged in equipment for easy of handling. Such an equipment packages include, but are not limited to, kits (e.g., a towelette package) and delivery apparatus (e.g., a sprayer). Examples of specific decontamination equipment packages that may be used in combination with a composition or method of the present invention include a ABC-M11 portable decontamination apparatus, which comprises DS2, a devise for spraying DS2, and a vehicle mounting bracket; a ABC-M12A1 power-driven, skid-mounted decontamination apparatus, which comprises a personnel shower unit, a pump, a tank, a M2 water heater, and delivers water, foam, DS2, STB, and/or deicing liquid; a M258A1 personal decontamination kit, which comprises towelettes soaked with a decontamination solution (i.e., 72% ethanol, 10% phenol, 5% NaOH, 0.2% ammonia, and 12% water), ampules of a decontaminating solution (5% ZnCl$_2$, 45% ethanol, 50% water) for adding to a towelette soaked with chloramines-B (PhS(O)$_2$NClNa), packing foil, and a plastic carrying case; a M280 individual equipment decontamination kit, which comprises twenty fold the contents of the M258A1 kit; a M291 skin decontamination kit, which comprises six XE-555 resin (i.e., styrene/divinyl benzene copolymer, a strong acid cation-exchange resin and a strong base anion-exchange resin for absorption and chemical detoxification) filled fiber pads packaged in foil; a M13 portable decontamination apparatus, which comprises DS2, a container and an equipment/vehicle mount, and is capable of dispensing DS2; a M17 lightweight, transportable decontamination apparatus, which comprises hoses, cleaning jets, personnel showers, a collapsible rubberized fabric tank, and is capable of dispensing water; or a combination thereof. The ABC-M11, M13 and M280 decontamination equipment packages are generally used for equipment (e.g., vehicles), the M258A1 and M17 decontamination equipment packages are generally used for equipment and/or personnel, and the ABC-M12A1 and M291 decontamination equipment packages are generally used for personnel (Yang, Y. C. et al., 1992).

9. Removing a Coating or Film

In certain embodiments, it may be desirable to remove a coating and/or film from a surface such as a non-film forming coating, a temporary film, a self-cleaning film, a coating and/or film that has been damaged, contaminated with an OP compound, or is otherwise no longer desired or no longer is suitable for use. Various coating removers (e.g., a paint remover) are known to those of ordinary skill in the art, and often comprise solvents described herein capable of dissolving a coating component (e.g., a binder) integral to a film's structural integrity. Standard procedures for determining the effectiveness of a coating remover have been described, for example, in "ASTM Book of Standards, Volume 06.02, Paint—Products and Applications; Protective Coatings; Pipeline Coatings," D6189-97, 2002.

EXAMPLE 1

Assay for Active Phosphoric Triester Hydrolase Expression in Cells

Routine analysis of parathion hydrolysis in whole cells is accomplished by suspending cultures in 10 milli-Molar ("mM") Tris hydrochloride at pH 8.0 comprising 1.0 mM sodium EDTA ("TE buffer"). Cell-free extracts are assayed using sonicated extracts in 0.5 milliLiters ("ml") of TE buffer. The suspended cells or cell extracts are incubated with 10 microLiters ("µl") of substrate, specifically 100 µg of parathion in 10% methanol, and p-nitrophenol production is monitored at a wavelength of 400 nm. To induce the opd gene under lac control, 1.0 µmol of isopropyl-β-D-thiogalactopyranoside (Sigma) per ml is added to the culture media.

EXAMPLE 2

Preparation of Enzyme Powder

In a typical preparation, a single colony of bacteria that expresses the opd gene is selected and cultured in a rich media. After growth to saturation, the cells are concentrated by centrifugation at 7000 rotations per minute ("rpm") for 10 minutes for example. The cell pellet is then resuspended in a volatile organic solvent such as acetone one or two times in order to desiccate the cells and to remove a substantial portion of the water contained in the cell pellet. The pellet may then be ground or milled to a powder form. The powder may be frozen or stored at ambient conditions for future use, or may be added immediately to a surface coating formulation. Additionally, the powder may be freeze dried, combined with a cryoprotectant (e.g., cryopreservative), or a combination thereof.

EXAMPLE 3

Two-Pack OPH Paint Coating: OPH Powder and Latex Paint

In an example of use of the powder prepared as described in Example 2, 3 mg of the milled powder was added to 3 ml of 50% glycerol. The suspension was then added to 100 ml of Olympic® premium interior flat latex paint (Olympic®, One PPG Place, Pittsburgh, Pa. 15272 USA). This paint with biomolecular composition was then used to demonstrate the activity of the paint biomolecular composition in hydrolysis of a pesticide or a nerve agent analog.

EXAMPLE 4

Application of OPH Paint to a Surface

In a first set of assays, a paint product as prepared in Example 3 was applied to a hard, metal surface. The surface used in the present example was a non-galvanized steel surface that was cleaned through being degreased, and pretreated with a primer coat. A control surface was painted with the identical paint with no biomolecular composition. Paraoxon, an organophosphorus nerve gas analog was used as an indicator of enzyme activity. Paraoxon, which is colorless, is degraded to form p-nitrophenol, which is yellow in color, plus diethyl phosphate, thus giving a visual indication of enzyme activity. In multiple assays, the surface with control paint remained white, indicating no production of p-nitrophenol, and the surface painted with the paint and biomolecular composition turned yellow within minutes, indicating an active OPH enzyme in the paint. This demonstration has shown that the surface remains active for more than 65 days, which was the maximum duration of the protocol.

In a further demonstration, the surfaces were treated as described above and each surface was then treated with paraoxon, an OP insecticide. Approximately 100 flies were then placed on each surface under a plastic cover. In each procedure, within three hours, virtually all the flies on the control surface with no paint biomolecular composition were killed by the paraoxon. In contrast, only approximately 5% of the flies on the enzyme comprising surface had died.

In a demonstration of enzyme stability in the paint, a series of wood dowels were dipped into the paint with OPH enzyme composition. The dowels were then placed in tubes containing paraoxon to indicate enzyme activity as described above. In each case, a positive yellow color was seen except in those dowels painted with no biomolecular composition as controls. The control solution remained clear in every case.

In order to demonstrate the shelf life of both the dry biomolecular composition and the paint with biomolecular composition, the biomolecular composition was aged from 0 to 20 days prior to mixing in the paint. The mixed paint and biomolecular composition was then also aged from 0 to 20 prior to painting individual dowels. The enzyme composition retained strong activity after 20 days aging prior to being mixed in the paint, and for 20 days after mixing the maximum time used in the assay.

EXAMPLE 5

Buffered Enzyme Paint

As the hydrolysis reaction that degrades nerve agents proceeds, the local pH decreases. Without limiting the invention to any particular mechanism, it is contemplated that due to the law of mass action, or to the optimum pH of the enzyme, the reaction is slower as the pH decreases. Because this effect could prevent or inhibit some surfaces from becoming completely decontaminated, active paint formulations have been prepared that include one or more buffering agents.

In initial procedures, the following compositions were used: 10 mg enzyme powder as described in Example 2, 100 µl 0.1 M buffer, 800 µl $H_2O$, and 100 µl paraoxon for a 1000 µl reaction volume.

Reactions were run for 1.5 to 2 hours and both pH and product concentration were measured. The concentration of product (p-nitrophenol) is measured by absorbance at 400 nm.

Ammonium bicarbonate, both monobasic and dibasic phosphate buffers, Trizma base and five zwitterionic buffers have been used in the active paint compositions. All the buffers were effective at allowing the reaction to proceed further to completion, thus demonstrating the advantage of addition of a buffering agent to the active paint compositions.

EXAMPLE 6

NATO Demonstration of Soman Detoxification Using OPH-Painted Surfaces

At the Sep. 22, 2002, meeting of the NATO Army Armaments Group in Cazaux, France, painted metal surfaces were assayed with soman using standard NATO procedures and protocols. For the assays, 10 cm×10 cm metal plates primed with standard NATO specification paints were coated with paint containing OPH. Control plates plus two different versions of the OPH enzyme composition differing in soman detoxification specificity were used. These surfaces were allowed to dry for several hours at room temperature and then assayed according to standard NATO assay protocol (described below), modified to account for the unique character of the surfaces treated with a paint comprising OPH.

The form of OPH in the biomolecular composition contains both the changes of the previously described H254R mutant and the H257L mutant, and is corresponding designated the "H254R, H257L mutant." The H254R, H257L mutant demonstrates a several-fold enhanced rates of R-VX catalysis relative to either the H254R mutant or the H257L mutant, and a 20-fold enhancement of activity relative to wild-type OPH. This version of the OPH biomolecular composition has been assayed in paints treated with soman or R-VX, and are described below.

Following standard protocols, OPD painted surfaces were uniformly contaminated with an isopropanol solution containing the chemical warfare agent soman. The concentration of soman on each contaminated surface was 1.0 mg/cm$^2$. The contaminated plates were maintained at or slightly above room temperature (≥20° C.) without any forced air-flow for various periods of time. A zero-time, 15 minutes, 30 minutes, and 45 minutes sample was taken for each control and biomolecular composition-containing plate series. In order to terminate the reaction and isolate residual soman on the plate surface, each plate was submerged in a container of isopropanol at the end-point and placed on a shaker to thoroughly extract any residual nerve agent. The solubilized portions were then quantified for soman. These assays showed that both the forms of OPH biomolecular composition were highly effective in detoxifying soman on metal surfaces. The two different OPH biomolecular compositions assayed detoxified the soman at levels over 65% and 77% after 45 minutes (Nato Army Armaments Group Project Group 31 on Non-Corrosive, Biotechnology-Based Decontaminants for CBW Agents, 2002). Additional assays with a CWA simulant indicated that had the NATO assay run for one to two hours, substantially all of the soman would have been detoxified.

EXAMPLE 7

Aberdeen Proving Ground

A demonstration of an OPH biomolecular composition has been conducted at SBCCOM in Aberdeen, Md. In these assays, a primed wooden stick was coated with paint containing OPH biomolecular composition. The painted sticks used were 2 millimeter ("mm") in diameter×15 mm in length. By estimating that the paint layer was 0.25 mm thick, the resulting surface area was approximately 125 mm$^2$. After coating the stick with paint containing OPH biomolecular composition and allowing the paint to dry, the coated stick was inserted into a microfuge tube containing 100 µl of 3.24 mM Russian-VX agent in saline and 900 µl phosphate buffer at pH 8.3. The tubes containing R-VX and the painted sticks were allowed to sit overnight in a hood at room temperature. Appropriate controls were run simultaneously.

The following morning, the contents of the microfuge tubes were assayed for free thiols by the Ellman method. 10 mM DTNB [molecular weight ("MW") 396.3] was prepared in 10 mM phosphate buffer at pH 8.0 for use as the indicator of enzyme activity. OPH paint's cleavage of R-VX releases a free thiol that reacts with DNTP to produce a colored product detectable spectrophotometrically at 405 nm. Ten µl of the microfuge tube contents, 100 µl DTNB solution and 890 µl phosphate buffer at pH 8.3 were read for thiol release at 405 nm using a Varian Carey 300 Spectrophotometer. The spectrophotometer was blanked with an unpainted stick control reaction. The molar equivalent of the R-VX hydrolyzed was determined using an extinction coefficient of 14,150 and the Beer-Lambert equation to calculate the product concentration. Results indicated that overnight exposure to OPH paint coated sticks resulted in decontamination of Russian VX from 32.4 µM in the original tube to less than 1 µM.

EXAMPLE 8

NATO Protocols for Organophosphorus CWA Decontamination

This example describes a method for determining the decontamination properties of a coating, specifically paint, comprising an phosphoric triester hydrolase biomolecular composition of the present invention. NATO assay requirements will be followed as closely as possible. Although actual assaying protocols among NATO countries vary somewhat, standard to all is the level of contamination. For exterior surfaces it is 10 grams per meter squared ("g/m$^2$"). For interiors it is 1 g/m$^2$. Basic elements of NATO assaying procedures are as follows:

A. Coated Surface

A 10×10 cm metal plate coated with a coating that may comprise a biomolecular composition of the present invention.

B. Contamination

Usually achieved with a multi-channel micropipette that can dispense 1 µl drops, with 100 drops per 10×10 cm metal plate.

C. Incubation

The plates will be placed into a sealed incubator, at 25° C. or 30° C., for a period ranging from 30 minutes to 3 hours.

D. Decontamination

The decontamination protocol varies according to the system being assayed. For example, spraying of decontamination solutions will last between 5 seconds to 20 seconds, depending on the pressure of the system.

E. Sampling

For standard solution-based decontamination, the assays will be normally prepared in a way that run-off decontaminant will be collected after it comes in contact with the plates and the CWA agent or CWA simulant. A set of plates will be removed for analysis at intervals, with the most common being 15 minutes and 30 minutes. Any residual liquid on the plates will be added to the run-off. For enzyme biomolecular composition assays, the plates will be not rinsed after decontamination, although the rinse is standard with other decontaminants. This rinsate would also be collected for analysis. A set of plates without decontamination will be used as 0 minute, 15 minute, and 30 minute controls.

F. Analysis

The run-off liquid and rinsate will be immediately extracted with a solvent, such as, for example, chloroform, hexane, etc., known to dissolve the CWA agent or CWA simulant. The plates themselves can be subjected to two types of analysis: contact hazard and off-gas hazard. For contact hazard, the plates will be covered with an absorbent material. For example, the French government uses silica gel TLC plates, and the government of the USA uses a dental dam as the absorbant material. In either case, the absorbant material is held in place with a weight and incubated for 15 minutes to 30 minutes at 25° C. or 30° C. The absorbent will be removed and extracted with solvent. The plates will be then extracted with solvent to determine residual agent absorbed into the paint, and thus the contact hazard. If surface decontamination efficiency, specifically the amount of residual agent detectable, is the only variable being assessed, the plates will be immediately extracted with solvent, eliminating the contact hazard step. All of the solvent samples will be analyzed by Gas Chromatography ("GC") with a flame photometric detector ("FPD") and a phosphorus filter for nerve agents. Some countries use Gas Chromatography-Mass Spectrometry ("GC-MS") for the analysis.

EXAMPLE 9

Large-Scale Batch Fermentation to Produce OPH

Batch Culture-Rich Medium comprised 24 g/L yeast extract; 12 g/L casein hydrolysate; 4 ml/L glycerol; 2.31 g/L $KH_2PO_4$; 12.54 g/L $K_2HPO_4$; 0.24 g/L $CoCl_2.6H_2O$; 2 g/L glucose; 0.2 ml/L PPG2000; and 100 µg/ml ampicillin.

Batch Culture-5 L scale was grown at the following conditions: 30° C.; 400-450 rpm agitation; DO controlled at 20%; uncontrolled initial pH between 6.8-6.9; 5 Lpm (1 vvm) aeration; and atmospheric pressure. Over a time period of 0 to 50 hours, the Escherichia coli strain's growth was measured by optical density at 600 nm, the specific paraoxonase activity was determined ($\mu$mol $ml^{-1}$ $min^{-1}$), the volumetric paraoxonase activity was determined ($\mu$mol $ml^{-1}$ $min^{-1}$), the pH measured over a range of pH 6 to pH 9, the agitation measured over a range of 0 rpm to 500 rpm, and the dissolved oxygen measured over a range of 0% to 100%.

Batch Culture-400 L scale was grown at the following conditions: 30° C.; 150-200 rpm agitation; DO at 0-100%; uncontrolled initial pH 6.58; 200-300 Lpm (0.5-0.75 vvm) aeration; and tank pressure at 0-10 psi. Over a time period of 0 to 30 hours, the Escherichia coli strain's growth was measured by optical density at 600 nm, the specific paraoxonase activity was determined ($\mu$mol $ml^{-1}$ $min^{-1}$), the volumetric paraoxonase activity was determined ($\mu$mol $ml^{-1}$ $min^{-1}$), the pH measured over a range of pH 6 to pH 8, the agitation measured over a range of 0 rpm to 200 rpm, the dissolved oxygen measured over a range of 0% to 100%, the aeration rate measured over a range of 0 to 300 Lpm, and the tamk pressure measured over a range of 0 psi to 12 psi.

EXAMPLE 10

Large-Scale Fed-Batch Fermentation to Produce OPH

Fed Batch Culture-Defined Medium comprised 13.3 g/L $KH_2PO_4$; 4 g/L $(NH_4)_2SO_4$; 1.7 g/L citric acid; 10 g/L glycerol; 1.2 g/L $MgSO_4.7H_2O$; 0.024 g/L $MnCl_2.4H_2O$; 2.26 mg/L $CuCl_2.H_2O$; 5 mg/L $H_3BO_3$; 4.5 mg/L Thiamine HCl; 4 mg/L $Na_2MoO_4.7H_2O$; 0.06 g/L Fe(III) citrate; 8.4 mg/L EDTA; 4 mg/L $CoCl_2.6H_2O$; 8 mg/L $Zn(acetate)_2.H_2O$; and 100 µg/ml ampicillin.

Feed: 500 g/L carbon source and 10 g/L $MgSO_4.7H_2O$.

Batch Culture-5 L scale was grown at the following conditions: 30° C.; 200-1000 rpm agitation; DO controlled at 20%; pH controlled at 6.5; 5 Lpm (1 vvm) aeration; and atmospheric pressure. Feed was initiated as the 16$^{th}$ hour, with the feed rate profile a constant rate with stepwise increments. Over a time period of 0 to 70 hours, the Escherichia coli strain's growth was measured by optical density at 600 nm, the specific paraoxonase activity was determined ($\mu$mol $ml^{-1}$ $min^{-1}$), the volumetric paraoxonase activity was determined ($\mu$mol $ml^{-1}$ $min^{-1}$), the pH measured over a range of pH 6 to pH 9, and the addition of the feed measured from 0 ml to 1000 ml.

EXAMPLE 11

Coating Formulation

It is contemplated that any described coating composition may be altered (e.g., by direct addition and/or coating component substitution) to incorporate the biomolecular composition of the present invention. The previous embodiments of the invention primarily described compositions and techniques for preparing, testing, and using a coating prepared de novo. However, it is contemplated that the biomolecular composition of the present invention may be incorporated into a standard coating by direct addition, as described in Example 3. In specific aspects, it is contemplated that such added biomolecular composition may comprise 0.001% to 40% or more, including all intermediate ranges and combinations thereof, by weight or volume, of the final composition produced by a combination of a coating and the biomolecular composition of the present invention.

Alternatively, it is contemplated that a previously described coating composition may be altered by substitution ("replacement") of one or more coating components, particularly a binder and/or a particulate material coating component (e.g., a pigment, a rheological control agent, a dispersant) by the biomolecular composition of the present invention. It is contemplated that 0.001% to 100%, including all intermediate ranges and combinations thereof, of the binder and/or particulate material coating component may be substituted by biomolecular composition of the present invention. Additionally, the concentration of a biomolecular composition of the present invention may exceed 100%, by weight or volume, of the substituted coating component. In specific aspects, a coating component may be substituted with a biomolecular composition of the present invention equivalent to 0.001% to 500%, including all intermediate ranges and combinations thereof, of the coating component. For example, a 20% (e.g., 2 kg) of a dispersant may be replaced by 10% (e.g., 1 kg) of the biomolecular composition of the present invention to produce a coating with similar dispersion properties as a non-substituted formulation. In an addition example, 70% of a specific pigment (e.g., 7 kg) may be replaced by the equivalent of 127% (e.g., 12.7 kg) of the biomolecular composition of the present invention to produce a coating with similar hiding power as a non-substituted formulation. The various assays described herein, or as would be known to one of ordinary skill in the art in light of the present disclosures, may be used to determine the properties of a coating and/or film produced by direct addition and/or coating component substitution by the biomolecular composition of the present invention.

The following is an example of a exterior gloss alkyd house paint that comprises various particulate materials (e.g., silica, a shading pigment, bentonite clay) that may incorporate a biomolecule composition of the present invention. This example of an exterior gloss alkyd house paint comprises a grind and a letdown. The grind comprises by weight or volume: a first alkyd 232.02 lb or 29.9 gallons; a second alkyd 154.2 lb or 20 gallons; an aliphatic solvent (e.g., duodecane) 69.55 lb or 1.7 gallons; lecithin 7.8 lb or 0.91 gallons; TiO2 185.25 lb or 5.43 gallons; 10 micron silica 59.59 lb or 2.7 gallons; bentonite clay 18.00 lb or 1.44 gallons; a second alkyd 97.22 lb or 12.61 gallons; a first alkyd 69.84 lb or 9.00 gallons; and mildewcide 7.8 lb or 0.82 gallons. The letdown comprises by weight or volume: aliphatic solvent (e.g., dudecane) 19.50 lb or 3.00 gallons; a first drier (e.g., 12% solution cobalt) 2.00 lb or 0.23 gallons; a second drier (e.g., 18% solution Zr) 2.92 lb or 0.32 gallons; a third drier 3 (e.g., 10% solution Ca) 8.00 lb or 0.98 gallons; methyl ethyl ketoxime (Anti skinning agent) 3.22 lb or 0.42 gallons; an aliphatic solvent 9.75 lb or 1.50 gallons; and a shading pigment 0.3 lb or 0.04 gallons. In some embodiments, the particulate material of the coating formulation may be partly or fully substituted by the biomolecule composition of the present invention. In other embodiments, the above formulation may be enhanced by direct addition of a biomolecule composition of the present invention.

In another example, the following exterior flat latex house paint may be modified to incorporate a biomolecule composition of the present invention. This example of an exterior flat latex house paint formulation, in typical order of addition, by weight or volume: water, 244.5 lb or 29.47 gallons; hydroxyethylcellulose, 3 lb or 0.34 gallons; glycols, 60 lb or 6.72 gallons; polyacrylate dispersant, 6.8 lb or 0.69 gallons; biocides, 10 lb or 1 gallons; non-ionic surfactant, 1 lb or 0.11 gallons; titanium dioxide, 225 lb or 6.75 gallons; silicate mineral, 160 lb or 7.38 gallons; calcined clay, 50 lb or 2.28 gallons; acrylic latex, @ 60%, 302.9 lb or 34.42 gallons; coalescent, 9.3 lb or 1.17 gallons; defoamers, 2 lb or 0.26 gallons; ammonium hydroxide, 2.2 lb or 0.29 gallons; 2.5% HEC solution, 76 lb or 9.12 gallons. In some embodiments, the particulate material (e.g., silicate mineral, calcined clay, titanium dioxide) of this coating formulation may be partly or fully substituted by the biomolecule composition of the present invention. In other embodiments, the above formulation may be enhanced by direct addition of a biomolecule composition of the present invention.

It is contemplated that any such previously described coating formulation may be modified to incorporate a biomolecular composition of the present invention. Examples of described coating compositions include over 200 industrial water-borne coating formulations (e.g., air dry coatings, air dry or force air dry coatings, anti-skid of non-slip coatings, bake dry coatings, clear coatings, coil coatings, concrete coatings, dipping enamels, lacquers, primers, protective coatings, spray enamels, traffic and airfield coatings) described in "Industrial water-based paint formulations," 1988, over 550 architectural water-borne coating formulations (e.g., exterior paints, exterior enamels, exterior coatings, interior paints, interior enamels, interior coatings, exterior/interior paints, exterior/interior enamels, exterior/interior primers, exterior/interior stains), described in "Water-based trade paint formulations," 1988, the over 400 solvent borne coating formulations (e.g., exterior paints, exterior enamels, exterior coatings, exterior sealers, exterior fillers, exterior primers, interior paints, interior enamels, interior coatings, interior primers, exterior/interior paints, exterior/interior enamels, exterior/interior coatings, exterior/interior varnishes) described in "Solvent-based paint formulations," 1977; and the over 1500 prepaint specialties and/or surface tolerant coatings (e.g., fillers, sealers, rust preventives, galvanizers, caulks, grouts, glazes, phosphatizers, corrosion inhibitors, neutralizers, graffiti removers, floor surfacers) described in Prepaint Specialties and Surface Tolerant Coatings, by Ernest W. Flick, Noyes Publications, 1991.

EXAMPLE 12

Ranges

To provide a description of the present invention that is both concise and clear, various examples of ranges have been identified herein with the phrase "including all intermediate ranges and combinations thereof". Examples of specific values (e.g., %, kDa, ° C., μm, kg/L, Ku) that can be within a cited range by the reference to "including all intermediate ranges and combinations thereof" include 0.000001, 0.00001, 0.0001, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.1, 1.2, 1.30, 1.31, 1.32, 1.33, 1.34, 1.35, 1.36, 1.37, 1.38, 1.39, 1.40, 1.41, 1.42, 1.43, 1.44, 1.45, 1.46, 1.47, 1.48, 1.49, 1.50, 1.51, 1.52, 1.53, 1.54, 1.55, 1.56, 1.57, 1.58, 1.59, 1.60, 1.61, 1.62, 1.63, 1.64, 1.65, 1.66, 1.67, 1.68, 1.69, 1.70, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1050, 1100, 1150, 1200, 1250, 1300, 1350, 1400, 1450, 1500, 1600, 1700, 1800, 1900, 2000, 3000, 4000, 5000, 6000, 7000, 8000, 9000, 10,000, or more.

However, general ranges for each type of unit (e.g., %, kDa, ° C., μm, kg/L, Ku) are contemplated. Examples of values that can be within a cited percentage range, as applicable, include 0.001% to 100%, including all intermediate ranges and combinations thereof. Examples of values that can be within a cited molecular mass range, as applicable, in kilo Daltons ("kDa"), include 0.50 kDa to 110 kDa, including all intermediate ranges and combinations thereof. Examples of values that can be within a cited temperature range, as applicable, in degrees Celsius ("° C."), that can be within a cited range include of 0° C. to 500° C., including all intermediate ranges and combinations thereof. Examples of values that can be within a thickness range (e.g., coating and/or film thickness upon a surface), as applicable, in micrometers ("μm"), that can be within a cited range include of 1 μm to 2000 μm, including all intermediate ranges and combinations thereof. Examples of values that can be within a cited density range, as applicable, in kilograms per liter ("kg/L"), include 0.50 kg/L to 20 kDa, including all intermediate ranges and combinations thereof. Examples of values that can be within a cited shear rate range, as applicable, in Ku, include 20 Ku to 300 Ku, including all intermediate ranges and combinations thereof.

EXAMPLE 13

Elastomers

It is contemplated that a biomolecular composition may also be incorporated into an elastomer. Elastomers ("rubbers") are polymers that can undergo large, but reversible, deformations upon a relatively low physical stress. It is contemplated that an elastomer composition may incorporate a biomolecular composition of the present invention, such as by preparation with the biomolecular composition and/or direct addition such as by a multi-pack composition. Elastomers (e.g., tire rubbers, polyurethane elastomers, polymers ending in an anionic diene, segmented polyerethane-urea copolymers, diene triblock polymers with styrene-alpha-methylstyrene copolymer end blocks, poly(p-methylstyrene-b-p-methylstyrene), polydimethylsiloxane-vinyl monomer block polymers, chemically modified natural rubber, polymers from hydrogenated polydienes, polyacrylic elastomers, polybutadienes, trans-polyisoprene, polyisobutene, cis-1,4-polybutadiene, polyolefin thermoplastic elastomers, block polymers, polyester thermoplastic elastomer, thermoplastic polyurethane elastomers) and techniques of elastomer synthesis and elastomer property analysis have been described, for example, in Walker, B. M., ed., *Handbook of Thermoplastic Elastomers*, Van Nostrand Reinhold Co., New York, 1979; Holden, G., ed., et. al., *Thermoplastic Elastomers*, $2^{nd}$ Ed., Hanser Publishers, Verlag, 1996.

EXAMPLE 14

Fillers and Filled Polymers

A filler is a bulk material in a composition. Extender pigments are used as a filler for coatings. In certain embodiments, a biomolecular composition may be used as a filler for various compositions. Examples of compositions that use fillers that are contemplated herein for incorporation of a biomolecular composition of the present invention, include a composition comprising a polymer, thermoplastic material, a thermostat material, an elastomer, or a combination thereof. Such filler comprising materials have been described in Gerard, J. F., ed., *Fillers and Filled Polymers—Macromolecular Symposia* 169, Wiley-VCH, Verlag, 2001; Slusarski, L., ed., *Fillers for the New Millenium—Macromolecular Symposia* 194, Wiley-VCH, Verlag, 2003; and Landrock, A. H., *Adhesives Technology Handbook*, Noyes Publications, New Jersey, 1985.

EXAMPLE 15

Adhesives and Sealants

An adhesive is a composition that is capable of holding at least two surfaces together in a strong and permanent manner. A sealant is a composition capable of attaching to at least two surfaces, filling the space between them to provide a barrier or protective coating. In certain embodiments, a biomolecular composition may be used as a component of an adhesive or a sealant, such as, for example, by direct addition, substitution of an adhesive or sealant component (e.g., a particulate material), or a combination thereof.

Examples of adhesives and sealants (e.g., caulks, acrylics, elastomers, phenolic resin, epoxy, polyurethane, anarobic and structural acrylic, high-temperature polymers, water-based industrial type adhesives, water-based paper and packaging adhesives, water-based coatings, hot melt adhesives, hot melt coatings for paper and plastic, epoxy adhesives, plastisol compounds, construction adhesives, flocking adhesives, industrial adhesives, general purpose adhesives, pressure sensitive adhesives, sealants, mastics, urethanes,) for various surfaces (e.g., metal, plastic, textile, paper), adhesive and sealant components (e.g., antifoams, antioxidants, extenders, fillers, pigments, flame/fire retardants, oils, polymer emulsions, preservatives, bactericides, fungicides, resins, rheological/viscosity control agents, starches, waxes, acids, aluminum silicates, antiskinning agents, calcium carbonates, catalysts, cross-linking agents, curing agents, clays, corn starch, starch derivatives, defoamers, antifoams, dispersing agents, emulsifying agents, epoxy resin diluents, lattices, polybutenes, polyvinyl acetates, preservatives, acrylic resins, epoxy resins, ester gums, ethylene/vinyl acetate resins, maleic resins, natural resins, phenolic resins, polyamide resins, polyethylene resins, polypropylene resins, polyterpene resins, powder coating resins, radiation coating resins, urethane resins, vinyl chloride resins, emulsion resins, dispersion resins, resin esters, rosins, silicas, silicon dioxide, stabilizers, surfactants/surface active agents, talcs, thickeners, thixotropic agents, waxes) techniques of preparation and assays for properties, have been described in Skeist, I., ed., *Handbook of Adhesives*, $3^{rd}$ Ed., Van Nostrand Reinhold, New York, 1990; Satriana, M. J. *Hot Melt Adhesives: Manufacture and Applications*, Noyes Data Corporation, New Jersey, 1974; Petrie, E. M., *Handbook of Adhesives and Sealants*, McGraw-Hill, New York, 2000; Hartshorn, S. R., ed., *Structural Adhesives—Chemistry and Technology*. Plenum Press, New York, 1986; Flick, E. W., *Adhesive and Sealant Compound Formulations*, $2^{nd}$ Ed., Noyes Publications, New Jersey, 1984; Flick, E., *Handbook of Raw Adhesives* $2^{nd}$ Ed., Noyes Publications, New Jersey, 1989; Flick, E., *Handbook of Raw Adhesives*, Noyes Publications, New Jersey, 1982; Dunning, H. R., *Pressure Sensitive Adhesives—Formulations and Technology*, $2^{nd}$ Ed., Noyes Data Corporation, New Jersey, 1977; and Flick, E. W., *Construction and Structural Adhesives and Sealants*, Noyes Publications, New Jersey, 1988.

EXAMPLE 16

Textiles

It is contemplated that a biomolecular composition may also be incorporated into a material applied to a textile, such as, for example, a textile finish. Materials for application to a textile, textile finishes (e.g., soil-resistant finishes, stain-resistant finishes) and finish components (e.g., antioxidants, defoamers, antimicrobials, wetting agents, flame retardants, softeners, soil repellents, hand modifiers, antistatic agents, biocides, fixatives, scouring agents, dispersants, defoamers, anticracking agents, binders, stiffeners, cohesive agents, fiber lubricants, emulsifiers, antistats, yarn to hard surface lubricants) as well as assays for determining their properties are described, for example, in Johnson, K., *Antistatic Compositions for Textiles and Plastics*, Noyes Data Corporation, New Jersey, 1976; Rouette, H. K., *Encyclopedia of Textile Finishing*, Springer, Verlag, 2001; "Textile Finishing Chemicals: An Industrial Guide", by Ernest W. Flick, Noyes Publications, 1990; and "Handbook of Fiber Finish Technology", by Philip E. Slade, Marcel Dekker, 1998. A specific example of a textile finish is the trademark formulations of water repellent and/or oil repellent finish known as Scotchguard™ (3M Corporate Headquarters, Maplewood, Minn., U.S.A.).

EXAMPLE 17

Waxes

It is contemplated that a biomolecular composition may also be incorporated into a material applied to a surface after manufacture, such as, for example, a wax. Waxes (e.g., natural waxes, fossil waxes, earth waxes, peat waxes, montana waxes, lignite paraffins, petroleum waxes, synthetic waxes, commercial modified, blended, and compounded waxes, emulsifiable waxes, waxy alcohols, waxy acids, metallic soaps, compounded waxes, paraffin wax compounds, ethyl cellulose and wax mixtures, compositions with resins and rubber) and methods of wax preparation and assays for wax properties have been described, for example, in Warth, A. H., *The Chemistry and Technology of Waxes*, Reinhold Publishing Corporation, New York, 1956; Bennet, H., *Industrial Waxes Volume II Compounded Waxes and Technology*, Chemical Publishing Co., New York, 1975.

EXAMPLE 18

Additional OPAAs

It additional embodiment is it contemplated that the following organisms produce an OPAA that may be used in a biomolecular composition of the present invention: *Acinetobacter calcoaceticus* ATCC 19606, *Aeromonas hydrophila* ATCC 7966, *Aeromonas proteolytica*, Arm. A isolate 1, Arm. A isolate 2, *Bacillus subtilis* (fr. Zuberer), *Bacillus subtilis*, ATCC 18685, *Bacillus subtilis* BRB41, *Bacillus subtilis* Q, *Bacillus thuringensis* (fr. Zuberer), *Burkholderia cepacia* LB400, *Burkholderia cepacia* T, *Citrobacter diversus*, *Citrobacter freundii* ATCC 8090, *Edwardsiella tarda* ATCC 15947, *Enterobacter aerogenes* ATCC 13048, *Enterobacter cloacae* 96-3, *Enterobacter liquefaciens* 363, *Enterobacter liquefaciens* 670, *Erwinia carotovora* EC189-67, *Erwinia herbicola*, *Erwinia herbicola* (*agglomerans*), *Escherichia coli* E63, *Hafnia alvei* ATCC 13337, *Klebsiella pneumoniae* ATCC 13883, *Lactobacillus casei* 686, *Lactococcus lactis* subsp. *lactis* pIL253, *Proteus morganaii*, *Proteus vulgaris* ATCC 13315, *Pseudomonas aeriginosa* ATCC 10145, *Pseudomonas aeriginosa* ATCC 27853, *Pseudomonas flourescens*, *Pseudomonas putida* ATCC 18633, *Pseudomonas putida* PpY101, *Pseudomonas* sp. P, *Salmonella typhimurium* ATCC 14028, *Serratia marcescens* ATCC 8100, *Serratia marcescens* HY, *Serratia marcescens* Nima, *Shigella flexneri* ATCC 12022, *Shigella sonnei* ATCC 25931, *Staphylococcus aureus* ATCC 25923, *Staphylococcus* sp. S, *Streptococcus faecalis* ATCC 19433, *Vibrio parahaemolyticus* TAMU 109, *Yersinia enterocolitica* ATCC 9610, *Yersinia enterocolitica* TAMU 84, *Yersinia frederiksenii* TAMU 91, *Yersinia intermedia* ATCC 29909, *Yersinia intermedii* TAMU 86, *Yersinia kristensenia* ATCC 33640, *Yersinia kristensenia* TAMU 95, *Yersinia* sp. ATCC 29912, *Vibrio proteolyticus* ATCC 15338, *Thermus* sp. ATCC 31674, *Streptomyces cinnamonensis* subsp. *Proteolyticus* ATCC 19893, *Deinococcus proteolyticus* ATCC 35074, *Clostridium proteolyticum* ATCC 49002, *Aeromonas jandaei* ATCC 49568, *Aeromonas veronii* biogroup *sobria* ATCC 9071, *Pseudoaltermonas haloplanktis* ATCC 23821, *Xanthomonas campestris* ATCC 33913, *Pseudoalteromonas espejiana* ATCC 27025, *Shewanella putrefasciens* ATCC 8071, *Stenotrophomonas maltophilus* ATCC 13637, *Ochrobactrum anthropi* ATCC 19286, *Desulfovibrio vulgaris*, or a combination thereof.

EXAMPLE 19

Dowel Assay-Paraoxonase

This example describes assay procedure for quantitative assessment of surface activity of a composition comprising a biomolecular composition using medicine sticks/dowels. The equipment used is a U.V. Spectrophotometer, a U.V. 1 cm pathlength cuvettes, 3 ml and 100 µl volume, and 1.5 ml eppendorf tubes. The reagents used include paraoxon (MW 275.21, ChemService cat#PS-610), 99% CHES ("2-[cyclohexylamino]ethanesulfonic acid"), (MW 207.3, Sigma cat # C-2880), and $CoCL_2 6H_2O$ (MW 237.9, Sigma cat # C-3169). 1 M $CoCl_2$, sterile, can be prepared as 23.79 g $CoCl_2$ per 100 ml $ddH_2O$ that is filter sterilized or autoclaved. 200 mM CHES, pH 9.0, sterile can be prepared as 4.15 g+80 ml ddH20, pH to 9.0 with NaOH, where the total volume with $ddH_2O$ is 100 ml, and can be filter sterilized or autoclaved. The assay buffer is 20 mM CHES, pH 9.0, 50 µM $CoCl_2$.

In a 1.5 mL Eppendorf tube add: paraoxon to 1 mM (ex: 126 µl of 12 mM paraoxon) and assay buffer to 1.5 ml (ex: 1374 µl CHES buffer). Add a 5 mm length of treated stick to start the reaction, mix by inverting. Take 10 µl samples at 1 minute intervals, diluting with 90 µL CHES buffer into a 100 µl cuvette. Record the absorbance at 400 nm ($A_{400nm}$), blanking against CHES buffer+paraoxon. A small amount of hydrolysis of paraoxon without biomolecular composition may occur. Mix by inversion before each time point.

Alternatively, in a 3 ml cuvette, add:paraoxon to 1 mM (ex: 168 µl of 12 mM paraoxon), and assay buffer to 2.0 ml (ex: 1832 µl CHES buffer). Add a 5 (or 15 mm) length of treated stick to start the reaction. Record the ($A_{400nm}$) at the following time points: 0, 15, 30, 45, 60, 120, 180, 240, 300, 360, 420 and 480 minutes. Mix by inversion at regular intervals. If absorbances above 2.5 are observed, dilute 10 µL samples with 90 µL CHES buffer in a 100 µL cuvette, as for fast reactions, above.

The following results (Table 5) demonstrate 90% degradation of the paraoxon over the time frame of measurement by a paroxonase bimolecular additive of the present invention as determined by the dowel assay.

TABLE 5

Results

| Time (seconds) | Replicates | | | umoles p-NP | Std Dev |
|---|---|---|---|---|---|
| | A | B | C | | |
| 0 | 0.0218 | 0.0218 | 0.0224 | 0.0220 | 0.0003 |
| 120 | 0.1794 | 0.1518 | 0.1253 | 0.1522 | 0.0271 |
| 240 | 0.4359 | 0.3953 | 0.3418 | 0.3910 | 0.0472 |
| 360 | 0.7529 | 0.6541 | 0.6218 | 0.6763 | 0.0683 |
| 480 | 0.9494 | 0.8971 | 0.8894 | 0.9120 | 0.0327 |
| 600 | 0.9724 | 0.9688 | 0.9659 | 0.9690 | 0.0032 |
| 720 | 0.9706 | 0.9706 | 0.9729 | 0.9714 | 0.0014 |
| 840 | 0.9700 | 0.9694 | 0.9782 | 0.9725 | 0.0049 |
| 960 | 0.9535 | 0.9535 | 0.9435 | 0.9502 | 0.0058 |
| 1080 | 0.9600 | 0.9935 | 0.9912 | 0.9816 | 0.0187 |
| 1200 | 0.9500 | 0.9665 | 0.9682 | 0.9616 | 0.0101 | p-NP = reaction product

REFERENCES

"ASTM Book of Standards, Volume 06.01, Paint—Tests for Chemical, Physical, and Optical Properties; Appearance" (2002) ASTM International, West Conshohocken, Pa., U.S.A.

"ASTM Book of Standards, Volume 06.02, Paint—Products and Applications; Protective Coatings; Pipeline Coatings" (2002) ASTM International, West Conshohocken, Pa., U.S.A.

"ASTM Book of Standards, Volume 06.03, Paint—Pigments, Drying Oils, Polymers, Resins, Naval Stores, Cellulosic Esters, and Ink Vehicles" (2002) ASTM International, West Conshohocken, Pa., U.S.A.

"ASTM Book of Standards, Volume 06.04, Paint—Solvents; Aromatic Hydrocarbons" (2002) ASTM International, West Conshohocken, Pa., U.S.A.

"Paint and Coating Testing Manual, Fourteenth Edition of the Gardner-Sward Handbook" (Koleske, J. V., Ed.) (1995) American Society for Testing and Materials, Philadelphia, Pa., U.S.A.

"Paint and Surface Coatings, Theory and Practice, Second Edition" (Lambourne, R. and Strivens, T. A., Eds.) (1999) Woodhead Publishing Ltd., Cambridge, England.

"Paints, Coatings and Solvents, Second, Completely Revised Edition" (Stoye, D. and Freitag, W., Eds.) (1998) Wiley-Vch, New York, U.S.A.

Albaret, A. et al., *Prot. Struct. Fund. Genet.* 28:543-555, 1997.

Albizo, J. M. and White, W. E. "The Hydrolysis of GD and VX by Acetone Dried Preparations of Cured and Plasmid-Containing *Pseudomonas Diminuta*" Chemical Research, Development & Engineering Center Scientific conference on Chemical Defense Research, November 18-21, pp. 643-649, 1986.

Andreopoulos, F. M. et al., *Biotech. Bioeng.* 65(5):579-588, 1999.

Andreopoulos, F. M. et al., *Biotech. Bioeng.* 65(5):579-588, 1999.

Ash, M. and Ash, I. "Handbook of Paint and Coating Raw Materials, Second Edition" (1996) Ashgate Publishing Company, Brookfield, Vt., U.S.A.

Ashani, et al., *Biochem. Pharm.* 55:159-168, 1998.

Azzoni, A. R. et al., *Biotech. Bioeng.* 80(3):268-276, 2002.

Baxter, G. D. et al., *Insect Biochem. and Molec. Bio.*, 28:581-589 (1998).

Baxter, G. D. et al., *Insect Biochem. and Molecular Bio.*, 32:815-820 (2002).

Bennet, H., *Industrial Waxes Volume II Compounded Waxes and Technology*, Chemical Publishing Co, New York, 1975.

Benning, M. M. et al., *Biochem.* 33:15001-15007, 1994.

Benning, M. M. et al., *Biochem.* 34:7973-7978, 1995.

Benning, M. M. et al., *J. Biol. Chem.* 275:30556-30560, 2000.

Benschop, H. P. and De Jong, L. P. A. *Acc. Chem. Res.* 21:368-374, 1988.

Benschop, H. P. et al., *Toxic. and Applied Pharm.* 72:61-74, 1984.

Billecke, S. S. et al., *Chemico-Biological Interactions* 119-120, 251-256, 1999.

Brinkmann, U. et al., *Gene* 85:109-114, 1989.

Broomfield, C. A., et al., *Chemico-Biochem. Interactions.*, 119-120:413-418 (1999).

Bugg, C. E. et al., *Sci. Am.*, 269:92-98,1993.

Caldwell, S. R. and Raushel, F. M., *Appl. Biochem Biotech* 31:59-74, 1991b.

Caldwell, S. R. and Raushel, F. M., *Biochem.* 30:744-7450, 1991c.

Caldwell, S. R. and Raushel, F. M., *Biotech. Bioeng.* 37:103-109, 1991a.

Campbell, P. M. et al., *Biochem. Molec. Biol.* 28:139-150, 1998.

Chae, M. Y. et al., *Bioorg. Med. Chem. Lett.* 4:1473-1478, 1994.

Chen, T. et al., *Biomacromolecules* 2:456-462, 2001.

Chen, W. and Mulchandani, A. *Tibtech* 16:71-76, 1998.

Cheng, T.-C. et al., *Appl. Environ. Microbiol.* 62(5):1636-1641, 1996.

Cheng, T.-C. et al., *Applied and Environ. Microbio.* 59(9): 3138-3140, 1993.

Cheng, T.-C. et al., *Chemico-Biological Interactions* 119-120:455-462, 1999.

Cheng, T.-C. et al., *J. Ind. Microbiol.* 18:49-55, 1997.

Chen-Goodspeed, M. et al., *Biochemistry* 40:1332-1339, 2001b.

Chen-Goodspeed, M. et al., *Biochemistry*, 40:1325-1331, 2001a.

Chiang, T. et al., *Bull. Env. Contam. Toxicol.* 34:809-814, 1985.

Cho, C. M. et al., *Applied and Enviro. Microbio.*, 2026-2030, 2002.

Claudianos, C. et al., *Insect Biochem. and Molecular Bio.* 29:675-686, 1999.

Cohen, A. A. and Shatzmiller, S. E., *J. Mol. Graph.* 11:166-173, 1993.

Coller, B. S. et al., *J. Biol Chem.* 268:20741-20743, 1993.

Combes, D. et al., *J. Mol. Biol.* 300:727-742, 2000.

Cousin, X. et al., *J. Biol. Chem.* 271(25):15099-15108, 1996.

Creighton, T. E. *Proteins: Structure and Molecular Properties*, W. H. Freeman & Co., San Francisco, pp 79-86, 1983.

Dave, K. I. et al., *Appl. Microbiol. Biotechnol.* 41:352-358, 1994b.

Dave, K. I. et al., *Biotechnol. Appl. Biochem.* 19:271-284, 1994a.

Dave, K. I. et al., *Chemical-Biological Interactions* 87:55-68, 1993.

Dean, P. M., *BioEssays*, 16:683-687, 1994.

DeFrank, J. J. and Cheng, T.-C., *J. Bacteriol* 173:1938-1943, 1991.

DeFrank, J. J. et al., *Chem.-Biol. Interact.* 87:141-148, 1993.

Desai, U. A. et al., *Protein Expr Purif* 25(1):195-202, 2002.

Diaz-Alejo, N. et al., *Chem.-Biol. Interact.* 108(3):187-196, 1998.

diSioudi, B. D. et al., *Chemico-Biological Interactions* 119-120:211-223, 1999b.
diSioudi, B. et al., *Biochemistry* 38:2866-2872, 1999a.
Donarski, W. J. et al., *Biochemistry* 28:4650-4655, 1989.
Drevon, G. F. and Russell, A. J., *Biomacromolecules* 1:571-576, 2000.
Drevon, G. F. et al., *Biomacromolecules* 2:664-671, 2001.
Drevon, G. F. et al., *Biotechnology and Bioengineering* 79(7):785-794, 2002.
Dumas, D. P. et al., *Biotech. Appl. Biochem.* 11:235-243, 1989a.
Dumas, D. P. et al., *Arch. Biochem. Biophys.* 277:155-159, 1990.
Dumas, D. P. et al., *Experientia*, 46:729-731, 1990.
Dumas, D. P. et al., *The Journal of Bio. Chem.* 264(33): 19659-19665, 1989b.
Dunning, H. R., *Pressure Sensitive Adhesives—Formulations and Technology*, $2^{nd}$ Ed., Noyes Data Corporation, New Jersey, 1977.
Duysen, E. G., *J. Pharm. Exp. Ther.* 302:751-758, 2002.
Edwards, R and Owen, W. J., *Planta* 175:99-106, 1998.
Efremenko, E. N. et al., *J. Biochem. Biophys Methods* 51:195-201, 2002.
Elashvili, I. and Defrank, J. J. "Phosphonate transporter mutation enhances the utilization of diisopropylphosphate (DIPP) and diisopropyl fluorophosphates (DFP) in *Escherichia coli* K-12. Proceedings of 1996 US Army ERDEC Scientific conference on chemical Defense Research, U. S. Army ERDEC, Aberdeen Proving Ground, Aberdeen, Md.
Elashvili, I. et al., *Appl Environ Microbiol* 64(7):2601-2608, 1998.
Ellman, G. L. et al., *Biochem Pharmacol* 7:88-95, 1961.
Endo, F. et al., *J. Biol. Chem.* 264(8):4476-4481, 1989.
Flick, E. W. "Handbook of Paint Raw Materials, Second Edition" (1989) Noyes Data Corporation/Noyes Publications, Park Ridge, N.J., U.S.A.
Flick, E. W., "Prepaint Specialties and Surface Tolerant Coatings," Noyes Publications (1991).
Flick, E. W., "Textile Finishing Chemicals: An Industrial Guide," Noyes Publications (1996).
Flick, E. W., *Adhesive and Sealant Compound Formulations*, $2^{nd}$ Ed., Noyes Publications, New Jersey 1984.
Flick, E. W., *Construction and Structural Adhesives and Sealants*, Noyes Publications, New Jersey, 1988.
Flick, E. W., *Industrial Surfactants*, Noyes Publications, New Jersey, 1988.
Flick, E., *Contemporary Industrial Coatings—Environmentally Safe Formulations*, Noyes Publications, New Jersey, 1985.
Flick, E., *Engineering Resins—An Industrial Guide*, Noyes Publications, New Jersey, 1988.
Flick, E., *Handbook of Raw Adhesives*, $2^{nd}$ Ed., Noyes Publications, New Jersey, 1989.
Flick, E., *Handbook of Raw Adhesives*, Noyes Publications, New Jersey, 1982.
Flick, E., *Water-Soluble Resins—An Industrial Guide*, Noyes Publications, New Jersey, 1986.
Fox, M. A., *Acc. Chem. Res.* 16:314-321, 1983.
Fox, T. G., *Bulletin of the American Physics Society*, 1:123, 1956.
Fujita, T. et al., *Biochim. Biophys. Acta* 1308 (1):49-57, 1996.
Gaberlein, S. et al., *Analyst* 125:2274-2279, 2000.
Gaberlein, S. et al., *Appl Microbiol Biotechnol* 54:652-658, 2000a.

Gallo, M. A. and Lawryk, N. J. (1991) Organic phosphorous pesticides. In: *The Handbook of Pesticide Toxicology* (Eds. Hayes, W. J. Jr. and Laws, E. R) Academic Press, San Diego, Calif. pp. 920-925.
Gao, J. et al., *J. Agric. Food Chem.* 48:614-6120, 2000.
Garden, J. M. et al., *Comp. Biochem. Physiol.* 52C:95-98, 1975.
Gerard, J. F., ed., *Fillers and Filled Polymers—Macromolecular Symposia* 169, Wiley-VCH, Verlag, 2001.
Gillette, M. L., "Using Acid-Base Indicators to Visually Estimate the pH of Solutions," Chemical Education Resources, Inc. (1985).
Glascock, C. B. and Weickert, M. J. *Gene*, 223(1-2):221-231, 1998.
Gopal, S. et al., *Biochem. and Biophys. Research Comm.* 279:516-519, 2000.
Gordon, R. K. et al., *Chemico-Biological Interactions* 119-120:463-470, 1999.
Grauso, M. et al., *FEBS Letter* 424:279-284, 1998.
Greene, T. W. and Wuts, P. G. M. Second Edition, pp. 309-315, John Wiley & Sons, Inc., USA, 1991.
Grimsley, J. K. "Enhancement of OPH production" Final report, U.S. Army Project DAAG-55-97-C-0005, 1997.
Grimsley, J. K. et al., *Biochemistry* 36(47):14366-14374, 1997.
Grimsley, J. K. et al., *Biotechnology Intl.* 2:235-242, 1999.
Hannig, G. and Makrides, S. C. *TIBTECH* 16:54-60, 1998.
Harel, M. et al., *J. Am. Chem. Soc.* 118:2340-2346, 1996.
Harel, M. et al., *Proc Natl Acad Sci USA* 89(22):10827-10831, 1992.
Harper, L. et al., *Appl. Env. Micro.* 54:2586-2589, 1988.
Hartleib, J. and Ruterjans, H *Biochim et Biophys Acta* 1546:312-324, 2001b.
Hartleib, J. and Ruterjans, *Prot. Expression and Purification* 21:210-219, 2001a.
Hartleib, J. et al., *Biochem J* 353:579-589, 2001.
Hartshorn, S. R., ed., *Structural Adhesives—Chemistry and Technology*, Plenum Press, New York, 1986.
Hassett, C. et al., *Biochemistry* 30:10141-10149, 1991.
Havens, P. L. and Rase, H. F. *Ind. Eng. Chem. Res.* 32:2254-2258, 1993.
Hill, C. M. et al., *Bioorganic Chemistry*, 29:27-35, 2001.
Hill, C. M. et al., *Bioorganic Medicinal Chemistry Letters* 10:1285-1288, 2000.
Holden, G., ed., et. al., *Thermoplastic Elastomers*, $2^{nd}$ Ed., Hanser Publishers, Verlag, 1996.
Hong, M. S. et al., *Bioremediation Journal* 2(2):145-157, 1998.
Hong, S.-B. and Raushel, F. M *Chemico-Bio. Interact.* 119-120:225-234, 1999b.
Hong, S.-B. and Raushel, F. M. *Biochem.* 35:10904-10912, 1996.
Hong, S.-B. and Raushel, F. M. *Biochem.* 38:1159-1165, 1999a.
Horne, I. et al., *Appl. Environ. Microbiol.* 68(7):3371-3376, 2002.
Hoskin, F. C. G. "An organophosphorus detoxifying enzyme unique to squid." In: Squid as Experimental Animals (Eds. Gilbert, D. L., Adelman W. J. Jr. and Arnold, J. M.), pp. 469-480. Plenum Press, New York, 1990.
Hoskin, F. C. G. and Roush, A. H., *Science* 215:1255-1257, 1982.
Hoskin, F. C. G. et al., *Biochemical Pharmacology* 46(7): 1223-1227, 1993.
Hoskin, F. C. G. et al., *Fundam. Appl. Toxicol.* 4:5165-5172, 1984.

Hoskin, F. C. G. et al., *Biochemical Pharmacology* 34(12): 2069-2072, 1985.
Hoskin, F. C. G. et al., *Biochemical Pharmacology* 49(5): 711-715, 1995.
Hoskin, F. C. G. et al., *Chemico-Biological Interactions* 119-120:399-404, 1999.
Hoskin, F. C. G. et al., Chemico-Biological Interactions 119-120:439-444, 1999.
Hruby, V. J., *Biopolymers*, 33:1073-1082, 1993.
Hung, S.-C. and Liao, J. C., *Appl. Biochem. Biotechnol.* 56(1):37-47, 1996.
In "Chemical Warfare Agents: Toxicity at Low Levels" (Satu M. Somani and James A. Romano, Jr., Eds.) CRC Press, Boca Raton, 2001. Chapter 1, Health Effects of Low-Level Exposure to Nerve Agents, p 2.
In "Chemical Warfare Agents: Toxicity at Low Levels" (Satu M. Somani and James A. Romano, Jr., Eds.) CRC Press, Boca Raton, 2001. Chapter 14, Emergency Response to a Chemical Warfare Agent Incident: Domestic Preparedness, First Response, and Public Health Considerations, p 414.
In "Chemical Warfare Agents: Toxicity at Low Levels" (Satu M. Somani and James A. Romano, Jr., Eds.) CRC Press, Boca Raton, 2001. Chapter 2, Toxicokinetics of Nerve Agents, pp 26-29.
In "Colour Index International" $3^{rd}$ Ed. *Pigment and Solvent Dyes*, Society of Dyers and Colourists American Association of Textile Chemists and Colorists, 1997.
In "Colour Index International" $3^{rd}$ Ed. Society of Dyers and Colourists American Association of Textile Chemists and Colorists, 1971.
In "Current Protocols in Cell Biology" (Morgan, K. Ed.) John Wiley & Sons, 2002.
In "Current Protocols in Cytometry" (Robinson, J. P. Ed.) John Wiley & Sons, 2002.
In "Current Protocols in Immunology" (Coico, R. Ed.) John Wiley & Sons, 2002.
In "Current Protocols in Molecular Biology" (Chanda, V. B. Ed.) John Wiley & Sons, 2002.
In "Current Protocols in Nucleic Acid Chemistry" (Harkins, E. W. Ed.) John Wiley & Sons, 2002.
In "Current Protocols in Pharmacology" (Taylor, G. Ed.) John Wiley & Sons, 2002.
In "Current Protocols in Protein Science" (Taylor, G. Ed.) John Wiley & Sons, 2002.
In "Industrial water-based paint formulations" by Ernest W. Flick, Park Ridge, N.J. Noyes, (1988), xvi, 277; p. 25.
In "Molecular Cloning" (Sambrook, J., and Russell, D. W., Eds.) 3rd Edition, Cold Spring Harbor, N.Y.: Cold Spring Harbor Laboratory Press, 2001.
In "Organic Coatings: Science and Technology" $2^{nd}$ edition, by Zeno W. Wicks Jr., Frank N. Jones, S. Peter Pappas, Publisher: Wiley-Interscience (John Wiley & Sons, Inc. 605 Third Avenue, New York, N.Y.) Table 31.1 Exterior White House Paint, p. 562.
In "Paint and surface coatings: Theory and Practice" $2^{nd}$ Edition (Lambourne, R. and Strivens, T. A. William, Eds) Andrew Publishing, Woodhead Publishing Ltd, Abington Hall, Abington, Cambridge CB1 6AH, England, 1999.
In "Paints, Coatings and Solvents" $2^{nd}$ Edition (Stoye, D. and Freitag, W., Eds) Wiley-Vch, New York, 1998.
Ishii, T. et al., *Biochim. Biophys. Acta* 1308(1):15-16, 1996.
Johnson, K., *Antistatic Compositions for Textiles and Plastics*, Noyes Data Corporation, New Jersey, 1976.
Josse, D. et al., *Chemico-Biological Interactions* 119-120: 71-78, 1999.
Josse, D. et al., *J. Appl. Toxicol.* 21:S7-S11, 2001.
Kaneva, I. et al., *Biotechnol. Prog.* 14:275-278, 1998.
Kim, C. et al., *Biotechnol Bioeng* 65:108-113, 1999.
Kim, J.-W. et al., *Biotechnol. Prog.* 18:429-436, 2002.
Koepke, J. et al., *Acta. Cryst.* D58:1757-1759, 2002.
Kolakowski, J. E. et al., *Biocatal. Biotransform.* 15:297-312, 1997.
Komives, C. et al., *Biotechnol. Prog.* 10:340-343, 1994.
Kuo, J. M. and Raushel, F. M., *Biochemistry* 33:4265-4272, 1994.
Kyte, J. and Doolittle, R. F. *J. Mol. Biol.*, 157:105-132, 1982.
Lai, K. et al., *Arch. Biochem. Biophys.* 318:59-64, 1995.
Lai, K. et al., *J. Biol. Chem.* 269:16579-16584, 1994.
Landis, W. G. et al., *J. Appl. Toxicol.* 7:35-41, 1987.
Landrock, A. H., *Adhesives Technology Handbook*, Noyes Publications, New Jersey, 1985.
Leduc, M. et al., *J. Bacteriol.* 161:627-635, 1985.
Lee, J. Y., et al., *Biotech. & Bioeng.* 43:1146-1152 (1994).
Lei, C. et al., *J Am Chem Soc* 124:11242-11243, 2002.
LeJeune, K. E. and Russell, A. J. *Biotech. and Bioeng.* 51(4):450-457, 1996.
LeJeune, K. E. and Russell, A. J., *Biotech and Bioeng* 62(6):559-665, 1999.
LeJeune, K. E. et al., *Ann. NY Acad. Sci.* 864:153-170, 1998a.
LeJeune, K. E. et al., *Biotechnology and Bioengineering* 54(2):105-114, 1997.
LeJeune, K. E. et al., *Biotechnology and Bioengineering* 64(2):250-254, 1999.
LeJeune, K. E., Wild, J. R., Russell, A. J. "Nerve agents degraded by enzymatic foams" 395(6697):27-28, 1998b.
Lenz, D. E. et al., *Biochim Biophys. Acta,* 321:189-196, 1973.
Lewis, V. E. et al., *Biochemistry* 27:1591-1597, 1988.
Li, W.-S. et al., *Bioorganic & Medicinal Chemistry*, 9:2083-2091, 2001.
Lineweaver, H. and Burke, D. "*J. Am. Chem. Soc.* 56:658-666, 1934.
Little, J. S. et al., *Biochem Pharmacol* 38(1):23-29, 1989.
Lockridge, O. et al., *Biochemistry* 36:786-795, 1997.
Luo, C. et al., *Biochemistry* 38:9937-9947, 1999.
Main, A. R., *Biochem J.* 74:10-20, 1960.
Makrides, S. C. *Microbiol. Rev.* 60:512-538, 1996.
Martinez, M. B. et al., *Biochem* 35(4):1179-1186, 1996.
Martinez, M. B. et al., *Biochem* 40(40):11965-11974, 2001.
Masson, P. et al., *J. Physiology (Paris)*, 92:357-362, 1999.
McClellan, J. S. et al., *Eur. J. Biochem.* 258:419-429, 1998.
McDaniel, S. and Wild, J. *Arch. Env. Contam. Toxic.* 17:189-194, 1988.
McDaniel, S. et al., *J. Bact.* 170:2306-2311, 1988a.
McDaniel, S., Ph.D. Dissertation, Texas A&M University, 1985.
McGuinn, W. D. et al., *Fundamental and Applied Toxicology* 21:38-43, 1993.
McTiernan, C. et al., *Proc. Natl. Acad. Sci.* 84:6682-6686, 1987.
Mehrotra, K. N., and Phokela, A., *Indian J. Entomol.* 34:355-358, 1974.
Millard, C. B. et al., *Biochemistry* 37(1):237-247, 1998.
Millard, C. B. et al., *Biochemistry*, 38:7032-7039, 1999.
Millard, C. B. et al., *Biochemistry.* 34(49):15925-15933, 1995.
Millard, C. B. et al., *Biochemistry.* 34(49):15925-15933, 1995.
Miller, C. E. Ph.D. dissertation, Texas A&M University, 1992.
Moore, G. J., *Trends Pharmacol. Sci.*, 15:124-129, 1994.

Mulbry, W. and Karns, J., *J. Bacteriol.* 171:6740-6746, 1989.
Mulbry, W. et al., *Appl. Env. Micro.* 51:926-930, 1986.
Mulchandani, A. et al., *Anal Chem* 70:4140-4145, 1998b.
Mulchandani, A. et al., *Anal Chem* 70:5042-5046, 1998c.
Mulchandani, A. et al., *Biosensors & Bioelectronics* 16:225-230, 2001.
Mulchandani, A. et al., *Biotechnol. Progr* 5:130-134, 1999a.
Mulchandani, A. et al., *Biotechnology and Bioengineering* 63(2):216-223, 1999b.
Mulchandani, A. et al., *Electroanalysis* 10:733-737, 1998a.
Mulchandani, P. et al., *Biosensors & Bioelectronics* 14:77-85, 1999.
Mulchandani, P. et al., *Biosensors & Bioelectronics* 16:433-437, 2001 b.
Mulchandani, P. et al., *Environ Sci Technol* 35:2562-2565, 2001a.
Munnecke, D. M., *Biotechnol. Bioeng.* 21:2247-2261, 1979.
Munnecke, D. M., *Process Biochemistry* 13:14-16, 31, 1978.
Nakahigashi, K. and Inokuchi, H. Nucleic Acids Res. 18(21):6439, 1990.
Nato Army Armaments Group Project Group 31 on Non-Corrosive, Biotechnology-Based Decontaminants for CBW Agents, Decision Sheet AC/225(PG/31)DS(2002)2, 26 Sep., 2002.
Newcomb, R. D. et al., *Proc. Natl. Acad. Sci. USA* 94:7464-7468, 1997.
Nijs, M. et al., *Appl Biochem Biotechnol* 49:75-91, 1994.
Ollis, D. L. et al., *Protein Engineering* 5:197-211, 1992.
Omburo, G. A. et al., *Biochemistry* 32:9148-9155, 1993.
Omburo, G. A. et al., *J. Biol. Chem.* 267:13278-13283, 1992.
Pei, L. et al., *Toxicology and Applied Pharmacology* 124: 296-301, 1994.
Petrie, E. M., *Handbook of Adhesives and Sealants*, McGraw-Hill, New York, 2000.
Petrikovics, I. et al., *Toxicology and Applied Pharmacology* 156:56-63, 1999.
Petrikovics, I. et al., *Drug Delivery* 7:83-89, 2000b.
Petrikovics, I. et al., *Toxicological Sciences* 57:16-21, 2000a.
Phillips, J. P. et al., *Proc. Natl. Acad. Sci. U.S.A.* 87:1-5, 1990.
Powell, M. F. et al., *Pharma. Res.*, 10:1268-1273, 1993.
Rainina, E. I. et al., *Biosensors Bioelectronics* 11:991-1000, 1996.
Rastogi, V. et al., *Biochem. and Biophys. Research Comm.* 241:294-296, 1997.
Raushel, Frank M., *Microbiology*, 5:288-295, 2002.
Raveh, L. et al., *Biochemical Pharmacology* 44(2):397-400, 1992.
Richins, R. D. et al., *Biotechnology and Bioengineering* 69(6):592-596, 2000.
Richins, R. D. et al., *Nature Biotechnology* 15:984-987, 1997.
Rodrigo, L. et al., *Biochem J.* 321:595-601, 1997.
Rogers, K. R. et al., *Biotech Prog* 15:517-521, 1999.
Rogers, S. G. et al., *Enzymology* 153: 253-292, 1987.
Rouette, H. K., *Encyclopedia of Textile Finishing*, Springer-Verlag, Berlin Heidelberg, 2001.
Rowland, S. S. et al., *Appl Environ Microbiol* 57(2):440-444, 1991.
Rowland, S. S. et al., *Appl. Microbiol. Biotechnol.* 38:94-100, 1992.
Russell, R. J. et al., *Analytical Chemistry* 71:4909-4912, 1999.
Satriana, M. J., *Hot Melt Adhesives: Manufacture and Applications*, Noyes Data Corporation, New Jersey, 1974.
Scharff, E. I. et al., *Acta Cryst.* D57:148-149, 2001.
Segel, I. H. Biochemical Calculations: How to Solve Mathematical Problems in General Biochemistry $2^{nd}$ Edition, John Wiley & Sons, Inc., New York, 1976.
Serdar, C. M. and Gibson, D. *Bio/Technology* 3:567-571, 1985.
Serdar, C. M. et al., *Appl Environ Microbiol* 44:246-249, 1982.
Serdar, C. M. et al., *Bio/Technology* 7:1151-1155, 1989.
Shafferman, A. et al., *Biochem. J.* 318:833-840, 1996.
Shim, H. et al., *J. Biol. Chem.* 273(28):17445-17450, 1998.
Shimazu, M. et al., *Biotech and Bioeng* 76(4):318-324, 2001 b.
Shimazu, M. et al., *Biotechnol. Prog.* 17:76-80, 2001a.
Shimazu, M. et al., *Biotechnology and Bioengineering* 81(1):74-79, 2002.
Singh, A. K. et al., *Biosensors & Bioelectronics* 14:703-713, 1999.
Skeist, I., ed., *Handbook of Adhesives*, $3^{rd}$ Ed., Van Nostrand Reinhold, New York, 1990.
Slade, P. E., et al., "Handbook of Fiber Finish Technology," Marcel Dekker (1998).
Slusarski, L., ed., *Fillers for the New Millenium—Macromolecular Symposia* 194, Wiley-VCH, Verlag, 2003.
Somara, S. et al., *Indian J Exp Biol* 40(7):774-779, 2002.
Soreq, H. et al., *Proc. Natl. Acad. Sci.* 87:9688-9692, 1990.
Srivastava, R. et al., *Applied Environ Microbio* 66(10):4366-5371, 2000.
Standard Practice for Cyclic Salt Fog/UV Exposure of Painted Metal, (Alternation Exposures in a Fog/Dry Cabinet and a UV/Condensation Cabinet) (ASTM D5894-96).
Standard Practice for Modifies Salt Spray (Fog) Testing. Appendix A5: Dilute Electrolyte Cyclic Fog/Dry Test (ASTM G85-94).
Standard Practice for Operating Light and Water-Exposure Apparatus (Fluorescent UV-Condensation Type) for Exposure of Nonmetallic Materials. (ASTM G53-88).
Standard Test Method for Evaluation of Painted or Coated Specimens Subjected to Corrosive Environments (ASTM D1654-92).
Steiert, J. G. et al., *Bio/Technology* 7:65-68, 1989.
Steurbaut, W., DeKimpe, N., Schreyen, L., Dejonckheere, W. *Bull Soc. Chim Belg.* 84:791, 1975.
Stevens, R. C. *Structure Fold Des.* 8(9):R177-R185, 2000.
Storkebaum, W. and Witzel, H., *Forschungsber. Landes Nordrhein-Westfalen* 2523:1-23, 1975.
Sussman, J. S. et al., *Science* 253:872-879, 1991.
Tchelet, R. et al., *Soil. Biol. Biochem.* 25:1665-1671, 1993.
Tomasek, P. H., et al., *J. Bacteriology*, 171(7):4038-4044 (1989).
Tuovinen, K. et al., Fundam Appl. Toxicol 23:578-584, 1994.
Ugaki, M. et al., *Nucl. Acid Res.*, 19:371-377, 1991.
Unger, T. F. *The Scientist*, 11(17):20, 1997.
Urry, D. W., *Prog Biophys Mol Biol* 57:23-57, 1992.
van der Wal, F. J. et al., *Appl. Environ. Microbiol.*, 64(2): 392-398, 1998.
Vanhooke, J. L. et al., *Biochemistry* 35:6020-6025, 1996.
Vitarius, J. A. and Sultatos, L. G. *Life Sciences*, 56(2):124-134, 1995.
Vontas, J. G., et al., *Insect Molec. Bio.*, 11(4):329-336 (2002).
Walker, A. W. and Keasling, J. D. *Biotech. and Bioeng.* 78(7):715-721, 2002.

Walker, B. M., ed., *Handbook of Thermoplastic Elastomers*, Van Nostrand Reinhold Co., New York, 1979.
Walsh, S. B., et al., *Biochem. J.*, 359:175-181 (2001).
Wan, E. W. and Baneyx, F. *Protein Expr. Purif.* 14(1):13-22, 1998.
Wang, A. A. et al., *Applied and Environ. Microbio.* 68(4): 1684-1689, 2002.
Wang, J. et al., *Biomacromolecules* 2:700-705, 2001.
Warth, A. H., *The Chemistry and Technology of Waxes*, Reinhold Publishing Corporation, New York, 1956.
Watkins, L. M. et al., *J. Biol. Chem.* 272(41):25596-25601, 1997a.
Watkins, L. M. et al., *Proteins: Struct., Funct., and Gen.* 29:553-561, 1997b.
Whitehouse, L. W., and Ecobichon, D. J., *Pestic. Biochem. Phys.* 5:314-322, 1975.
Wicks, Jr., Z. W., Jones, F. N., Pappas, S. P. "Organic Coatings, Science and Technology, Volume 1: Film Formation, Components, and Appearance" (1992) John Wiley & Sons, Inc., New York, U.S.A.
Wicks, Jr., Z. W., Jones, F. N., Pappas, S. P. "Organic Coatings, Science and Technology, Volume 2: Applications, Properties and Performance" (1992) John Wiley & Sons, Inc., New York, U.S.A.
Wierdl, M. et al., *Biochem. Pharm.* 59:773-781, 2000.
Wild, J. R. et al., *Proc. U.S. Army Chem. Res. Devel. Eng. Center Sci. Conf. Chem. Defense Res.* 18-21 November, p. 629-634, 1986.
Wiley, R. A. and Rich, D. H. *Med. Res. Rev.*, 13:327-384, 1993.
Wu, C.-F. et al., *Appl Microbiol Biotechnol* 54:78-83, 2000b.
Wu, C.-F., *Biotechnol. Prog.* 17:606-611, 2001a.
Wu, C.-F., *Biotechnology and Bioengineering* 75(1):100-103, 2001b.
Wu, C.-F., *Biotechnology and Bioengineering* 77(2):212-218, 2002.
Wu, F. et al., *J. Am. Chem. Soc.* 122:10206-10207, 2000a.
Xu, B. et al., *J. Ferment. Bioeng.* 81:473-481, 1996.
Yang, F. et al., *Biotechnol. Prog.* 11:471-474, 1995.
Yang, Y.-C. et al., *Chem. Rev.* 92:1729-1743, 1992.
Yang, Y.-C. et al., *J. Am. Chem. Soc.* 112:6621-6627, 1990.
Yang, Y.-C. et al., *J. Org. Chem.* 61:8407-8413, 1996.
Yang, Z. et al., *Biotechnol Bioeng* 45:10-17, 1995.
Yang, Z. et al., *Enzyme Microb Technol* 18:82-89, 1996.
Yoshimoto, T. et al., *J. Biochem.* 105(3):412-416, 1989.
Zhang, Y. et al., *Biotech. Bioengineering* 64:221-231, 1998.
Zhongli, C. et al., *Applied and Environmental Microbiology* 67(10):4922-4925, 2001.
Zhu, K. Y., et al., *Insect Biochem. Molec.*, 25(10):1129-1138 (1995).

What is claimed is:

1. A paint comprising an enzymatically active esterase classified in an enzyme subclass designated by Enzyme Commission number EC 3.1.8.1;
   wherein the paint comprises a cell wall material;
   wherein the enzymatically active esterase comprises the aryldialkylphosphatase encoded by the gene set forth by Genbank accession number M20392 or M22863 or an enzymatically active fragment of said aryldialkylphosphatase;
   wherein the aryldialkylphosphatase or fragment has catalytic activity for at least 2months after the paint has undergone solid, adherent film formation on a surface.

2. The paint of claim 1, wherein the cell wall material is in the form of a cell fragment microorganism based particulate material.

3. The paint of claim 1, wherein the enzymatically active esterase comprises a $Co^{2+}$, $Fe^{2+}$, $Cu^{2+}$, $Mn^{2+}$, $Cd^{2+}$, or $Ni^{2+}$ at the enzyme active site.

4. The paint of claim 1, wherein the paint comprises one or more of a binder, a liquid component, a colorant, an additive, or a combination thereof.

5. The paint of claim 4, wherein the binder comprises a thermoplastic binder, a thermosetting binder, or a combination thereof.

6. The paint of claim 4, comprising an additive selected from the group consisting of an accelerator, an adhesion promoter, an antifoamer, anti-insect additive, an antioxidant, an anti-skinning agent, a buffer, a catalyst, a coalescing agent, a corrosion inhibitor, a crosslinking agent, a defoamer, a dehydrator, a dispersant, a drier, electrical additive, an emulsifier, a filler, a flame/fire retardant, a flatting agent, a flow control agent, a gloss aid, a leveling agent, a marproofing agent, a preservative, a silicone additive, a slip agent, a surfactant, a light stabilizer, a rheological control agent, a wetting additive, and combinations thereof.

7. The paint of claim 6, wherein the additive comprises 0.001% to 20.0% by weight, of the paint.

8. The paint of claim 7, wherein the binder comprises a polymer resin, wherein the additive comprises a combination of additives, wherein the combination of additives comprises a crosslinking agent and at least two ultraviolet light stabilizers whereby at least one light stabilizer is a sterically hindered amine, and at least one light stabilizer is a UV absorber, said UV absorber present at a concentration in excess of 5% by weight.

9. The paint of claim 8, wherein said sterically hindered amine is bis(1,2,2,6,6,-pentamethyl-4-poperidinyl) ester or bis(2,2,6,6,-tetramethyl-1-isooctyloxy-4-piperidinyl) ester.

* * * * *